(12) United States Patent
Messinger et al.

(10) Patent No.: US 8,288,367 B2
(45) Date of Patent: Oct. 16, 2012

(54) SUBSTITUTED ESTRATRIENE DERIVATIVES AS 17BETA HSD INHIBITORS

(75) Inventors: Josef Messinger, Sehnde (DE); Uwe Schoen, Burgdorf (DE); Heinrich-Hubert Thole, Hannover (DE); Bettina Husen, Hannover (DE); Pasi Koskimies, Turku (FI); Mikko Unkila, Kaarina (FI)

(73) Assignee: Solvay Pharmaceuticals GmBH, Hannover (DE)

( * ) Notice: Subject to any disclaimer, the term of this patent is extended or adjusted under 35 U.S.C. 154(b) by 1269 days.

(21) Appl. No.: 11/947,025

(22) Filed: Nov. 29, 2007

(65) Prior Publication Data

US 2008/0255075 A1 Oct. 16, 2008

Related U.S. Application Data

(60) Provisional application No. 60/861,753, filed on Nov. 30, 2006.

(51) Int. Cl.
*A61K 31/56* (2006.01)
*C07J 1/00* (2006.01)
(52) U.S. Cl. ........ 514/169; 514/177; 552/502; 552/505; 552/650
(58) Field of Classification Search .................. 552/502, 552/505, 650; 514/169, 177
See application file for complete search history.

(56) References Cited

U.S. PATENT DOCUMENTS

| | | | |
|---|---|---|---|
| 3,347,878 A | 10/1967 | Boswell | |
| 3,413,321 A | 11/1968 | Boswell, Jr. | |
| 5,571,933 A | 11/1996 | Li et al. | |
| 5,677,292 A | 10/1997 | Li et al. | |
| 5,866,603 A | 2/1999 | Li et al. | |
| 6,043,236 A | 3/2000 | Brattsand et al. | |
| 6,541,463 B1 | 4/2003 | Labrie et al. | |
| 2003/0170292 A1 | 9/2003 | Yong et al. | |

FOREIGN PATENT DOCUMENTS

| | | |
|---|---|---|
| EP | 0 367 576 | 5/1990 |
| EP | 0 977 555 | 2/2000 |
| WO | WO 99/46279 | 9/1999 |
| WO | WO 00/07996 | 2/2000 |
| WO | WO 01/42181 A1 | 6/2001 |
| WO | WO 02/26706 A2 | 4/2002 |
| WO | WO 02/32409 A2 | 4/2002 |
| WO | WO 03/017973 A1 | 3/2003 |
| WO | WO 03/022835 A1 | 3/2003 |
| WO | WO 03/033487 A1 | 4/2003 |
| WO | WO 03/101972 A1 | 12/2003 |
| WO | WO 2004/046111 A1 | 6/2004 |
| WO | WO 2004/060488 A1 | 7/2004 |
| WO | WO 2004/080271 A2 | 9/2004 |
| WO | WO 2004/085345 A2 | 10/2004 |
| WO | WO 2004/085457 A2 | 10/2004 |
| WO | WO 2004/085459 A1 | 10/2004 |
| WO | WO 2004/110459 A1 | 12/2004 |
| WO | WO 2005/032527 A2 | 4/2005 |
| WO | WO 2005/047303 A2 | 5/2005 |
| WO | WO 2005/084295 A2 | 9/2005 |
| WO | WO 2006/003012 A1 | 1/2006 |
| WO | WO 2006/003013 A2 | 1/2006 |
| WO | WO 2006/027347 A1 | 3/2006 |
| WO | WO 2006/063585 A1 | 6/2006 |
| WO | WO 2006/125800 A1 | 11/2006 |

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta et al. (Advanced Drug Delivery Reviews, 48 (2001), pp. 3-26).*
Ahmed V, Liu Y, Silvestro C, Taylor SD (2006) "Boronic acids as inhibitors of steroid sulfatase" Bioorg. Med. Chem. 14(24):8564-8573.
Andersen J, Bolvig S, Liang X (2005) „Efficient One-Pot Synthesis of 1-Aryl 1,2,3-Triazoles from Aryl Halides and Terminal Alkynes in the Presence of Sodium Azide Synlett, 2005, 19:2941.
Andersson S (1995) „Molecular genetics of androgenic 17β-Hydroxysteroid Dehydrogenases. J. Steroid Biochem. Molec. Biol., 55:533-534.
Boivin RP, Luu-The V, Lachance R, Labrie F, Poirier D. (2000) "Structure-activity relationships of 17alpha-derivatives of estradiol as inhibitors of steroid sulfatase." J Med Chem. 2000 Nov 16;43(23):4465-78. Burow ME, Boue SM, Collins-Burow BM, Melnik LI, Duong BN, Carter-Wientjes CH, Li S, Wiese TE, Cleveland TE, McLachlan JA (2001) Phytochemical glyceollins, isolated from soy, mediate antihormonal effects through estrogen receptor alpha and beta. J. Clin. Endocrinol. Metab. 86 (4), 1750-1758.
Ciobanu LC & Poirier D (2006) "Synthesis of libraries of 16beta-aminopropyl estradiol derivatives for targeting two key steroidogenic enzymes" ChemMedChem. 1(11):1249-59.

(Continued)

*Primary Examiner* — Barbara P Badio
(74) *Attorney, Agent, or Firm* — Crowell & Moring LLP

(57) ABSTRACT

Substituted estratriene compounds of formula (I) useful in therapy, especially in the treatment or inhibition of a steroid hormone dependent disorder requiring the inhibition of a 17β-hydroxysteroid dehydrogenase (17β-HSD) type 1, type 2 and/or type 3 enzyme, as well as their salts, pharmaceutical compositions containing such compounds and processes for preparing such compounds.

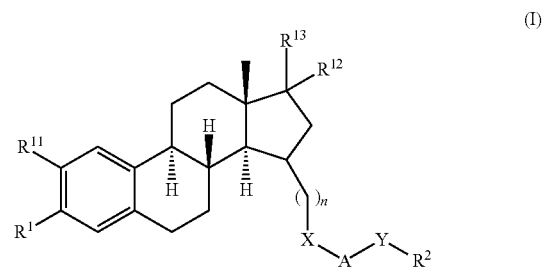

(I)

34 Claims, No Drawings

OTHER PUBLICATIONS

Cushman et al (1995) "Synthesis, antitubulin and antimitotic activity, and cytotoxicity of analogs of 2-methoxyestradiol, an endogenous mammalian metabolite of estradiol that inhibits tubulin polymerization by binding to the coichicine binding site." J Med Chem. 38(12):2041-9.

Cushman et al (2002) "The effect of exchanging various substituents at the 2-position of 2-methoxyestradiol on cytotoxicity in human cancer cell cultures and inhibition of tubulin polymerization." J Med Chem. 45(21):4748-54.

Day et al (2003) "The effects of 2-substituted oestrogen sulphamates on the growth of prostate and ovarian cancer cells." J Steroid Biochem Mol Biol. 2003 84(2-3):317-25.

Dong et al. (1998) "173-hydroxysteroid dehydrogenases in human bone cells" J. Bone Min. Res., 13:1539-1546.

Einspanier A, Lieder K, Bruns A, Husen B, Thole H, Simon C. (2006) "Induction of endometriosis in the marmoset monkey (*Callithrix jacchus*)" Mol Hum Reprod. May 2006;12(5):291-9. Epub Apr. 11, 2006.

Ettmayer P, Amidon GL, Clement B, Testa B (2004) "Lessons learned from marketed and investigational pro-drugs", J.Med.Chem. 47(10): 2393-2404.

Geissler WM et al. (1994) "Male pseudohermaphroditism caused by mutations of testicular 17beta-hydroxysteroid dehydrogenase 3." Nat Genet., 7:34-9.

Gonzalez et al (1982) "Synthesis and pharmacological evaluation of 8alpha-estradiol derivatives" Steroids 40(2):171-188.

Gruemmer R, Schwarzer F, Bainczyk K, Hess-Stumpp H, Regidor PA, Schindler AE, Winterhager E (2001) "Peritoneal endometriosis: validation of an in vivo model". Hum. Reprod. 16 (8), 1736-1743.

Husen B, Huhtinen K, Poutanen M, Kangas L, Messinger J, Thole Fl (2006) "Evaluation of inhibitors for 17beta-hydroxysteroid dehydrogenase type 1 in vivo in immunodeficient mice inoculated with MCF-7 cells stably expressing the recombinant human enzyme" Mol Cell Endocrinol. Mar. 27, 2006;248(1-2):109-13. Epub Jan. 10, 2006.

Koffman et al (1991) "Evidence for involvement of tyrosine in estradiol binding by rat uterus estrogen receptor." J. Steroid. Biochem. Mol. Biol. 38(2):135.

Labaree et al. (2003) "Synthesis and Evaluation of B-, C- and D-ring substituted estradiol carboxylic acid esters as locally active estrogens" J. Med. Chem. 46:1886-1904.

Labrie et al (1997) "The key role of 17 beta-hydroxysteroid dehydrogenases in sex steroid biology." Steroids, 62:148-58.

Labrie et al. (2000) "Role of 17 beta-hydroxysteroid dehydrogenases in sex steroid formation in peripheral intracrine tissues" Trends Endocrinol Metab., 11:421-7.

Lawrence et al (2005) "Novel and potent 17beta-hydroxysteroid dehydrogenase type 1 inhibitors." J Med Chem. 48(8):2759-62.

Lesma G; Sacchetti A, Silvani A (2006) "Palladium-Catalyzed Hydroxycarbonylation of Aryl and Vinyl Triflates by in situ Generated Carbon Monoxide under Microwave Irradiation" Synthesis 4: 594-96.

Ley et al (1994) "Tetrapropylammonium perruthenate, Pr4N+RuO4-, TPAP: a catalytic oxidant for organic synthesis" Synthesis. 07:639-666.

Li PK, Pillai R and Dibbelt L (1995) "Estrone sulfate analogs as estrone sulfatase inhibitors" Steroids 60(3): 299-306.

Liu et al (1992) "Synthesis of high affinity fluorine-substituted ligands for the androgen receptor. Potential agents for imaging prostatic cancer by positron emission tomography." J Med Chem. 35(11):2113-29.

Lunn & Farkas (1968) "The adamantyl carbonium ion as a dehydrogenating agent, its reactions with estrone" Tetrahedron 24(23):6773-6776.

Mindnich et al (2004) "The role of 17 beta-hydroxysteroid dehydrogenases" Mol Cell Endocrinol. 218(1-2):7-20. Review.

Mohanakrishnan & Cushman (1999) "Pd(0)-Mediated Cross Coupling of 2-Iodoestradiol with Organozinc Bromides: A General Route to the Synthesis of 2-Alkynyl, 2-Alkenyl and 2-Alkylestradiol Analogs" Synlett 1999(07):1097-1099.

Morera E & Ortar G (1998) "A palladium-catalyzed carbonylative route to primary amides" Tetrahedron Letters, 39(18): 2835-2838.

Nambara et al. (1976) "Synthesis of Estetrol Monoglucuronides" Steroids 27:111-122.

Oefelein MG & Cornum R (2000) "Failure to achieve castrate levels of testosterone during luteinizing hormone releasing hormone agonist therapy: the case for moni-toring serum testosterone and a treatment decision algorithm." J Urol.; 164:726-9.

Pelletier & Poirier (1996) "Synthesis and evaluation of estradiol derivatives with 16a-(bromoalkylamide), 16a-(bromoalkyl) or 16a-(bromoalkynyl) side chain as inhibitors of 173-hydroxysteroid dehydrogenase type 1 without estrogenic activity" Bioorg Med Chem, 4(10):1617-1628.

Poirier (2003) "Inhibitors of 17 beta-hydroxysteroid dehydrogenases" Curr Med Chem. 10:453-77.

Poirier et al (1991) "Synthesis of 173-estradiol derivatives with N-Butyl, N-methyl alkylamide side chain at position 15." Tetrahedron, 47(37):7751-7766.

Poirier et al (1996) "D-Ring alkylamine derivatives of estradiol: effect on ER-binding affinity and antiestrogenic activity" Bioorg Med Chem Lett 6(21):2537-2542.

Poirier et al (1998) "A 6(3-(Thiaheptanamide) Derivative of Estradiol as inhibitor of 173-Hydroxysteroid Dehydrogenase Type 1", J. Steroid Biochem. Molec. Biol., 64:83-90.

Poirier D, Ciobanu LC, Berube M. (2002) "A multidetachable sulfamate linker successfully used in a solid-phase strategy to generate libraries of sulfamate and phenol derivatives" Bioorg Med Chem Lett. Oct. 21, 2002; 12(20):2833-8.

Puranen et al (1994) "Site-directed mutagenesis of the putative active site of human 17 beta-hydroxysteroid dehydrogenase type 1" Biochem. J. 304:289-93.

Rao & Cessac (2002) "A new, practical synthesis of 2-methoxyestradiols." Steroids. 67(13-14): 1065-70.

Sam et al. (1998) "C16 and C17 Derivatives of Estradiol as Inhibitors of 17RHydroxysteroid Dehydrogenase Type 1: Chemical Synthesis and Structure-Activity Relationships", Drug Design and Discovery, 15:157-180.

Schoen U, Messinger J, Buchholz M, Reinecker U, Thole H, Prabhu MKS, Konda A (2005) "An improved synthesis of 3-aminoestrone" Tetrahedron Letters 46(42): 7111-7115.

Stella P (2004) "Prodrugs as therapeutics" Expert Opin. Ther. Patents, 14(3): 277-280.

Tamaya et al. (1985) "Comparison of cellular levels of steroid receptors in uterine leiomyoma and myometrium." Acta Obstet Gynecol Scand., 64:307-9.

Tremblay & Poirier (1998) "Overview of a Rational Approach to Design Type 117(3-Hydroxysteroid Dehydrogenase Inhibitors Without Estrogenic Activity: Chemical Synthesis and Biological Evaluation", J. Steroid Biochem. Molec. Biol., 66:179-191.

Yoshikawa et al. (2002) "Diastereo- and Enantioselective Direct Catalytic Aldo! Reaction of 2-Hydroxyacetophenones with Aldehydes Promoted by a Heteropolymetallic Complex: Catalytic Asymmetric Synthesis of anti-1,2-Diols" J. Org. Chem. 67(8); 2556-2565.

Yuen AKL & Hutton CA (2005) "Deprotection of pinacolyl boronate esters via hydrolysis of intermediate potassium trifluoroborates" Tetrahedron letters, 46(46): 7899-7903.

Zeitoun K, Takayama K, Sasano H, Suzuki T, Moghrabi N, Andersson S, Johns A, Meng L, Putman M, Carr B, Bulun Se (1998) "Deficient 17beta-hydroxysteroid dehydrogenase type 2 expression in endometriosis: failure to metabolize 17beta-estradiol." J Clin Endocrinol Metab. Dec. 1998;83(12):4474-80.

* cited by examiner

SUBSTITUTED ESTRATRIENE DERIVATIVES AS 17BETA HSD INHIBITORS

CROSS REFERENCE TO RELATED APPLICATIONS

This application claims priority from U.S. provisional patent application No. 60/861,753, filed Nov. 30, 2006, the entire disclosure of which is incorporated herein by reference.

FIELD OF INVENTION

The present invention relates to novel, substituted estratriene derivatives which represent inhibitory compounds of the 17β-hydroxysteroid dehydrogenase type 1 (17β-HSD1), type 2 (17β-HSD2) or type 3 (17β-HSD3) enzyme, as well as to the salts of these compounds, to pharmaceutical preparations containing these compounds and to processes for the preparation of these compounds. Furthermore, the invention concerns the therapeutic use of said novel substituted estratriene derivatives, particularly their use in the treatment or prevention of steroid hormone dependent diseases or disorders requiring the inhibition of the 17β-HSD1, 17β-HSD2 or 17β-HSD3 enzymes and/or requiring the lowering of the endogenous 17β-estradiol and/or androgen concentration.

BACKGROUND OF THE INVENTION

The publications and other materials used herein to illuminate the background of the invention, and in particular, cases to provide additional details respecting the practice, are incorporated by reference.

Mammalian 17β-hydroxysteroid dehydrogenases (17β-HSDs) are NAD(H) or NADP(H) dependent enzymes which convert inactive 17-keto-steroids into their active 17β-hydroxy-forms or catalyse the oxidation of the 17β-hydroxy-forms into the 17-keto-steroids. Because both estrogens and androgens have the highest affinity for their receptors in the 17β-hydroxy form, 17β-HSD enzymes play an essential role in the tissue-selective regulation of the activity of sex steroid hormones. At present, 10 human members of the 17β-HSD enzyme family have been described (types 1-5, 7, 8, 10-12), whereby each type of 17β-HSD has a selective substrate affinity, directional (reductive or oxidative) activity in intact cells, and a particular tissue distribution.

Due to their essential role in the tissue-selective regulation of the activity of sex steroid hormones, 17β-HSDs can be involved in the occurrence and development of estrogen-sensitive pathologies (f. ex. breast, ovarian, and endometrium cancers etc.) and androgen-sensitive pathologies (f. ex. prostate cancer, benign prostatic hyperplasia, acne, hirsutism, etc). Furthermore, many types of 17β-HSD have been shown to be involved in the pathogenesis of particular human disorders such as pseudohermaphroditism (17β-HSD3), polycystic kidney disease (17β-HSD8) and bifunctional enzyme deficiency (17β-HSD4) [reviewed by: Mindnich et al (2004)]. Therefore treatment of sex steroid-sensitive diseases by administration of specific inhibitors of the 17β-HSDs enzymes have been suggested, optionally in combination with potent and specific anti-estrogens and anti-androgens [Labrie et al. (1997)].

The best characterized member of the 17β-HSD family is the 17β-HSD1 [EC 1.1.1.62]. The 17β-HSD1 enzyme catalyzes in vitro the reduction and the oxidation between estrone (E1) and estradiol (E2). However, under physiological in vivo conditions the enzyme only catalyses the reductive reaction from the estrone (E1) to the estradiol (E2). The 17β-HSD1 was found to be expressed in a variety of hormone-dependent tissues, e.g. placenta, mammary gland tissue or uterus and endometrium tissue, respectively.

Estradiol itself is, especially in comparison to the significantly less active estrone, a very potent hormone, which regulates the expression of a variety of genes by binding to the nuclear estrogen receptor and plays an essential role in the proliferation and differentiation of the target cell. Physiological as well as pathological cell proliferations can be estradiol dependent. Especially many breast cancer cells are stimulated by a locally raised estradiol concentration. Furthermore, the occurrence or course of benign pathologies such as endometriosis, uterine leiomyomas (fibroids or myomas), adenomyosis, menorrhagia, metrorrhagia and dysmenorrhoea is dependent from the existence of significantly high estradiol levels.

Endometriosis is a well-known gynaecological disorder that affects 10 to 15% of women in the reproductive age. Endometriosis is an estrogen-dependent disease, which does not occur before puberty and is rare after the menopause. It is a benign disease defined as the presence of viable endometrial gland and stroma cells outside the uterine cavity. It is most frequently found in the pelvic area. In women developing endometriosis, the endometrial cells entering the peritoneal cavity by retrograde menstruation (the most likely mechanism) have the capacity to adhere to and invade the peritoneal lining, and are then able to implant and grow. The implants respond to steroid hormones of the menstrual cycle in a similar way as the endometrium in the uterus. Estrogen synthesis within endometriotic foci is increased due to aberrantly high local levels of aromatase and 17μ-HSD1, accompanied by reduced expression of the estradiol inactivating enzyme 17βHSD2 [Zeitoun et al. (1998)]. These higher local estrogen concentrations induce in turn the production of prostaglandin E2, which then stimulates further aromatase activity. Consequently, this vicious circle leads to additional estrogen production. The infiltrating lesions and the blood from these lesions which are unable to leave the body cause inflammation of the surrounding tissue. The most common symptoms of endometriosis are dysmenorrhoea, dyspareunia and (chronic) abdominal pain. Up to now, no reliable non-invasive test is available to diagnose endometriosis. Laparoscopy has to be performed to diagnose the disease. Endometriosis is classified according to the 4 stages set up by the American Fertility Society (AFS). Stage I corresponds to minimal disease while stage IV is severe, depending on the location and the extent of the endometriosis. Endometriosis is found in up to 50% of the women with infertility. Moderate to severe endometriosis can cause tubal damage and adhesions leading to infertility. The aims of treatment of endometriosis are pain relief, resolution of the endometriotic tissue and restoration of fertility (if desired). The two common treatments are surgery or anti-inflammatory and/or hormonal therapy or a combination thereof.

Uterine leiomyomas (fibroids or myomas), benign clonal tumours, arise from smooth muscle cells of the human uterus. They are clinically apparent in up to 25% of women and are the single, most common indication for hysterectomy. They cause significant morbidity, including prolonged and heavy menstrual bleeding, pelvic pressure and pain, urinary problems, and, in rare cases, reproductive dysfunction. Myomas are found submucosally (beneath the endometrium), intramurally (within the myometrium) and subserosally (projecting out of the serosal compartment of the uterus), but mostly are mixed forms of these 3 different types. The presence of estrogen receptors in leiomyoma cells has been studied by Tamaya et al. [Tamaya et al. (1985)]. They have shown that the ratios of estrogen receptor compared to progesterone and androgen receptor levels were higher in leiomyomas than in the corresponding normal myometrium. Surgery has long been the main treatment for myomas. Furthermore, medical therapies that have been proposed to treat myomas include administration of a variety of steroids such as the androgenic steroids danazol or gestrinone and progestogens, or of compounds modulating the steroid hormone plasma levels like e.g. GnRH agonists and GnRH antagonists, whereby the administration is often associated a variety of serious side-effects.

Dysfunctional uterine bleeding disorders (dysfunctional or abnormal uterine bleeding, metrorrhagia and menorrhagia, hypermenorrhea) are forms of pathological bleeding that are not attributable to organic changes in the uterus (such as, e.g., endometrial carcinoma, myomas, polyps, etc.), systemic coagulation disorders, or a pathological pregnancy (e.g., ectopic pregnancy, impending abortion). The average blood loss during normal menstruation is about 30 ml, whereby the period lasts for an average of 5 days. If the blood loss exceeds 80 ml, it is classified as pathological. Metrorrhagias are defined as bleeding that may or may not be accompanied by pain and that cannot be linked to menstruation or cycle. Menorrhagia is menstruation that may or may not be accompanied by pain, normally every 27-28 days, which, when it lasts over 7 days, is associated in most cases with an increased blood loss. Menorrhagia is a syndrome of unknown origin and one of the most common problems in gynecology. 60% of women refereed with menorrhagia have a hysterectomy within five years. Hypermenorrhea is defined as menstruation that may or may not be accompanied by pain, normally every 27-28 days for 4-5 days with an elevated blood loss. Forms of dysfunctional uterine bleeding (mainly metrorrhagias and menorrhagias) are typical of adolescence and of the time of menopause, in which follicle-stimulating disorders, anovulation, and yellow-body and follicle persistence occur in clusters. The incidence of dysfunctional uterine bleeding is high and represents one of the most frequent reasons for gynecological consultation for women of reproductive age.

Everything that has been said above in relation to the treatment of uterine leiomyomas, endometriosis and dysfunctional uterine bleeding equally applies to other benign gynaecological disorders, notably adenomyosis and dysmenorrhea. These benign gynaecological disorders are all estrogen sensitive and are treated in a comparable way as described herein before in relation to uterine leiomyomas, endometriosis and dysfunctional uterine bleeding. The available pharmaceutical treatments, however, suffer from the same major drawbacks, i.e. they have to be discontinued once the side-effects become more serious than the symptoms to be treated and symptoms reappear after discontinuation of the therapy.

Since the aforementioned malign and benign pathologies are all 17β-estradiol dependent, a reduction of the endogenous 17β-estradiol concentration in the respective tissue will result in an impaired or reduced proliferation of 17β-estradiol responsive cells in said tissues. Therefore, it may be concluded that selective inhibitors of the 17β-HSD1 enzyme are well suited for their use to impair endogenous productions of estrogens, in particular of 17β-estradiol, in myomas, endometriotic, adenomyotic and endometrial tissue. The application of a compound acting as selective inhibitor on the 17β-HSD1 which preferentially catalyses the reductive reaction will result in a lowered intracellular estradiol-concentration, since the reductive conversion of the estrone into the active estradiol is reduced or suppressed. Therefore, reversible or even irreversible inhibitors of the 17β-HSD1 may play a significant role in the prophylaxis and/or treatment of steroid-hormone, in particular 17β-estradiol, dependent disorders or diseases. Furthermore, the reversible or even irreversible inhibitors of the 17β-HSD1 should have no or only pure antagonistic binding activities to the estradiol receptor, in particular to the estrogen receptor α subtype, since agonistic binding of the estrogen receptor would lead to activation and subsequently to the proliferation and differentiation of the target cell. In contrast, antagonists of the estrogen receptor, so called anti-estrogens, bind competitively to the specific receptor protein thus preventing access of endogenous estrogens to their specific binding site.

At present it is described in the literature that several malignant disease as breast cancer, prostate cancer, ovarian cancer, uterine cancer, endometrial cancer and endometrial hyperplasia may be treated by the administration of a selective 17β-HSD1 inhibitor. Furthermore, a selective 17β-HSD1 inhibitor may be useful for the prevention of the aforementioned hormone-dependent cancers, especially breast cancer (e.g. WO2004/080271). Furthermore, international patent application WO2003/017973 describes the use of a selective estrogen enzyme modulator (SEEM) in the manufacture of a drug delivery vehicle for intravaginal administration to treat or prevent a benign gynaecological disorder such as endometriosis in a mammalian female.

Several reversible or irreversible inhibitors of the 17β-HSD1 enzyme of steroidal and even non-steroidal origin are already known from the literature. The characteristics of these inhibitory molecules, which mainly have a substrate or cofactor-like core structure, have been reported in the literature [reviewed in: Poirier D (2003)].

The following compounds or compound classes have already been described as 17β-HSD1 inhibitors: For example, Tremblay and Poirier describe an estradiol derivative, 16-[carbamoyl-(bromo-methyl)-alkyl]-estradiol, and tested the same in respect of its inhibition of the estradiol formation catalysed by the enzyme 17β-HSD1 [Tremblay & Poirier (1998)]. Poirier and colleagues describe a 6β-thiaheptan-butyl-methyl-amide derivative of estradiol as a potent and selective inhibitor of the 17β-HSD1 enzyme [Poirier et al. (1998)]. Furthermore, Poirier and colleagues describe new derivatives of 17β-estradiol with long N-butyl, N-methyl alkylamide side chains of three different lengths (n=8, 10 or 12) at position 15, which might be potential inhibitors of the 17β-HSD1 enzyme [Poirier et al. (1991)]. Similar compounds were also disclosed within European patent application EP0367576. However, the biological activity of these compounds was only tested with regard to estrogen receptor binding affinity, estrogenic and anti-estrogenic activity [Poirier et al. (1996)], but not with regard to their ability to inhibit the 17β-HSD1 enzyme. In addition, Pelletier and Poirier describe novel 17β-estradiol derivatives with different bromo-alkyl side chains, which might be potential inhibitors of the 17β-HSD1 enzyme [Pelletier & Poirier (1996)]. Sam and colleagues describe several estradiol derivatives with a halogenated alkyl side chain in 16α or 17α position of the steroidal D-ring which possess 17β-HSD1 inhibiting properties [Sam et al. (1998)]. Furthermore, the finding that some anti-estrogens, such as tamoxifen, possess weak 17β-HSD1 inhibiting properties suggested that it may be possible to develop a potent 17β-HSD1 inhibitor that is also anti-estrogenic [reviewed in: Poirier D. (2003)]. Several of the aforementioned already known compounds also display anti-estrogenic properties (e.g. the 6,6-thiaheptan-butyl-methyl-amide derivative of estradiol described by Poirier and colleagues [Poirier et al. (1998)]). The synthesis of 16β-aminopropyl substituted estradiol derivatives as moderate 17β-HSD1 inhibitory compounds was described by Poirier et al [Poirier et al, 2002 and Ciobanu & Poirier, 2006]. None of the aforementioned compounds has been clinically used so far.

Furthermore, the international patent application WO2004/085457 discloses a variety of estron derivatives with different substituents in C2, C3, C6, C16 and/or C17 position as potent 17β-HSD1 inhibitors. For some of the compounds it was shown that the substitution of steroid based 17β-HSD1 inhibitors at the C2 position with small hydrophobic groups renders the compounds less estrogenic and are favourable for 17β-HSD1 over 17β-HSD2 discrimination [Lawrence et al (2005)].

The international application WO2005/047303 discloses novel 3,15 substituted 17β-estradiol derivatives with different kind of side chains at position 15, which are potent and selective 17β-HSD1 inhibitors.

Furthermore novel 3,15 substituted 17β-estradiol derivatives with additional modifications of the steroidal core at positions C2, C3 and/or C17 have been described within international application WO2006/125800 as potent 17β-HSD1 inhibitory compounds.

Additional compounds representing potential 17β-HSD1 inhibitors were disclosed within international applications WO2006/003012 and WO2006/003013 in the form of novel 2-substituted D-homo-estra-1,3,5(10)-trienes and novel 2-substituted estra-1,3,5(10)-trien-17-ones.

A further well characterized member of the 17β-HSD family is the 17β-HSD type 3 enzyme (17β-HSD3). The 17β-HSD3 has a distinct feature compared to other 17β-HSDs: it is found to be expressed almost exclusively the testis, whereas the other isoenzymes are expressed more widely in several tissues. 17β-HSD3 has a crucial role in androgen biosynthesis. It converts 4-androstene-3,17-one (A) to testosterone (T). The biological significance of the 17β-HSD3 is of undeniable physiological importance. Mutations in the gene for 17β-HSD3 have found to lead to decreased T formation in the fetal testis and consequently to a human intersex disorder termed male pseudohermaphroditism [Geissler et al. (1994)].

With regard to the indication prostate cancer, the primary cancer cells mostly retain their responsiveness to androgens in their regulation of proliferation, differentiation, and programmed cell death for some period. At present, androgen deprivation is the only effective systemic hormonal therapy available for prostate cancer. The development of selective inhibitors against 17β-HSD3 is a new therapeutic approach for the treatment of androgen dependent disease [Labrie et al. (2000)]. Furthermore, Oefelein et al. reported that the depot GnRH analogue fails, in nearly 20% of cases, to achieve castrate levels of T in men [Oefelein M G & Cornum R (2000)]. In order to improve the response rate to endocrine therapy for men with prostate cancer it may be important to selectively inhibit testicular 17β-HSD3 activity. Besides prostate cancer, many other androgen-sensitive diseases, i.e. diseases whose onset or progress is aided by androgenic activity, may be treated by selectively inhibiting 17β-HSD3 activity. These diseases include but are not limited to prostadynia, benign prostatic hyperplasia, prostatitis, acne, seborrhea, hirsutism, androgenic alopecia, precocious puberty, adrenal hyperplasia, and polycystic ovarian syndrome. Furthermore, considering the fact that 17β-HSD3 is found mainly in the testis, the development of potent inhibitors could be of interest for blocking spermatogenesis and as an anti-fertility agent for males.

Acne is a polyetiological disease caused by the interplay of numerous factors, such as inheritance, sebum, hormones, and bacteria. The most important causative factor in acne is sebum production; in almost all acne patients sebaceous glands are larger and more sebum is produced than in persons with healthy skin. The development of the sebaceous gland and the extent of sebum production is controlled hormonally by androgens; therefore, androgens play a crucial role in the pathogenesis of acne. In man, there are two major sources supplying androgens to target tissues: (i) the gonades which secrete testosterone, (ii) the adrenals producing dehydroepiandrosterone (DHEA) which is secreted as the sulfate conjugate (DHEAS). Testosterone and DHEAS are both converted to the most active androgen, dihydrotestosterone (DHT), in the target tissue, e.g. in the skin. There is evidence that these pathways of local synthesis of DHT in the skin are more important than direct supply with active androgens from the circulation. Therefore, reduction of endogeneous levels of androgens in the target tissue by specific inhibitors should be of therapeutic benefit in acne and seborrhoea. Furthermore, it opens the perspective to treat these disorders through modulation of local androgen levels by topical treatment, rather than influencing circulating hormone levels by systemic therapies.

Androgenetic male alopecia is very common in the white races, accounting for about 95% of all types of alopecia. Male-pattern baldness is caused by an increased number of hair follicles in the scalp entering the telogen phase and by the telogen phase lasting longer. It is a genetically determined hair loss affected through androgens. Elevated serum DHEA but normal testosterone levels have been reported in balding men compared with non-balding controls, implying that target tissue androgen production is important in androgenetic alopecia.

Hirsutism is the pathological thickening and strengthening of the hair which is characterized by a masculine pattern of hair growth in children and women. Hirsutism is androgen induced, either by increased formation of androgens or by increased sensitivity of the hair follicle to androgens.

Several reversible or irreversible inhibitors of the 17β-HSD3 enzymes of steroidal and even non-steroidal origin are already known from the literature. The characteristics of these inhibitory molecules have been reported in the literature [reviewed in: Poirier D. (2003)]. Furthermore, the international patent application WO01/42181 discloses benzyl-tetralins, the chemical structure of which is related to that of the phytoestrogen biochanin, as 17β-HSD3 inhibitors. Moreover, international patent applications WO99/46279, WO2003/022835, WO2003/033487, WO2004/046111, WO2004/060488, WO2004/110459, WO2005/032527 and WO2005/084295 disclose compounds which have a 17β-HSD3 inhibitory activity, for the treatment of hormone sensitive diseases.

Microsomal 17β-hydroxysteroid dehydrogenase of human endometrium and placenta (designated 17β-HSD type 2 or 17β-HSD2) was cloned by expression cloning, and found to be equally active using androgens and estrogens as substrates for oxidation [Andersson (1995)]. The recombinant 17β-HSD2 converts the highly active 17β-hydroxysteroids such as estradiol (E2), testosterone (T), and dehydrotestosterone (DHT) to their inactive keto forms. In addition, the 17β-HSD2 can, to a lesser extent, also convert 20β-hydroxyprogesterone (20βP) to progesterone (P). The broad tissue distribution together with the predominant oxidative activity of 17β-HSD2 suggest that the enzyme may play an essential role in the inactivation of highly active 17β-hydroxysteroids, resulting in diminished sex hormone action in target tissues. Dong and colleagues showed significant 17β-HSD2 activity in cultured human osteoblasts and osteoblast-like osteosarcoma cells MG63 and TE85, but not in SaOS-2 [Dong et al. (1998)]. The potential for interconversion of E1 to E2, T to A, and DHT to A by bone cells could therefore represent important mechanism for the local regulation of intracellular ligand supply for the estrogen and androgen receptors in the osteoblasts and other steroid sensitive cells. This modulation of steroid levels may be employed for a wide variety of indications, including the following: for the prevention and treatment of osteoporosis, for the treatment of ovarian cancer, breast cancer or endometrial cancer, for the treatment of prostate cancer and/or for the treatment of androgen-dependent hair-loss.

Several reversible or irreversible inhibitors of the 17β-HSD2 enzymes of steroidal and even non-steroidal origin are already known from the literature. The characteristics of these inhibitory molecules have been reported in the literature [reviewed in: Poirier D. (2003)]. In addition, the international patent application WO02/26706 discloses 17β-HSD2 inhibitors of non-steroidal origin.

In addition, 17β-HSD1, 17β-HSD2 or 17β-HSD3 inhibitors may be useful for the prevention and treatment of further estrogen- or androgen-dependent diseases or disorders and/or diseases or disorders requiring the lowering of the endogeneous estrogen or androgen concentration in a generalized or tissue-specific manner, such as inflammatory and autoimmune diseases, e.g. rheumatoid arthritis, type I and II diabetes, systemic lupus erythematosus, multiple sclerosis, myastenia gravis, thyroiditis, vasculitis, ulcerative colitis, and Crohn's disease, psoriasis, contact dermatitis, eczema, tissue wounds, skin wrinkles and/or cataracts, asthma, graft versus host disease, and organ rejection following transplantation. 17β-HSD inhibitors might be also useful for the enhancement of cognitive function, especially in the treatment of senile dementia, including Alzheimer's disease. Further estrogen-dependent diseases which may be treated and/or prevented with an effective amount of a compound of the invention are squamous cell carcinoma and colon cancer.

Several different kind of estrogen or androgen derivatives have been disclosed in the literature as being inhibitors or activators of further enzymes of sex steroid conversion:

For example, related U.S. Pat. Nos. 5,571,933, 5,677,292 and 5,866,603 disclose inhibitors of the steroid sulfatase enzyme, whereby the compounds are estrone derivatives bearing a —NH—SO$_2$-aryl, a —NH—CO—(C$_1$-C$_6$-alkyl) or a —NH—CO—CF$_3$ side chain at the C3 position of the steroidal core.

Furthermore, U.S. Pat. No. 6,541,463 discloses androsterone and estratrienee derivatives carrying mainly modifications in the C17 position, which were developed as inhibitors of the 17β-HSD5 enzyme and optionally additionally of the 17β-HSD3 enzyme. Some of the examples disclosed (EM-1404, EM-1403, EM-1401, EM-1388) carry a carboxy, a carboxy-methyl or an amide group in the C3 position of the steroidal core. However, these compounds have been developed as selective inhibitors of the 17β-HSD5 enzyme and do not show significant inhibitory potential of the 17β-HSD1, 17β-HSD2 or 17β-HSD3 enzyme.

The synthesis of different B-, C- and D-ring substituted estradiol carboxylic esters was described by Labaree et al. [2003]. However, these esters were only analysed with regard to their estrogenic potential. The related international patent application WO2004/085345 discloses 15α substituted estradiol compounds bearing a —(CH$_2$)$_m$—CO—O—R side chain, wherein R is H, a C$_1$-C$_5$ alkyl group, optionally substituted with at least one halogen group, such as CH$_2$CH$_2$F, or other group (e.g. CH$_2$CHF$_2$, CH$_2$CF$_3$ or CF$_3$ group); and m is from 0-5. These 15α estradiol esters are described as locally active estrogens without significant systemic action.

Estratriene derivatives with a modification of the D-ring as dual inhibitors of the 17β-HSD1 and of the steroid sulfatase enzyme have been described in international patent application WO02/32409.

International patent application WO2004/085459 also discloses a variety of estrone derivatives with different substituents in C2, C3, C4 and/or C17 position as potent steroid sulfatase inhibitors.

Furthermore, international application WO2006/027347 discloses 15β-substituted estradiol derivatives having selective estrogen receptor activity towards the estrogen receptor α-subtype.

Estrone and estradiol derivatives carrying a boronic acid substitution in C3 position were recently disclosed by Ahmed et al. as inhibitors of the steroid sulfatase enzyme [Ahmed et al. (2006)].

Accordingly, there is still a need for the development of compounds which are suited for the treatment and/or prevention of the aforementioned steroid hormone dependent diseases or disorders by selectively inhibiting the 17β-HSD1, 17β-HSD3 or 17β-HSD2 enzyme, depending on the disease intended to be treated, while desirably failing to substantially inhibit other members of the 17β-HSD protein family. In particular, it is an aim of the present invention to develop selective inhibitors of the 17β-HSD1 enzyme, whereby in addition the compounds have no or only pure antagonistic binding affinities to the estrogen receptor (both subtypes α and β). Preferably, the selective inhibitors of the 17β-HSD1 enzyme should have no inhibitory potential on the 17β-HSD2 enzyme. Furthermore, an increased metabolic stability of the compounds would be desirable, in order to prevent conversion of the compounds to metabolites with less inhibitory potential on the 17β-HSD1 enzyme.

SUMMARY OF THE INVENTION

Therefore, it is an object of the present invention to develop novel inhibitors of the 17β-HSD1, 17β-HSD3 or 17β-HSD2 enzyme, which have valuable pharmacological properties and which are suited for the treatment of sex steroid hormone dependent diseases and disorders. In particular, it is an object of the present invention to develop novel inhibitors of the 17β-HSD1 or 17β-HSD2 enzyme, which have valuable pharmacological properties and which are suited for the treatment of estrogen dependent diseases and disorders, and it is a further object of the present invention to develop novel inhibitors of the 17β-HSD3 enzyme, which have valuable pharmacological properties and which are suited for the treatment of androgen dependent diseases and disorders.

It has now been found that novel substituted estratriene derivatives as described herein would be valuable in therapy, especially in the treatment or prevention of steroid hormone dependent diseases or disorders requiring the lowering of the endogeneous estradiol concentration, in animals, in particular mammals, and humans. In particular, compounds of formula (I) represent potent inhibitors of the 17β-HSD1, 17β-HSD2 and/or 17β-HSD3 enzyme, whereas selective inhibitors of the 17β-HSD1 should have no inhibitory potential on the 17β-HSD2 enzyme. Accordingly, the compounds of the invention possess valuable pharmacological properties for the treatment and/or prophylaxis of malignant steroid dependent diseases or disorders such as breast cancer, prostate cancer, ovarian cancer, uterine cancer, endometrial cancer and endometrial hyperplasia, but also for the treatment and/or prophylaxis of benign steroid dependent diseases or disorders such as endometriosis, uterine fibroids, uterine leiomyoma, adenomyosis, dysmenorrhoea, menorrhagia, metrorrhagia, urinary dysfunction, prostadynia, benign prostatic hyperplasia, prostatitis, acne, seborrhea, hirsutism, androgenic alopecia, precocious puberty, adrenal hyperplasia, polycystic ovarian syndrome and/or lower urinary tract syndrome. Further estrogen-dependent diseases which may be treated and/or prevented with an effective amount of a compound of the invention are osteoporosis, multiple sclerosis, rheumatoid arthritis, systemic lupus erythematosus, myastenia gravis, thyroiditis, vasculitis, ulcerative colitis, Crohn's disease, graft versus host and host versus graft disease (organ rejection following transplantation), type I and II diabetes, asthma, squamous cell carcinoma, colon cancer, cognitive dysfunctions, senile dementia, Alzheimer's disease, psoriasis, contact dermatitis, eczema, tissue wounds, skin wrinkles and/or cataracts. Furthermore, compounds of formula (I) may be useful for blocking spermatogenesis and as an anti-fertility agent for males.

Accordingly, the present invention relates to a compound corresponding to formula I,

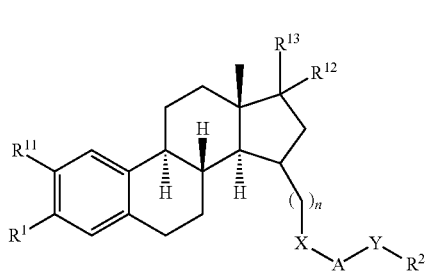

wherein
—X-A-Y— together represent a group selected from
(a) —CO—$NR^4$—,
(b) —CO—O—,
(c) —CO—,
(d) —CO—NH—$NR^4$—,
(e) —$NR^3$—CO—$NR^4$—,
(f) —$NR^3$—CO—O—,
(g) —$NR^3$—CO—,
(h) —$NR^3$—CO—NH—$SO_2$—,
(i) —$NR^3$—$SO_2$—$NR^4$—,
(j) —$NR^3$—$SO_2$—O—,
(k) —$NR^3$—$SO_2$—
(l) —O—CO—$NR^4$,
(m) —O—CO—,
(n) —O—CO—NH—$SO_2$—$NR^4$—,
(o) —O—, and
(p) a group

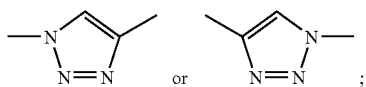

$R^3$ represents —H or —$(C_1\text{-}C_4)$alkyl;
$R^1$ is selected from the group consisting of:
(a) —$B(OR^9)(OR^{10})$
(b) —CO—$OR^6$
(c) —CO—$NR^7R^8$
(d) —$NR^7R^8$
(e) —$NR^5$—CO—$R^6$
(f) —$NR^5$—$SO_2$—$R^6$;

$R^5$ represents —H or —$(C_1\text{-}C_4)$alkyl; and
$R^6$, $R^7$, $R^8$, $R^9$ and $R^{10}$ are independently selected from the group consisting of:
(a) —H
(b) optionally substituted —$(C_1\text{-}C_{14})$alkyl,
(c) optionally substituted aryl or aryl-$(C_1\text{-}C_{14})$alkyl,
(d) optionally substituted heteroaryl or heteroaryl-$(C_1\text{-}C_{14})$alkyl, and
(e) optionally substituted cycloheteroalkyl or cycloheteroalkyl-$(C_1\text{-}C_{14})$alkyl, or
$R^7$ and $R^8$ together with the nitrogen atom, to which they are attached, a heterocyclic 4, 5, 6, 7 or 8 membered ring, which is optionally saturated, partly unsaturated or aromatic; which optionally contains 1, 2 or 3 additional heteroatoms selected from the group consisting of N, O or S, the number of additional N atoms being 0, 1, 2 or 3 and the number of O and S atoms each being 0, 1 or 2; and which ring is optionally part of a multiple condensed ring system, wherein the ring or the ring-system is optionally substituted;
and if $R^1$ is —$NR^5$—CO—$R^6$, then $R^5$ and $R^6$ together with the nitrogen atom to which $R^5$ is attached and the carbonyl group to which $R^6$ is attached may also form a 4, 5, 6, 7 or 8 membered lactam ring,
and if $R^1$ is —$NR^5$—$SO_2$—$R^6$, then $R^5$ and $R^6$ together with the nitrogen atom to which $R^5$ is attached and the sulfoxyd group to which $R^6$ is attached may also form a 4, 5, 6, 7 or 8 membered sultam ring, or
$R^9$ and $R^{10}$ together with the boronic acid group to which they are attached form a 5 or 6 membered ring, which is optionally substituted with 1, 2, 3 or 4—$(C_1\text{-}C_4)$alkyl groups;
n represents 1, 2, 3, 4, 5 or 6, or
if —X-A-Y— represents —CO—$NR^4$—, —CO—O—, —CO— or —CO—NH—$NR^4$—, then n may also represent 0;
$R^{11}$ represents H, —$(C_1\text{-}C_{14})$alkyl, $(C_1\text{-}C_{14})$alkoxy, or $(C_1\text{-}C_{14})$alkoxy-$(C_1\text{-}C_{14})$alkyl;
$R^{12}$ and $R^{13}$ together represent =O, or $R^{12}$ and $R^{13}$ each individually represents F;
$R^2$ and $R^4$ are independently selected from:
(a) —H;
(b) optionally substituted —$(C_1\text{-}C_{14})$alkyl,
(c) optionally substituted acyl, under the proviso that —X-A-Y— together represent —CO—NH—$NR^4$— or a group

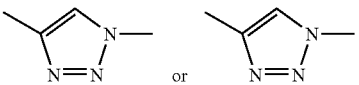

(d) optionally substituted aryl or aryl-$(C_1\text{-}C_{14})$alkyl,
(e) optionally substituted heteroaryl or heteroaryl-$(C_1\text{-}C_{14})$alkyl, and
(f) optionally substituted cycloheteroalkyl or cycloheteroalkyl-$(C_1\text{-}C_{14})$alkyl;
or $R^2$ and $R^4$ together with the nitrogen atom to which $R^2$ and $R^4$ are attached form a heterocyclic 4, 5, 6, 7 or 8 membered ring, which is optionally saturated, partly unsaturated or aromatic; which optionally contains 1, 2 or 3 additional heteroatoms selected from N, O and S, the number of additional N atoms being 0, 1, 2 or 3 and the number of O and S atoms each being 0, 1 or 2; and which ring is optionally part of a multiple condensed ring-system, wherein the ring or the ring-system is optionally substituted;

and/or all stereoisomers, and/or pharmaceutically acceptable salts, and/or metabolites, and/or solvates, and/or prodrugs thereof.

Pharmaceutically acceptable salts as well as all tautomers, stereoisomers, racemates, enantiomers of the compounds of the invention and mixtures thereof, unless the formula depicting the compound explicitly shows a particular stereochemistry, are also within the scope of the invention. Such isomers can be isolated by standard resolution techniques, including fractional crystallization and chiral column chromatography. Furthermore the compounds of the invention also include isotopically-labeled and radio-labeled compounds, as well as commonly used pro-drugs and active metabolites of these compounds.

In one embodiment, the present invention relates to a compound, wherein $R^{12}$ and $R^{13}$ individually represent F and which therefore has the following formula (Ia)

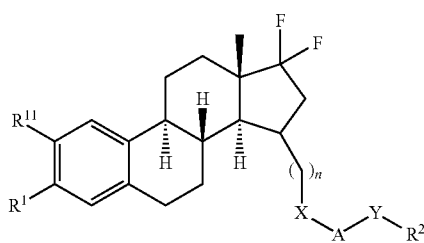

(Ia)

In an alternative embodiment, the present invention relates to a compound, wherein $R^{12}$ and $R^{13}$ together represent =O and which therefore has the following formula (Ib)

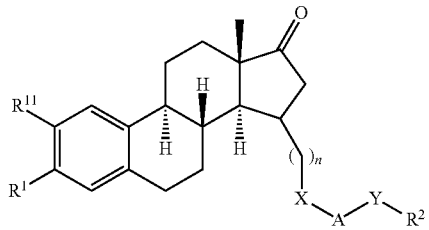

(Ib)

In one embodiment, the present invention relates to a compound of the general formula I, which is an optically pure 15α enantiomer having the formula (II)

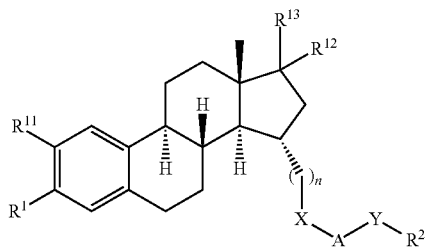

(II)

or a pharmaceutically acceptable salt thereof. In a further embodiment, the present invention relates to the 15α enantiomer having formula (II), wherein n represents 1, 2, 3 or 4.

In another embodiment, the present invention relates to a compound of the general formula I, which is an optically pure 15β enantiomer having the formula (III)

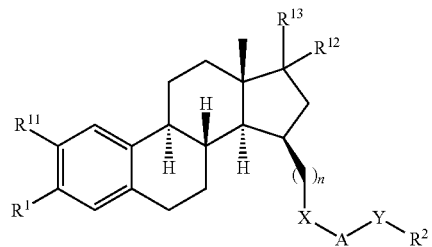

(III)

or a pharmaceutically acceptable salt thereof. In a further embodiment, the present invention relates to the 15β enantiomer having formula (III), wherein n represents 2, 3, 4, or 5.

One embodiment of the present invention relates to compounds of formula I, Ia, Ib, II or III, wherein —X-A-Y— together represent a group selected from
(a) —CO—NR$^4$—,
(b) —CO—O—,
(c) —CO—,
(d) —CO—NH—NR$^4$—,
(e) —NH—CO—NH—,
(f) —NH—CO—O—,
(g) —NH—CO—,
(h) —NH—CO—NH—SO$_2$—,
(i) —NH—SO$_2$—NH—,
(j) —NH—SO$_2$—O—,
(k) —NH—SO$_2$
(l) —O—CO—NH—,
(m) —O—CO—,
(n) —O—CO—NH—SO$_2$—NR$^4$—,
(o) —O—, and
(p) a group

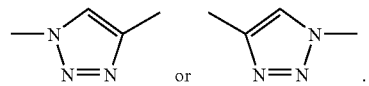

In a preferred subgroup of this embodiment, —X-A-Y— together represent a group selected from —CO—NR$^4$— and a group

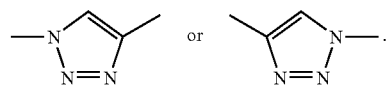

One embodiment of the present invention relates to compounds of formula I, Ia, Ib, II or III, wherein $R^2$ and $R^4$ are independently selected from:
(a) —H, wherein, if —X-A-Y— together represents —CO—O— or —CO—, then $R^2$ is different from —H,
(b) —(C$_1$-C$_{12}$)alkyl, which is optionally substituted with one or more substituents independently selected from the group consisting of halogen, —CN, —OR$^{14}$, —SR$^{14}$, —NR$^{15}$R$^{16}$, —CONR$^{15}$R$^{16}$, —SO$_2$NR$^{15}$R$^{16}$, —CO—R$^{17}$, —COOR$^{14}$—NH—CO—R$^{17}$ and —O—SO$_2$—R$^{18}$; the number of said substituents being 1, 2, 3, 4 or 5 for halogen, and 1 or 2 for any combination of substituents;
(c) acyl —(C=O)—Z, wherein Z represents hydrogen, (C$_1$-C$_4$)alkyl, aryl, aryl-(C$_1$-C$_4$)alkyl or heteroaryl-(C$_1$-C$_4$)alkyl;

in which each aryl or aryl-$(C_1-C_4)$alkyl is optionally substituted in the aryl moiety with 1, 2 or 3 substituents independently selected from the group consisting of hydroxyl, halogen, —O—$(C_1-C_4)$alkyl, —$(C_1-C_4)$alkyl or halogenated —$(C_1-C_4)$alkyl;

(d) aryl and aryl-$(C_1-C_{12})$alkyl, in which the aryl moiety is optionally substituted with one or more substituents independently selected from the group consisting of halogen, —OR$^{14}$, —$(C_1-C_6)$alkyl, halogenated —$(C_1-C_6)$alkyl, —COOR$^{14}$, —$(C_1-C_6)$alkyl-COOR$^{14}$, —CONR$^{15}$R$^{16}$, —CN, —CO—R$^{17}$, —SR$^{14}$, —SO$_2$—R$^{18}$, —SO$_2$NR$^{15}$R$^{16}$, —NO$_2$, —NR$^{15}$R$^{16}$—NH—CO—R$^{17}$ and heteroaryl; the number of said substituents being 1, 2, 3, 4 or 5 for halogen, and 1, 2 or 3 for any combination of said substituents, and in which each heteroaryl is optionally substituted with 1 or 2 substituents independently selected from oxo, halogen, —$(C_1-C_4)$alkyl and halogenated —$(C_1-C_4)$alkyl; or in which the aryl moiety is optionally substituted by two groups which are attached to adjacent carbon atoms and are combined into a saturated or partly unsaturated cyclic 5, 6, 7, or 8 membered ring system, optionally containing 1, 2 or 3 heteroatoms selected from the group consisting of N, O and S, the number of N atoms being 0, 1, 2 or 3 and the number of O and S atoms each being 0, 1 or 2;

and in which the $(C_1-C_{12})$alkyl moiety is optionally substituted by 1, 2 or 3 halogens or 1 or 2 hydroxyl groups;

(e) heteroaryl and heteroaryl-$(C_1-C_{12})$alkyl, in which the heteroaryl moiety is optionally substituted with one or more substituents independently selected from the group consisting of halogen, —OR$^{14}$, —$(C_1-C_6)$alkyl, halogenated —$(C_1-C_6)$alkyl, —$(C_1-C_6)$alkyl-C OOR$^{14}$, —COOR$^{14}$, —CONR$^{15}$R$^{16}$, —CN, —CO—R$^{17}$, —SR$^{14}$, —SO$_2$—R$^{18}$, —SO$_2$NR$^{15}$R$^{16}$, —NR$^{15}$R$^{16}$, —NH—CO—R$^{17}$, aryl-$(C_1-C_4)$-alkyl and aryl, the number of said substituents being 1, 2, 3, 4 or 5 for halogen, and 1, 2 or 3 for any combination of said substituents, and in which each aryl is optionally substituted with 1, 2 or 3 substituents independently selected from the group consisting of hydroxyl, halogen, —$(C_1-C_6)$alkoxy, —$(C_1-C_6)$alkyl, halogenated —$(C_1-C_6)$alkyl and halogenated —$(C_1-C_6)$alkoxy;

and in which the $(C_1-C_{12})$alkyl moiety is optionally substituted by 1, 2 or 3 halogens;

(f) cycloheteroalkyl and cycloheteroalkyl-$(C_1-C_{12})$alkyl, in which the cycloheteroalkyl moiety is optionally substituted with one or more substituents independently selected from the group consisting of oxo, —$(C_1-C_6)$-alkyl, aryl, aryl-$(C_1-C_4)$-alkyl, —OR$^{14}$, —COOR$^{14}$, —$(C_1-C_6)$alkyl-COOR$^{14}$, —SR$^{14}$, —CN, —SO$_2$NR$^{15}$R$^{16}$, —NR$^{15}$R$^{16}$, —CONR$^{15}$R$^{16}$, —CO—R$^{17}$ and —NH—CO—R$^{17}$, the number of said substituents being 1, 2, 3, 4 or 5 for halogen, and 1, 2 or 3 for any combination of said substituents, and in which each aryl group is optionally substituted with 1, 2 or 3 substituents independently selected from the group consisting of hydroxyl, halogen, $(C_1-C_6)$alkoxy, —$(C_1-C_6)$alkyl, halogenated —$(C_1-C_6)$alkyl and halogenated —$(C_1-C_6)$alkoxy;

or R$^2$ and R$^4$ together with the nitrogen atom to which R$^2$ and R$^4$ are attached form a heterocyclic 4, 5, 6, 7 or 8 membered ring, which is optionally saturated or partly unsaturated; which optionally contains 1, 2 or 3 additional heteroatoms selected from N, O and S, the number of additional N atoms being 0, 1, 2 or 3 and the number of O and S atoms each being 0, 1 or 2; and which ring is optionally part of a multiple condensed ring-system, which ring or ring-system is optionally substituted with 1, 2 or 3 substituents independently selected from the group consisting of oxo, —$(C_1-C_6)$alkyl, halogen, —OR$^{14}$, —COOR$^{14}$, —$(C_1-C_6)$alkyl-COOR$^{14}$, —SR$^{14}$, —CN, —NR$^{15}$R$^{16}$, —CONR$^{15}$R$^{16}$, —SO$_2$NR$^{15}$R$^{16}$, aryl, aryl-$(C_1-C_4)$-alkyl, heteroaryl and cycloheteroalkyl, in which each $(C_1-C_6)$alkyl group is optionally substituted with 1, 2 or 3 substituents independently selected among hydroxyl, halogen, —$(C_1-C_4)$alkoxy or halogenated —$(C_1-C_4)$alkoxy, in which each aryl or heteroaryl moiety is optionally substituted with 1, 2 or 3 substituents independently selected from the group consisting of hydroxyl, halogen, —$(C_1-C_6)$alkyl, —$(C_1-C_6)$alkoxy, halogenated —$(C_1-C_6)$alkyl, halogenated —$(C_1-C_6)$alkoxy, —$(C_1-C_6)$alkyl-COOR$^{14}$ and —COOR$^4$, or in which each aryl moiety optionally substituted by two groups which are attached to adjacent carbon atoms and are combined into a saturated or partly unsaturated cyclic 5, 6 or 7 membered ring system, optionally containing 1 or 2 heteroatoms selected from N, O and S, the number of N atoms being 0, 1 or 2 and the number of O and S atoms each being 0, 1 or 2; and in which each cycloheteroalkyl is optionally substituted with 1, 2 or 3 substituents independently selected from the group consisting of oxo, —$(C_1-C_6)$alkyl, aryl, aryl-$(C_1-C_4)$alkyl, hydroxyl, —$(C_1-C_6)$alkoxy, —$(C_1-C_6)$alkyl-COOR$^{14}$ and —COOR$^{14}$;

or which ring is optionally substituted by two groups which are attached to the same carbon atom and are combined into a saturated or partly unsaturated cyclic 4, 5, 6, 7 or 8 membered ring system, optionally containing 1, 2 or 3 heteroatoms selected from N, O and S, the number of N atoms being 0, 1, 2 or 3 and the number of O and S atoms each being 0, 1 or 2, and which cyclic ring system is optionally substituted by 1 or 2 substituents independently selected from the group consisting of oxo, $(C_1-C_6)$alkyl, aryl and aryl-$(C_1-C_4)$-alkyl.

Herein R$^{14}$, R$^{15}$, R$^{16}$, R$^{17}$ and R$^{18}$ are independently selected from the group consisting of —H, —$(C_1-C_4)$alkyl, halogenated —$(C_1-C_4)$alkyl, aryl and aryl-$(C_1-C_4)$alkyl, or wherein R$^{15}$ and R$^{16}$ together with the nitrogen atom to which they are attached form a heterocyclic 5, 6 or 7 membered ring, optionally containing 1 or 2 additional heteroatoms selected from N, O and S, the number of N atoms being 0, 1 or 2 and the number of O and S atoms each being 0 or 1.

In a further embodiment thereof, when R$^2$ and R$^4$ together with the nitrogen atom to which R$^2$ and R$^4$ are attached form an optionally substituted heterocyclic 4, 5, 6, 7 or 8 membered ring or ring-system, this ring or ring system is selected from the group consisting of

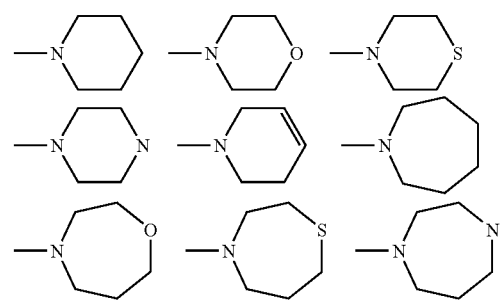

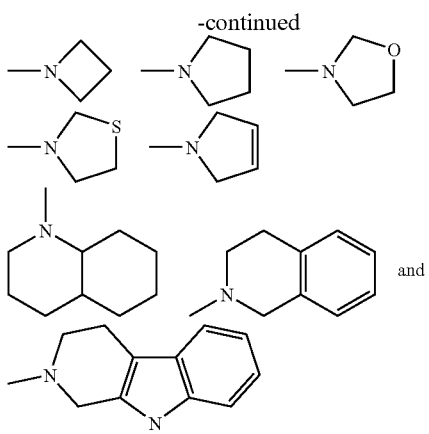

In a preferred embodiment n represents (a) 1, 2, 3, 4, 5 or 6, if —X-A-Y— together represent —NH—CO—NR$^4$—, —NH—CO—O—, —NH—CO—, —NH—CO—NH—SO$_2$—, —NH—SO$_2$—NR$^4$—, —NH—SO$_2$—O—, —NH—SO$_2$—, —O—CO—NR$^4$—, —O—CO—, —O—CO—NH—SO$_2$—NR$^4$—, or —O—, or (b) 0, 1, 2, 3, 4, or 5, if —X-A-Y— together represent —CO—NR$^4$—, —CO—O—, —CO—, or —CO—NH—NR$^4$—.

In one preferred embodiment of the present invention, the residues R$^2$ and R$^4$ in the compounds of the general formula I may independently represent —H, wherein, if —X-A-Y— together represents —CO—O— or —CO—, then R$^2$ is different from —H.

In a further embodiment, the invention relates compounds of formula I, Ia, Ib, II or III, wherein R$^6$, R$^7$, R$^8$, R$^9$ and R$^{10}$ are independently selected from the group consisting of:

(a) —H (b) —(C$_1$-C$_{12}$)alkyl, which is optionally substituted by halogen, —CN, —OR$^{14}$, —SR$^{14}$, —NR$^{15}$R$^{16}$, —CONR$^{15}$R$^{16}$—SO$_2$NR$^{15}$R$^{16}$—CO—R$^{17}$—COOR$^{14}$—NH—CO—R$^{17}$, or —O—SO$_2$—R$^{18}$; the number of said substituents being up to five for halogen, and 1 or 2 for any combination of substituents;

(c) aryl and aryl-(C$_1$-C$_{12}$)alkyl, in which the aryl moiety of the aryl or aryl-(C$_1$-C$_{12}$)alkyl group is optionally substituted with one or more substituents independently selected from the group consisting of halogen, —OR$^{19}$, —(C$_1$-C$_6$)alkyl, halogenated —(C$_1$-C$_6$)alkyl, —COOR$^{19}$, —(C$_1$-C$_6$)alkyl-COOR$^{19}$, —CONR$^{20}$R$^{21}$, —CN, —CO—R$^{22}$, —SR$^{19}$, —SO$_2$—R$^{23}$, SO$_2$NR$^{20}$R$^{21}$, —NO$_2$, —NR$^{20}$R$^{21}$, —NH—CO—R$^{22}$ and heteroaryl; the number of said substituents being 1, 2, 3, 4 or 5 for halogen, and 1, 2 or 3 for any combination of said substituents, and in which each heteroaryl is optionally substituted with 1 or 2 substituents independently selected from oxo, halogen, —(C$_1$-C$_4$)alkyl and halogenated —(C$_1$-C$_4$)alkyl; or in which the aryl moiety of the aryl or aryl-(C$_1$-C$_{12}$)alkyl group is optionally substituted by two groups which are attached to adjacent carbon atoms and are combined into a saturated or partly unsaturated cyclic 5, 6, 7, or 8 membered ring system, optionally containing 1, 2 or 3 heteroatoms selected from the group consisting of N, O and S, the number of N atoms being 0, 1, 2 or 3 and the number of O and S atoms each being 0, 1 or 2, and which ring system is optionally substituted with 1 or 2 oxo groups; and in which the (C$_1$-C$_{12}$)alkyl moiety is optionally substituted by 1, 2 or 3 halogens or 1 or 2 hydroxyl groups;

(d) heteroaryl and heteroaryl-(C$_1$-C$_{12}$)alkyl, in which the heteroaryl moiety is optionally substituted with one or more substituents independently selected from the group consisting of halogen, oxo, —OR$^{19}$, —(C$_1$-C$_6$)alkyl, halogenated —(C$_1$-C$_6$)alkyl, —COOR$^{19}$, -(C$_1$-C$_6$)alkyl-COOR$^{19}$, —CONR$^{20}$R$^{21}$, —CN, —CO—R$^{22}$, —SR$^{19}$, —SO$_2$—R$^{23}$, —SO$_2$NR$^{20}$R$^{21}$, —NR$^{20}$R$^{21}$, —NH—CO—R$^{22}$, aryl-(C$_1$-C$_4$)-alkyl and aryl, the number of said substituents being 1, 2, 3, 4 or 5 for halogen, and 1, 2 or 3 for any combination of said substituents, and in which each aryl is optionally substituted with 1, 2 or 3 substituents independently selected from the group consisting of hydroxyl, halogen, —(C$_1$-C$_6$)alkoxy, —(C$_1$-C$_6$)alkyl, halogenated —(C$_1$-C$_6$)alkyl and halogenated —(C$_1$-C$_6$)alkoxy;

and in which the (C$_1$-C$_{12}$)alkyl moiety is optionally substituted by 1, 2 or 3 halogens;

(e) cycloheteroalkyl and cycloheteroalkyl-(C$_1$-C$_{12}$)alkyl, in which the cycloheteroalkyl moiety is optionally substituted with one or more substituents independently selected from the group consisting of oxo, —(C$_1$-C$_6$)-alkyl, aryl, aryl-(C$_1$-C$_4$)-alkyl, —OR$^{19}$, —COOR$^{19}$, —(C$_1$-C$_6$)alkyl-COOR$^{19}$, —SR$^{19}$, —CN, —SO$_2$NR$^{20}$R$^{21}$, —NR$^{20}$R$^{21}$, —CONR$^{20}$R$^{21}$, —CO—R$^{22}$ and —NH—CO—R$^{22}$, the number of said substituents being 1, 2, 3, 4 or 5 for halogen, and 1, 2 or 3 for any combination of said substituents, and in which each aryl group is optionally substituted with 1, 2 or 3 substituents independently selected from the group consisting of hydroxyl, halogen, (C$_1$-C$_6$)alkoxy, —(C$_1$-C$_6$)alkyl, halogenated —(C$_1$-C$_6$)alkyl and halogenated —(C$_1$-C$_6$)alkoxy;

or R$^7$ and R$^8$ together with the nitrogen atom to which they are attached, form a heterocyclic 4, 5, 6, 7 or 8 membered ring, which is optionally saturated, partly unsaturated or aromatic; which optionally contains 1, 2 or 3 additional heteroatoms selected from the group consisting of N, O or S, the number of additional N atoms being 0, 1, 2 or 3 and the number of O and S atoms each being 0, 1 or 2; and which ring is optionally part of a multiple condensed ring system, and which ring or ring-system is optionally substituted by 1, 2 or 3 substituents independently selected from the group consisting of oxo, —(C$_1$-C$_6$)alkyl, halogen, —OR$^{19}$, —COOR$^{19}$, —(C$_1$-C$_6$)alkyl-COOR$^{19}$, —SR$^{19}$, —CN, —NR$^{20}$R$^{21}$, —CONR$^{20}$R$^{21}$—SO$_2$NR$^{20}$R$^{21}$, aryl and aryl-(C$_1$-C$_4$)-alkyl, in which each (C$_1$-C$_6$)alkyl group is optionally substituted with 1, 2 or 3 substituents independently selected among hydroxyl, halogen, —(C$_1$-C$_4$)alkoxy or halogenated —(C$_1$-C$_4$)alkoxy, in which each aryl moiety is optionally substituted with 1, 2 or 3 substituents independently selected from the group consisting of hydroxyl, halogen, —(C$_1$-C$_6$)alkyl, —(C$_1$-C$_6$)alkoxy, halogenated —(C$_1$-C$_6$)alkyl, halogenated —(C$_1$-C$_6$)alkoxy, —(C$_1$-C$_6$)alkyl-COOR$^{19}$ and —COOR$^{19}$; or wherein R$^{19}$, R$^{20}$, R$^{21}$, R$^{22}$ and R$^{23}$ are independently selected from the group consisting of —H, —(C$_1$-C$_4$)alkyl, halogenated —(C$_1$-C$_4$)alkyl, aryl and aryl-(C$_1$-C$_4$)alkyl, or wherein R$^{20}$ and R$^{21}$ together with the nitrogen atom to which they are attached form a heterocyclic 5, 6 or 7 membered ring, optionally containing 1 or 2 additional heteroatoms selected from N, O and S, the number of N atoms being 0, 1 or 2 and the number of O and S atoms each being 0 or 1, and if R$^1$ is —NR$^5$—CO—R$^6$, then R$^5$ and R$^6$ together with the nitrogen atom to which $R^5$ is attached and the carbonyl group to which $R^5$ is attached may also form a heterocyclic 4, 5, 6, 7 or 8 membered lactam ring, and if $R^1$ is —$NR^5$—$SO_2$—$R^6$, then $R^5$ and $R^6$ together with the nitrogen atom to which $R^5$ is attached, and the sulfoxyd group to which $R^6$ is attached, may also form a heterocyclic 4, 5, 6, 7 or 8 membered sultam ring, or $R^9$ and $R^{10}$ together with the boron atom to which they are attached form a heterocyclic 5 or 6 membered ring, which is optionally substituted with 1, 2, 3 or 4-$(C_1$-$C_4)$alkyl groups.

A further preferred embodiment of the present invention relates to compounds of formula I, Ia, Ib, II or III, wherein $R^1$ is selected from the group consisting of:

(a) —$B(OH)_2$.
(b) —CO—OH
(c) —CO—$NR^7R^8$,
(d) —$NR^7R^3$, and
(e) —$NR^5$—CO—$R^6$.

In this context, one embodiment is directed to compounds of formula I, Ia, Ib, II or III, wherein $R^1$ is —CO—$NR^7R^8$, and $R^7$ and $R^8$ are independently selected from the group consisting of —H and —$(C_1$-$C_6)$alkyl.

In this context, another embodiment is directed to compounds of formula I, Ia, Ib, II or III, wherein $R^1$ is —$NR^5$—CO—$R^6$, and $R^5$ and $R^6$ together with the nitrogen atom to which $R^5$ is attached and the carbonyl group to which $R^5$ is attached form a heterocyclic 5 or 6 membered lactam ring.

In this context, another embodiment is directed to compounds of formula I, Ia, Ib, II or III, wherein $R^1$ is —$NR^7R^8$. In a subgroup of this embodiment, additionally $R^7$ and $R^8$ are preferably independently selected from the group consisting of:

(a) —H
(b) —$(C_1$-$C_6)$alkyl;
(c) phenyl and phenyl-$(C_1$-$C_4)$alkyl, in which the phenyl moiety is optionally substituted with 1 or 2 substituents independently selected from the group consisting of halogen, —$OR^{19}$, —$(C_1$-$C_4)$alkyl, halogenated —$(C_1$-$C_4)$alkyl, —CN and —$SO_2NR^{20}R^{21}$; or
 in which the phenyl moiety is optionally substituted by two groups which are attached to adjacent carbon atoms and are combined into a saturated or partly unsaturated cyclic 5 or 6 membered ring system, optionally containing 1 or 2 heteroatoms selected from the group consisting of O and S, the number of O and S atoms each being 0, 1 or 2, and which ring system is optionally substituted with 1 or 2 oxo groups;
(d) heteroaryl and heteroaryl-$(C_1$-$C_4)$alkyl, which heteroaryl moiety is optionally substituted with 1 or 2 oxo groups;
(e) cycloheteroalkyl and cycloheteroalkyl-$(C_1$-$C_4)$alkyl, in which the cycloheteroalkyl moiety is optionally substituted with an oxo group;

or $R^7$ and $R^8$ together with the nitrogen atom, to which they are attached, form a heterocyclic 5, 6 or 7 membered ring, which is optionally saturated, partly unsaturated or aromatic, which optionally contains 1 or 2 additional heteroatoms selected from the group consisting of N, O or S, the number of additional N atoms being 0, 1 or 2 and the number of O and S atoms each being 0 or 1; and which ring is optionally part of a multiple condensed ring system, and which ring or ring-system is optionally substituted by 1 or 2 substituents independently selected from the group consisting of oxo, —$(C_1$-$C_4)$alkyl, —$OR^{19}$, aryl and aryl-$(C_1$-$C_2)$-alkyl, in which each aryl moiety is optionally substituted with 1, 2 or 3 substituents independently selected from the group consisting of hydroxyl, halogen, —$(C_1$-$C_4)$alkyl, —$(C_1$-$C_4)$alkoxy, halogenated —$(C_1$-$C_4)$alkyl and halogenated —$(C_1$-$C_4)$alkoxy;

wherein $R^{19}$, $R^{20}$ and $R^{21}$ are independently selected from the group consisting of —H, —$(C_1$-$C_4)$alkyl and halogenated —$(C_1$-$C_4)$alkyl, or wherein $R^{20}$ and $R^{21}$ together with the nitrogen atom to which they are attached form a heterocyclic 5 or 6 membered ring, optionally containing 1 additional heteroatom selected from N, O and S.

In an additional embodiment of the present invention, compounds of formula I, Ia, Ib, II or III are disclosed, wherein $R^2$ and $R^4$ are independently selected from:

(a) —H, wherein, if —X-A-Y— together represents —CO—O— or —CO—, then $R^2$ is different from —H,
(b) —$(C_1$-$C_6)$alkyl and —$(C_1$-$C_6)$cycloalkyl, which are optionally substituted with 1 or 2 substituents independently selected from the group consisting of halogen and —$OR^{14}$;
(c) phenyl and phenyl-$(C_1$-$C_4)$alkyl, in which the phenyl moiety is optionally substituted with 1 or 2 substituents independently selected from the group consisting of halogen, —$OR^{14}$, —$(C_1$-$C_6)$alkyl and halogenated —$(C_1$-$C_6)$alkyl, or
 in which the phenyl moiety is optionally substituted by two groups which are attached to adjacent carbon atoms and are combined into a saturated or partly unsaturated cyclic 5 or 6 membered ring system, optionally containing 1 or 2 heteroatoms independently selected from the group consisting of N, O and S, the number of N, O and S atoms each being 0, 1 or 2;
(d) heteroaryl and heteroaryl-$(C_1$-$C_4)$alkyl, in which the heteroaryl moiety is optionally substituted with 1 or 2 substituents independently selected from the group consisting of halogen, —$OR^{14}$, —$(C_1$-$C_6)$alkyl and halogenated —$(C_1$-$C_6)$alkyl;

or $R^2$ and $R^4$ together with the nitrogen atom, to which $R^2$ and $R^4$ are attached form a heterocyclic 5, 6 or 7 membered ring, which is optionally saturated or partly unsaturated; which optionally contains 1 or 2 additional heteroatoms selected from N, O and S, the number of additional N atoms being 0, 1 or 2 and the number of O and S atoms each being 0 or 1; and which ring is optionally part of a multiple condensed ring-system, which ring or ring-system is optionally substituted with 1 or 2 substituents independently selected from the group consisting of oxo, —$(C_1$-$C_6)$alkyl, halogen and —$OR^{14}$, wherein $R^{14}$ is selected from the group consisting of —H, —$(C_1$-$C_4)$alkyl and halogenated —$(C_1$-$C_4)$alkyl.

Another embodiment in this context is directed to the ring or ring system optionally formed by $R^2$ and $R^4$ together with the nitrogen atom, to which $R^2$ and $R^4$ are attached: This ring or ring system may be selected from the group consisting of

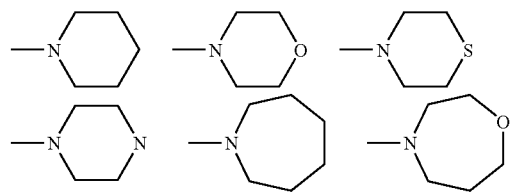

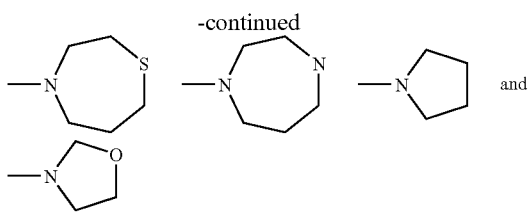

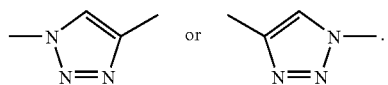

wherein the ring or the ring-system is optionally substituted as defined herein.

Another embodiment of the present invention relates to compounds of formula I, Ia, Ib, II or III, wherein $R^{11}$ represents H, —($C_1$-$C_4$)alkyl, ($C_1$-$C_4$)alkoxy, or ($C_1$-$C_4$)alkoxy-($C_1$-$C_4$)alkyl. In a subgroup of this embodiment, $R^{11}$ represents H, ethyl, propyl, methoxyethyl, methoxy, ethoxy or methoxyethoxy. Preferably, $R^{11}$ represents H.

Preferred are compounds of formula I, Ia, Ib, II or III, wherein n represents 2, 3 or 4, preferably n represents 2 or 3.

In an additional embodiment of the present invention, compounds of formula I, Ia, Ib, II or III are disclosed, wherein n represents 2. In this context are those compounds preferred, wherein the compound is an optically pure enantiomer having the formula (III-b)

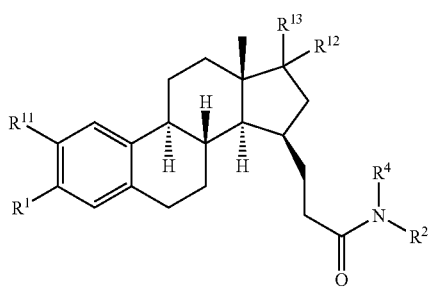

In an alternative embodiment of the present invention, compounds of formula I, Ia, Ib, II or III are disclosed, wherein n represents 3. In this context are those compounds preferred, wherein the compound is an optically pure enantiomer having the formula (II-b)

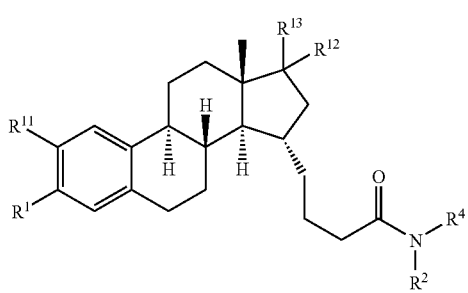

Another embodiment of the invention relates to compounds of formula I, Ia, Ib, II or III, wherein —X-A-Y— together represent —CO—NHR$^4$—.

Another embodiment of the invention relates to compounds of formula I, Ia, Ib, II or III, wherein —X-A-Y— together represent a group A further embodiment relates to compounds of formula I, Ia, Ib, II or III, wherein $R^{12}$ and $R^{13}$ together represent =O.

A further embodiment relates to compounds of formula I, Ia, Ib, II or III, wherein $R^{12}$ and $R^{13}$ each individually represent F.

In one embodiment, the invention relates to a compound of the following formula XLII

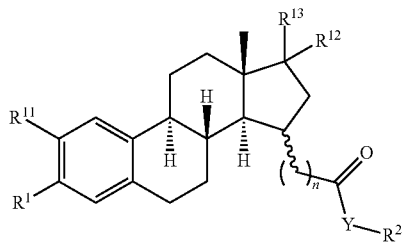

wherein
Y represents —NR$^4$—, —O—, a bond or —NH—NR$^4$,
i.e. compounds of formula I, wherein —X-A-Y— together represent a group selected from
(a) —CO—NR$^4$—,
(b) —CO—O—,
(c) —CO—, and
(d) —CO—NH—NR$^4$,
the preferred meanings of $R^1$, $R^2$, $R^4$, $R^{11}$, $R^{12}$ and $R^{13}$ are as indicated herewithin, and
n represents 0, 1, 2, 3, 4, or 5.

In one embodiment, the invention relates to a compound corresponding to formula VI

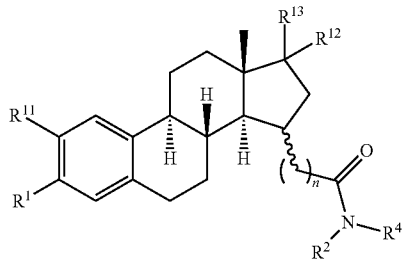

i.e. a compound of formula I, wherein —X-A-Y— together represent —CO—NR$^4$—, and wherein the preferred meanings of $R^1$, $R^2$, $R^4$, $R^{11}$, $R^{12}$ and $R^{13}$ are as indicated herewithin, and n represents 0, 1, 2, 3, 4, or 5, preferably n represents 2, 3 or 4.

In this embodiment,
$R^2$ more preferably represents
(i) —($C_1$-$C_4$)alkyl, which is optionally substituted with one or two ($C_1$-$C_4$)alkoxy groups;
(ii) —($C_3$-$C_8$)cycloalkyl;
(iii) phenyl or —($C_1$-$C_4$)alkyl-phenyl,
which phenyl is optionally substituted with one or two substituents independently selected from hydroxyl, halogen, cyano and ($C_1$-$C_4$)alkoxy; or which phenyl is optionally substituted by two groups which are attached to adjacent carbon atoms and are combined into a saturated cyclic 5 or 6-membered ring system, containing 1 or 2 O-atoms; or
(iv) heteroaryl or —$(C_1$-$C_4)$alkyl-heteroaryl, wherein the heteroaryl is thiazolyl, pyridinyl, indolyl, or indazolyl; which heteroaryl is optionally substituted with one or two —$(C_1$-$C_4)$alkyl groups;
and $R^4$ is independently selected from —H, —$(C_1$-$C_4)$-alkyl or —$(C_1$-$C_4)$-alkyl-phenyl, wherein the phenyl group is optionally substituted with one or two $(C_1$-$C_4)$ alkoxy groups; or
$R^2$ and $R^4$ together with the nitrogen atom to which $R^2$ and $R^4$ are attached form a ring, which is selected from the group consisting of morpholine, piperidine, and piperazine,
wherein the ring is optionally substituted with a —$(C_1$-$C_4)$alkyl group.

Mostly preferred are compounds according to general formula VI, wherein
$R^2$ represents a —$(C_1$-$C_4)$alkylphenyl, preferably a benzyl group, or a thiazolyl group, optionally substituted with —$(C_1$-$C_4)$-alkyl, preferably methyl, and $R^4$ represents —H; or
$R^2$ and $R^4$ together with the nitrogen atom to which $R^2$ and $R^4$ are attached form a morpholine group, and
n represents 2 or 3.

In a further embodiment the invention relates to a compound corresponding to formula XL,

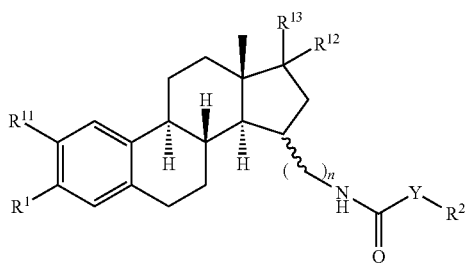

(XL)

wherein Y represents —NH—, a bond, or —O—; i.e compounds of formula I, wherein —X-A-Y— together represent —NH—CO—NH—, —NH—CO—O—, or —NH—CO—; the preferred meanings of $R^1$, $R^2$, $R^4$, $R^{11}$, $R^{12}$ and $R^{13}$ are as indicated herewithin; and n represents 1, 2, 3, 4, 5 or 6, preferably 1, 2, 3 or 4.

A further embodiment of the invention relates to a compound of the following formula XVII,

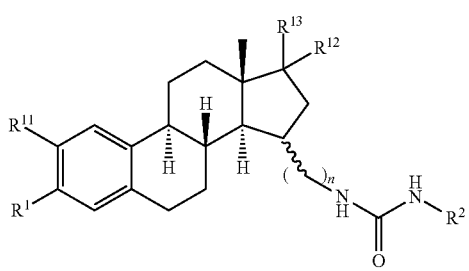

(XVII)

wherein the preferred meanings of $R^1$, $R^2$, $R^{11}$, $R^{12}$ and $R^{13}$ are as indicated herewithin; and n preferably represents 1, 2, 3, or 4, even more preferably 3 or 4.

In this embodiment, $R^2$ preferably represents
(i) —$(C_1$-$C_4)$alkyl,
(ii) —$(C_3$-$C_8)$cycloalkyl,
(iii) —$(C_1$-$C_4)$alkyl-$(C_3$-$C_8)$cycloalkyl,
(iv) aryl, wherein the aryl is phenyl or naphthyl,
which phenyl is optionally substituted with one or two substituents independently selected from the group consisting of hydroxyl, halogen, —CO—O$(C_1$-$C_4)$ alkyl and $(C_1$-$C_4)$alkoxy; or
which phenyl is optionally substituted by two groups which are attached to adjacent carbon atoms and are combined into a saturated cyclic 5 or 6-membered ring system, containing 1 or 2 O atoms, or
(v) —$(C_1$-$C_4)$alkyl-phenyl.

A further embodiment of the invention relates to a compound corresponding to formula XXIII,

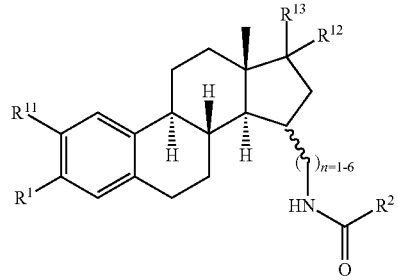

(XXIII)

wherein the preferred meanings of $R^1$, $R^2$, $R^{11}$, $R^{12}$ and $R^{13}$ are as indicated herewithin; and n preferably represents 1, 2, 3, or 4.

In this embodiment, $R^2$ preferably represents
(i) —$(C_1$-$C_4)$alkyl,
(ii) —$(C_3$-$C_8)$cycloalkyl,
(iii) —$(C_1$-$C_4)$alkyl-$(C_3$-$C_8)$cycloalkyl,
(iv) —$(C_1$-$C_4)$alkyl, substituted with one or two substituents independently selected from the group consisting of —O—$(C_1$-$C_4)$alkyl and —O—$(C_1$-$C_4)$alkyl-phenyl,
(v) phenyl,
which phenyl is optionally substituted with one, two or three substituents independently selected from the group consisting of halogen and $(C_1$-$C_4)$alkoxy;
(vi) —$(C_1$-$C_4)$alkyl-phenyl; or
(vii) adamanty.

In another embodiment, the present invention relates to compounds of formula (I), wherein —X-A-Y— together represent a group selected from —NH—$SO_2$—NH—, —NH—$SO_2$—O—, and —NH—$SO_2$—, and n represents 1, 2, 3, or 4.

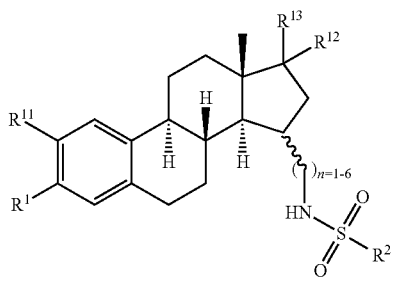
(XXIV)

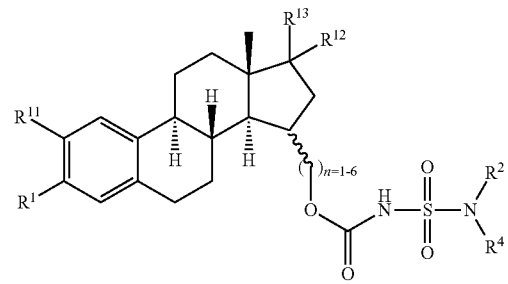
(XXVIII)

wherein the preferred meanings of $R^1$, $R^2$, $R^{11}$, $R^{12}$ and $R^{13}$ are as indicated herewithin; and n preferably represents 1, 2, 3, or 4.

In this embodiment, $R^2$ preferably represents
(i) aryl, wherein the aryl is selected among phenyl and naphthyl,
   which aryl is optionally substituted with one or two substituents independently selected from the group consisting of halogen, nitro, $(C_1$-$C_4)$alkoxy, and —$(C_1$-$C_4)$ alkyl; or
(ii) heteroaryl, wherein the heteroaryl is furyl, thienyl, or thiazolyl, or indolyl,
   which heteroaryl is optionally substituted with one or two substituents independently selected from the group consisting of —$SO_2$-phenyl and $(C_1$-$C_4)$alkyl.

In another embodiment, the present invention relates to compounds of formula (I), wherein —X-A-Y— together represent a group selected from —O—CO—NH—, —O—CO—, and —O—CO—NH—$SO_2$—$NR^4$—, and n represents 1, 2, 3, 4, 5 or 6.

A further embodiment of the invention relates to a compound corresponding to formula XXVI,

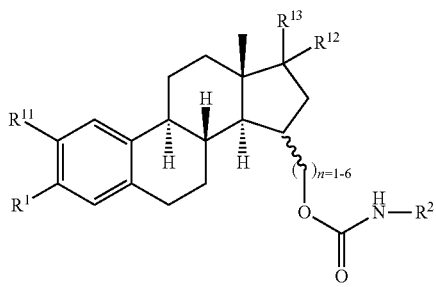
(XXVI)

wherein the preferred meanings of $R^1$, $R^2$, $R^{11}$, $R^{12}$ and $R^{13}$ are as indicated herewithin; and n preferably represents 3, 4, 5 or 6.

In this embodiment, $R^2$ preferably represents phenyl or naphthyl,
which phenyl is optionally substituted with one or two substituents independently selected from the group consisting of hydroxyl, halogen, nitro, —CO—O($C_1$-$C_4$)alkyl and ($C_1$-$C_4$)alkoxy and halogenated ($C_1$-$C_4$)alkyl; or
which phenyl is optionally substituted by two groups which are attached to adjacent carbon atoms and are combined into a saturated cyclic 5 or 6-membered ring system, containing 1 or 2 O atoms.

A further embodiment of the invention relates to a compound of the following formula XXVIII, wherein the preferred meanings of $R^1$, $R^2$, $R^4$, $R^{11}$, $R^{12}$ and $R^{13}$ are as indicated herewithin; and n preferably represents 3, 4, 5 or 6.

In this embodiment,
$R^2$ preferably represents
   (i) —$(C_1$-$C_4)$alkyl,
   (ii) —$(C_3$-$C_8)$cycloalkyl,
   (iii) —$(C_1$-$C_4)$alkyl-phenyl,
   (iv) phenyl, or
   (v) heteroaryl or —$(C_1$-$C_4)$alkyl-heteroaryl, wherein the heteroaryl is furyl, thienyl, thiazolyl, pyridinyl, indolyl, or benzoimidazolyl;
and preferably $R^4$ is independently selected from H, —($C_1$-$C_4$)-alkyl and —$(C_1$-$C_4)$alkyl-phenyl; or
$R^2$ and $R^4$ together with the nitrogen atom to which $R^2$ and $R^4$ are attached may form a ring, which is selected from the group consisting of morpholine, thiomorpholine and piperazyl, and which is optionally substituted with ($C_1$-$C_4$)-alkyl.

A further embodiment of the invention relates to a compound corresponding to formula XXXI,

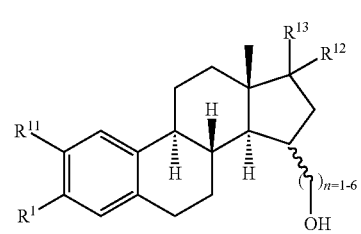
(XXXI)

wherein the preferred meanings of $R^1$, $R^{10}$, $R^{11}$, $R^{12}$ and $R^{13}$ are as indicated herewithin; and n represents 1, 2, 3, 4, 5 or 6, preferably 3 or 4.

A further embodiment of the invention relates to a compound of formula I, Ia, Ib, II or III, wherein
$R^1$ represents —CO—OH or —CO—$NR^7R^3$, wherein $R^7$ and $R^8$ are independently selected from —H and —$(C_1$-$C_4)$ alkyl;
—X-A-Y— together represent —CO—$NR^4$—;
$R^{11}$ represents —H;
$R^{12}$ and $R^{13}$ together represent =O, or $R^{12}$ and $R^{13}$ each individually represent F;
n represents 2 or 3; and
$R^2$ and $R^4$ have the meanings as indicated herewithin.

A further embodiment of the invention relates to a compound of formula I, Ia, Ib, II or III, wherein
$R^1$ represents —$B(OH)_2$,
—X-A-Y— together represent —CO—$NR^4$—;
$R^{11}$ represents —H;

$R^{12}$ and $R^{13}$ together represent =O, or $R^{12}$ and $R^{13}$ each individually represent F;

n represents 2 or 3; and $R^2$ and $R^4$ have the meanings as indicated herewithin.

A further embodiment of the invention relates to a compound of formula I, Ia, Ib, II or III, wherein $R^1$ represents —$NR^5$—CO—$R^6$, wherein $R^5$ and $R^6$ together with the nitrogen atom to which $R^5$ is attached and the carbonyl group to which $R^6$ is attached form a heterocyclic 5 membered lactam ring;

—X-A-Y— together represent —CO—$NR^4$—;

$R^{11}$ represents —H;

$R^{12}$ and $R^{13}$ together represent =O, or $R^{12}$ and $R^{13}$ each individually represent F;

n represents 2 or 3, and $R^2$ and $R^4$ have the meanings as indicated herewithin.

A further embodiment of the invention relates to a compound of formula I, Ia, Ib, II or III, wherein $R^1$ represents —$NR^7R^8$, —X-A-Y— together represent —CO—$NR^4$—;

$R^{11}$ represents —H;

$R^{12}$ and $R^{13}$ together represent =O, or $R^{12}$ and $R^{13}$ each individually represent F;

n represents 2 or 3;

$R^2$ and $R^4$ have the meanings as indicated herewithin, and $R^7$ and $R^8$ have the meanings as indicated herewithin.

In this embodiment, $R^7$ and $R^8$ are preferably independently selected from the group consisting of:
(a) —H
(b) —($C_1$-$C_6$)alkyl;
(c) phenyl and phenyl-($C_1$-$C_2$)alkyl, in which the phenyl moiety is optionally substituted with 1 or 2 substituents independently selected from the group consisting of halogen, —$OR^{19}$, —($C_1$-$C_4$)alkyl, halogenated —($C_1$-$C_4$)alkyl, —CN and —$SO_2NR^{20}R^{21}$; or
in which the phenyl moiety is optionally substituted by two groups which are attached to adjacent carbon atoms and are combined into a saturated or partly unsaturated cyclic 5 or 6 membered ring system, optionally containing 1 or 2 heteroatoms selected from the group consisting of O and S, the number of O and S atoms each being 0, 1 or 2, and which ring system is optionally substituted with 1 or 2 oxo groups;
(d) heteroaryl and heteroaryl-($C_1$-$C_2$)alkyl, in which the heteroaryl moiety is selected from the group consisting of indolyl, quinolinyl, benzothienyl and pyridinyl, which heteroaryl moiety is optionally substituted with 1 or 2 oxo groups;
(e) cycloheteroalkyl and cycloheteroalkyl-($C_1$-$C_4$)alkyl, in which the cycloheteroalkyl moiety is selected from the group consisting of pyrrolidinyl and oxazolidinyl, and in which the cycloheteroalkyl moiety is optionally substituted with an oxo group;

or $R^7$ and $R^8$ together with the nitrogen atom to which they are attached, form a heterocyclic 5 or 6 membered saturated ring, which is saturated or partly unsaturated, which optionally contains 1 additional heteroatom selected from the group consisting of N and O; and which ring is optionally part of a multiple condensed ring system, and which ring or ring-system is optionally substituted by a substituent selected from the group consisting of oxo, phenyl and phenyl-($C_1$-$C_2$)-alkyl, in which each phenyl moiety is optionally substituted with a substituent selected from the group consisting of halogen and —($C_1$-$C_4$)alkoxy;

wherein $R^{19}$, $R^{20}$ and $R^{21}$ are independently selected from the group consisting of —H, —($C_1$-$C_4$)alkyl and halogenated —($C_1$-$C_4$)alkyl, or wherein $R^{20}$ and $R^{21}$ together with the nitrogen atom to which they are attached form a heterocyclic 6 membered ring, optionally containing 1 additional heteroatom selected from N and O.

In the aforementioned embodiments, $R^2$ and $R^4$ are preferably independently selected from the group consisting of:
(a) —H,
(b) —($C_1$-$C_4$)alkyl, which is optionally substituted with —$OR^{14}$,
(c) —($C_1$-$C_6$)cycloalkyl;
(d) phenyl and phenyl-($C_1$-$C_2$)alkyl, in which the phenyl moiety is optionally substituted with 1 or 2 substituents independently selected from the group consisting of halogen and —$OR^{14}$, or
in which the phenyl moiety is optionally substituted by two groups which are attached to adjacent carbon atoms and are combined into a saturated cyclic 5 or 6 membered ring system, optionally containing 1 or 2 heteroatoms independently selected from the group consisting of N, O and S, the number of N, O and S atoms each being 0, 1 or 2;
(e) heteroaryl and heteroaryl-($C_1$-$C_2$)alkyl, in which the heteroaryl moiety is selected from the group consisting of imidazolyl, pyridinyl, indolyl and thiazolyl, and in which the heteroaryl moiety is optionally substituted with —($C_1$-$C_4$)alkyl;

or $R^2$ and $R^4$ together with the nitrogen atom to which $R^2$ and $R^4$ are attached, form a heterocyclic 5, 6 or 7 membered saturated ring, which optionally contains 1 additional heteroatom selected from N and O; which ring is optionally substituted with —($C_1$-$C_4$)alkyl;

wherein $R^{14}$ is selected from the group consisting of —H, —($C_1$-$C_4$)alkyl and halogenated —($C_1$-$C_4$)alkyl.

A further embodiment of the invention relates to a compound of formula I, Ia, Ib, II or III, wherein $R^1$ represents —$B(OH)_2$, —X-A-Y— together represent a group

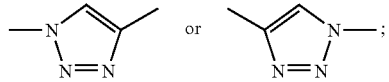

$R^{11}$ represents H, ethyl, propyl, methoxyethyl, methoxy, ethoxy or methoxyethoxy, preferably H;

$R^{12}$ and $R^{13}$ together represent =O, or $R^{12}$ and $R^{13}$ each individually represent F;

n represents 2 or 3; and $R^2$ has the meanings as indicated herewithin.

In this embodiment, $R^2$ is preferably selected from the group consisting of
(a) —($C_1$-$C_6$)alkyl,
(b) ($C_1$-$C_6$)cycloalkyl-($C_1$-$C_4$)alkyl, and
(c) phenyl and phenyl-($C_1$-$C_2$)alkyl, in which the phenyl moiety is optionally substituted with 1 or 2 substituents independently selected from the group consisting of halogen, —($C_1$-$C_4$)alkyl, halogenated —($C_1$-$C_4$)alkyl, —$OR^{14}$, and —$COOR^{14}$, wherein $R^{14}$ is selected from the group consisting of —H, —($C_1$-$C_4$)alkyl and halogenated —($C_1$-$C_4$)alkyl.

Preferred embodiments of the invention relate to the following compounds:

No. 1 15alpha-(4-morpholin-4-yl-4-oxobutyl)-17-oxoestra-1(10),2,4-triene-3-carboxamide No. 2 15alpha-(4-morpholin-4-yl-4-oxobutyl)-17-oxoestra-1 (10),2,4-triene-3-carboxylic acid No. 3 15beta-{3-[(5-methyl-1,3-thiazol-2-yl)amino]-3-oxopropyl}-17-oxoestra-1(10),2,4-triene-3-carboxamide No. 4 15beta-{3-[(5-methyl-1,3-thiazol-2-yl)amino]-3-oxopropyl}-17-oxoestra-1(10),2,4-triene-3-carboxylic acid No. 5 N-butyl-N-methyl-15beta-{3-[(5-methyl-1,3-thiazol-2-yl)amino]-3-oxopropyl}-17-oxoestra-1(10),2,4-triene-3-carboxamide No. 6 17,17-difluoro-15alpha-(4-morpholin-4-yl-4-oxobutyl)estra-1(10),2,4-triene-3-carboxamide No. 7 17,17-difluoro-15alpha-(4-morpholin-4-yl-4-oxobutyl)estra-1(10),2,4-triene-3-carboxylic acid No. 8 17,17-difluoro-15beta-{3-[(5-methyl-1,3-thiazol-2-yl)amino]-3-oxopropyl}estra-1(10),2,4-triene-3-carboxamide No. 9 17,17-difluoro-15beta-{3-[(5-methyl-1,3-thiazol-2-yl)amino]-3-oxopropyl}estra-1(10),2,4-triene-3-carboxylic acid No. 10 [15alpha-(4-morpholin-4-yl-4-oxobutyl)-17-oxoestra-1(10),2,4-trien-3-yl]boronic acid No. 11 [15alpha-{3-[(5-methyl-1,3-thiazol-2-yl)amino]-3-oxopropyl}-17-oxoestra-1(10),2,4-trien-3-yl]boronic acid No. 12 [15alpha-{4-[(3,4-dihydroxybenzyl)amino]-4-oxobutyl}-17-oxoestra-1(10),2,4-trien-3-yl]boronic acid No. 13 [15alpha-[4-(1,3-benzodioxol-5-ylamino)-4-oxobutyl]-17-oxoestra-1(10),2,4-trien-3-yl]boronic acid No. 14 [15alpha-[4-(cyclopropylamino)-4-oxobutyl]-17-oxoestra-1(10),2,4-trien-3-yl]boronic acid No. 15 [15alpha-(4-{[2-(7-methyl-1H-indol-3-yl)ethyl]amino}-4-oxobutyl)-17-oxoestra-1(10),2,4-trien-3-yl]boronic acid No. 16 [15alpha-{4-[(5-methyl-1,3-thiazol-2-yl)amino]-4-oxobutyl}-17-oxoestra-1(10),2,4-trien-3-yl]boronic acid No. 17 [15alpha-[4-(cyclohexylamino)-4-oxobutyl]-17-oxoestra-1(10),2,4-trien-3-yl]boronic acid No. 18 [15alpha-(4-{[(1-methyl-1H-imidazol-4-yl)methyl]amino}-4-oxobutyl)-17-oxoestra-1(10),2,4-trien-3-yl]boronic acid No. 19 [15alpha-{4-[(1,3-benzodioxol-5-ylmethyl)amino]-4-oxobutyl}-17-oxoestra-1(10),2,4-trien-3-yl]boronic acid No. 20 [17-oxo-15alpha-(4-oxo-4-piperidin-1-ylbutyl)estra-1(10),2,4-trien-3-yl]boronic acid No. 21 [17-oxo-15alpha-{4-oxo-4-[(pyridin-3-ylmethyl)amino]butyl}estra-1(10),2,4-trien-3-yl]boronic acid No. 22 [15alpha-{4-[benzyl(methyl)amino]-4-oxobutyl}-17-oxoestra-1(10),2,4-trien-3-yl]boronic acid No. 23 [15alpha-[4-(benzylamino)-4-oxobutyl]-17-oxoestra-1(10),2,4-trien-3-yl]boronic acid No. 24 [15alpha-[4-(diethylamino)-4-oxobutyl]-17-oxoestra-1(10),2,4-trien-3-yl]boronic acid No. 25 [15alpha-{4-[(2-methoxyethyl)amino]-4-oxobutyl}-17-oxoestra-1(10),2,4-trien-3-yl]boronic acid No. 26 [15alpha-(4-{[2-(3,4-dimethoxyphenyl)ethyl](methyl)amino}-4-oxobutyl)-17-oxoestra-1(10),2,4-trien-3-yl]boronic acid No. 27 [15alpha-{4-[(2,4-difluorobenzyl)amino]-4-oxobutyl}-17-oxoestra-1(10),2,4-trien-3-yl]boronic acid No. 28 [15alpha-[4-(4-isopropylpiperazin-1-yl)-4-oxobutyl]-17-oxoestra-1(10),2,4-trien-3-yl]boronic acid No. 29 [(15beta-[3-(cyclopropylamino)-3-oxopropyl]-17-oxoestra-1(10),2,4-trien-3-yl]boronic acid No. 30 [(15beta-(3-{[2-(7-methyl-1H-indol-3-yl)ethyl]amino}-3-oxopropyl)-17-oxoestra-1(10),2,4-trien-3-yl]boronic acid No. 31 [(15beta-{3-[(5-methyl-1,3-thiazol-2-yl)amino]-3-oxopropyl}-17-oxoestra-1(10),2,4-trien-3-yl]boronic acid No. 32 [(15beta-[3-(cyclohexylamino)-3-oxopropyl]-17-oxoestra-1(10),2,4-trien-3-yl]boronic acid No. 33 [(15beta-(3-morpholin-4-yl-3-oxopropyl)-17-oxoestra-1(10),2,4-trien-3-yl]boronic acid No. 34 [(15beta-{3-[(1,3-benzodioxol-5-ylmethyl)amino]-3-oxopropyl}-17-oxoestra-1(10),2,4-trien-3-yl]boronic acid No. 35 [17-oxo-15beta-(3-oxo-3-piperidin-1-ylpropyl)estra-1(10),2,4-trien-3-yl]boronic acid No. 36 [17-oxo-15beta-{3-oxo-3-[(2-pyridin-2-ylethyl)amino]propyl}estra-1(10),2,4-trien-3-yl]boronic acid No. 37 [(15beta-{3-[benzyl(methyl)amino]-3-oxopropyl}-17-oxoestra-1(10),2,4-trien-3-yl]boronic acid No. 38 [17-oxo-15beta-{3-oxo-3-[(pyridin-3-ylmethyl)amino]propyl}estra-1(10),2,4-trien-3-yl]boronic acid No. 39 [(15beta-[3-(diethylamino)-3-oxopropyl]-17-oxoestra-1(10),2,4-trien-3-yl]boronic acid No. 40 [(15beta-[3-(benzylamino)-3-oxopropyl]-17-oxoestra-1(10),2,4-trien-3-yl]boronic acid No. 41 [(15beta-(3-{[2-(3,4-dimethoxyphenyl)ethyl](methyl)amino}-3-oxopropyl)-17-oxoestra-1(10),2,4-trien-3-yl]boronic acid No. 42 [(15beta-{3-[(2-methoxyethyl)amino]-3-oxopropyl}-17-oxoestra-1(10),2,4-trien-3-yl]boronic acid No. 43 [(15beta-[3-(4-isopropylpiperazin-1-yl)-3-oxopropyl]-17-oxoestra-1(10),2,4-trien-3-yl]boronic acid No. 44 [(15beta-{3-[(3,5-dimethoxybenzyl)amino]-3-oxopropyl}-17-oxoestra-1(10),2,4-trien-3-yl]boronic acid No. 45 [(15beta-[3-(1,3-benzodioxol-5-ylamino)-3-oxopropyl]-17-oxoestra-1(10),2,4-trien-3-yl]boronic acid No. 46 [17,17-difluoro-15alpha-{3-[(5-methyl-1,3-thiazol-2-yl)amino]-3-oxopropyl}estra-1(10),2,4-trien-3-yl]boronic acid No. 47 [17,17-difluoro-15alpha-(4-morpholin-4-yl-4-oxobutyl)estra-1(10),2,4-trien-3-yl]boronic acid No. 48 [15alpha-[4-(cyclohexylamino)-4-oxobutyl]-17,17-difluoroestra-1(10),2,4-trien-3-yl]boronic acid No. 49 [15alpha-[4-(diethylamino)-4-oxobutyl]-17,17-difluoroestra-1(10),2,4-trien-3-yl]boronic acid No. 50 [15alpha-{4-[(1,3-benzodioxol-5-ylmethyl)amino]-4-oxobutyl}-17,17-difluoroestra-1(10),2,4-trien-3-yl]boronic acid No. 51 [15alpha-(4-{[2-(3,4-dimethoxyphenyl)ethyl](methyl)amino}-4-oxobutyl)-17,17-difluoroestra-1(10),2,4-trien-3-yl]boronic acid No. 52 [17,17-difluoro-15alpha-{4-oxo-4-[(2-pyridin-2-ylethyl)amino]butyl}estra-1(10),2,4-trien-3-yl]boronic acid No. 53 [17,17-difluoro-15alpha-{4-oxo-4-[(pyridin-3-ylmethyl)amino]butyl}estra-1(10),2,4-trien-3-yl]boronic acid No. 54 [15alpha-[4-(benzylamino)-4-oxobutyl]-17,17-difluoroestra-1(10),2,4-trien-3-yl]boronic acid No. 55 [17,17-difluoro-15alpha-{4-[(2-methoxyethyl)amino]-4-oxobutyl}estra-1(10),2,4-trien-3-yl]boronic acid No. 56 [17,17-difluoro-15alpha-(4-{[2-(7-methyl-1H-indol-3-yl)ethyl]amino}-4-oxobutyl)estra-1(10),2,4-trien-3-yl]boronic acid No. 57 [17,17-difluoro-15alpha-(4-oxo-4-piperidin-1-ylbutyl)estra-1(10),2,4-trien-3-yl]boronic acid No. 58 [(8x,9x,14x,15b)-17,17-difluoro-15-{3-[(5-methyl-1,3-thiazol-2-yl)amino]-3-oxopropyl}estra-1(10),2,4-trien-3-yl]boronic acid No. 59 [15beta-[3-(cyclohexylamino)-3-oxopropyl]-17,17-difluoroestra-1(10),2,4-trien-3-yl]boronic acid No. 60 [15beta-{3-[(1,3-benzodioxol-5-ylmethyl)amino]-3-oxopropyl}-17,17-difluoroestra-1(10),2,4-trien-3-yl]boronic acid No. 61 [17,17-difluoro-15beta-{3-oxo-3-[(2-pyridin-2-ylethyl)amino]propyl}estra-1(10),2,4-trien-3-yl]boronic acid No. 62 [17,17-Difluoro-15beta-{3-oxo-3-[(pyridin-3-ylmethyl)amino]propyl}estra-1(10),2,4-trien-3-yl]boronic acid No. 63 [15beta-[3-(benzylamino)-3-oxopropyl]-17,17-difluoroestra-1(10),2,4-trien-3-yl]boronic acid No. 64 [17,17-Difluoro-15beta-{3-[(2-methoxyethyl)amino]-3-oxopropyl}estra-1(10),2,4-trien-3-yl]boronic acid No. 65 [15beta-{3-[(2,4-difluorobenzyl)amino]-3-oxopropyl}-17,17-difluoroestra-1(10),2,4-trien-3-yl]boronic acid No. 66 [15beta-{3-[(3,5-dimethoxybenzyl)amino]-3-oxopropyl}-17,17-difluoroestra-1(10),2,4-trien-3-yl]boronic acid No. 67 [17,17-difluoro-15beta-(3-{[2-(7-methyl-1H-indol-3-yl)ethyl]amino}-3-oxopropyl)estra-1(10),2,4-trien-3-yl]boronic acid No. 68 [17,17-Difluoro-15beta-(3-{[(1-methyl-1H-imidazol-4-yl)methyl]amino}-3-oxopropyl)estra-1(10),2,4-trien-3-yl]boronic acid No. 69 [17,17-difluoro-15beta-(3-oxo-3-piperidin-1-ylpropyl)estra-1(10),2,4-trien-3-yl]boronic acid No. 70 [15beta-{3-[benzyl(methyl)amino]-3-oxopropyl}-17,17-difluoroestra-1(10),2,4-trien-3-yl]boronic acid No. 71 [15beta-[3-(diethylamino)-3-oxopropyl]-17,17-difluoroestra-1(10),2,4-trien-3-yl]boronic acid No. 72 [15beta-(3-{[2-(3,4-dimethoxyphenyl)ethyl](methyl)amino}-3-oxopropyl)-17,17-difluoroestra-1(10),2,4-trien-3-yl]boronic acid No. 73 [17,17-difluoro-15beta-[3-(4-isopropylpiperazin-1-yl)-3-oxopropyl]estra-1(10),2,4-trien-3-yl]boronic acid No. 74 [15beta-[3-(1,3-benzodioxol-5-ylamino)-3-oxopropyl]-17,17-difluoroestra-1(10),2,4-trien-3-yl]boronic acid No. 75 3-{[3-methoxy-5-(trifluoromethyl)phenyl]amino}-15alpha-(4-morpholin-4-yl-4-oxobutyl)estra-1(10),2,4-trien-17-one No. 76 15alpha-(4-morpholin-4-yl-4-oxobutyl)-3-{[3-(morpholin-4-ylsulfonyl)phenyl]amino}estra-1(10),2,4-trien-17-one No. 77 3-[4-(3-methoxyphenyl)piperazin-1-yl]-15alpha-(4-morpholin-4-yl-4-oxobutyl)estra-1(10),2,4-trien-17-one No. 78 3-{[3,5-bis(trifluoromethyl)phenyl]amino}-15alpha-(4-morpholin-4-yl-4-oxobutyl)estra-1(10),2,4-trien-17-one No. 79 15alpha-(4-morpholin-4-yl-4-oxobutyl)-3-{[3-(2-oxopyrrolidin-1-yl)propyl]amino}estra-1(10),2,4-trien-17-one No. 80 15alpha-(4-morpholin-4-yl-4-oxobutyl)-3-(2-oxo-1,3-oxazolidin-3-yl)estra-1(10),2,4-trien-17-one No. 81 3-(1H-indol-5-ylamino)-15alpha-(4-morpholin-4-yl-4-oxobutyl)estra-1(10),2,4-trien-17-one No. 82 15alpha-(4-morpholin-4-yl-4-oxobutyl)-3-pyrrolidin-1-ylestra-1(10),2,4-trien-17-one No. 83 15alpha-(4-morpholin-4-yl-4-oxobutyl)-3-(quinolin-3-ylamino)estra-1(10),2,4-trien-17-one No. 84 15alpha-(4-morpholin-4-yl-4-oxobutyl)-3-(4-phenylpiperazin-1-yl)estra-1(10),2,4-trien-17-one No. 85 3-{[15alpha-(4-morpholin-4-yl-4-oxobutyl)-17-oxoestra-1(10),2,4-trien-3-yl]amino}benzonitrile No. 86 3-(4-benzylpiperazin-1-yl)-15alpha-(4-morpholin-4-yl-4-oxobutyl)estra-1(10),2,4-trien-17-one No. 87 3-[(3,4-difluorophenyl)amino]-15alpha-(4-morpholin-4-yl-4-oxobutyl)estra-1(10),2,4-trien-17-one No. 88 3-[methyl(2-pyridin-2-ylethyl)amino]-15alpha-(4-morpholin-4-yl-4-oxobutyl)estra-1(10),2,4-trien-17-one No. 89 15alpha-(4-morpholin-4-yl-4-oxobutyl)-3-[(3-oxo-1,3-dihydro-2-benzofuran-5-yl)amino]estra-1(10),2,4-trien-17-one No. 90 3-(3,4-dihydroisoquinolin-2(1H)-yl)-15alpha-(4-morpholin-4-yl-4-oxobutyl)estra-1(10),2,4-trien-17-one No. 91 3-[(1,1-dioxido-1-benzothien-6-yl)amino]-15alpha-(4-morpholin-4-yl-4-oxobutyl)estra-1(10),2,4-trien-17-one No. 92 3-[4-(3-chlorophenyl)piperazin-1-yl]-15alpha-(4-morpholin-4-yl-4-oxobutyl)estra-1(10),2,4-trien-17-one No. 93 15alpha-(4-morpholin-4-yl-4-oxobutyl)-3-(pentylamino)estra-1(10),2,4-trien-17-one No. 94 15alpha-(4-morpholin-4-yl-4-oxobutyl)-3-(2-oxopyrrolidin-1-yl)estra-1(10),2,4-trien-17-one No. 95 3-anilino-15alpha-(4-morpholin-4-yl-4-oxobutyl)estra-1(10),2,4-trien-17-one No. 96 15alpha-(4-morpholin-4-yl-4-oxobutyl)-3-pyrrolidin-1-ylestra-1(10),2,4-trien-17-one No. 97 3-(1,3-benzodioxol-5-ylamino)-15alpha-(4-morpholin-4-yl-4-oxobutyl)estra-1(10),2,4-trien-17-one No. 98 3-(benzylamino)-15alpha-(4-morpholin-4-yl-4-oxobutyl)estra-1(10),2,4-trien-17-one or a pharmaceutically acceptable salt thereof.

Pharmaceutically acceptable salts of the compounds of the invention as well as commonly used pro-drugs and active metabolites of these compounds are also within the scope of the invention.

The invention also provides methods of preparing the compounds of the invention and the intermediates used in those methods.

Additionally, the invention relates to a compound of the invention for use as a medicament.

Furthermore, the invention relates to the use of an effective amount of a compound of the invention for the treatment or prevention of a steroid hormone dependent disease or disorder in an animal, preferably a mammal, or human. Preferably the steroid hormone dependent disease or disorder is an estradiol dependent disease or disorder. Alternatively, the steroid dependent disease or disorder is an androgen-dependent disease or disorder.

In addition, the invention relates to the use of a compound of the invention for the manufacture of a medicament for the treatment or prevention of a steroid hormone dependent disease or disorder in a mammal, in particular a human. Preferably the steroid hormone dependent disease or disorder is an estradiol dependent disease or disorder. Alternatively, the steroid dependent disease or disorder is an androgen-dependent disease or disorder.

In a further embodiment of the invention, the steroid hormone dependent disease or disorder requires the inhibition of a 17β-HSD1, 17β-HSD2 and/or 17β-HSD3 enzyme, preferably the human 17β-HSD1, 17β-HSD2 and/or 17β-HSD3 enzyme. Preferably, the steroid hormone dependent disease or disorder requires the inhibition of the human 17β-HSD1 enzyme.

Furthermore, the invention also relates to a method of treating a mammal such as a human having a condition related to 17β-HSD1, 17β-HSD2 and/or 17β-HSD3 activity or which condition can be treated by inhibition of one, two or all of said enzymes, comprising administering to the mammal an amount of a compound of this invention, or a salt or a prodrug thereof, which amount is effective to treat the condition.

Administration of compounds of this invention in combination with other pharmaceuticals used in treatment of the listed conditions is contemplated.

The conditions to be treated include but are not limited to malign estradiol dependent disease or disorder such as breast cancer, ovarian cancer, uterine cancer, endometrial cancer, and endometrial hyperplasia. Preferably, the malign disease or disorder is characterized by a detectable level of 17β-HSD1 within a cancer tissue sample. A detectable level of 17β-HSD1 means that a certain level of 17β-HSD1 mRNA or of 17β-HSD1 protein can be detected by conventional molecular biology methods such as hybridization, PCR reactions, Northern or Western Blotting etc. An alternative detection method for 17β-HSD1 expression is the measurement of the corresponding enzyme activity. According to a further aspect of the invention, the estradiol dependent disease is breast cancer and the mammal is a human post-menopausal female.

Furthermore, the conditions to be treated include but are not limited to benign estradiol dependent diseases or disorders such as endometriosis, uterine fibroids, uterine leiomyoma, adenomyosis, dysmenorrhea, menorrhagia, metrorrhagia and urinary dysfunction. In a further embodiment, the invention relates to use of an effective amount of a compound of the invention for the treatment or prevention of one of the aforementioned benign gynaecological diseases or disorders in a mammal whereby the mammal is a human, preferably a female and most preferably a pre- or peri-menopausal female.

According to a further aspect of the present invention, the steroid hormone dependent disease or disorder is an androgen-dependent disease or disorder. Preferably, said androgen-dependent disease or disorder is selected from the group consisting of prostate cancer, prostadynia, benign prostatic hyperplasia, urinary dysfunction, lower urinary tract syndrome, prostatitis, acne, seborrhea, androgenetic alopecia, hirsutism, precocious puberty, adrenal hyperplasia and polycystic ovarian syndrome.

Furthermore, the compounds of the invention can be useful in the manufacture of a pharmaceutical composition for blocking spermatogenesis and/or for use as an anti-fertility agent for males.

According to a further aspect of the invention, the steroid hormone dependent disease or disorder to be treated is an estrogen- or androgen dependent disease or disorder requiring the lowering of the endogeneous estrogen or androgen concentration in a generalized or tissue-specific manner.

Therefore, further steroid-dependent diseases which may be treated with an effective amount of a compound of the invention are selected from the group consisting of squamous cell carcinoma, colon cancer, osteoporosis, rheumatoid arthritis, multiple sclerosis, myastenia gravis, thyroiditis, vasculitis, ulcerative colitis, Crohn's disease, type I and II diabetes, psoriasis, contact dermatitis, skin wrinkles, eczema, tissue wounds, systemic lupus erythematosus, graft versus host disease, organ rejection following transplantation, cataracts and asthma.

According to a further embodiment, a compound of the present invention may be used for the enhancement of cognitive function, i.e. in the treatment or prevention of cognitive dysfunctions, such as senile dementia, including Alzheimer's disease.

The disclosed compounds are also useful as diagnostic agents (e.g. in diagnostic kits or for use in clinical laboratories) for screening for the presence or absence of 17β-HSD1, 17β-HSD2 and/or 17β-HSD3 enzyme activity. Isotopically-labeled compound of formula (I) or pharmaceutically acceptable salts thereof, including compounds of formula (I) isotopically-labeled to be detectable by PET or SPECT, are also included within the scope of the invention, and same applies to compounds of formula (I) labeled with [$^{13}$C]-, [$^{3}$H]-, [$^{125}$I]- or other radioactive atoms, suitable for enzyme activity or metabolism studies.

The compounds of the invention possess inhibiting activity on the 17β-HSD1, 17β-HSD2 and/or 17β-HSD3 enzyme. The inhibiting activities of the compounds of the invention are readily demonstrated, for example, using one or more of the assays described herein or known in the art. An advantage of the present invention is that the compounds of the present invention can act as selective 17β-HSD1, 17β-HSD2 or 17β-HSD3 inhibitors Preferably, the compounds of the invention possess inhibiting activity on one of the 17β-HSD1, 17β-HSD2 or 17β-HSD3 enzyme, but does not inhibit the respective other enzymes. These inhibitory activities make them suited for the treatment of particular steroid hormone dependent diseases as explained in more detail above. An advantage of the compounds of the present invention is that they may be potent in vivo and suited for the therapeutic use in mammals, especially humans. Some of the compounds of the present invention may additionally be non-estrogenic compounds. Here, the term "non-estrogenic" means exhibiting no or substantially no estrogenic activity on the estrogen receptor. Another advantage is that some of the compounds may not be capable of being metabolised to compounds which display or induce hormonal activity. Some of the compounds of the present invention are also advantageous in that they may be orally active.

DETAILED DESCRIPTION OF PREFERRED EMBODIMENTS

Definitions

The following terms are used to describe the present invention and in particular, to describe various constituents of the chemical composition useful in this invention. The terms are defined as follows:

As used herein, the terms "comprising" and "including" are used herein in their open, non-limiting sense.

The word "compound" shall here be understood to cover any and all isomers (e.g., enantiomers, stereoisomers, diastereomers, rotomers, tautomers) or any mixture of isomers, prodrugs, and any pharmaceutically acceptable salt of said compound, unless the formula depicting the compound explicitly shows a particular stereochemistry.

Where the plural form is used for compounds, salts, and the like, this is taken to mean also a single compound, salt, or the like.

The term "17β-hydroxysteroid dehydrogenase type I" or "17β-HSD1" for short is used for the enzyme EC 1.1.1.62 and reduces estrone (E1) to the biologically active estrogen, estradiol (E2).

The terms "inhibit" and "inhibition" include the meaning of to reduce and/or eliminate and/or mask and/or prevent a certain enzyme action.

The term "17β-HSD1 inhibitor" as used herein with respect to the compound of the present invention means a compound that can inhibit 17β-HSD1 activity, such as to reduce and/or eliminate and/or mask and/or prevent the action of 17β-HSD1. The 17β-HSD1 inhibitor may act as an reversible or irreversible inhibitor of 17β-HSD1. The ability of compounds to inhibit 17β-HSD1 activity can be assessed using cell lines recombinantly expressing the human 17β-HSD1 enzyme or using the recombinantly produced and purified 17β-HSD1 enzyme. Details on a suitable Assay Protocol are presented in the Examples section. It is to be noted that the compound of the present invention may have other beneficial properties in addition to or in the alternative to its ability to inhibit 17β-HSD1 activity; in particular a 17β-HSD1 inhibitor may have antagonistic activity towards the nuclear estrogen receptor.

The term "17β-HSD2 inhibitor" as used herein with respect to the compound of the present invention means a compound that can inhibit 17β-HSD2 activity, such as to reduce and/or eliminate and/or mask and/or prevent the action of 17β-HSD2. The 17β-HSD2 inhibitor may act as an reversible or irreversible inhibitor of 17β-HSD2. The ability of compounds to inhibit 17β-HSD2 activity can be assessed using cell lines recombinantly expressing the human 17β-HSD2 enzyme or using the recombinantly produced and purified 17β-HSD2 enzyme. Details on a suitable Assay Protocol are known to the skilled artisan. It is to be noted that the compound of the present invention may have other beneficial properties in addition to or in the alternative to its ability to inhibit 17β-HSD2 activity.

The term "17β-HSD3 inhibitor" as used herein with respect to the compound of the present invention means a compound that can inhibit 17β-HSD3 activity, such as to reduce and/or eliminate and/or mask and/or prevent the action of 17β-HSD3. The 17β-HSD3 inhibitor may act as an reversible or irreversible inhibitor of 17β-HSD3. The ability of compounds to inhibit 17β-HSD3 activity can be assessed using cell lines recombinantly expressing the human 17β-HSD3 enzyme or using the recombinantly produced and purified 17β-HSD3 enzyme. Details on a suitable Assay Protocol are presented in the Examples section. It is to be noted that the compound of the present invention may have other beneficial properties in addition to or in the alternative to its ability to inhibit 17β-HSD3 activity; in particular a 179-HSD3 inhibitor may have antagonistic activity towards the nuclear androgen receptor.

The terms "selective" and "selectivity" as used herein with respect to the compounds of the present invention means a compound that can inhibit 17β-HSD1, 17β-HSD2 and/or 17β-HSD3, and shows a higher inhibition value for these particular targets than with regard to other enzyme targets, in particular other HSD enzymes. Preferably a compound of the present invention has at least about a 100 fold selectivity to the desired target, preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

The term "substituted" means that the specified group or moiety bears one or more substituents. Where any group may carry multiple substituents and a variety of possible substituents is provided, the substituents are independently selected and need not be the same. The term "unsubstituted" means that the specified group bears no substituents. The term "optionally substituted" means that the specified group may or may not not be further substituted by one or more substituents.

With reference to substituents, the term "independently" means that when more than one of such substituents is possible, such substituents may be the same or different from each other.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

Any asymmetric carbon atoms may be present in the (R)—, (S)— or (R,S)-configuration preferably in the (R)— or (S)-configuration, whichever is most active, unless the stereochemistry is explicitly depicted in the corresponding compound formula. Substituents at a double bond or a ring may be present in cis- (=Z—) or trans (=E-) form, unless the stereochemistry is explicitly depicted in the corresponding compound formula.

The compounds of formula (I) have a defined stereochemistry within the steroidal core structure according to the natural configuration for estrogenic steroids such as estrone:

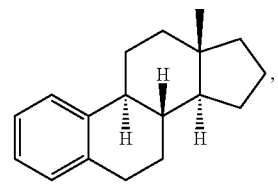

The stereochemistry within the steroidal core structure is always shown in the corresponding compound formula and should not vary within the scope of the present invention, whereas the stereochemistry at the carbon atoms in the steroidal core carrying additional side chains and the stereochemistry of any asymmetric carbon atom within the side chains themselves is not fixed. Therefore, the term "compounds of formula (I)" or "compounds of formula (II)" etc also comprises the stereoisomers of the depicted compounds, unless a particular stereochemistry is explicitly shown within the formula. The stereochemistry shown in the respective formula prevails over the general term "stereoisomers".

The compounds of the formula I contain at least one additional chiral carbon atom, namely the carbon atom carrying the side chain in the 15-position of the steroide structure. The compounds can thus be present at least in two optically active stereoisomeric forms or as a racemate. The present invention includes both the racemic mixtures and the isomerically pure compounds of the formula I. The position of the substituents within the C15 position is characterized by α or β. A C15α derivative according to the present invention is represented by a compound of the following formula (II)

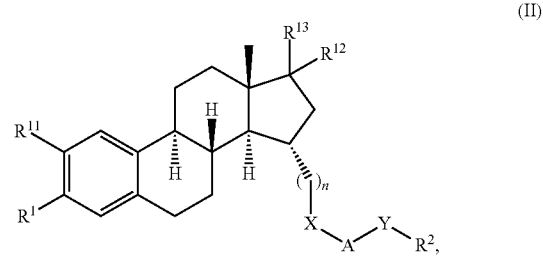

whereas a C15β derivative according to the present invention is represented by a compound of the following formula (III)

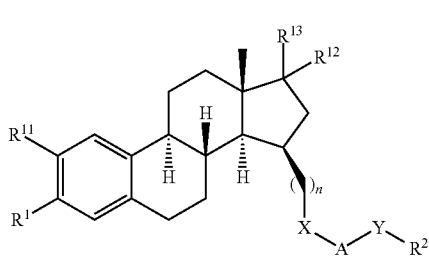

(III)

The compounds of the present invention may contain further asymmetric centers on the molecule, depending upon the nature of the various substituents. In certain instances, asymmetry may also be present due to restricted rotation about the central bond adjoining the two aromatic rings of the specified compounds. It is intended that all isomers (including enantiomers and diastereomers), either by nature of asymmetric centers or by restricted rotation as described above, as separated, pure or partially purified isomers or racemic mixtures thereof, be included within the ambit of the instant invention, unless a particular stereochemistry is explicitly depicted in the formula representing a respective compound.

The term "halogen" refers to fluorine (F, Fluoro-), bromine (Br, Bromo-), chlorine (Cl, Chloro), and iodine (I, Iodo-) atoms. Preferred in the context of the present invention are F, Cl and Br. The terms "dihalogen", "trihalogen" and "perhalogen" refer to two, three and four substituents, respectively, each individually selected from the group consisting of fluorine, bromine, chlorine, and iodine atoms.

The term "hetero" as in 'heteroalkyl, heteroaromatic' etc, means containing one or more N, O or S atoms.

The term "hydroxyl" refers to the group —OH
The term "thiol" refers to the group —SH
The term "oxo" refers to the group =O
The term "carbamoyl" refers to the group —CO—NH$_2$
The term "sulfoxy" or "sulfonyl" refers to the group —SO$_2$—
The term "sulfinyl" refers to the group —SO—
The term "sulfamoyl" refers to the group —SO$_2$—NH$_2$
The term "nitro" refers to the group —NO$_2$
The term "nitrile" or "cyano" refers to the group —CN
The term "oxime" refers to the group =N—O-Alkyl or =N—OH.

The terms "oxy", "thio" (or "sulfanyl") and "carbo" as used herein as part of another group respectively refer to an oxygen atom, a sulfur atom and a carbonyl (C=O) group, serving as linker between two groups, such as for instance hydroxyl (—OH), alkoxy (—O-alkyl), alkylthio (—S-alkyl), carboxy (—CO—O—), etc.

For the purpose of the present invention, the carbon content of various hydrocarbon containing moieties is indicated by a prefix designating the minimum and maximum number of carbon atoms in the moiety, i.e., the prefix $C_i$-$C_j$ defines the number of carbon atoms present from the integer "i" to the integer "j" inclusive. Thus $C_1$-$C_4$-alkyl refers to alkyl of 1-4 carbon atoms, inclusive, or methyl, ethyl, propyl, butyl and isomeric forms thereof.

The term "alkyl" stands for a hydrocarbon radical which may be linear, cyclic or branched, with single or multiple branching. If not otherwise indicated, the alkyl group comprises 1 to 14 carbon atoms, exemplified by the term ($C_1$-$C_{14}$) alkyl, preferably 1-12 carbon atoms, exemplified by the term ($C_1$-$C_{12}$)alkyl. In one embodiment, the term "alkyl" stands for a linear or branched (with single or multiple branching) alkyl chain of 1 to 8 carbon atoms, exemplified by the term ($C_1$-$C_8$)alkyl, more preferably of 1 to 6 carbon atoms exemplified by the term ($C_1$-$C_6$)alkyl, and even more preferred of 1 to 4 carbon atoms exemplified by the term ($C_1$-$C_4$)alkyl. The term ($C_1$-$C_8$)alkyl is further exemplified by such groups as methyl; ethyl; n-propyl; isopropyl; n-butyl; sec-butyl; isobutyl; tert-butyl; n-pentyl; isopentyl; neopentyl; tert-pentyl; 2- or 3-methylpentyl; n-hexyl; isohexyl, heptyl, octyl and the like. Any alkyl group, in particular the ($C_1$-$C_8$)alkyl group, may be partially unsaturated, forming such alkenyl or alkynyl groups as, for example, vinyl, propenyl (allyl), butenyl, pentenyl, pentynyl, 1-butynyl, 2-butynyl, hexenyl, octadienyl, and the like. The term "alkyl" further comprises cycloalkyl groups; in particular, the ($C_1$-$C_8$)alkyl group comprises cyclo($C_3$-$C_8$)alkyl groups which refer to cyclopropyl, cyclobutyl, cyclopentyl, cyclohexyl, cycloheptyl, cyclooctyl and isomeric forms thereof such as methylcyclopropyl; 2- or 3-methylcyclobutyl; 2-, or 3-methylcyclopentyl, and the like. The cycloalkyl group may also be partly unsaturated, forming such groups as, for example, cyclohexenyl, cyclopentenyl, cyclooctadienyl, and the like. Furthermore, the term alkyl, pin particular the terms "($C_1$-$C_{12}$)alkyl" and "($C_1$-$C_{14}$)alkyl", comprise cycloalkyl-alkyl groups comprising 4 to 12 carbon atoms, preferably "—($C_1$-$C_4$)alkyl-cyclo($C_3$-$C_8$)alkyl" which refers to an alkyl group of 1 to 4 carbon atoms as described above substituted with a cyclo($C_3$-$C_8$)alkyl group as described above, forming such groups as for example cyclopropylmethyl, cyclohexylmethyl, cyclopentylethyl or cyclohexenylethyl. The terms "($C_1$-$C_{12}$)alkyl" and "($C_1$-$C_{14}$) alkyl" further comprise bicyclic ring systems of 6 to 10 carbon atoms, preferably Bicyclo[2.1.1]hexyl, Bicyclo[2.2.1] heptyl, Bicyclo[3.2.1]octyl, Bicyclo[2.2.2]octyl, Bicyclo [3.2.2]nonanyl, Bicyclo[3.3.1]nonanyl, Bicyclo[3.3.2] decanyl; and the like, preferably Bicyclo[2.2.1]heptyl, and fused ring systems of up to 10 carbon atoms such as adamantyl, noradamantyl and the like.

The alkyl group may optionally be substituted by 1, 2, 3, 4 or 5, more preferably 1, 2 or 3 substituents independently selected from the group consisting of halogen, hydroxyl, optionally substituted aryl, optionally substituted heteroaryl, optionally substituted cycloheteroalkyl, thiol, nitro, nitrile, alkoxy, aryloxy, arylalkyloxy, amino, amido, alkylthio, arylthio, arylalkylthio, sulfamoyl, sulfonamide, acyl, carboxyl, and acylamino, as defined herein. These groups may be attached to any carbon atom of the alkyl moiety.

The term "alkoxy" refers to a group —O-alkyl, wherein the alkyl chain may be optionally further substituted as defined herein. Preferably, the term "alkoxy" refers to —O—($C_1$-$C_6$) alkyl (or ($C_1$-$C_6$)alkoxy), with the ($C_1$-$C_6$)alkyl group as defined above and optionally substituted with 1, 2 or 3 hydroxyl groups.

The term "aryloxy" refers to a group —O—Ar, where Ar represents aryl as defined herein, which is optionally substituted in the aryl group with one or more independently selected substituents as defined herein, in particular hydroxyl, halogen, ($C_1$-$C_4$)alkyl, ($C_1$-$C_4$)alkoxy, halogenated ($C_1$-$C_4$) alkyl, or halogenated ($C_1$-$C_4$)alkoxy; the number of said substituents being 1, 2, 3 4 or 5 for halogen, and 1, 2 or 3 for any combination of said other substituents. Preferably, aryloxy refers to phenoxy, optionally substituted as defined above.

The term "arylalkyloxy" refers to a group —O-alkyl-Ar, preferably —O—($C_1$-$C_4$)alkyl-Ar, wherein Ar represents aryl, which is optionally substituted in the aryl group with one or more independently selected substituents as defined herein, in particular hydroxyl, halogen, ($C_1$-$C_4$)-alkyl, ($C_1$-$C_4$)-alkoxy, halogenated ($C_1$-$C_4$)alkyl, or halogenated ($C_1$-$C_4$)alkoxy; the number of said substituents being 1, 2, 3 4 or 5 for halogen, and 1, 2 or 3 for any combination of said other substituents. Preferably, arylalkyloxy refers to benzyloxy, optionally substituted as defined above.

The term "acyl" or "carbonyl" refers to a group —(C═O)—R, where R may be hydrogen, optionally substituted alkyl, optionally substituted aryl or aryl-alkyl, optionally substituted heteroaryl or heteroaryl-alkyl, as defined herein. Preferably, the term "acyl" refers to a group —(C═O)—R', where R' represents hydrogen, ($C_1$-$C_4$)alkyl, phenyl, or aryl-($C_1$-$C_4$)alkyl, preferably benzyl or phenethyl, or heteroaryl-($C_1$-$C_4$)alkyl, preferably indolyl-methyl; whereby the phenyl moiety may be optionally substituted with one or more independently selected substituents, especially hydroxyl, halogen, ($C_1$-$C_4$)alkoxy, ($C_1$-$C_4$)-alkyl or halogenated ($C_1$-$C_4$)alkyl, the number of said substituents being 1, 2, 3 4 or 5 for halogen, and 1, 2 or 3 for any combination of said other substituents.

The term "carboxyl" refers to a group —(C═O)—OR, wherein R may be hydrogen, optionally substituted alkyl (preferably substituted with hydroxyl, halogen or ($C_1$-$C_4$)-alkoxy), optionally substituted aryl or aryl-alkyl, preferably aryl-($C_1$-$C_4$)alkyl, or optionally substituted heteroaryl or heteroaryl-alkyl, preferably heteroaryl-($C_1$-$C_4$)alkyl, each as defined herein.

The term "amino" as used herein alone or as part of another group refers to a nitrogen atom that may be either terminal or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine. In particular, the term "amino" refers to the group —NRR', where R and R' are residues as particularly defined herein, and may independently be hydrogen, optionally substituted alkyl, optionally substituted aryl or aryl-alkyl, or optionally substituted heteroaryl or heteroaryl-alkyl, each as defined herein.

The term "amido" refers to the group —(C═O)—NRR', where R and R' are residues as particularly defined herein, and may independently be hydrogen, optionally substituted alkyl, optionally substituted aryl or aryl-alkyl, or optionally substituted heteroaryl or heteroaryl-alkyl, each as defined herein.

The term "acylamino" or "carbonylamino" refers to the group —NR—CO—R', where R and R' are residues as particularly defined herein, and may independently be hydrogen, optionally substituted alkyl, optionally substituted aryl or aryl-alkyl, preferably aryl-($C_1$-$C_4$)alkyl, or optionally substituted heteroaryl or heteroaryl-alkyl, preferably heteroaryl-($C_1$-$C_4$)alkyl, each as defined herein. Preferably, acylamino refers to —NH—CO—($C_1$-$C_4$)-alkyl.

The term "sulfonamide" refers to the group —$SO_2$—NRR', wherein R and R' are residues as particularly defined herein, and may independently be selected from hydrogen or ($C_1$-$C_4$)alkyl.

Halogenated alkyl, halogenated alkoxy and halogenated alkylthio are substituents in which the alkyl moieties (preferably ($C_1$-$C_6$)alkyl, more preferred ($C_1$-$C_4$)alkyl, and most preferred methyl) are substituted either partially or in full with halogens, generally with chlorine and/or fluorine. Preferred examples of such substituents are trifluoromethyl, trifluoromethoxy, trifluoromethylthio, dichloromethyl, pentafluoroethyl, dichloropropyl, fluoromethyl and difluoromethyl.

The term "cycloheteroalkyl" refers to a 4, 5, 6, 7 or 8 membered heterocyclic ring containing at least one heteroatom, such as N, O or S, the number of N atoms being 0, 1, 2 or 3 and the number of O and S atoms each being 0, 1 or 2, which system may be saturated, partly unsaturated or hydroaromatic, and which ring can be part of a multiple condensed ring-system in which some rings may be aromatic. Examples of such cycloheteroalkyls include pyrrolidinyl, tetrahydrofuryl, tetrahydrothiophenyl, tetrahydropyridinyl, azetidinyl, thiazolidinyl, oxazolidinyl, piperidinyl, morpholinyl, thiomorpholinyl, piperazinyl, azepanyl, diazepanyl, oxazepanyl, thiazepanyl, dihydro-1H-pyrrolyl, 3,6-dihydro-2H-pyridinyl, 1,3-dihydro-benzoimidazolyl and the like. Preferred examples of such cycloheteroalkyl groups are pyrrolidinyl, morpholinyl, tetrahydrofuryl, piperidinyl or azepanyl.

The term "cycloheteroalkyl-alkyl" refers to an alkyl group substituted with up to three independently selected cycloheteroalkyl groups; preferably the term "cycloheteroalkyl-alkyl" refers to "cycloheteroalkyl-($C_1$-$C_{14}$)alkyl", "cycloheteroalkyl-($C_1$-$C_{12}$)alkyl", "cycloheteroalkyl-($C_1$-$C_8$)alkyl" or "cycloheteroalkyl-($C_1$-$C_4$)alkyl", wherein the cycloheteroalkyl moiety is as defined herein, preferably cycloheteroalkyl is piperidinyl, pyrrolidinyl, or morpholinyl, forming such groups as for example morpholinylethyl, morpholinylpropyl, piperidinylethyl or pyrrolidinylethyl. The cycloheteroalkyl moiety may optionally be substituted as defined herein.

The cycloheteroalkyl group may optionally be substituted by 1, 2 or 3 substituents, independently selected from the group consisting of oxo, alkyl, optionally substituted aryl or aryl-($C_1$-$C_4$)-alkyl, hydroxyl, ($C_1$-$C_6$)alkoxy, halogenated ($C_1$-$C_6$)alkyl, halogenated ($C_1$-$C_6$)alkoxy, carboxyl-($C_1$-$C_6$)alkyl, thiol, nitrile, sulfamoyl, sulfonamide, carboxyl, aryloxy or arylalkyloxy, ($C_1$-$C_6$)alkylthio, arylthio or arylalkylthio, amino, amido, acyl, and acylamino, as defined herein. The substituents of the cycloheteroalkyl groups may be attached to any carbon atom of the cycloheteroalkyl moiety. Substituted cycloheteroalkyl is preferably substituted as particularly defined herein.

The terms "aryl" or "Ar" refer to an aromatic carbocyclic group comprising 6 to 14, more preferably 6 to 10 carbon atoms and having at least one aromatic ring or multiple condensed rings in which at least one ring is aromatic. Preferably, aryl is phenyl, naphthyl, indanyl, indenyl, fluorenyl or 1,2,3,4-tetrahydro-naphthalen-1-yl or biphenyl.

The term "arylalkyl" refers to an alkyl group substituted with up to three independently selected aryl groups; preferably the term "arylalkyl" refers to "aryl-($C_1$-$C_{14}$)alkyl" and "diaryl-($C_1$-$C_{14}$)alkyl", "aryl-($C_1$-$C_{12}$)alkyl" and "diaryl-($C_1$-$C_{12}$)alkyl", "aryl-($C_1$-$C_8$)alkyl" and "diaryl-($C_1$-$C_8$)alkyl", "aryl-($C_1$-$C_4$)alkyl" and "diaryl-($C_1$-$C_4$)alkyl", respectively, wherein the aryl is as defined herein, preferably aryl is phenyl or naphthyl, forming such groups as for example benzyl, diphenylmethyl, phenethyl, phenylpropyl, diphenylpropyl, phenylbutyl, naphthylmethyl or naphthylethyl. The alkyl chain may be further substituted as defined above; for example the alkyl chain may carry an additional hydroxyl group. Furthermore, the alkyl chain may be partially unsaturated, such as a vinyl group. The aryl moiety may optionally be substituted as defined herein.

The term "heteroaryl" refers to an aromatic carbocyclic group of having a single 4, 5, 6, 7 or 8 membered ring or multiple condensed rings comprising 6 to 14, more preferably 6 to 10, ring atoms and containing at least one heteroatom selected from N, O and S, within at least one ring, the number of N atoms being 0, 1, 2 or 3 and the number of O and S atoms each being 0, 1 or 2; in which group at least one heterocyclic ring is aromatic. Examples of such groups include pyrrolyl, thienyl, furyl, imidazolyl, thiazolyl, isothiazolyl, oxazolyl, isoxazolyl, imidazo[2,1-b][1,3]thiazolyl, pyrazolyl, pyridinyl, pyrimidinyl, pyrazinyl, pyridazinyl, 1,3,5-triazinyl, indolyl, indazolyl, indolizinyl, isoindolyl, purinyl, quinolinyl, isoquinolinyl, 1,2,3,4-tetrahydroisoquinolinyl, quinazolinyl, quinoxalinyl, benzothiazolyl, benzimidazolyl, 1,3-dihydro-benzoimidazolyl, benzofuryl, benzo[b]thienyl and the like. Preferably, heteroaryl is quinolinyl, furyl, benzoimidazolyl, pyridinyl, thienyl, indolyl, benzo[b]thiophene, pyridinyl, imidazolyl, pyrazolyl or thiazolyl.

The term "heteroaryl-alkyl" refers to an alkyl group substituted with up to three independently selected heteroaryl groups; preferably the term "heteroaryl-alkyl" refers to "heteroaryl-($C_1$-$C_{14}$)alkyl", "heteroaryl-($C_1$-$C_{12}$)alkyl", "heteroaryl-($C_1$-$C_8$)alkyl" and "heteroaryl-($C_1$-$C_4$)alkyl", wherein the heteroaryl is as defined herein, preferably heteroaryl is furyl, indolyl, benzoimidazolyl, pyridinyl, thienyl or imidazolyl, forming such groups as for example benzoimidazolylmethyl, pyridinylmethyl, thienylmethyl, furylmethyl, indolylethyl, thienylethyl, pyridinylethyl, or imidazolylpropyl. The heteroaryl moiety may optionally be substituted as defined herein.

Aryl and/or heteroaryl groups may optionally be substituted by one or more substituents independently selected from the group consisting of halogen, hydroxyl, ($C_1$-$C_6$) alkoxy, ($C_1$-$C_6$)alkyl, halogenated ($C_1$-$C_6$)alkyl, halogenated ($C_1$-$C_6$)alkoxy, carboxyl-($C_1$-$C_6$)alkyl, oxo, thiol, nitro, nitrile, sulfamoyl, sulfonamide, carboxyl, aryloxy or arylalkyloxy, ($C_1$-$C_6$)alkylthio, arylthio or arylalkylthio, alkylsulfonyl, arylsulfonyl, amino, amido, acyl, and acylamino, as defined herein, the number of said substituents being 1, 2, 3, 4 or 5 for halogen, and 1, 2 or 3 for any combination of said other substituents; whereby the aryloxy, arylalkyloxy, arylthio or arylalkylthio group may be further optionally substituted in the aryl moiety with independently selected substituents as defined herein. The heteroaryl group may further be optionally substituted with an aryl group, which may be optionally substituted in the aryl moiety with independently selected substituents as defined herein. The aryl group may further be optionally substituted with a heteroaryl group or a second aryl group.

The aryl may be further substituted by two groups which are attached to adjacent carbon atoms and are combined into a saturated or partly unsaturated cyclic 5, 6, 7 or 8 membered ring system, optionally containing 1, 2 or 3 heteroatoms selected from the group consisting of N, O and S, the number of N atoms being 0, 1, 2 or 3 and the number of O and S atoms each being 0, 1 or 2. Preferably, the two groups which are attached to adjacent carbon atoms, are combined into a saturated cyclic 5 or 6 membered ring system, optionally containing 1, 2 or 3 heteroatoms selected from the group consisting of N and O, the number of N atoms being 0, 1, 2 or 3 and the number of O atoms being 0, 1 or 2. This cyclic ring system may optionally be further substituted by one or two oxo group. Preferred examples of such a substituted aryl groups are benzo[1,3]dioxol and 1,3-dihydro-benzoimidazol-2-one.

The statement is made that when two side chains are found on a single nitrogen atom, they can be combined, including the nitrogen atom to which they are attached, into a heterocyclic ring of 4, 5, 6, 7 or 8 atoms, which ring is optionally saturated, partly unsaturated or aromatic, and which optionally contains 1, 2 or 3 additional heteroatoms selected from the group consisting of N, O and S, the number of additional N atoms being 0, 1, 2 or 3 and the number of O and S atoms each being 0, 1 or 2; and which ring is optionally part of a multiple condensed ring-system, in which some rings may be aromatic. Preferred examples of such heterocyclic ring systems, including the N, to which the respective side chains are attached, comprise:

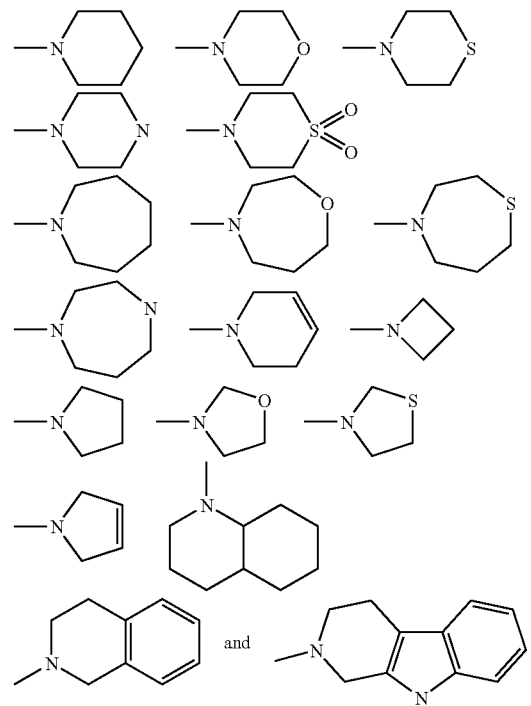

Even more preferred examples of such heterocyclic ring systems, including the N, to which the respective side chains are attached, comprise:

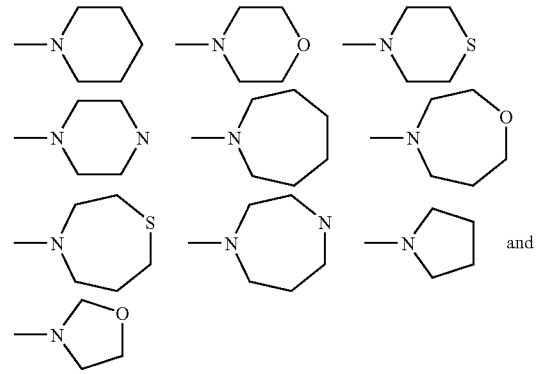

The aforementioned heterocyclic ring or ring system is optionally substituted by 1, 2 or 3 substituents, which can be attached to any carbon or nitrogen atom of the heterocyclic ring system. Preferred examples of substituted heterocyclic ring systems are:

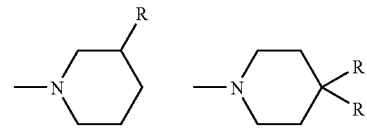

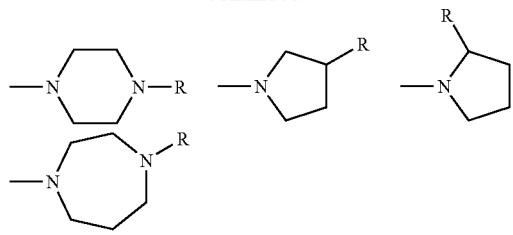

The optional 1, 2 or 3 independently selected substituents for the heterocyclic ring system may be chosen among optionally substituted alkyl, halogen, hydroxyl, oxo, thiol, nitro, nitrile, ($C_1$-$C_6$)-alkoxy, aryl, heteroaryl, optionally substituted cycloheteroalkyl, aryloxy, arylalkyloxy, amino, amido, alkylthio, arylthio, arylalkylthio, sulfamoyl, sulfonamide, acyl, carboxyl, and acylamino, as defined herein, whereby all aryl or heteroaryl moieties may be optionally substituted with 1, 2, 3, 4 or 5, preferably 1, 2 or 3 independently selected substituents as defined herein.

Furthermore, the aforementioned heterocyclic ring system may be substituted by two groups which are attached to the same carbon atom and are combined into a saturated or partly unsaturated cyclic 4, 5, 6, 7, or 8 membered ring system, optionally containing 1, 2 or 3 heteroatoms, selected from the group consisting of N, O and S, the number of N atoms being 0, 1, 2 or 3 and the number of O and S atoms each being 0, 1 or 2. This cyclic ring system may optionally be further substituted by up to three substitutents independently selected from oxo, ($C_1$-$C_6$)-alkyl, aryl, preferably phenyl, and aryl-($C_1$-$C_4$)-alkyl, preferably benzyl. Preferred examples of such substituted heterocyclic ring systems are 1,4-dioxa-8-aza-spiro[4.5]decane, 1,3,8-triaza-spiro[4.5]decane, 1,3,8-triaza-spiro-[4.5]decan-4-one, 1-phenyl-1,3,8-triaza-spiro[4.5]decane, and 1-phenyl-1,3,8-triaza-spiro-[4.5]decan-4-one.

The term "prodrug" as used herein, represents derivatives of the compounds of the invention that are drug precursors which, following administration to a patient by any known route, release the drug in vivo via a chemical or physiological process. As used herein, the term "pro-drug" include metabolic precursors. Pro-drugs are bioreversible derivatives of drug molecules used to overcome some barriers to the utility of the parent drug molecule. These barriers include, but are not limited to, solubility, permeability, stability, presystemic metabolism and targeting limitations (Medicinal Chemistry: Principles and Practice, 1994, Ettmayer et al. [2004], Stella P [2004]). In particular, pro-drugs are derivatives of the compounds of the invention in which functional groups carry additional substituents which may be cleaved under physiological conditions in vivo and thereby releasing the active principle of the compound (e.g., a pro-drug on being brought to a physiological pH or through an enzyme action is converted to the desired drug form). Pro-drugs of the compounds mentioned above are also within the scope of the present invention. Pro-drugs that are metabolised to compounds having formula (I) belong to the invention. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. In particular this relates to compounds with primary or secondary amino or hydroxy groups. Such compounds can be reacted with organic acids to yield compounds having formula (I) wherein an additional group is present which is easily removed after administration, for instance, but not limited to amidine, enamine, a Mannich base, a hydroxyl-methylene derivative, an O-(acyloxymethylene carbamate) derivative, carbamate, ester, amide or enaminone.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention, or separately by reacting compounds of the invention with pharmaceutically acceptable non-toxic bases or acids, including inorganic or organic bases and inorganic or organic acids.

The term "metabolites" refers to active compounds derived from catabolism of a compound of formula I upon introduction into a biological milieu, such as a human. The term "metabolites" includes primary metabolites as well as secondary metabolites of a compound of formula I.

The term "solvates" pertains to the association of suitable organic solvent molecules with molecules or ions of a compound of formula I. As used herein, the term "solvates" refers both to stable solvates, containing a defined number of solvent molecules pro molecule of a compound of formula I, and inclusion complexes, which are less stable and contain a variable number of solvent molecules pro molecule of a compound of formula I.

The term "composition" as used herein is intended to encompass a product comprising the specified ingredients in the predetermined amounts or proportions, as well as any product which results, directly or indirectly, from combination of the specified ingredients in the specified amounts.

The phrase "(therapeutically) effective amount" as used herein refers to an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically acceptable excipient(s)/carrier(s) utilized, and like factors within the knowledge and expertise of the attending physician. Thus, it is not useful to specify an exact effective amount in advance.

The term "treatment" as used herein refers to any treatment of a mammalian, preferably human condition or disease, and includes: (1) preventing the disease or condition from occurring in a subject which may be predisposed to the disease but has not yet been diagnosed as having it, (2) inhibiting the disease or condition, i.e., arresting its development, (3) relieving the disease or condition, i.e., causing regression of the condition, or (4) relieving the conditions caused by the disease, i.e., stopping the symptoms of the disease.

The term 'medical therapy' as used herein is intended to include prophylactic, diagnostic and therapeutic regimens carried out in vivo or ex vivo on humans or other mammals.

The term "subject" as used herein, refers to an animal, preferably a mammal, most preferably a human, who has been the object of treatment, observation or experiment.

Administration Forms

The compounds of the invention are primarily intended for treatment in a mammal, preferably in humans and other primates, of steroid hormone dependent diseases or disorders, in particular estradiol dependent diseases or disorders, wherein the steroid hormone dependent disease or disorder preferably requires the inhibition of a 17β-HSD enzyme, preferably the 17β-HSD1, 17β-HSD2 or 17β-HSD3 enzyme.

The compounds may be administered orally, dermally, parenterally, by injection, by pulmonal or nasal delivery, or sublingually, rectally or vaginally in dosage unit formulations. The term "administered by injection" includes intravenous, intraarticular, intramuscular (e.g. by depot injection where the active compounds are released slowly into the blood from the depot and carried from there to the target organs), intraperitoneal, intradermal, subcutaneous, and intrathecal injections, as well as use of infusion techniques. Dermal administration may include topical application or transdermal administration. One or more compounds may be present in association with one or more non-toxic pharmaceutically acceptable auxiliaries such as excipients, adjuvants (e.g. buffers), carriers, inert solid diluents, suspending agents, preservatives, fillers, stabilizers, anti-oxidants, food additives, bioavailability enhancers, coating materials, granulating and disintegrating agents, binding agents etc., and, if desired, other active ingredients.

The pharmaceutical composition may be formulated for example as immediate release, sustained release, pulsatile release, two or more step release, depot or other kind of release formulations.

The manufacture of the pharmaceutical compositions according to the invention may be performed according to methods known in the art and will be explained in further detail below. Commonly known and used pharmaceutically acceptable auxiliaries as well as further suitable diluents, flavorings, sweetening agents, coloring agents etc. may be used, depending on the intended mode of administration as well as particular characteristics of the active compound to be used, such as solubility, bioavailability etc. Suitable auxiliaries and further ingredients may be such as recommended for pharmacy, cosmetics and related fields and which preferably are listed in the European Pharmacopoeia, FDA approved or cited in the "GRAS" list (FDA List of food additives that are 'generally recognized as safe' (GRAS)).

One mode of application of the compounds of general formula (I) or of pharmaceutical compositions comprising one or more of said compounds is oral administration, e.g., by tablets, pills, dragees, hard and soft gel capsules, granules, pellets, aqueous, lipid, oily or other solutions, emulsions such as oil-in-water emulsions, liposomes, aqueous or oily suspensions, syrups, elixiers, solid emulsions, solid dispersions or dispersible powders. For the preparation of pharmaceutical compositions for oral administration, the compounds suitable for the purposes of the present invention as defined above can be admixed with commonly known and used adjuvants and excipients such as for example, gum arabic, talcum, starch, sugars, gelatine, surface-active agents, magnesium stearate, aqueous or non-aqueous solvents, paraffin derivatives, cross-linking agents, dispersants, emulsifiers, lubricants, conserving agents, flavoring agents, solubility enhancers or bioavailability enhancers. In the pharmaceutical composition, the active ingredients may also be dispersed in a microparticle, e.g. a nanoparticulate, composition.

For parenteral administration, the active agents can be dissolved or suspended in a pharmaceutically acceptable diluent, such as, e.g., water, buffer, oils, with or without solubilizers, surface-active agents, dispersants or emulsifiers. More generally spoken, for parenteral administration the active agent can be in the form of an aqueous, lipid, oily or other kind of solution or suspension or even administered in the form of liposomes or nano-suspensions.

Transdermal application can be accomplished by suitable patches, as generally known in the art, specifically designed for the transdermal delivery of active agents, optionally in the presence of specific permeability enhancers. Furthermore, also emulsions, ointments, pastes, creams or gels may be used for transdermal delivery.

Another suitable mode of administration is via intravaginal devices (e.g. vaginal rings) or intrauterine systems (IUS) containing reservoirs for controlled release of active agents over extended periods of time. For rectal or vaginal administration of the drug the compounds may also be administered in the form of suppositories. These compositions can be prepared by mixing the drug with a suitable non-irritating excipient which is solid at ordinary temperatures but liquid at the rectal or vaginal temperature and will therefore melt in the rectum or vagina to release the drug.

Another mode of application is by implantation of a depot implant comprising an inert carrier material, such as biologically degradable polymers or synthetic silicones such as e.g. silicone rubber. Such implants are designed to release the active agent in a controlled manner over an extended period of time (e.g. 3 to 5 years).

It will be appreciated by those skilled in the art that the particular method of administration will depend on a variety of factors, all of which are considered routinely when administering therapeutics. It will also be understood, however, that the actual dosages of the agents of this invention for any given patient will depend upon a variety of factors, including, but not limited to the activity of the specific compound employed, the particular composition formulated, the mode of administration, time of administration, route of administration and the particular site, host, and disease being treated, and furthermore the age of the patient, the body weight of the patient, the general health of the patient, the gender of the patient, the diet of the patient, rate of excretion, drug combinations, and the severity of the condition undergoing therapy. It will be further appreciated by one skilled in the art that the optimal course of treatment, i.e., the mode of treatment and the daily number of doses of a compound of Formula I or a pharmaceutically acceptable salt thereof given for a defined number of days, can be ascertained by those skilled in the art using conventional treatment tests. Optimal dosages for a given set of conditions may be ascertained by those skilled in the art using conventional dosage-determination tests in view of the experimental data for a given compound. For oral administration, an exemplary daily dose generally employed will be from about 0.01 µg/kg to about 100 mg/kg of total body weight, whereby courses of treatment may be repeated at appropriate time intervals. Administration of pro-drugs may be dosed at weight levels that are chemically equivalent to the weight levels of the fully active compounds. The daily dosage for parenteral administration will generally be from about 0.01 µg/kg to about 100 mg/kg of total body weight. A daily rectal dosage regimen will generally be from about 0.01 µg/kg to about 200 mg/kg of total body weight. A daily vaginal dosage regimen will generally be from about 0.01 µg/kg to about 100 mg/kg of total body weight. The daily topical dosage regimen will generally be from about 0.1 µg to about 100 mg administered between one to four times daily. The transdermal concentration will generally be that required to maintain a daily dose of from 0.01 µg/kg to 100 mg/kg of total body weight.

Abbreviations and Acronyms

As employed herein, the following terms have the indicated meanings.

| | |
|---|---|
| μM | micromolar |
| ACN | acetonitrile |
| Aq | aqueous |
| Bn | benzyl |
| BOC | tert-butoxycarbonyl |
| Brine | saturated sodium chloride solution |
| Celite ® | CAS No 68855-54-9 |
| conc. | concentrated |
| d | day(s) |
| DAST | N,N-diethylaminosulfur trifluoride |
| DCM | dichloromethane = $CH_2Cl_2$ |
| DHP | 3,4-dihydro-[2H]-pyran |
| DIAD | diisopropyl azodicarboxylate |
| DIBAH | Diisobutyl aluminiumhydrid |
| DIPEA | N,N-diisopropylethylamine |
| DMAP | 4-dimethylaminopyridin |
| DME | dimethyl ethylene glycol = 1,2-dimethoxyethane |
| DMF | N,N-dimethylformamide |
| DMSO | dimethylsulfoxide |
| E1 | estrone |
| E2 | estradiol |
| EDCI | 1-(3,3-dimethylaminopropyl)-3-ethylcarbodiimide |
| ER | estrogen receptor |
| EtOAc | ethyl acetate |
| Fu-salt | $[(t\text{-}Bu)_3PH]BF_4$ |
| h | hour(s) |
| HMPA | hexamethylphosphoramide |
| Hermann's catalyst | trans-di-μ-aceto-bis[2-(di-o-tolylphosphino)benzyl]dipalladium (II) |
| HOBT | 1-Hydroxybenzotriazole Hydrate |
| HPLC | High Performance Liquid Chromatography |
| HSD | hydroxysteroid dehydrogenase |
| Hünig base | N,N-Diisopropyl-N-ethyl-amine = $N(iPr)_2Et$ = EDIPA) |
| IPA | iso-propyl acetate |
| m-CPBA | m-chloroperoxybenzoic acid |
| mg | milligram(s) |
| min | minute(s) |
| mm | millimolar |
| MOM | methoxy methyl |
| MsCl | methanesulfonyl chloride (mesyl chloride) |
| MTBE | methyl tert.-butylether |
| NAD(P)[H] | nicotinamide-adenine-dinucleotide (phosphate) [reduced NAD(P)] |
| n-BuLi | n-butyl lithium |
| nM | nanomolar |
| NMM | N-methylmorpholine |
| NMO | N-methylmorpholine N-oxide |
| NMR | nuclear magnetic resonance |
| PG | protection group |
| pTosOH | para-toluene sulfonic acid |
| Rt | Retention time (LC/MS) |
| RT | room temperature |
| sat | saturated |
| T3P | propylphosphonic acid anhydride |
| TBAF | tetrabutylammonium-fluoride |
| TBDMS | tert-butyl dimethyl siloxy |
| TBME | tert-butyl methyl ether |
| TEA | triethylamine |
| TEOF | Triethylorthoformat ($CH(OEt)_3$) |
| TFA | trifluoroacetic acid |
| THF | tetrahydrofuran |
| THP | tetrahydropyran |
| TLC | thin-layer chromatography |
| TMSCI | trimethylsilylchloride/$Me_3SiCl$ |
| TPAP | tetrapropylammonium perruthenate |

Numbering of Compound Formulas and Intermediates

The general structure formulas are typically designated with a number in roman format, followed by α or β indicating the stereochemistry at the C15 atom of the estrone core if necessary. If the number of methylene groups attached at the C15 position is specified (i.e. the value of "n"), the roman number plus α or β is followed by a hyphen and a number indicating the amount of methylene groups. This "number" is set in parantheses. The prefix C2 in front of the parantheses indicates that the compound may be substituted in C2 by a residue $R^{11}$. A prefix F,F in front of the number indicates that the —CO— function in C17 may be replaced by —$CF_2$—. A modification of the C3 hydroxy function is designated in the compound formula following the parantheses.

For example, compound IV is the general acid building block:

(IV)

Therefore, a compound IVβ-3 would represent a derivative of IV with β stereochemistry at C15 and three methylene groups, i.e.:

(IVβ-3)

For example, a compound C2-(IVβ-3) would represent a derivative of IV with β stereochemistry at C15, three methylene groups and a substituent in C2, i.e.:

C2-(IVβ-3)

For example, a compound F,F-C2-(IVβ-3) would represent a derivative of IV with β stereochemistry at C15, three methylene groups, a substituent in C2 and a difluoro group in C17 position, i.e.:

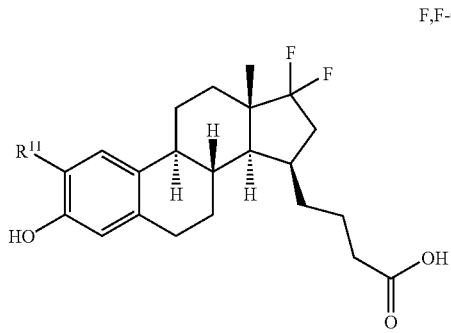

F,F-C2-(IVb-3)

For example, a compound F,F-C2-(IVβ-3)-B(OH)$_2$ would represent a derivative of IV with β stereochemistry at C15, three methylene groups, a substituent in C2, a difluoro group in C17 position and a boronic acid group in C3 position, i.e.:

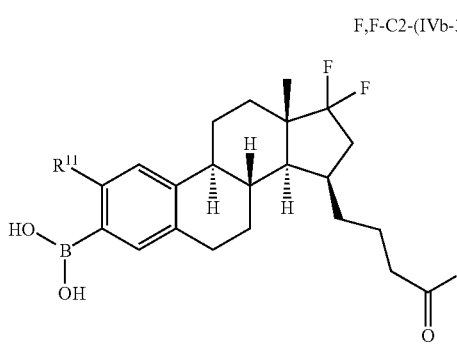

F,F-C2-(IVb-3)-B(OH)$_2$

General Preparative Methods

The compounds of the present invention may be prepared by use of known chemical reactions and procedures. Nevertheless, the following general preparative methods are presented to aid the reader in synthesizing the 17β-HSD1, 17β-HSD2 and/or 17β-HSD3 inhibitors, with specific details provided below in the experimental section to illustrate working examples.

All variable groups of these methods are as described in the generic description if they are not specifically defined below.

It is recognized that compounds of the invention with each claimed optional functional group may not be prepared by each of the below-listed methods. Within the scope of each method, optional substituents may appear on reagents or intermediates which may act as protecting or otherwise non-participating groups. Utilizing methods well known to those skilled in the art, these groups are introduced and/or removed during the course of the synthetic schemes which provide the compounds of the present invention.

Flow Diagrams

The synthesis of substituted estrone derivatives bearing a side chain of the amide, ester, carbonyl, hydrazone, alcohol, ether, urea, carbamate, "retro"-amide, sulfonyl urea, sulfamide, sulfamate, "retro"-sulfonamide, "retro"-carbamate, "retro"-ester or sulfonylcarbamate type in position C15 is extensively described within the international application WO2005/047303, which is hereby incorporated by reference in its entity. Alternatively, the compounds of the invention may carry a triazole moiety in the C15 sidechain, the synthesis of which compounds is disclosed in detail within International patent application PCT/EP2007/059785 (not yet published).

The additional modifications of the steroidal core at positions C2 and/or C17, which can also characterize the compounds of the present invention, are extensively described within the international application WO2006/125800, which is hereby incorporated by reference in its entity.

In addition, the compounds of the present invention are characterized by replacement of the C3 hydroxy function of the steroidal core with a boronic acid, carboxylic acid, carboamide, amino, amide or sulfonamide moiety.

The modifications of the steroidal core leading to the compounds of the present invention may be introduced in the following order of general chemical modifications (General Synthesis Scheme I)

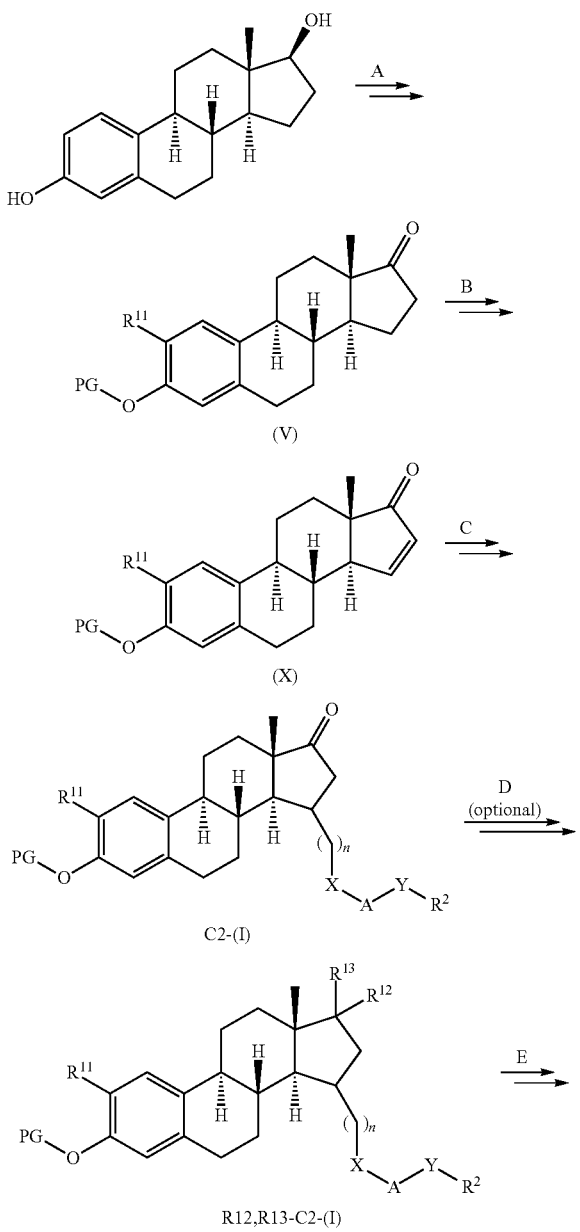

-continued

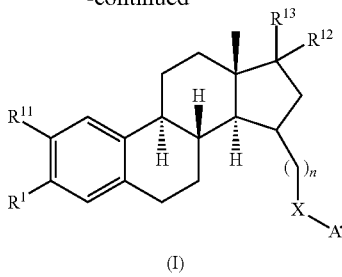

(I)

wherein $R^1$, $R^2$, $R^{11}$, $R^{12}$, $R^{13}$, X, A and Y have the meanings as defined herein, and PG is a common protecting group.

The introduction of the $R^{11}$ substituent in C2 position—if present in the final compound—has to take place first, starting from the 17β-estradiol using methods well known in the art (Steps A). In parallel, the C17-OH function is oxidized to the corresponding keto function. If necessary, a suitable protecting group may be introduced at this point in order to protect the oxygen in C3 position. Then, the estrone derivative of formula (V) is converted into the central intermediate, the 15, 16-unsaturated estrone of formula X (Steps B), which is further derivated in the C15 position by introduction of the basic side chain ("so called building blocks"). These building blocks are reacted with the appropriate compounds carrying the $R^2/R^4$ substitutents to lead to the desired C15 substituted compound (Steps C). If desired, the obtained educt may be further modified within the C17 position by replacement of the oxygen with a difluoro group (Steps D). Finally, the protection group in C1 position is substituted with an alternative $R^1$ side chain to deliver the compounds of the invention (Steps E).

For synthesis of some compounds of the invention and in order to enable library synthesis, it might be necessary that some of the reaction steps explained under "STEPS C—the introduction of the C15 side chain" have to be carried out after having introduced the difluoro group in C17 and/or after having introduced the new substituent (or an intermediate thereof) in C3 position as depicted in the following general synthesis scheme II.

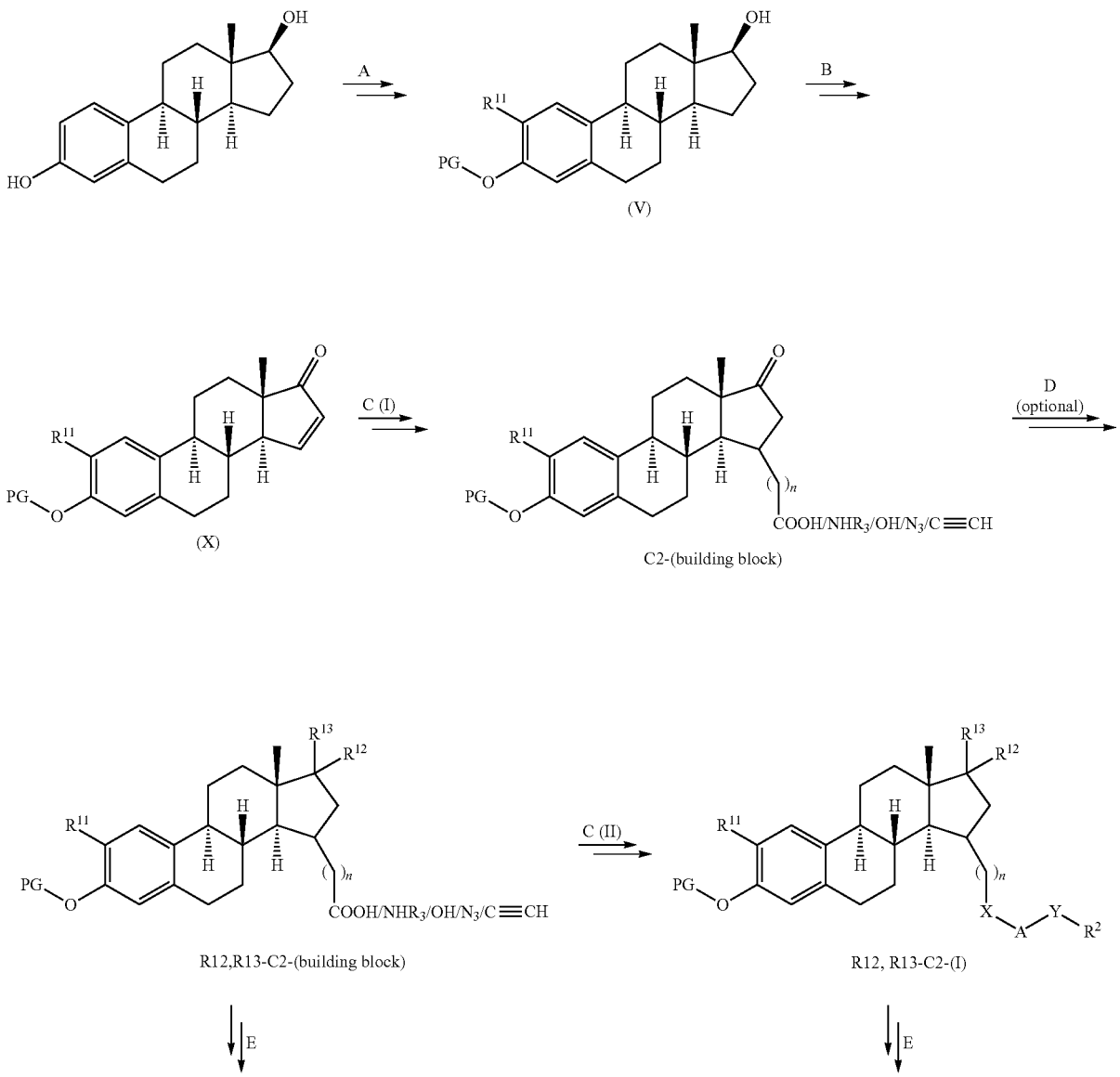

-continued

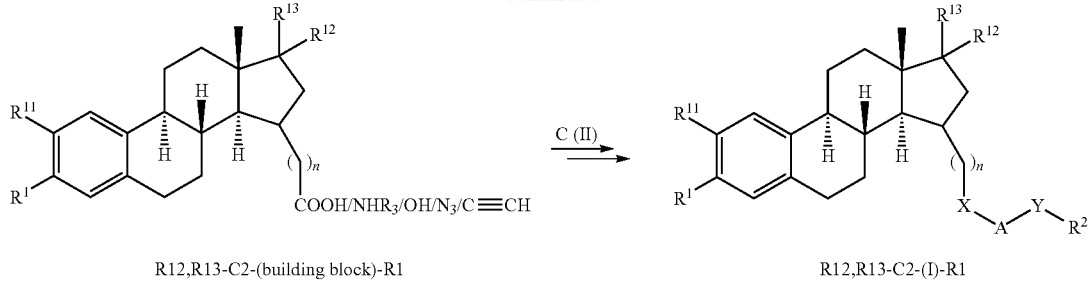

R12,R13-C2-(building block)-R1     C (II) →     R12,R13-C2-(I)-R1 wherein $R^1$, $R^2$, $R^3$, $R^{11}$, $R^{12}$, $R^{13}$, X, A and Y have the meanings as defined herein, and PG is a common protecting group, and wherein any reactive group, especially in the C15 side chain, might be optionally protected by a conventional protecting or otherwise non-participating group if necessary, also if not explicitly indicated within this scheme.

Step A—Introduction of a $R^{11}$ Side Chain in C2 Position of 17β-Estradiol or Estrone The optional "Step A" modification was fully disclosed in international patent application WO2006/125800.

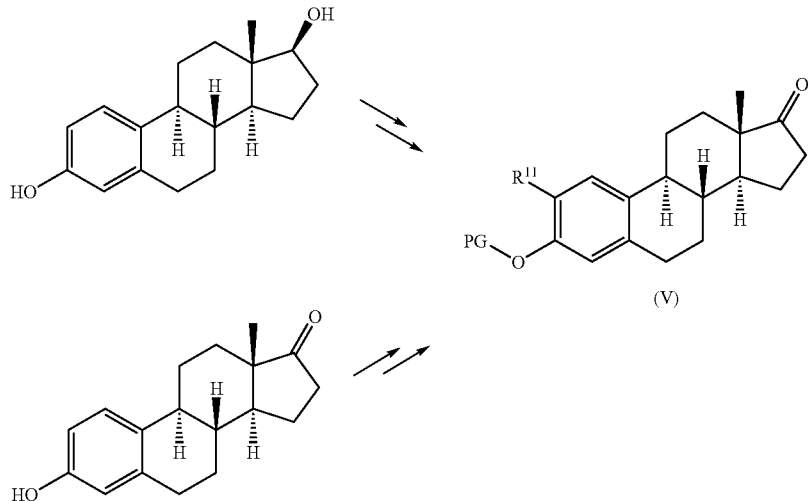

(V)

The introduction of the $R^{11}$ substituent in C2 position—if present in the final compound—has to take place first, starting from the 17β-estradiol using methods well known in the art (Steps A). In parallel, the C17-OH function is oxidized to the corresponding keto function. If necessary, a suitable protecting group may be introduced at this point in order to protect the oxygen in C3 position. Then, the estrone derivative of formula (V) is converted into the central intermediate, the 15, 16-unsaturated estrone of formula X (Steps B), which is further derivated in the C15 position by introduction of the basic acid, alcohol, amid or alkenyl side chain delivering the so called building blocks (Steps C(I)). Then, the difluoro group might be introduced into C17 position of the steroidal core (Step D). Alternatively or additionally, at this step the boronic acid or carboxylic acid or amino group in C3 position might be introduced (Step E). The so-obtained building blocks are reacted with the appropriate compounds carrying the $R^2/R^4$ substitutents to lead to the desired C15 substituted compound (Steps C(II)). Finally, the protection group in C1 position is substituted with an alternative $R^1$ side chain to deliver the compounds of the invention (Steps E) or any still necessary modifications at the C3 position are carried out.

wherein $R^{11}$ has the meanings as defined herein, and PG is a common protecting group.

The introduction of various side chains in the estrone core is known from the literature, e.g. Rao et al (2002) describe the synthesis of 2-methoxyestradiol, and the synthesis of 2-ethoxy-estradiol was disclosed by Verdier-Pinard et al (2000). 2-Ethyl-estrone may be prepared from estrone by Friedel-Crafts acetylation of estrone-3-O-methyl ether and catalytic hydrogenation, followed by demethylation, which produced the desired product. Alternatively, the introduction of substituents on the 2-position may be obtained by using a Fries-rearrangement starting with estradiol and the reagent $(RCO)_2O$ with R=lower alkyl, as described by Rao et al. (2002): After acylation, the compounds should be converted into the R—CO-substituted derivatives in C2 position. Reduction of the acyl function may be achieved by reduction with Pd/C and $H_2$ [Gonzalez et al (1982)]. Alternatively, the acetoxy-group in C2-position could be oxidized with PhI $(CF_3CO_2)_2$ according to [Yoshikawa et al. (2002)]. The newly introduced hydroxy group may be further alkylated, followed by reduction of the ketone, resulting in an alkoxy-alkyl substituted estradiol derivative. An alternative strategy to introduce an alkoxy-alkyl group is exemplified for the methoxyethyl group: After MOM-protection of the 17β-estradiol, the MOM-protected estradiol is iodinated [Mohanakrishnan & Cushman (1999)]. Then, the MOM-group is replaced with a TBDMS group. Negishi coupling with allylbromide gives the 2-allyl substituted estrone derivative, which can be oxidised and methylated (including some protective group manipulations). Further synthetic ways to 2-alkyl-substituted estrone or estradiol derivatives have been displayed previously [see e.g. Mohanakrishnan & Cushman (1999); Day et al. (2003); Cushman et al (1995), and Lunn & Farkas (1968)] The synthesis of further estrone derivatives with various substituents in 2-position was disclosed by Cushman et al (2002).

During the introduction of the C2 side chain, the 3-hydroxy function of the steroidal core is typically protected with a methyl or benzyl group (exemplified by PG). For example, the methyl derivative can be prepared using MeJ and acetone, whereas the corresponding Benzyl-derivative may be prepared using Benzylbromid, DIPEA and acetone. Enone intermediates with other substituents in $R^1$ (=PG), in particular optionally substituted $C_1$-$C_4$-alkyl, can be prepared accordingly by using the appropriate optionally substituted $C_1$-$C_4$-alkyl-bromide or $C_1$-$C_4$-alkyl-iodide.

Step B—Synthesis of the 15,16-Unsaturated Estrone of Formula X (Intermediate I)

The "Step B" reaction was fully disclosed in international patent applications WO2005/047303 for estrone and WO2006/125800 for C2 substituted estrone derivatives.

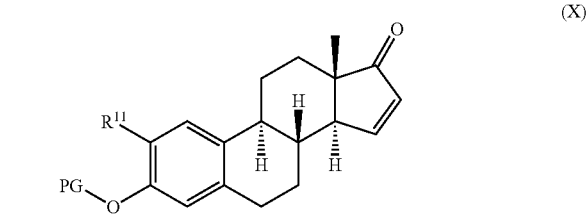

(X)

Starting from the corresponding 2-substituted estrone of formula (V) the ketal of the formula (IX) can be prepared according to Nambara [Nambara et al. (1976)] as depicted within the following SCHEME 1. If not yet protected, the introduction of PG groups in C3 position can be achieved according to a procedure described by Labaree (2003).

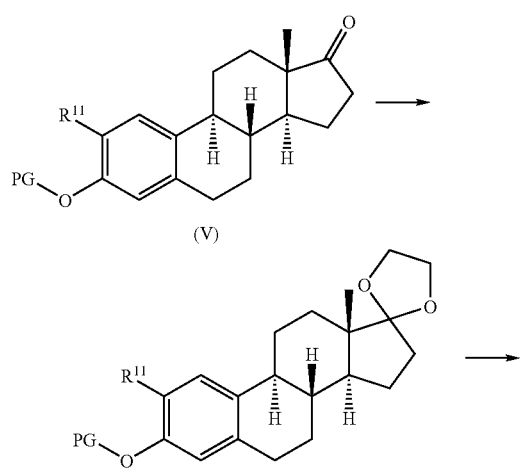

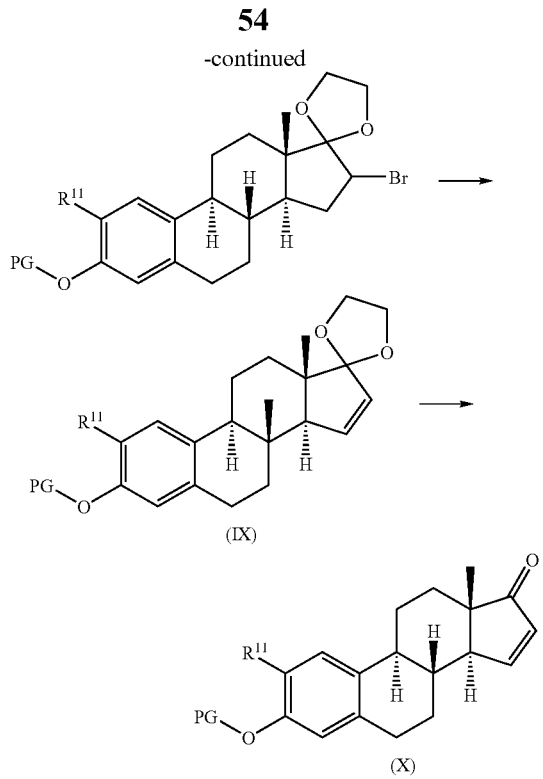

wherein $R^{11}$ has the meanings as defined herein, and PG is a common protecting group.

The C17 keto function of the C2 substituted and protected estrone derivative of formula (V) is protected as acetal, followed by bromination. The elimination of the bromide yielded the desired 15,16-unsaturated estron. Finally, the ketal derivative is hydrolysed to give the appropriate enone-derivative X.

Alternatively, the enone intermediate of formula X can be prepared from the corresponding estrone derivative according to a procedure described by Poirier et al. (1991).

Step C—Introduction of the Side Chain in C15 Position

The "Step C" modification—the introduction of the side chain in C15 position—is carried out in two major steps: In a first step C(I) the 15,16-unsaturated Estrone of formula X is converted into a so-called building block carrying an alkyl side chain in C15 position with a terminal amino, carboxy, or alcohol function. The synthesis of some exemplary building blocks is depicted in the Experimental Section "Intermediates", and was fully disclosed for nearly all kinds of building blocks in international patent application WO2005/047303 for estrone and WO2006/125800 for C2 substituted estrone derivatives. How to obtain estrone intermediates with azide or alkine side chain in C15 position was disclosed within unpublished International patent application PCT/EP2007/059785.

The second step C(II) of the "Step C" modification—the conversion of the building blocks into the desired derivatives carrying the complete side chain in C15 position—is exemplified below by using one of the following synthetic schemes as shown in Flow Diagrams I to XV. Again, the synthesis of some exemplary intermediates or even final compounds of formula (I) carrying particular side chains is depicted in the Experimental Section "Intermediates" or under "Examples". The synthesis of a variety of different C15 side chains was fully disclosed in international patent application WO2005/047303 for estrone and WO2006/125800 for C2 substituted and/or C17 modified estrone derivatives.

Certain formula I compounds, in which X-A-Y represents —CO—NH— or —CO—NR$^4$— and n represents an integer from 0 to 5, may be prepared by a reaction as shown in Flow Diagram Ia.

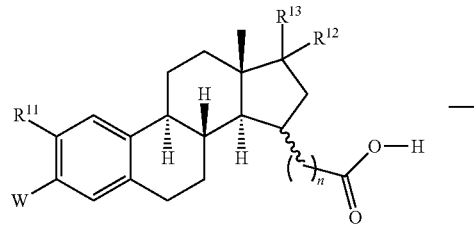

(IV)

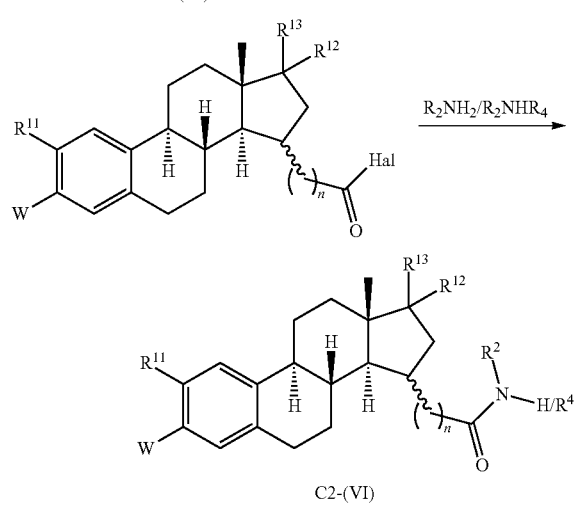

wherein W represents R$^1$ or —O-PG, and R$^1$, R$^2$, R$^4$, R$^{11}$, R$^{12}$ and R$^{13}$ have the meanings as defined herein, and PG is a common protecting group. The free acid (IV) may be converted to the reactive acyl halide, in particular the acid chloride, by reaction with SOCl$_2$, COCl$_2$, PCl$_5$ or PBr$_3$ or the like. The amide derivatives C2-(VI) may be prepared by a base catalyzed addition-elimination reaction, where the halogen residue is substituted with the appropriate amine R$^2$NH$_2$ or R$^2$NHR$^4$ in the presence of a base, for example DIPEA. Alternatively, especially suited for derivatives with n>2, the amide derivatives may be prepared directly from the free acids by nucleophilic substitution with the appropriate amine. Alternatively, the amide derivatives may be prepared directly from the free acids by nucleophilic substitution with the appropriate amine as shown in Flow Diagram Ib:

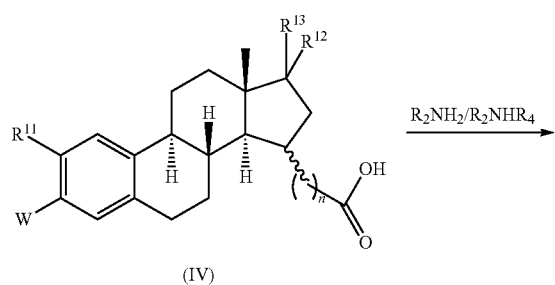

(IV)

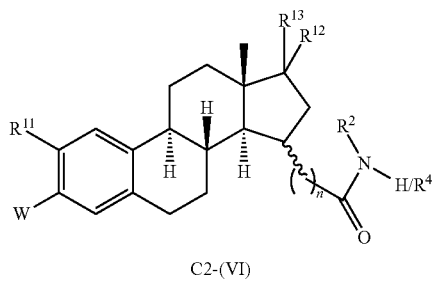

C2-(VI)

wherein W represents R$^1$ or —O-PG, and R$^1$, R$^2$, R$^4$, R$^{11}$, R$^{12}$ and R$^{13}$ have the meanings as defined herein, and PG is a common protecting group.

Certain formula I compounds, in which —X-A-Y— represent —CO—O—, and n represents an integer from 0 to 5, may be prepared by a reaction as shown in Flow Diagram II:

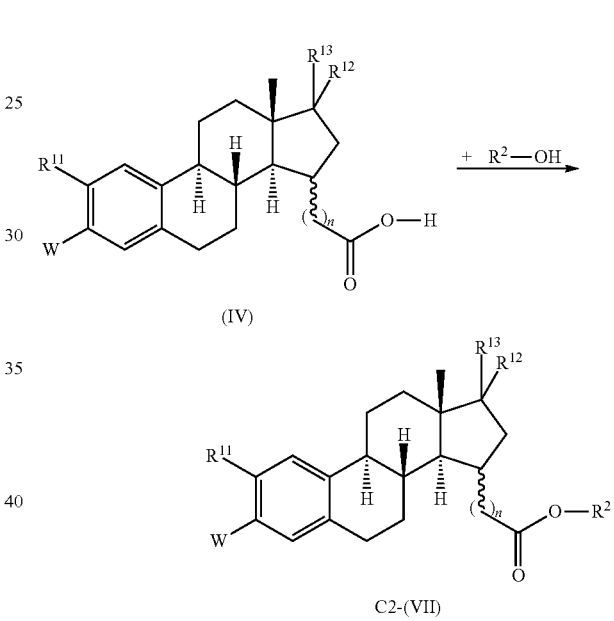

wherein W represents R$^1$ or —O-PG, and R$^1$, R$^2$, R$^{11}$, R$^{12}$ and R$^{13}$ have the meanings as defined herein, and PG is a common protecting group. The ester derivatives C2-(VII) may be prepared from the free acid (IV) by esterification with the appropriate alcohol R$^2$—OH.

Certain formula I compounds, in which —X-A-Y— represent —CO—, and n represents an integer from 0 to 5, may be prepared by a reaction as shown in Flow Diagram III:

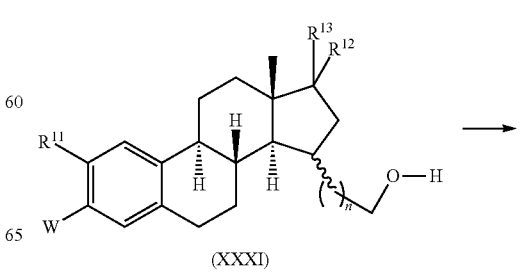

(XXXI)

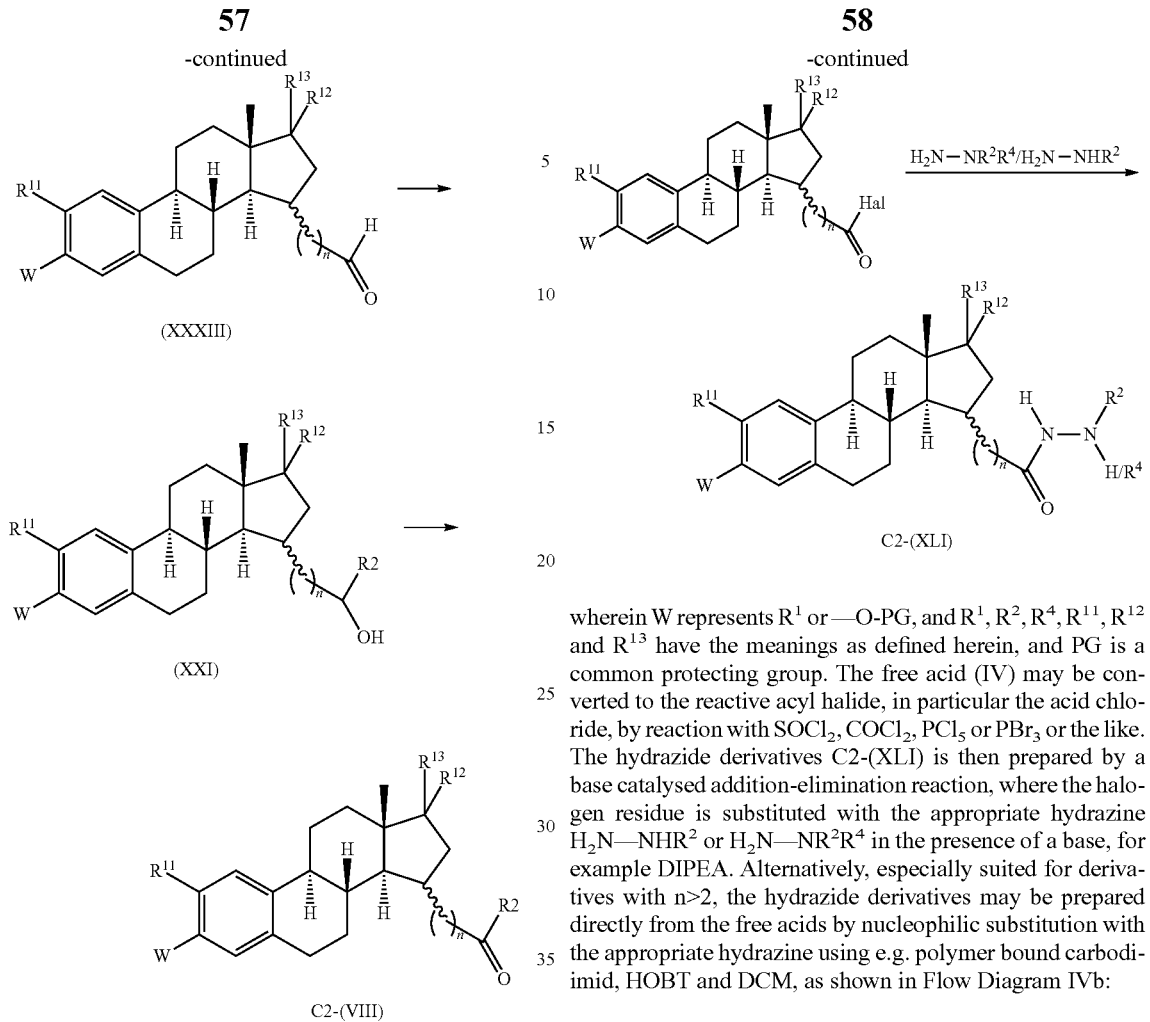

(XXXIII)

(XXI)

C2-(VIII)

wherein W represents $R^1$ or —O-PG, and $R^1$, $R^2$, $R^{11}$, $R^{12}$ and $R^{13}$ have the meanings as defined herein, and PG is a common protecting group. The alcohol (XXXI) may be converted to the corresponding aldehyde (XXXIII) via Dess-Martin Oxidation. Subsequently the aldehyde may be converted by a nucleophilic addition-elimiation reaction with a Grignard or other organometallic reagent, substituted with the appropriate $R^2$ residue to the corresponding secondary alcohol (XXI), which thereafter can be oxidized again to the desired ketone C2-(VIII).

Certain formula I compounds, in which —X-A-Y— represents —CO—NH—$NR^4$— or —CO—NH—NH—, and n represents an integer from 0 to 5, may be prepared by a reaction as shown in Flow Diagram IVa.

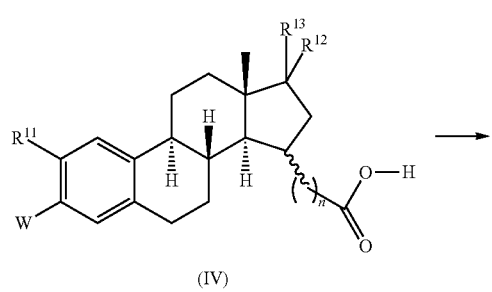

(IV)

C2-(XLI)

wherein W represents $R^1$ or —O-PG, and $R^1$, $R^2$, $R^4$, $R^{11}$, $R^{12}$ and $R^{13}$ have the meanings as defined herein, and PG is a common protecting group. The free acid (IV) may be converted to the reactive acyl halide, in particular the acid chloride, by reaction with $SOCl_2$, $COCl_2$, $PCl_5$ or $PBr_3$ or the like. The hydrazide derivatives C2-(XLI) is then prepared by a base catalysed addition-elimination reaction, where the halogen residue is substituted with the appropriate hydrazine $H_2N$—$NHR^2$ or $H_2N$—$NR^2R^4$ in the presence of a base, for example DIPEA. Alternatively, especially suited for derivatives with n>2, the hydrazide derivatives may be prepared directly from the free acids by nucleophilic substitution with the appropriate hydrazine using e.g. polymer bound carbodiimid, HOBT and DCM, as shown in Flow Diagram IVb:

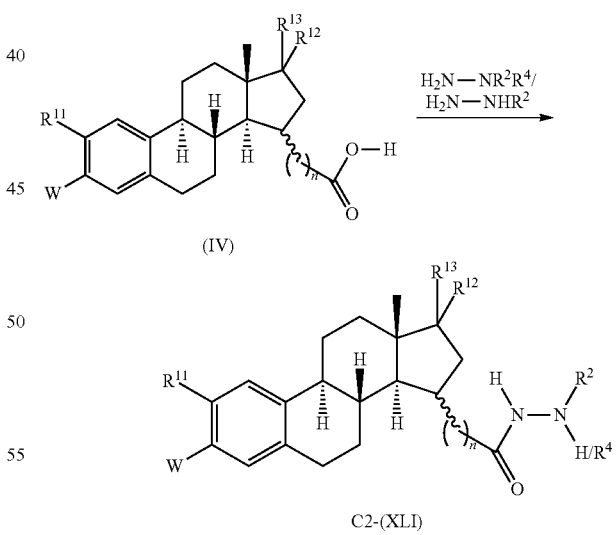

C2-(XLI)

wherein W represents $R^1$ or —O-PG, and $R^1$, $R^2$, $R^4$, $R^{11}$, $R^{12}$ and $R^{13}$ have the meanings as defined herein, and PG is a common protecting group.

Certain formula I compounds, in which —X-A-Y— represents —NH—CO—NH—, and n represents an integer from 1 to 6, may be prepared by a reaction as shown in Flow Diagram Va:

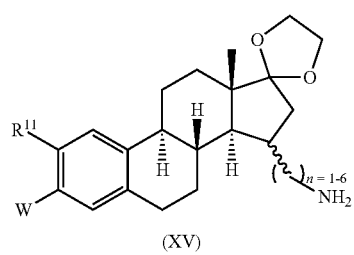

(XV)

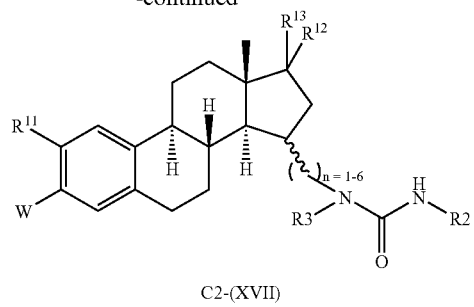

C2-(XVII)

wherein W represents $R^1$ or —O-PG, and $R^1$, $R^2$, $R^3$, $R^4$, $R^{11}$, $R^{12}$ and $R^{13}$ have the meanings as defined herein, and PG is a common protecting group.

Certain formula I compounds, in which —X-A-Y— represents —NH—SO$_2$—NH—, and n represents an integer from 1 to 6, may be prepared by a reaction as shown in Flow Diagram VI

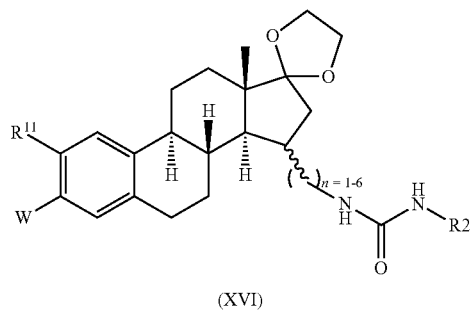

(XVI)

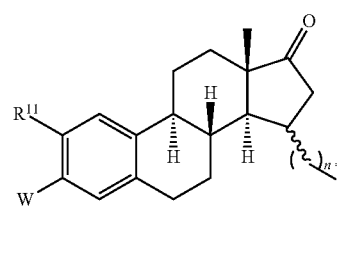

C2-(XVII)

wherein W represents $R^1$ or —O-PG, and $R^1$, $R^2$ and $R^{11}$ have the meanings as defined herein, and PG is a common protecting group. The urea derivatives of the general formula C2-(XVII) may be prepared by the reaction of the amine building block (XV) with an appropriately substituted Isocyanate ($R^2$—N=C=O). After the addition, the ketal function is converted into the keto function. Alternatively, the amine may be first reacted with carbodiimidazol or triphosghen to form a reactive carbamoyl compound, which than can react further with a suitable amine $R^2R^4$—NH. A further synthesis variant may use the unprotected amine (XXIX) as starting material for the reaction with an appropriately substituted Isocyanate ($R^2$—N=C=O) as shown in Flow Diagram Vb

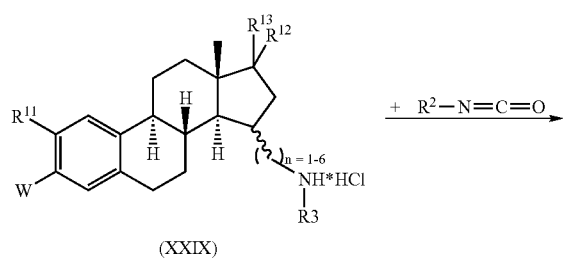

(XXIX)

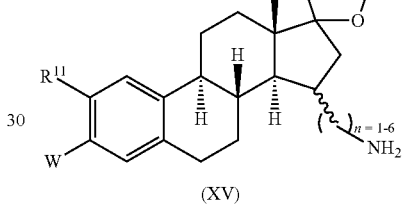

(XV)

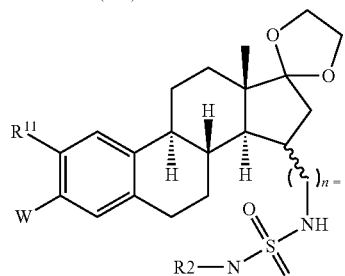

(XVIII)

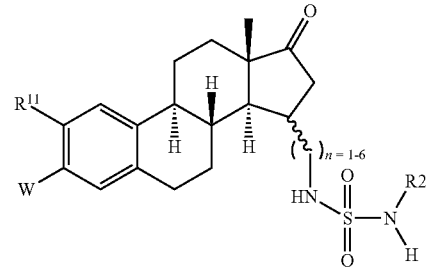

C2-(XIX)

wherein W represents $R^1$ or —O-PG, and $R^1$, $R^2$ and $R^{11}$ have the meanings as defined herein, and PG is a common protecting group. In a first step, the amine building block (XV) may be converted into a protected, for example Boc-protected, sulfamide compound by a reaction with the appropriately protected chlorosulfonyl isocyanate. In a second step, the protected sulfamide compound is allowed to react with the appropriate Bromo-reagent ($R^2$—Br) to provide the still protected, substituted sulfamide derivative of the formula (XVIII). After deprotection, the desired N-substituted sulfamide derivative of formula C2-(XIX) is obtained.

Certain formula I compounds, in which —X-A-Y— represents —NH—CO—O—, and n represents an integer from 1 to 6, may be prepared by a reaction as shown in Flow Diagram VII:

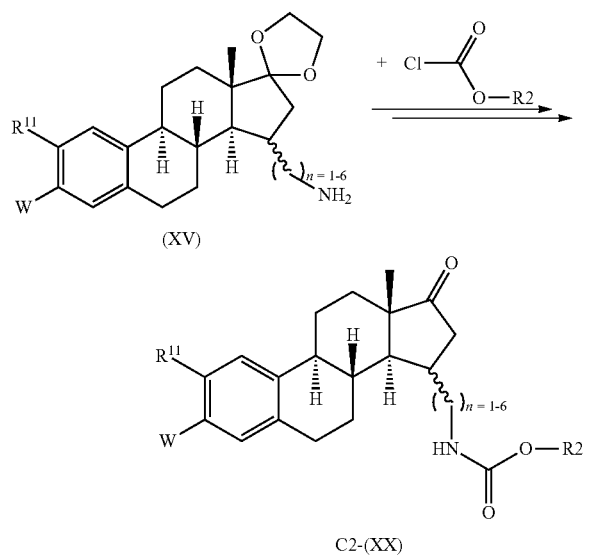

C2-(XX)

wherein W represents $R^1$ or —O-PG, and $R^1$, $R^2$ and $R^{11}$ have the meanings as defined herein, and PG is a common protecting group. The carbamate derivatives of the general formula C2-(XX) may be prepared by the reaction of the amine building block (XV) with an appropriate chloroformic acid ester ($R^2$—CO—Cl). After the addition-elimination reaction, in a second step the ketal function is converted into the keto function.

Certain formula I compounds, in which —X-A-Y— represents —NH—SO$_2$—O—, and n represents an integer from 1 to 6, may be prepared by a reaction as shown in Flow Diagram VIII:

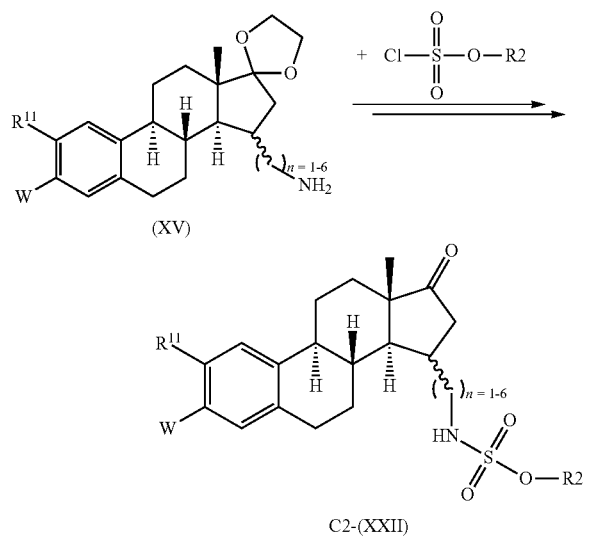

C2-(XXII)

wherein W represents $R^1$ or —O-PG, and $R^1$, $R^2$ and $R^{11}$ have the meanings as defined herein, and PG is a common protecting group. The sulfamate derivatives of the general formula C2-(XXII) may be prepared by the reaction of the amine building block (XV) with an appropriate chlorosulfonic acid ester ($R^2$—O—SO$_2$—Cl). After the addition-elimination reaction, in a second step the ketal function is converted into the keto function.

Certain formula I compounds, in which —X-A-Y— represents —NH—CO—, and n represents an integer from 1 to 6, may be prepared by a reaction as shown in Flow Diagram IXa:

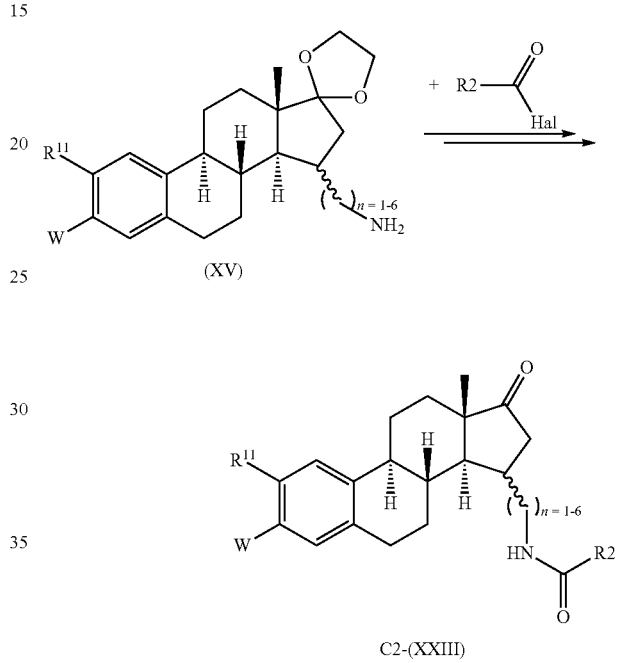

C2-(XXIII)

wherein W represents $R^1$ or —O-PG, and $R^1$, $R^2$ and $R^{11}$ have the meanings as defined herein, and PG is a common protecting group. The "retro"-amide derivatives of the general formula C2-(XXIII) may be prepared by the reaction of the amine building block (XV) with an appropriate acid halide, e.g. an acid chloride ($R^2$—CO—Cl). After the addition-elimination reaction, in a second step the ketal function is converted into the keto function. Alternatively, the reaction with an appropriate acid halide, e.g. an acid chloride ($R^2$—CO—Cl), can be performed using the amino-hydrochloride salt of the estrone (XXIX) as starting material as shown in the following Flow Diagram IXb:

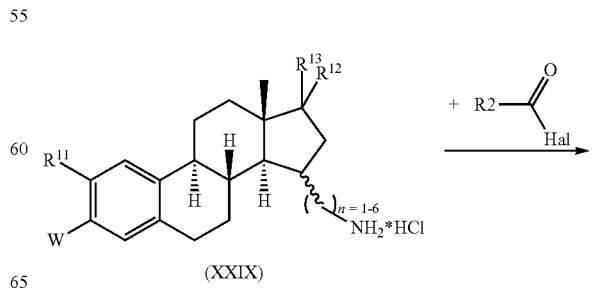

(XXIX)

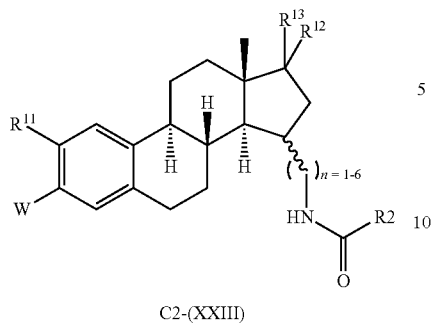

C2-(XXIII)

wherein W represents $R^1$ or —O-PG, and $R^1$, $R^2$, $R^{11}$, $R^{12}$ and $R^{13}$ have the meanings as defined herein, and PG is a common protecting group.

Certain formula I compounds, in which —X-A-Y— represents —NH—SO$_2$—, and n represents an integer from 1 to 6, may be prepared by a reaction as shown in Flow Diagram Xa:

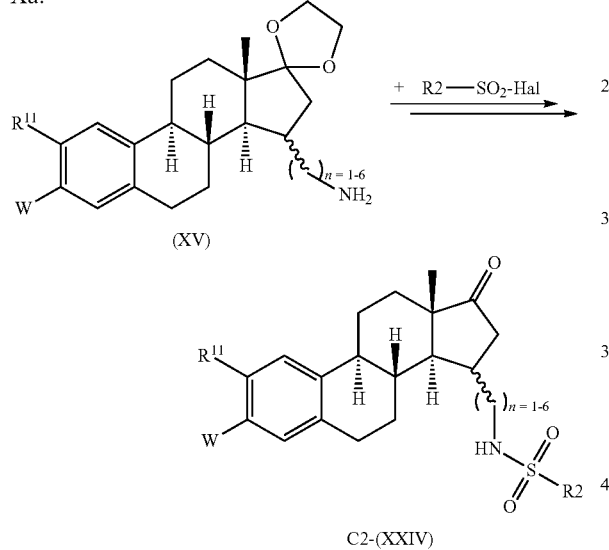

C2-(XXIV)

wherein W represents $R^1$ or —O-PG, and $R^1$, $R^2$ and $R^{11}$ have the meanings as defined herein, and PG is a common protecting group. The sulfonamide derivatives of the general formula C2-(XXIV) may be prepared by the reaction of the amine building block (XV) with an appropriate sulfonic acid halide, e.g. a sulfonic acid chloride ($R^2$—SO$_2$—Cl). After the addition-elimination reaction, in a second step the ketal function is converted into the keto function. Alternatively, the reaction with an appropriate sulfonic acid halide, e.g. sulfonic acid chloride ($R^2$—SO$_2$—Cl), can be performed using the aminohydrochloride salt of the estrone (XXIX) as starting material as shown in the following Flow Diagram Xb:

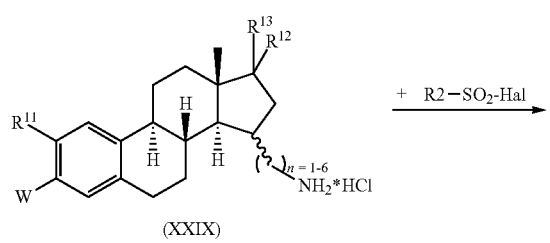

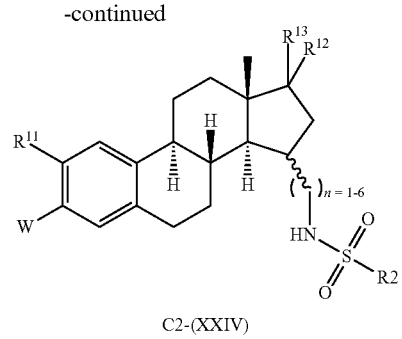

C2-(XXIV)

wherein W represents $R^1$ or —O-PG, and $R^1$, $R^2$, $R^{11}$, $R^{12}$ and $R^{13}$ have the meanings as defined herein, and PG is a common protecting group.

Certain formula I compounds, in which —X-A-Y— represents —NH—CO—NH—SO$_2$—, and n represents an integer from 1 to 6, may be prepared by a reaction as shown in Flow Diagram XI:

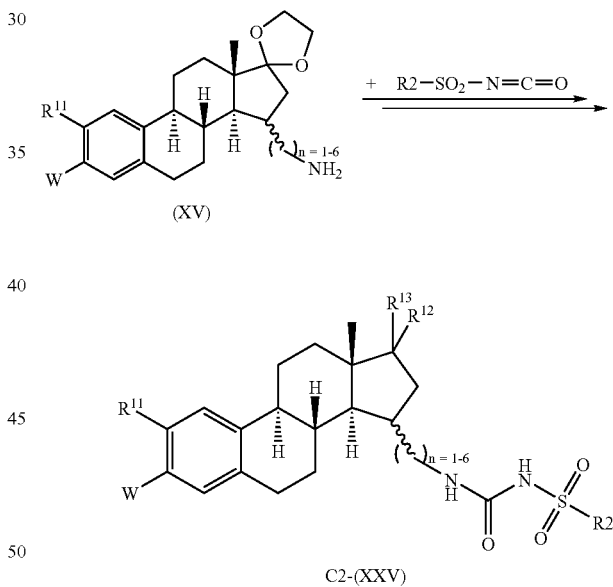

C2-(XXV)

wherein W represents $R^1$ or —O-PG, and $R^1$, $R^2$ and $R^{11}$ have the meanings as defined herein, and PG is a common protecting group. The sulfonyl urea derivatives of the general formula C2-(XXV) may be prepared by the reaction of the amine building block (XV) with an appropriately substituted sulfonyl isocyanate ($R^2$—SO$_2$—N=C=O). After the addition, the ketal function is converted into the keto function.

Certain formula I compounds, in which —X-A-Y— represents —O—CO—NR$^4$— and n represents an integer from 1 to 6, may be prepared by a reaction as shown in Flow Diagram XII:

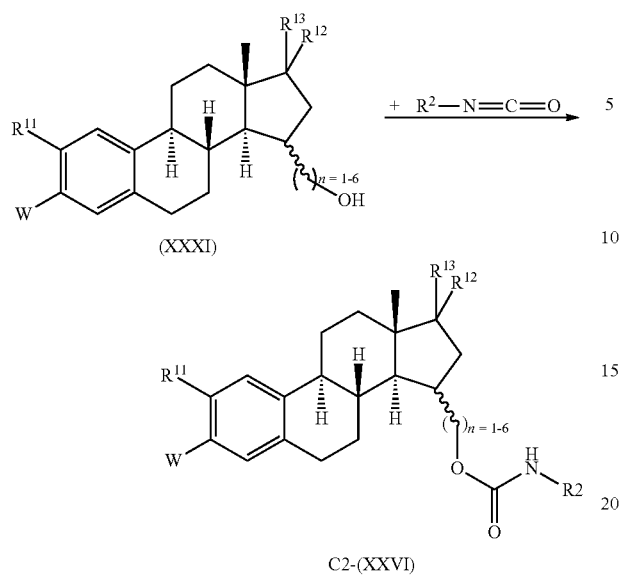

(XXXI)

C2-(XXVI)

wherein W represents $R^1$ or —O-PG, and $R^1$, $R^2$, $R^{11}$, $R^{12}$ and $R^{13}$ have the meanings as defined herein, and PG is a common protecting group. The "retro"-carbamate derivatives of the general formula C2-(XXVI) may be prepared by the reaction of the estrone alcohol building block (XXXI) with an appropriately substituted isocyanate ($R^2$—N=C=O) and subsequent purification.

Certain formula I compounds, in which —X-A-Y— represents —O—CO— and n represents an integer from 1 to 6, may be prepared by a reaction as shown in Flow Diagram XIII:

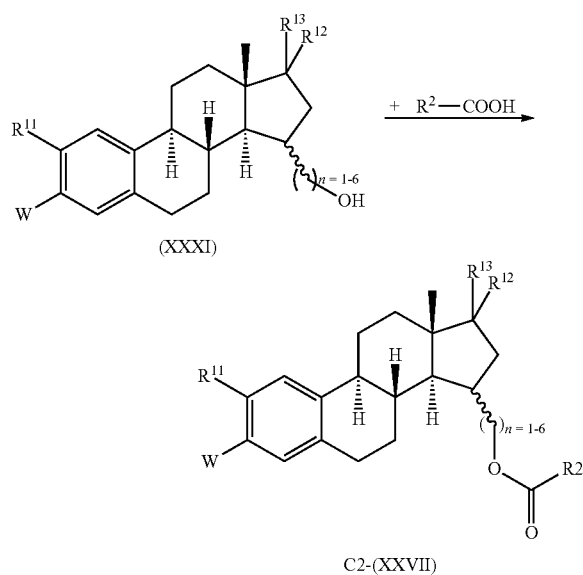

(XXXI)

C2-(XXVII)

wherein W represents $R^1$ or —O-PG, and $R^1$, $R^2$, $R^{11}$, $R^{12}$ and $R^{13}$ have the meanings as defined herein, and PG is a common protecting group. The "retro"-ester derivatives of the general formula C2-(XXVII) may be prepared by the esterification of the estrone alcohol building block (XXXI) with the appropriate carboxylic acid $R^2$—COOH and subsequent purification.

Certain formula I compounds, in which —X-A-Y— represents —O—CO—NH—SO$_2$—NR$^4$—, and n represents an integer from 1 to 6, may be prepared by a reaction as shown in Flow Diagram XIV:

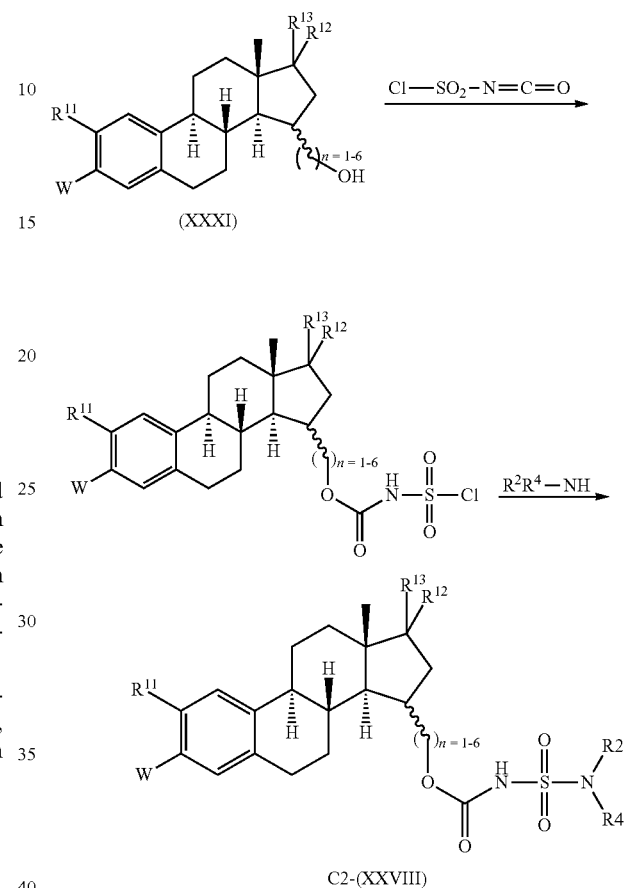

(XXXI)

C2-(XXVIII)

wherein W represents $R^1$ or —O-PG, and $R^1$, $R^2$, $R^4$, $R^{11}$, $R^{12}$ and $R^{13}$ have the meanings as defined herein, and PG is a common protecting group. The sulfonylcarbamate derivatives of the general formula C2-(XXVIII) may be prepared by a two-step synthesis: In a first step, the estrone alcohol building block (XXXI) is converted to the chlorosulfonylcarbamate intermediate by reaction with chlorosulfonyl isocyanate. Subsequently, the intermediate is allowed to react with the appropriate primary or secondary amine HNR$^2$R$^4$ in in order to give the desired sulfonylcarbamate derivative.

Certain formula I compounds, in which X-A-Y represents —O—, and $R^2$ is different from H may be prepared by a reaction as shown in Flow Diagram XV:

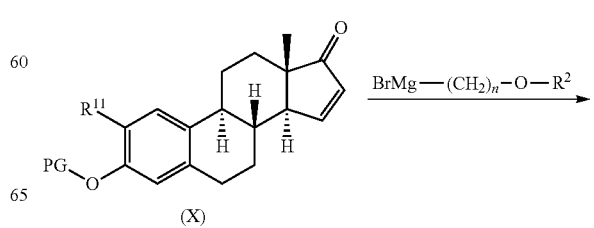

(X)

-continued

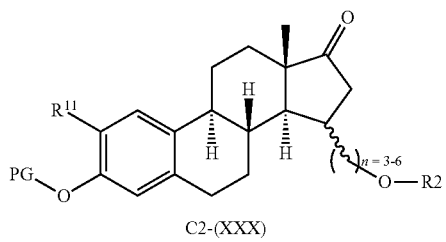

C2-(XXX)

wherein $R^2$ and $R^{11}$ have the meanings as defined herein, and PG is a common protecting group. The ether derivatives of the general formula C2-(XXX) may be prepared the reaction of an appropriate Grignard reagent $BrMg$—$(CH_2)_n$—$O$—$R^2$ (for n=3-6) with the 15,16-unsaturated estrone derivative of formula X. Alternatively, ether derivatives may be prepared by derivatisation of the corresponding alcohol of the general formula (XXXI).

The synthesis of certain formula I compounds, in which X-A-Y represents —O—, $R^2$ represents H, and n represents an integer from 1 to 6, according to general formula C2-(XXXI) is known in the state of the art:

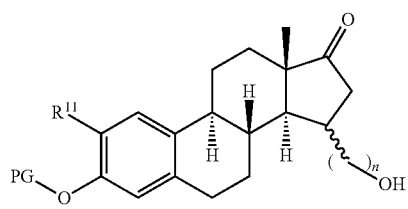

C-(XXXI)

wherein $R^{11}$ has the meaning as defined herein, and PG is a common protecting group.

The synthesis of certain formula I compounds, in which X-A-Y represents a group

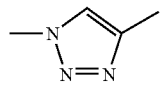

and n represents an integer from 1 to 6, may be prepared by a reaction as shown in Flow Diagram XVIa

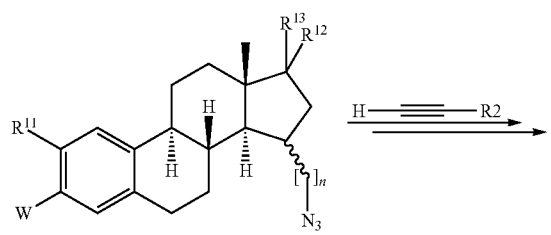

-continued

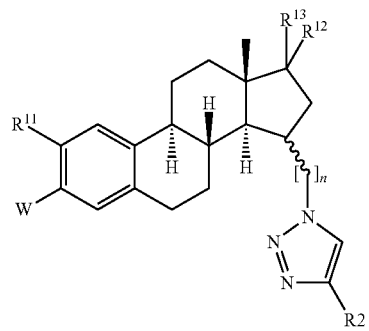

wherein W represents $R^1$ or —O-PG, and $R^1$, $R^2$, $R^{11}$, $R^{12}$ and $R^{13}$ have the meanings as defined herein, and PG is a common protecting group. The synthesis of the C15 substituted azide derivate might be achieved by conventional synthesis methods as already depicted within international patent application WO2005/047303, in patent application WO2006/125800, in unpublished International patent application PCT/EP2007/059785 and as described herein in the "intermediates" section. Then the coupling of the azide with a terminal alkinyl delivering the desired triazole derivatives may be carried out by using a method for the formation of 1,4 disubstituted triazoles well known to one skilled in the art of organic synthesis (see e.g. WO2006/063585 and WO2003/101972 and references cited therein).

The synthesis of certain formula I compounds, in which X-A-Y represents a group

and n represents an integer from 1 to 6, may be prepared by a reaction as shown in Flow Diagram XVIb

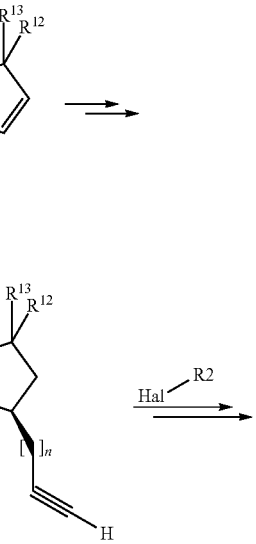

-continued

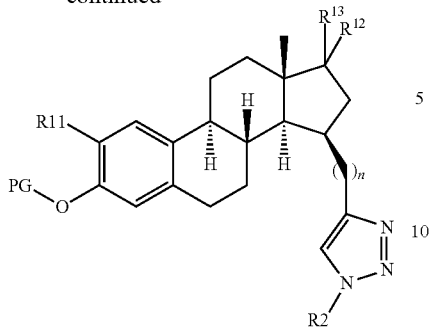

wherein $R^{11}$, $R^{12}$ and $R^{13}$ have the meanings as defined herein, and PG is a common protecting group. The synthesis of the C15 substituted alkine derivate might be achieved by conventional synthesis methods by coupling the respective 15,16-unsaturated estron with the corresponding alkine compound in a Grignard reaction (e.g. as depicted within international patent application WO2005/047303, in patent application WO2006/125800, and unpublished International patent application PCT/EP2007/059785). Then the triazoles are prepared from the alkine substituted estron derivate and the corresponding $R^2$ halides via in situ generated azides (as depicted in unpublished International patent application PCT/EP2007/059785). The one pot synthesis for specific aryl triazoles is described in detail in Andersen et al. (2005).

The synthesis of certain formula I compounds, in which X-A-Y represents a group

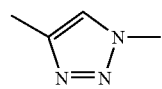

and n represents an integer from 3 to 4, may be prepared by a reaction as shown in Flow Diagram XVIc

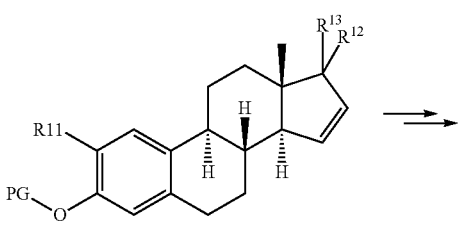

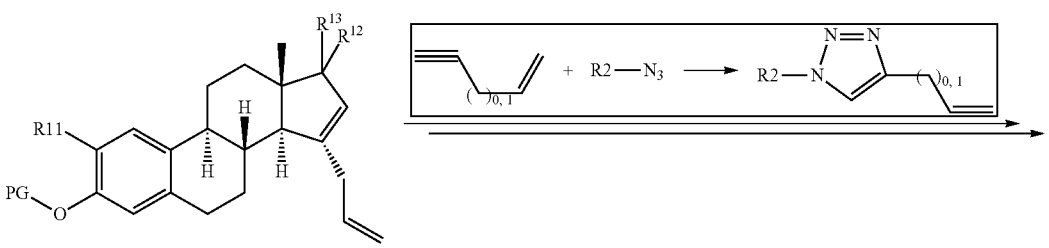

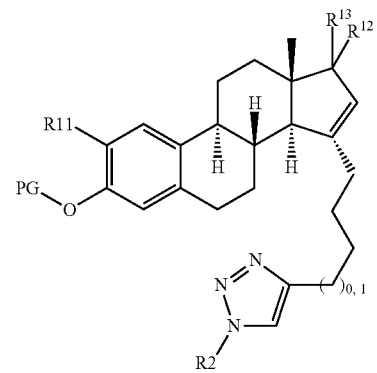

wherein $R^{11}$, $R^{12}$ and $R^{13}$ have the meanings as defined herein, and PG is a common protecting group. Starting from the 15,16-unsaturated estron derivative, the preparation of the 15, 16 unsaturated allyl derivate is described in detail in WO2006/125800$^{Error!\ Bookmark\ not\ defined.}$. Then, the introduction of the triazole moiety, being synthesized from the corresponding allyl alkine in reaction with the desired azide, is achieved by chain elongation (e.g. via olefin metathesis using a Grubb II catalyst). Finally, the reduction of the double bond leads to the still O-protected Triazoles.

Step D—Difluorination of the C17-Keto Function

The aim of this step is the difluorination of the C17 carbonyl function to obtain one of the following intermediate compounds according to reaction SCHEMES 2 or 3:

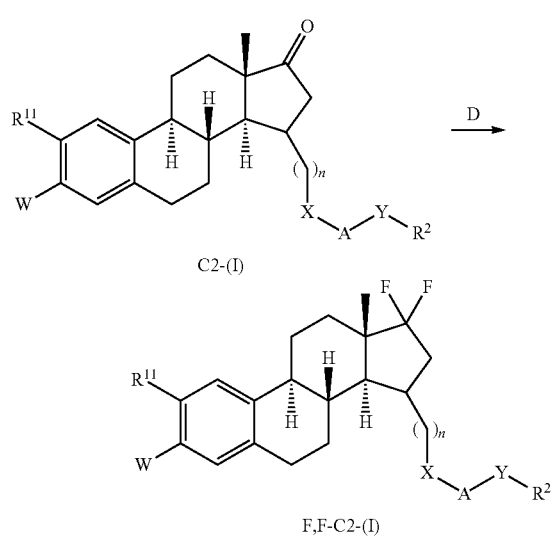

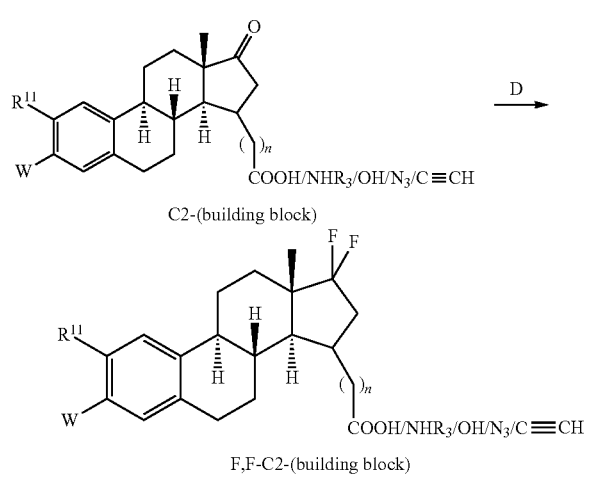

wherein W represents —O-PG or $R^1$, and $R^1$, $R^2$, $R^3$, $R^{11}$, X, A and Y have the meanings as defined herein, and PG is a common protecting group. Since the C15-side chain as well as optionally the C2 and or C3 side chain might have been already introduced, it is clear for the skilled artisan, that, where necessary, functional groups should be protected in known manner and the protecting group or groups removed at the end of the reaction.

The difluorination of the C17 atom of the estrone core is a reaction well known in the art and was already disclosed in U.S. Pat. Nos. 3,413,321 and 3,347,878. Furthermore, the difluorination of the C17 atom of the estrone core may be achieved using the DAST (N,N-diethylaminosulfur trifluoride) reagent [Liu et al (1992)].

Step E—Modification of the C3 Hydroxy Function

The compounds of the present invention are characterized by replacement of the C3 hydroxy function of the steroidal core by a boronic acid, carboxylic acid, carboamide, amino, amide or sulfonamide moiety, i.e. the compounds of formula (I) carry a $R^1$ residue represented by (a) —B(OR$^9$)(OR$^{10}$)
(b) —CO—OR$^6$
(c) —CO—NR$^7$R$^8$
(d) —NR$^7$R$^8$
(e) —NR$^5$—CO—R$^6$, or
(f) —NR$^5$—SO$_2$—R$^6$ This substitution step E is carried out with the building blocks as starting material and/or after introduction of the finally desired C15 side chain (step C(II)) as depicted in the following SCHEME 4:

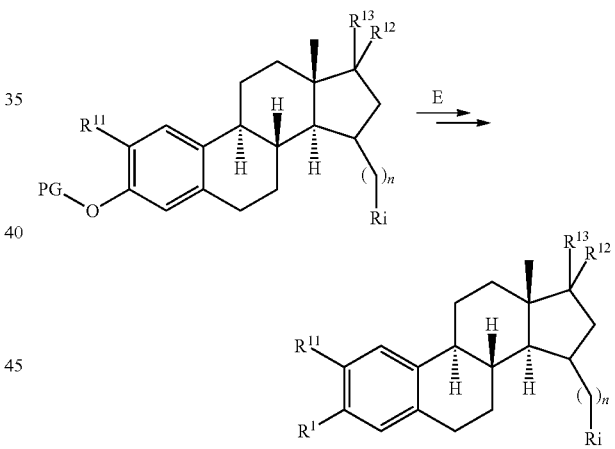

wherein Ri represents an optionally protected group —COOH, —OH, —NHR$^3$, —N$_3$, =CH$_2$ or =CH group or X-A-Y—R$^2$, and X-A-Y, $R^1$, $R^2$, $R^4$, $R^{11}$, $R^{12}$ and $R^{13}$ have the meanings as defined herein, and PG is a common protecting group. Any reactive groups might be protected with conventional protection groups during the course of this reaction. Since the C15-side chain as well as optionally the C2 and or C3 side chain might have been already introduced, it is clear for the skilled artisan, that, where necessary, functional groups should be protected in known manner and the protecting group or groups removed at the end of the reaction.

(a) Introduction of a Boronic Acid or Boronic Ester Group in C3 Position

The step E(a) reaction to obtain a steroid derivative in which the 3-OH of estrone is replaced by B(OH)$_2$ can be achieved according to the protocol disclosed by Ahmed et al (2006) and as displayed in the following SCHEME 5:

73

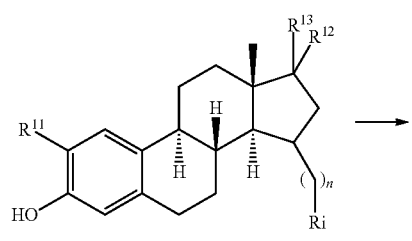

74

-continued

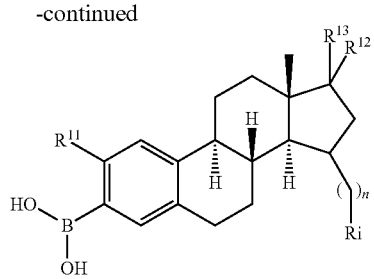

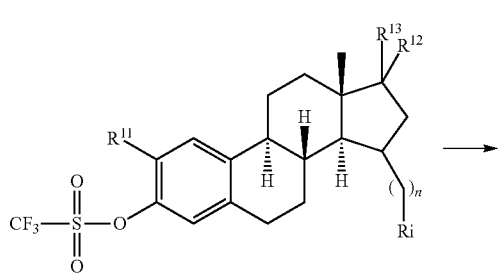

wherein Ri represents an optionally protected group —COOH, —OH, —NHR$^3$, —N$_3$, =CH$_2$ or ≡CH group or X-A-Y—R$^2$, and X-A-Y, R$^2$, R$^{11}$, R$^{12}$ and R$^{13}$ have the meanings as defined herein, and PG is a common protecting group. Any reactive groups might be protected with conventional protection groups during the course of this reaction. First a steroid derivative was converted into the corresponding C3 triflate [obtainable e.g. as described in Li et al (1995) or as described herewithin in the section Intermediates "Step E"]. Then, the estrone triflate was reacted with pinacolborane in the presence of a palladium catalyst to give the corresponding boronate ester. Subsequent reaction of the ester with NaIO4 in ammonium acetate/water for several days gave the desired boronic acid compound. Alternatively, the borone cross-coupling can be achieved by coupling with either bis(pinacolato)diborone or bis(neopentylgluconato)diboron at 100° C. for 14 h, or with pinacolborane in the presence of 10% DMSO. Saponification of the boronic acid can also be achieved with LiOH or in 3N HCl under addition of phenylboronic acid (coated on polymer). Alternatively, the pinacolyl boronate ester is converted into the corresponding potassium trifluoroborate salt through treatment with excess potassium hydrogen fluoride, and subsequently treatment of the potassium trifluoroborate salt i with trimethylsilyl chloride in water/acetonitrile mixture afforded the free boronic acid [Yuen & Hutton (2005)]. The exact conditions may vary depending on the actual substitution of the steroid core.

In general, diverse boronic ester derivatives can be synthesized according to the following general SCHEME 6A:

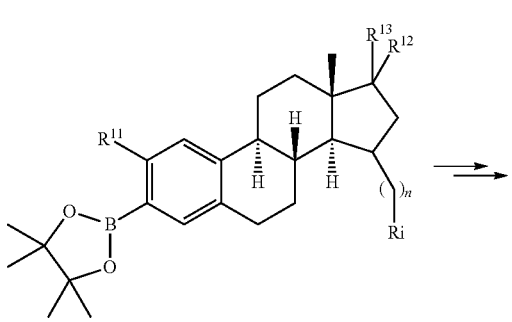

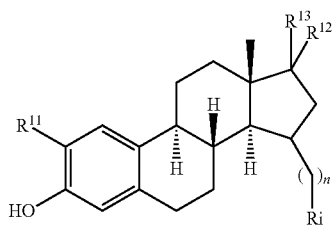

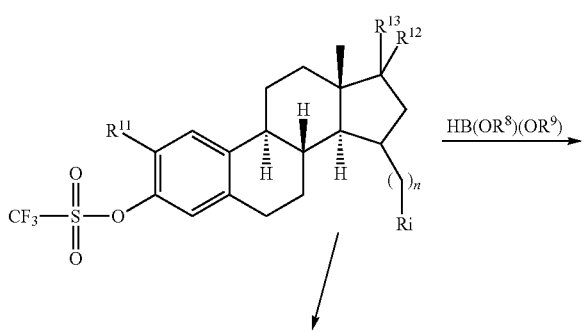

HB(OR$^8$)(OR$^9$)

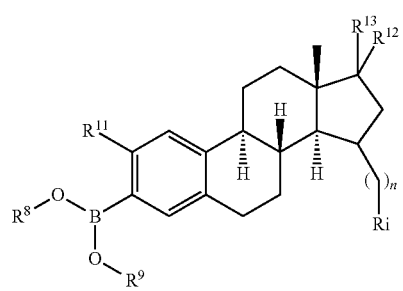

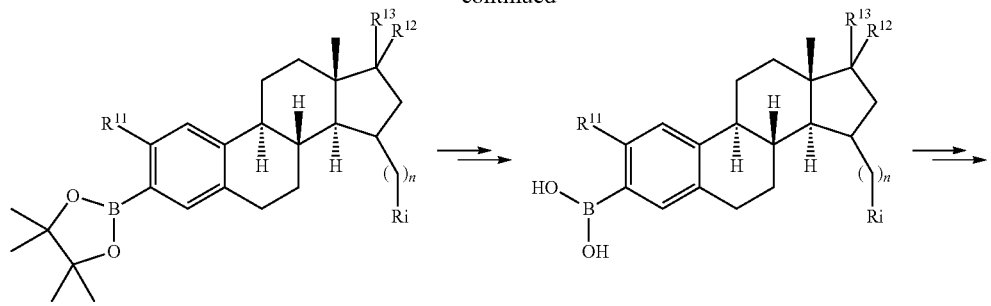

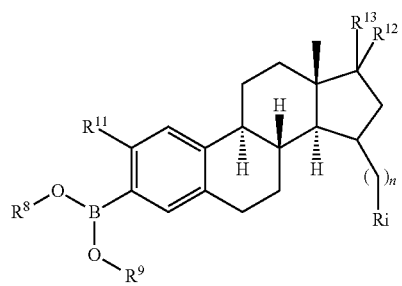

wherein Ri represents an optionally protected group —COOH, —OH, —NHR$^3$, —N$_3$, =CH$_2$ or ≡CH group, or X-A-Y—R$^2$, and X-A-Y, R$^2$, R$^8$, R$^9$, R$^{11}$, R$^{12}$ and R$^{13}$ have the meanings as defined herein, but R$^8$ and R$^9$ cannot represent —H. In one alternative, the C3 triflate of the estrone derivative is directly reacted with a borane ester delivering the desired compounds, whereas the second alternative uses the pathway described in SCHEME 5 and subsequent esterification of the free boronic acid.

(b) Introduction of a Carboxylic Acid Group in C3 Position

The step E(b) reaction to obtain a steroid derivative in which the 3-OH of estrone is replaced by —CO—O—R$^6$, wherein R$^6$ has the meaning as defined herewithin, can be achieved according to the protocol disclosed by Lesma et al (2006) and variations thereof as displayed in the following SCHEME 6B:

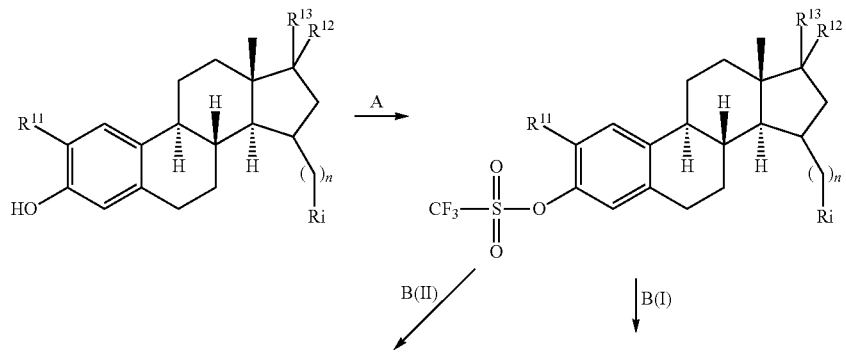

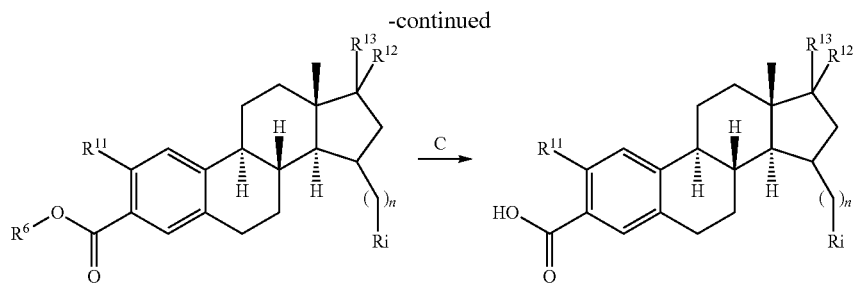

wherein Ri represents an optionally protected —COOH, —OH, —NHR$^3$, —N$_3$, =CH$_2$, ≡CH or X-A-Y—R$^2$ group, and X-A-Y, R$^2$, R$^{11}$, R$^{12}$ and R$^{13}$ have the meanings as defined herein. Any reactive groups might be protected with conventional protection groups during the course of this reaction. First a steroid derivative was converted into the corresponding C3 triflate (step A) [obtainable e.g. as described in Li et al (1995) or as described herewithin in the section Intermediates "Step E"]. Then, alkoxycarbonylation of the substituted steroid triflates is carried out using palladium (0) as metal catalyst (in situ generated from Pd(II) and a suitable phosphine ligand) and Mo(CO)$_6$ as a commercially available, stable and solid carbon monoxide source in a microwave system. When the reaction is carried out in water, the corresponding carboxylic acids are directly available (step B(I)). Alternatively, when adding the corresponding R$^6$—OH alcohol in a suitable solvent, the corresponding carboxylic acid ester is obtained (step B(II)). Depending on the additional substitutions of the steroidal core, it might be necessary first to produce the carboxylic acid ester, which is then finally hydrolysed to give the desired free carboxylic acid (step C).

(c) Introduction of a Amide Group in C3 Position

The step E(c) reaction to obtain a steroid derivative in which the 3-OH of estrone is replaced with —CO—NR$^7$R$^8$, wherein R$^7$ and R$^8$ have the meanings as defined herewithin, can be achieved starting from the corresponding free carboxylic acid obtained according to SCHEME 6B as displayed in the following SCHEME 6C-I,

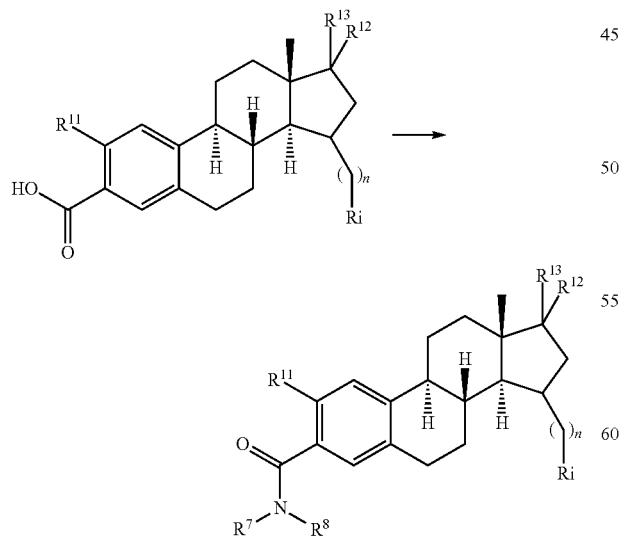

wherein Ri represents an optionally protected —COOH, —OH, —NHR$^3$, —N$_3$, =CH$_2$, ≡CH or X-A-Y—R$^2$ group, and X-A-Y, R$^2$, R$^7$, R$^8$, R$^{11}$, R$^{12}$ and R$^{13}$ have the meanings as defined herein. Any reactive groups might be protected with conventional protection groups during the course of this reaction. The carboxylic acid is converted into the desired amide via a well known nucleophilic substitution reaction with the corresponding primary or secondary amine R$^7$R$^8$—NH as nucleophilic substituent carried out in a suitable aprotic solvent, in the presence of a suitable coupling reagent (e.g. HOBT) and/or a compound with a carbodiimide functionality (e.g. PS-Carbodiimide or EDCl) and an appropriate unreactive base if desired, added to activate the carboxylic acid.

An alternative synthesis pathway directly starts from the C3 hydroxy steroid derivative and can be achieved according to the protocol disclosed by Morera & Ortar (1998) and variations thereof as to the following SCHEME 6C-II

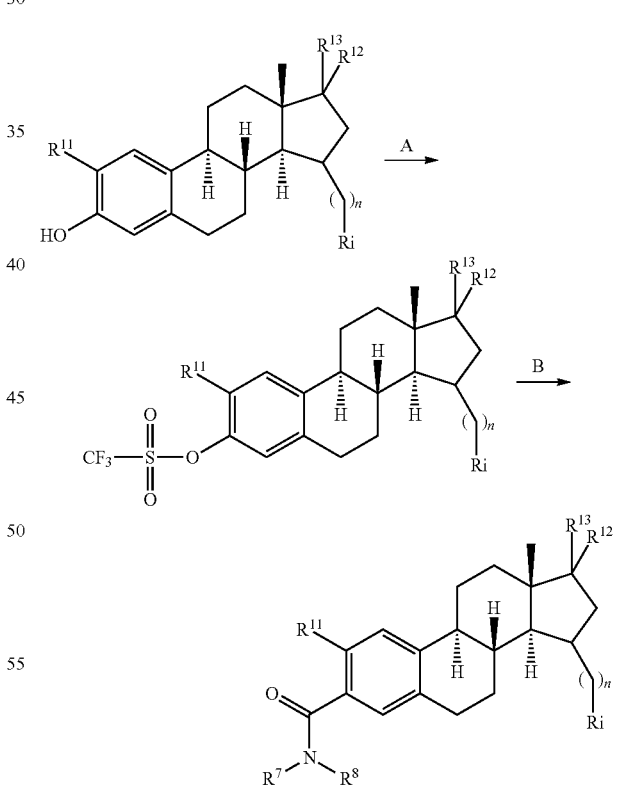

wherein Ri represents an optionally protected group —COOH, —OH, —NHR$^3$, —N$_3$, =CH$_2$≡CH group or X-A-Y—R$^2$, and X-A-Y, R$^2$, R$^7$, R$^8$, R$^{11}$, R$^{12}$ and R$^{13}$ have the meanings as defined herein. Any reactive groups might be protected with conventional protection groups during the course of this reaction. First a steroid derivative is converted into the corresponding C3 triflate (step A) [obtainable e.g. as described in Li et al (1995) or as described herewithin in the section Intermediates "Step E"]. Then, aminocarbonylation of the substituted steroid (=aryl) triflates is carried out using palladium (0) as metal catalyst and a suitable carbon monoxide source (e.g. carrying out the reaction under CO atmosphere or, more convenient Mo(CO)$_6$ as described above for SCHEME 6B) in the presence of the corresponding amine $R^7R^8$—NH in a suitable solvent delivering the desired amide.

(d) Introduction of an Amino Group in C3 Position

The step E(d) reaction to obtain a steroid derivative in which the 3-OH of estrone was replaced by —$NR^7R^8$, wherein $R^7$ and $R^8$ have the meanings as defined herewithin, can be achieved according to the protocol disclosed by Schoen et al (2005) and variations thereof as displayed in the following SCHEME 6D:

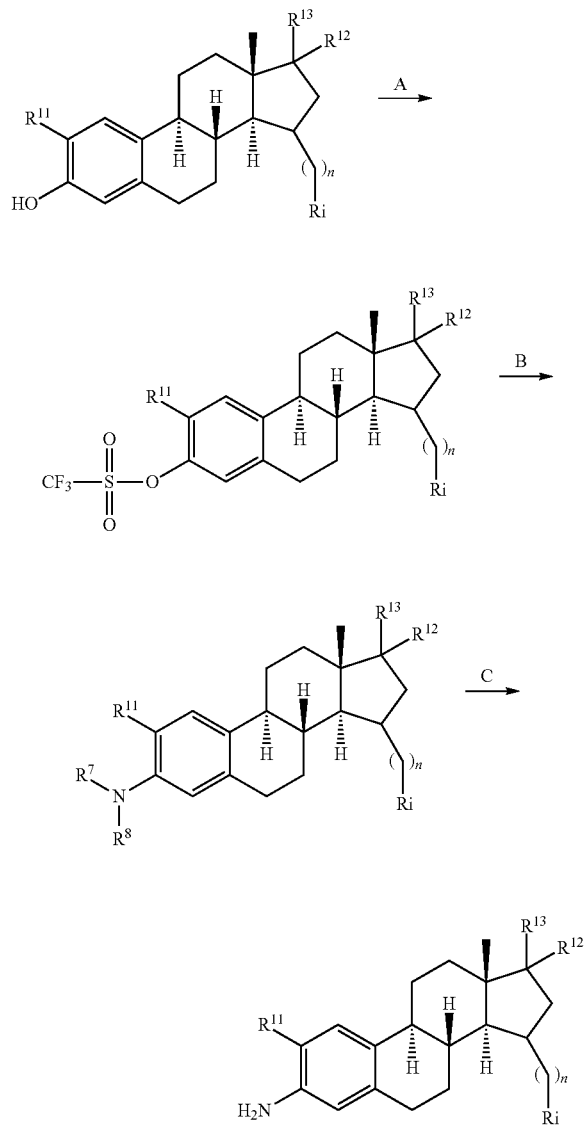

wherein Ri represents an optionally protected group —COOH, —OH, —NHR$^3$, —N$_3$, =CH$_2$ or ≡CH group or X-A-Y—R$^2$, and X-A-Y, R$^2$, R$^7$, R$^8$, R$^{11}$, R$^{12}$ and R$^{13}$ have the meanings as defined herein. Any reactive groups might be protected with conventional protection groups during the course of this reaction. First a steroid derivative is converted into the corresponding C3 triflate (step A) [obtainable e.g. as described in Li et al (1995) or as described herewithin in the section Intermediates "Step E"]. Then, amination of the substituted steroid (=aryl) triflates is carried out using palladium (0) as metal catalyst and the corresponding $R^7R^8$—NH amine (step B). Optimally, the reaction is carried out in a microwave system using DMF as solvent. If desired, the secondary or tertiary amine can be subsequently hydrogenated to deliver the corresponding primary amine (step C).

(e) Introduction of a Carbo Amide Group in C3 Position

The step E(e) reaction to obtain a steroid derivative in which the 3-OH of estrone is replaced with —NR$^5$—CO—R$^6$, wherein R$^5$ and R$^6$ have the meanings as defined herewithin, can be achieved starting from the corresponding primary or secondary amine obtained according to SCHEME 6D as displayed in the following SCHEME 6E,

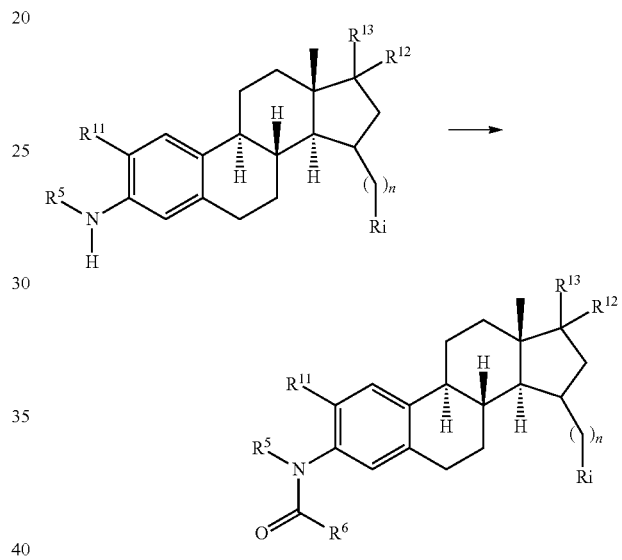

wherein Ri represents an optionally protected —COOH, —OH, —NHR$^3$, —N$_3$, =CH$_2$, ≡CH or X-A-Y—R$^2$ group, and X-A-Y, R$^2$, R$^5$, R$^6$, R$^{11}$, R$^{12}$ and R$^{13}$ have the meanings as defined herein. Any reactive groups might be protected with conventional protection groups during the course of this reaction. The amine is converted into the desired carbo amide via a well known nucleophilic substitution reaction with the corresponding carboxylic acid R$^6$—COOH or carboxylic acid halide R$^6$—CO-Hal carried out in a suitable aprotic, inert solvent. If a carboxylic acid R$^6$—COOH is used, the reaction has to be carried out in the presence of a suitable coupling reagent (e.g. HOBT) and/or a compound with a carbodiimide functionality (e.g. PS-Carbodiimide or EDCl) and an appropriate unreactive base if desired, to activate the carboxylic acid. If a carboxylic acid halide R$^6$—CO-Hal is used, the reaction has to be carried out in the presence of an unreactive base, e.g. Hünig base.

(f) Introduction of a Sulfonamide Amino Group in C3 Position

The step E(f) reaction to obtain a steroid derivative in which the 3-OH of estrone is replaced with —NR$^5$—SO$_2$—R$^6$, wherein R$^5$ and R$^6$ have the meanings as defined herewithin, can be achieved starting from the corresponding primary or secondary amine obtained according to SCHEME 6D as displayed in the following SCHEME 6F,

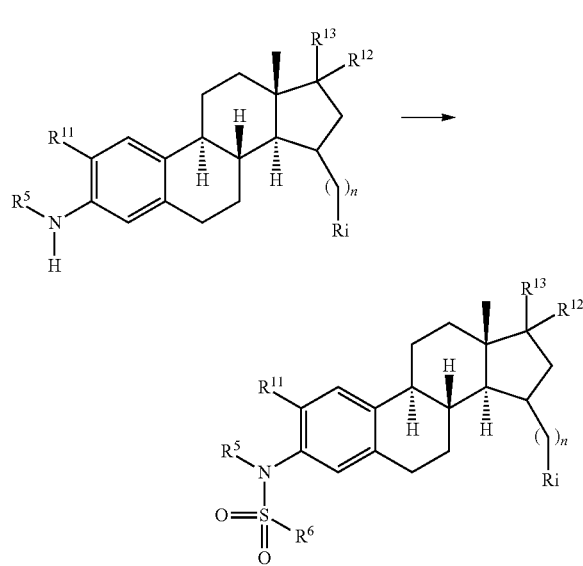

wherein Ri represents an optionally protected —COOH, —OH, —NHR$^3$, —N$_3$, =CH$_2$, ≡CH or X-A-Y—R$^2$ group, and X-A-Y, R$^2$, R$^5$, R$^6$, R$^{11}$, R$^{12}$ and R$^{13}$ have the meanings as defined herein. Any reactive groups might be protected with conventional protection groups during the course of this reaction. The amine is converted into the desired sulfonamide via a well known nucleophilic substitution reaction with the corresponding sulfonic acid halide R$^6$—SO$_2$-Hal carried out in a suitable aprotic, inert solvent and in the presence of an unreactive base, e.g. Hünig base.

EXPERIMENTAL

Examples of preparations of compounds of the invention are provided in the following detailed synthetic procedures.

In single compound synthesis as well as in combinatorial synthesis, all reactions were stirred magnetically or shaken with an orbital shaker unless otherwise indicated. Sensitive liquids and solutions were transferred via syringe or cannula, and introduced into reaction vessels through rubber septa, in these cases the reaction were carried out under a positive pressure of dry argon or dry nitrogen. Commercial grade reagents and solvents were used without further purification.

Unless otherwise stated, the term "concentration under reduced pressure" refers to use of a Buchi or Heidolph rotary evaporator ("Rotavapor") or vacuum centrifuges ("GeneVac" or "Christ alpha RVC") at approximately 15 mm of Hg. All temperatures are reported uncorrected in degrees Celsius (° C.). Unless otherwise indicated, all parts and percentages are by volume.

Thin-layer chromatography (TLC) was performed on Merck® pre-coated glass-backed silica gel or aluminium sheets 60A F-254 250 µm plates. Visualization of plates was effected by one or more of the following techniques: (a) ultraviolet illumination (254 nm or 266 nm), (b) exposure to iodine vapor, (c) spraying of the plate with Schlittler's reagent solution followed by heating, (d) spraying of the plate with anisaldehyde solution followed by heating, and/or (e) spraying of the plate with Rauxz reagent solution followed by heating. Column chromatography (flash chromatography) was performed using 230-630 mesh ICN, SiliTech 60A silica gel.

Melting points (mp) were determined using a Reichert Thermovar melting point apparatus or a Mettler DSC822 automated melting point apparatus and are uncorrected.

Proton ($^1$H) nuclear magnetic resonance (NMR) spectra were measured with a Bruker ARX (400 MHz) or Bruker ADVANCE (500 MHz) spectrometer with either Me$_4$Si (δ 0.00) or residual protonated solvent (CHCl$_3$ δ 7.26; CHD$_2$OD δ 3.30; DMSO-d$_5$ δ 2.50) as standard. Carbon ($^{13}$C) NMR spectra were measured with a Bruker ARX (100 MHz) or Bruker ADVANCE (126 MHz) spectrometer with either Me$_4$Si (δ 0.00) or solvent (CDCl$_3$ δ 77.05; CD$_3$OD δ 49.0; DMSO-d$_6$ δ 39.45) as standard.

HPLC electrospray mass spectra (LC-MS) were obtained using the following method and equipment: Samples were separated by reversed phase high pressure liquid chromatography (RP-HPLC) coupled to a quadrupol MS. HPLC was performed at a flow of 1000 µl/min using XterraMS C18 columns (i.d. 4.6 mm, length 50 mm, particle size 2.5 µm) or Phenomenex Luna C18(2) 30*4.6 mm columns. For most samples, a gradient from 0% eluent B to 95% B was run in 10 min, with eluent A consisting of water, 10 mM ammoniumacetate at pH 5+5% acetonitrile and eluent B consisting of acetonitrile. Two different setups were used: 1. Waters Alliance 2795 coupled to a Waters ZQ MS, a Waters 2996 diode array detector (DAD) and an evaporative light scattering detector (ELSD, EL-ELS1000, PolymerLabs). Ionization: electrospray positive and negative mode ES +/−; or 2. LC200 pump (PE) coupled to an API100 MS (Applied Biosystems Sciex), a variable wavelength detector Waters 2487 set to 225 nm, and an ELSD (Sedex 75), ES+. In both setup versions spectra were scanned with a scan range of m/z 100 to 800 or 100 to 900.

NMR spectra and LC-MS data of the compounds were consistent with the assigned structures.

Intermediates

I. Estrone Derivatives Substituted in C2 Position of the Steroidal Core of Formula (V) (Step A)

3-Benzyloxy-estra-1,3,5(10)-trien-2,17,β-diol (V-C2-A)

3-Benzyloxy-estra-1,3,5(10)-trien-2,17-diol can be prepared starting from estradiol by introduction of the hydroxy side chain in C2 position as described by Rao et al. (2002) in which a Fries rearrangement and a Baeyer Villiger reaction is used. Its detailed synthesis is displayed in international patent application WO2006/125800.

3-Benzyloxy-2-methoxy-estra-1,3,5(10)-triene-17one (V-C2-B)

3-Benzyloxy-2-methoxy-estra-1,3,5(10)-triene-17one was prepared starting from (V-C2-A) according to the procedure described by Rao et al. (2002) and within U.S. Pat. No. 6,043,236. Its detailed synthesis is displayed in international patent application WO2006/125800.

3-Benzyloxy-2-ethyl-estra-1,3,5(10)-triene-17one (V-C2-C)

3-Benzyloxy-2-ethyl-estra-1,3,5(10)-triene-17one was prepared starting from (C$_{2-4}$) by performing a Wolff-Kishner reduction to obtain the ethyl side chain. The oxidation of the C17 hydroxyl function was achieved by TPAP oxidation using the procedures of Ley et al (1994). Alternatively, 3-Benzyloxy-2-ethyl-estra-1,3,5(10)-triene-17-one was prepared starting from (C$_{2-3}$) by reduction of the acyl function which was achieved by reaction with Pd/C and H$_2$ [Gonzalez et al (1982)], subsequent benzylation of the 3-hydroxy function, deprotection of the C17 hydroxy function and TPAP oxidation. Its detailed synthesis is displayed in international patent application WO2006/125800.

3-Benzyloxy-2-ethoxy-estra-1,3,5(10)-triene-17one (V-C2-D) and 3-Benzyloxy-2-(2-methoxy-ethoxy)-estra-1,3,5(10)-triene-17one (V-C2-E)

In the first step, the 2-hydroxy function of 3-Benzyloxy-estra-1,3,5(10)-triene-2,17β-diol (C2-A) was alkylated using ethylsulfate and LiOH or methoxyethanol under Mitsunobu conditions. Subsequently, the alcohol was oxidated with TPAP and NMO to the corresponding estrone derivative. Their detailed synthesis is displayed in international patent application WO2006/125800.

3-Benzyloxy-2-(2-methoxy-ethyl)-estra-1,3,5(10)-triene-17one (V-C2-F)

Its detailed synthesis is disclosed published PCT application no. WO2006/125800.

3-Benzyloxy-2-propyl-estra-1,3,5(10)-triene-17one (V-C2-G) and 3-Hydroxy-2-propyl-estra-1,3,5(10)-triene-17-one (V-C2-G-a)

3-Benzyloxy-2-propyl-estra-1,3,5(10)-triene-17one was prepared starting from estradiol by introduction of the propionate side chain in C2 position as described by Rao et al. (2002) using a Fries rearrangement. Then the keto function is reduced to obtain the propyl side chain by reaction with Pd/C and $H_2$ [Gonzalez et al (1982)]. The subsequent oxidation of the $C_{1-7}$ hydroxyl function was achieved by TPAP oxidation using the procedures of Ley et al. (1994). Then the benzyloxy group is reduced to the hydroxyl function. The detailed synthesis protocol is displayed in international patent application WO2006/125800.

II. 15,16-unsaturated and C2 substituted Estrone derivatives of formula (X) (Step B)

The estrone of general formula V was converted into the corresponding 15,16 unsaturated derivative by the 4-step reaction as depicted in SCHEME 1 according to Nambara 1976: After protection of the C17 keto function as acetal (ethylene glycol, TEOF and p-TosOH in toluene, work-up with water and TEA), the acetal was brominated (with pyridinium perbromate and ethylene glycol in DME, work-up with $Na_2S_2O_3$). Subsequently, HBr was eliminated by reaction with K-O-tert-butyl in DMSO. Finally, the deprotection of the acetal was achieved with p-TosOH in DME and water.

III. Introduction of the Basic Side Chain in C15 Position—Synthesis of the So-called "Building Blocks"

The detailed synthesis of the following intermediates, wherein $R^{11}$ represents H, is fully disclosed in published PCT application no. WO2005/47303, whereas the detailed synthesis of intermediates, wherein $R^{11}$ is different from H, is fully disclosed in published PCt application no. WO2006/125800, which applications are both incorporated by reference herein. Furthermore, the detailed synthesis of intermediates, wherein $R^{12}$ and $R^{13}$ each represent F is also disclosed within international patent application WO2006/125800.

IIIa. The Optionally 2-Substituted Ketal Derivative of the Estron-15α-yl-carbaldehyde of Formula XIII-0

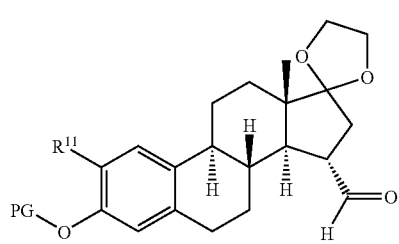

(XIII-0)

The protected aldehyde intermediate of formula XIII-0 with PG=$CH_3$ (XIIIb) or PG=Benzyl (XIIIc) can be prepared according to a procedure depicted within the following SCHEME 7:

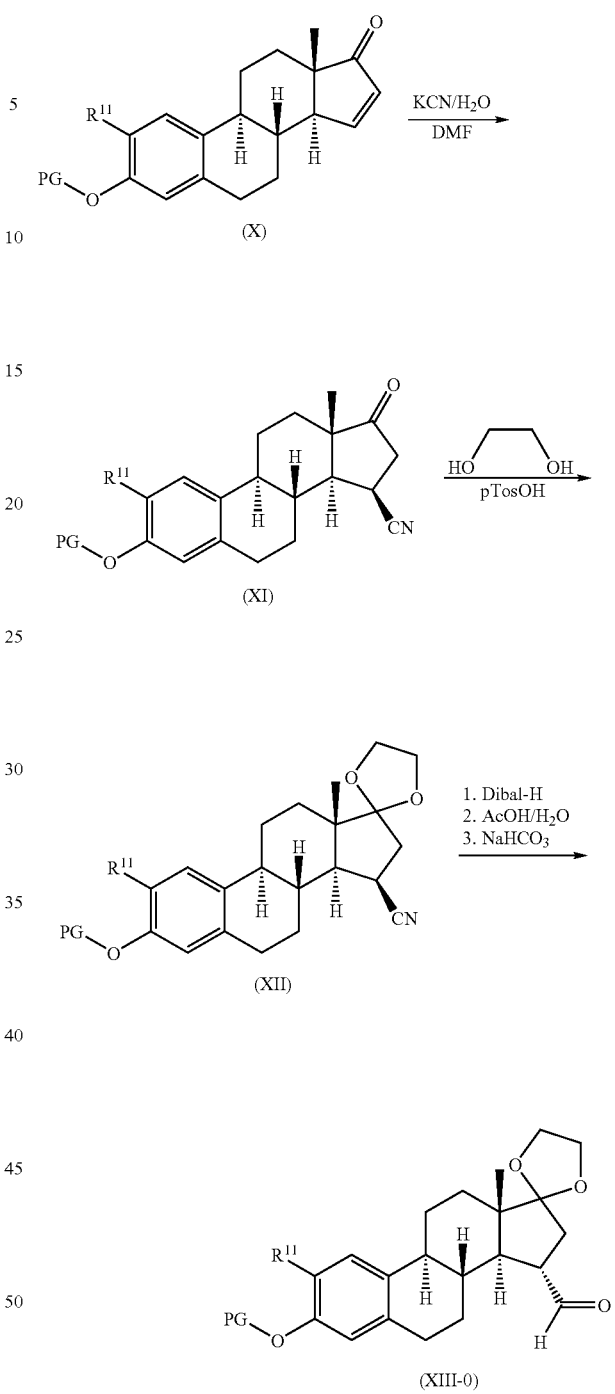

The optionally 2-substituted 15,16-unsaturated estrone of formula (X) is converted into the corresponding cyano-estrone (XI) by a cyanide Michael addition at the D-ring. The nitrile was introduced in the beta configuration as was proven by 2D-NMR. Epimerization of this stereocenter had been accomplished in a following step. First the ketone functionality was protected as the acetal (XII), followed by conversion of the nitrile to the corresponding aldehyde (XIII-0) by the addition of DIBAH to the nitrile and the consecutive hydrolysis of the imine product. At this stage the epimerization took place for about 90% (2D-NMR). Consecutive washing of the mixture with aqueous bicarbonate gave the α-isomer with a d.e≦98%.

IIIb. Optionally 2-Substituted Compounds of Formula IV:
Estron-15-yl-$C_0$-$C_5$-alkyl-carboxylic Acid
Acid Building Block IV-0: (n=0)

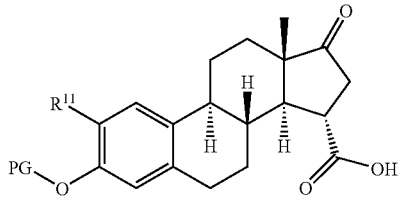
(IV-0)

The individual steps in the synthesis of acid building block of the formula IV-0b are depicted in the following SCHEME 8.

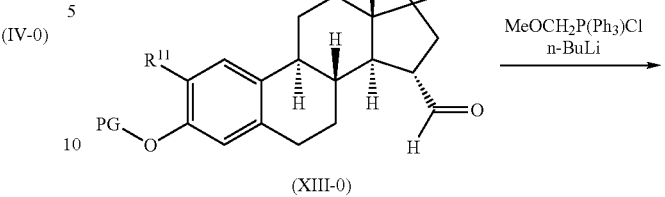

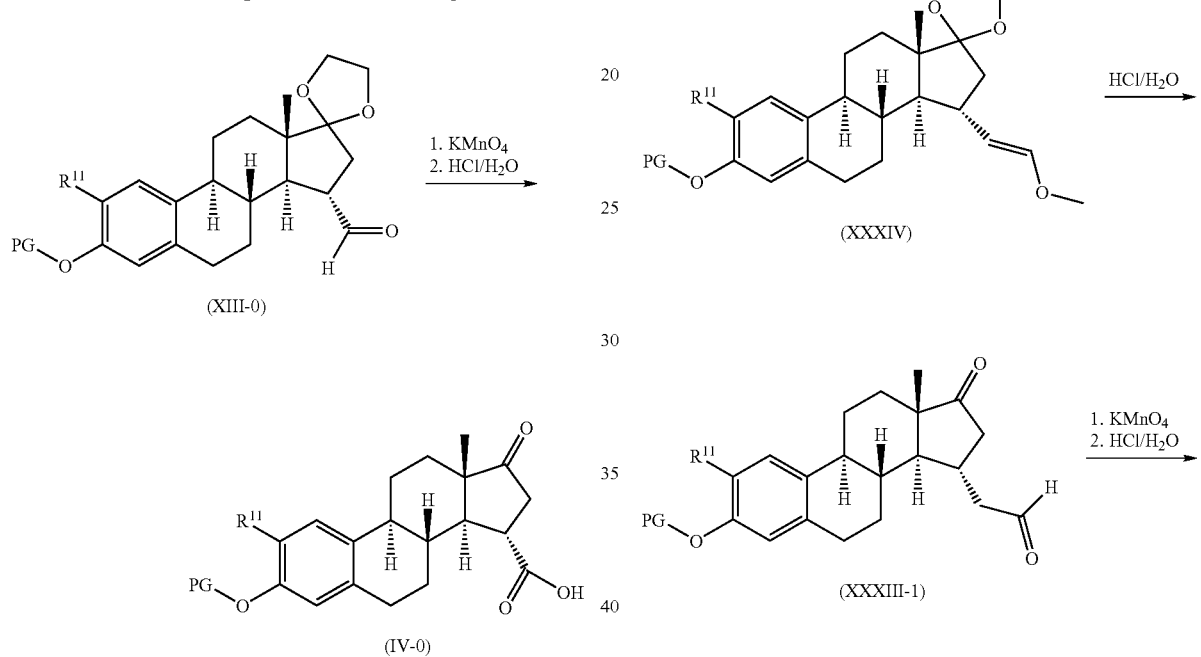

The ketal derivative of the optionally 2-substituted 17-oxo-estra-1,3,5(10)-trien-15α-yl-carbaldehyde of formula XIII-0 is oxidized to the corresponding carboxylic acid and converted into the unprotected 15α-substituted estrone derivative of formula IV-0.

Acid Building Block IV-1: (n=1):

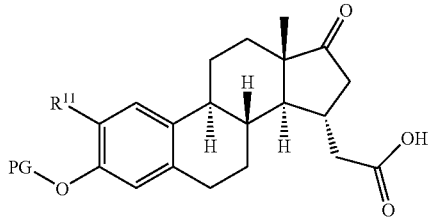
(IV-1)

The acid building block IV-1 may be synthesized via two different routes. The individual steps of the first synthesis route of acid building block IV-1 are depicted in the following SCHEME 9. The same kind of procedure can be applied for n=2 and for other side chains within the PG position.

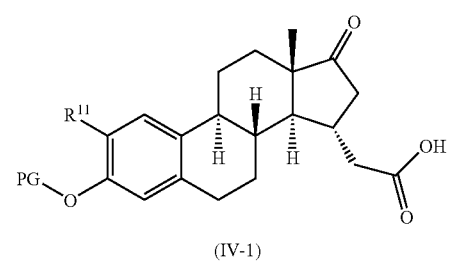
(IV-1)

The ketal derivative of the 17-oxo-estra-1,3,5(10)-trien-15α-yl-carbaldehyde of formula XIII-0 is converted into the methyl enol ether of the formula XXXIV via a Wittig reaction with MeOCH$_2$LiP(Ph)$_3$. Hydrolysis with HCl$_{(aq)}$ delivered the unprotected acetaldehyde derivative XXXIII-1. The acetaldehyde derivative is then further oxidized to the corresponding carboxylic acid IV-1.

Alternative Synthesis Route for the Acid Building Block IV-1: (n=1):

IV-1b: (n=1 and PG=CH$_3$): 3-Methoxy-17-oxo-estra-1,3,5 (10)-trien-15α-yl-acetic acid Alternatively, compound IV-1b can be prepared directly from the enone derivative of formula X according to the following synthesis SCHEME 10:

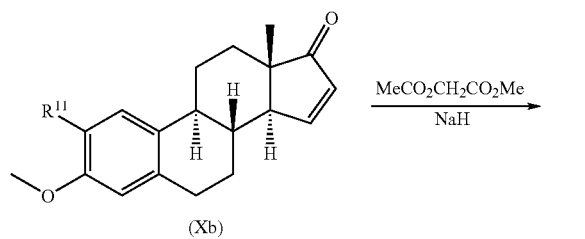

A Michael addition of the dimethylmalonate-anion to the enone derivative delivered the diester XXXVIb, which was converted into the acid building block of formula IV-b by alkaline ester hydrolysis and decarboxylation in refluxing acetic acid.

Optionally 2-Substituted Acid Building Block with β Stereochemistry at C15:

Optionally 2-Substituted Acid Building Blocks IVβ-3, IVβ-4, IVβ-5, IVβ-6 (n=3, 4, 5, 6):

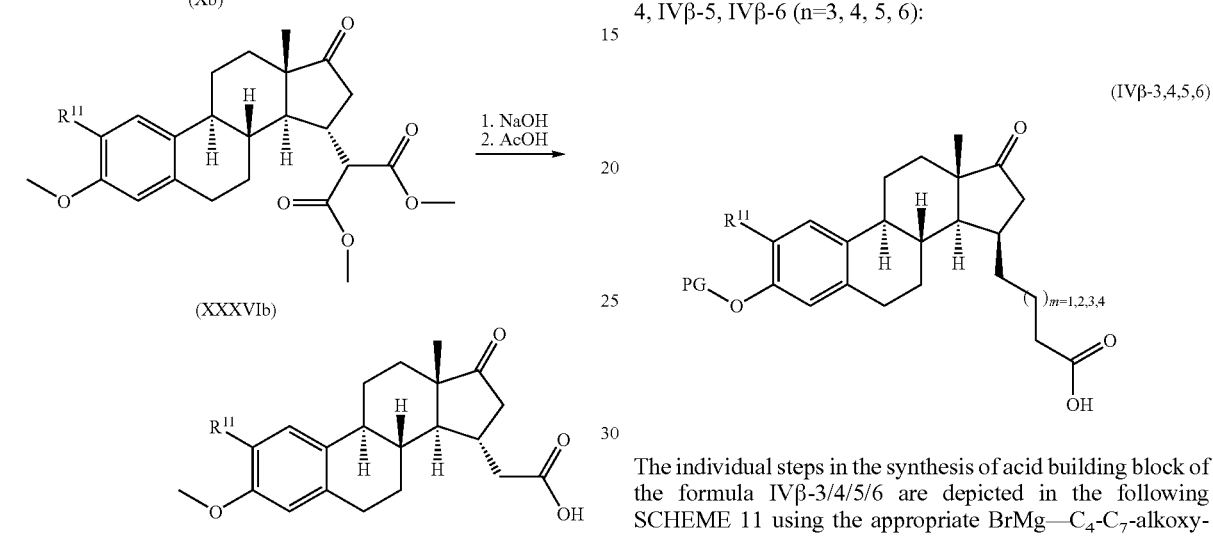

The individual steps in the synthesis of acid building block of the formula IVβ-3/4/5/6 are depicted in the following SCHEME 11 using the appropriate BrMg—$C_4$-$C_7$-alkoxy-THP as Grignard Reagent. Furthermore, this reaction scheme also delivers the estrone-alcohol building block in form of the intermediate of formula XXXIβ-4.

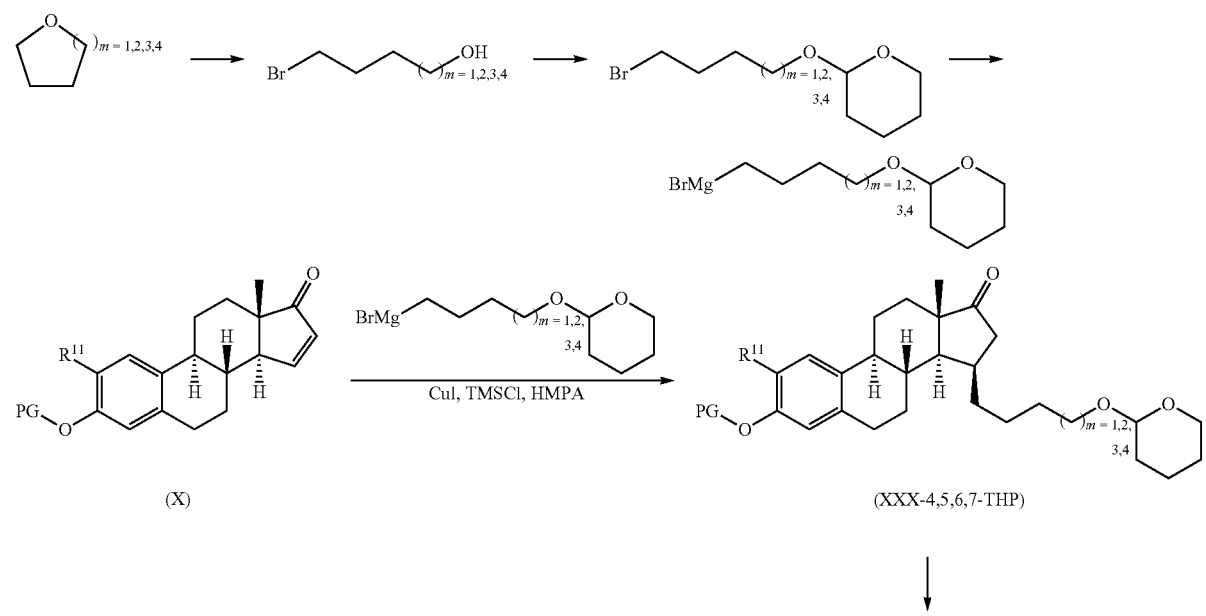

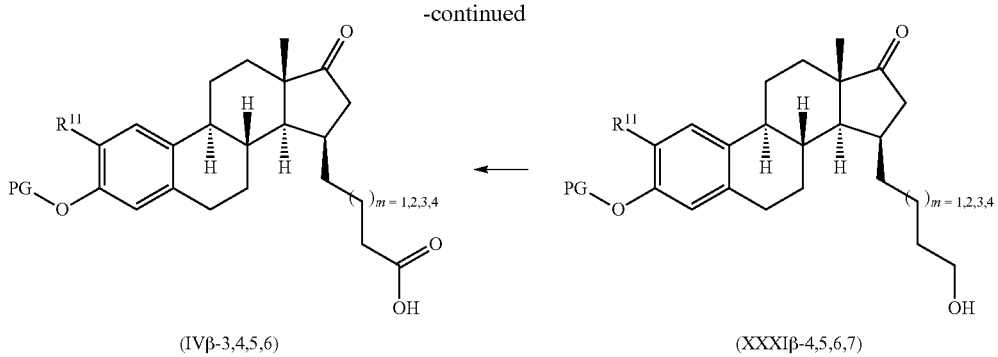

(IVβ-3,4,5,6)  (XXXIβ-4,5,6,7)

The 15,16-unsaturated Estrone derivative of formula X is subjected to a 1,4 addition using a freshly prepared Gringard Reagent delivering the corresponding alkoxy-THP derivative XXX-4,5,6,7-THP. This is further hydroxylated p-TosOH/MeOH to give the alcohol derivative XXXI-4,5,6,7b, which is converted, without purification, into the free acid IV-3b by a Jones oxidation.

Acid Building Block IVβ-2 (n=2): Optionally 2-Substituted 3-(3-Hydroxy-17-oxo-estra-1,3,5(10)-trien-15β-yl)-propanoic Acid

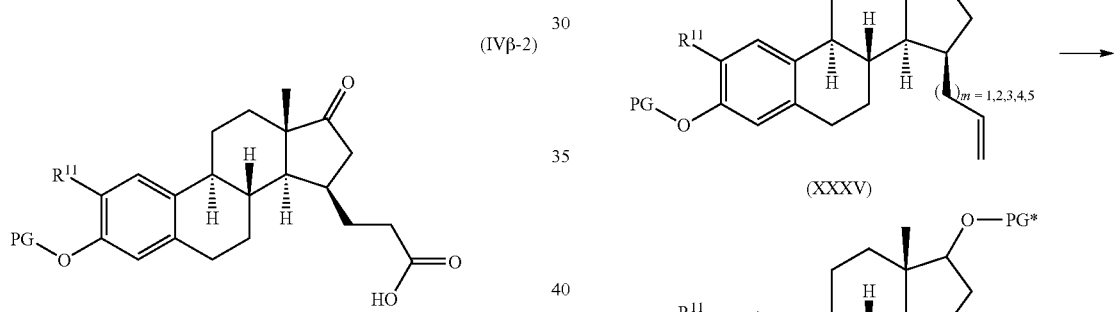

(IVβ-2)

The optionally 2-substituted carboxylic acid IVβ-2 can be prepared by oxidation of the alcohol derivative of formula XXXIβ-3 (synthesis see below) according to the preparation of the carboxylic acid IVβ-3.

Optionally 2-Substituted Acid Building Blocks IVβ-2, IVβ-3, IVβ-4, IVβ-5, IVβ-6 (n=3-6)

(IVb-2,3,4,5,6)

An alternative synthesis possibility for the acid building blocks IVβ-2, IVβ-3, IVβ-4, IVβ-5, IVβ-6 is depicted in the following SCHEME 13.

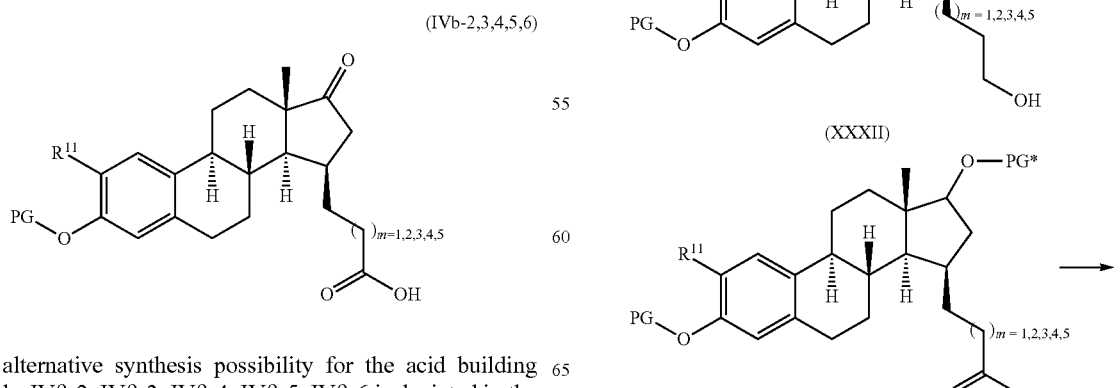

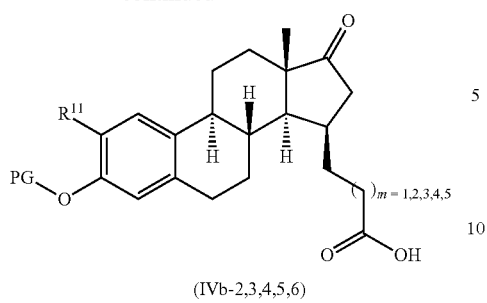

(IVb-2,3,4,5,6)

The 15,16-unsaturated estrone derivative of formula X may be converted selectively in a single step into the corresponding alkenyl (XIII) via a copper mediated addition using a freshly prepared Gringard Reagent. After protection of the ketone (by conversion into a ketal or alternatively by reduction with NaBH4 and subsequent protection of the alcohol), the alkenyl is hydroxylated (XXXII). Subsequently, the resulting compound was subjected to a Jones' oxidation to provide the corresponding acid. Deprotection of the ketone (by removal of the ketal or oxidation) delivered the desired compound IVβ.

Optionally 2-Substituted Acid Building Block with a Stereochemistry at C15:

IVα-3a (n=3 and PG=H): 4-(3-Hydroxy-17-oxo-estra-1,3,5(10)-trien-15α-yl)-butyric Acid

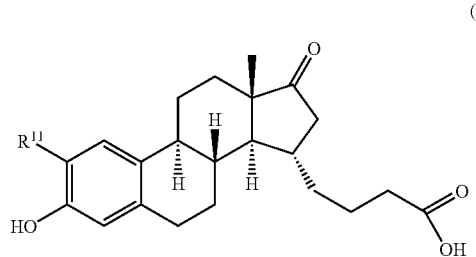

(IVα-3a)

The individual steps in the synthesis of the optionally 2-substituted acid building block of the formula IVα-3a are performed according to any of the procedures depicted in SCHEMES 14 and 15. Furthermore, reaction scheme 14 also delivers the still ketal-protected estrone-alcohol building block in form of the intermediate of formula XLIVα-1c. Debenzylation and deprotection delivers the estrone-alcohol XXXIα-1a.

SCHEME 14

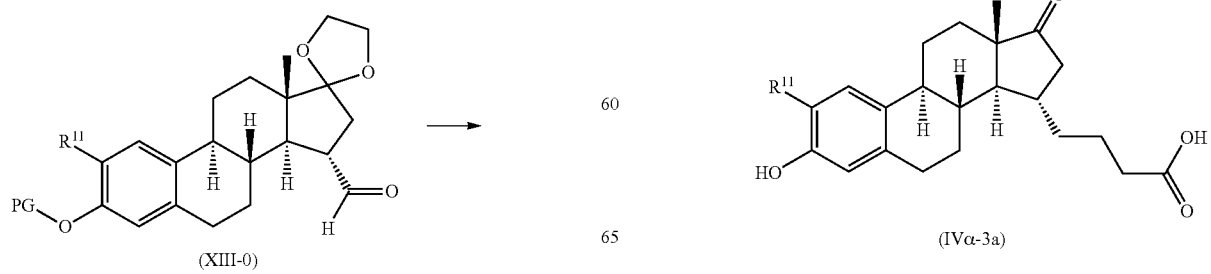

(XIII-0)

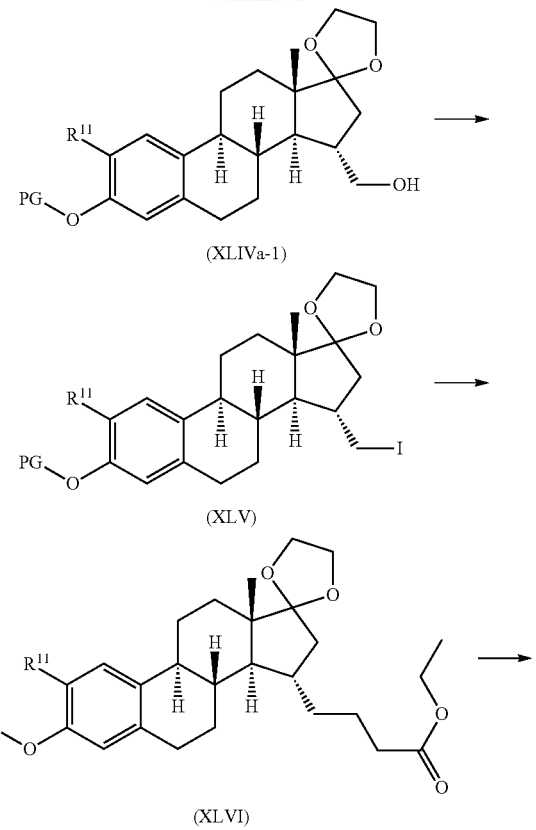

(XLIVa-1)

(XLV)

(XLVI)

(XLVII)

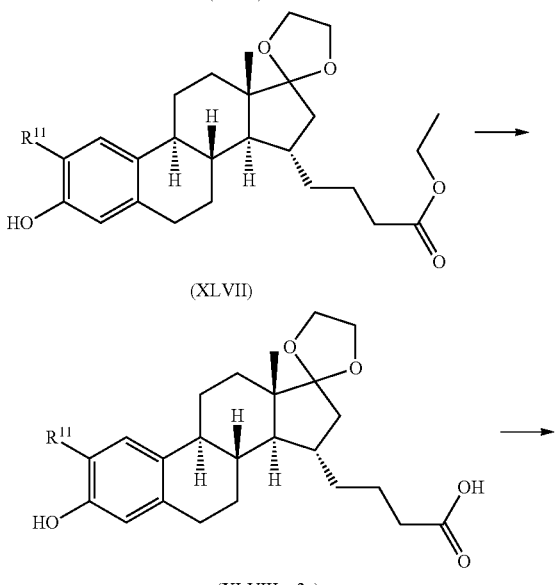

(XLVIIIα-3a)

(IVα-3a)

Reduction of the aldehyde XIII-0 with NaBH₄ gave the alcohol XLIVα-1, which was further treated with iodine, triphenylphosphine and imidazole to give the iodide XLV. Subsequently, ethylacrylate was coupled to iodine XLV and gave compound XLVI after purification by column chromatography. Reduction of compound XLVI was performed under H₂ atmosphere to give compound XLVII, which was transformed into the protected carboxylic acid building block XLVIIIα-3a by saponification. The carboxylic acid IVα-3a was obtained by deprotection.

SCHEME 15

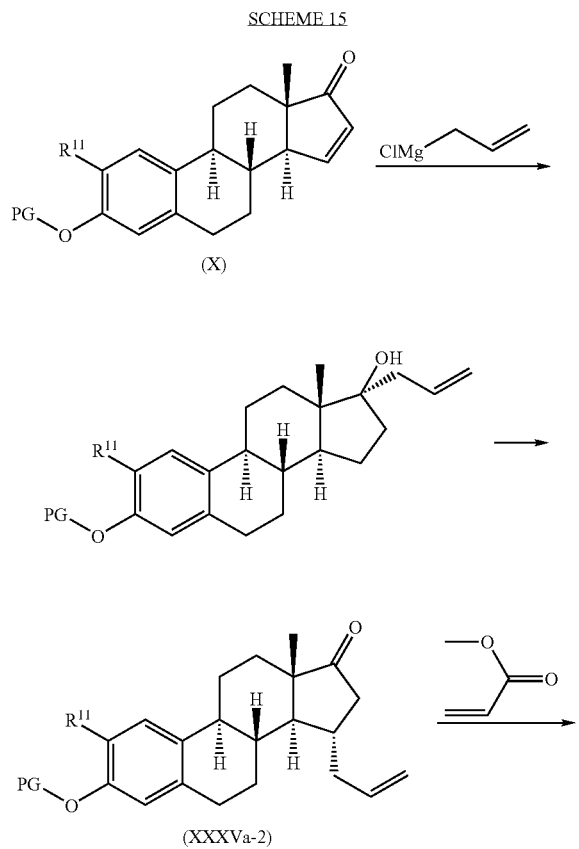

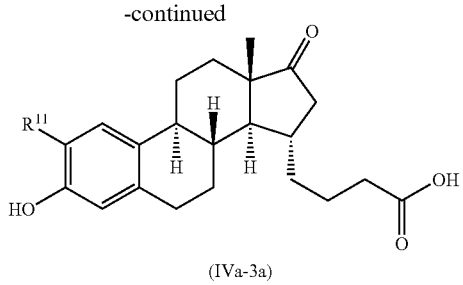

(IVa-3a)

The allyl group was introduced into the optionally C2 substituted, 15,16-unsaturated Estrone derivative of formula Xc by reaction with allylmagnesium chloride or bromide, followed by an oxy-cope rearrangement catalysed by KH and 18-Crown-6. Subsequently, the resulting compound XXX-2c was reacted with acrylic acid methyl ester using a Grubb II catalyst, known as olefin metathesis. The free acid (IVα-3a) is obtained by hydrogenation, deprotection, and, in the last step, hydrolysation of the methyl ester with LiOH.

IIIc. Compounds of Formula XXXI (Alcohol Derivatives):
Optionally 2-substituted 15-hydroxy-$C_1$-$C_6$-alkyl-estrone derivatives Alcohol Building Block XXXIα-1 (n=1)

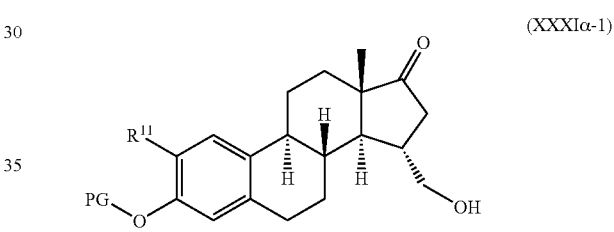

(XXXIα-1)

The synthesis of the alcohol derivatives XXXIα-1 can be achieved starting from the protected aldehyde intermediate of formula XIII-0 using NaBH₄ followed by ketal hydrolysis gave the corresponding alcohol XXXIα-1. If desired, the protection group PG can be cleaved of delivering the free hydroxy function.

Alcohol Building Blocks XXXIb-3,4,5,6

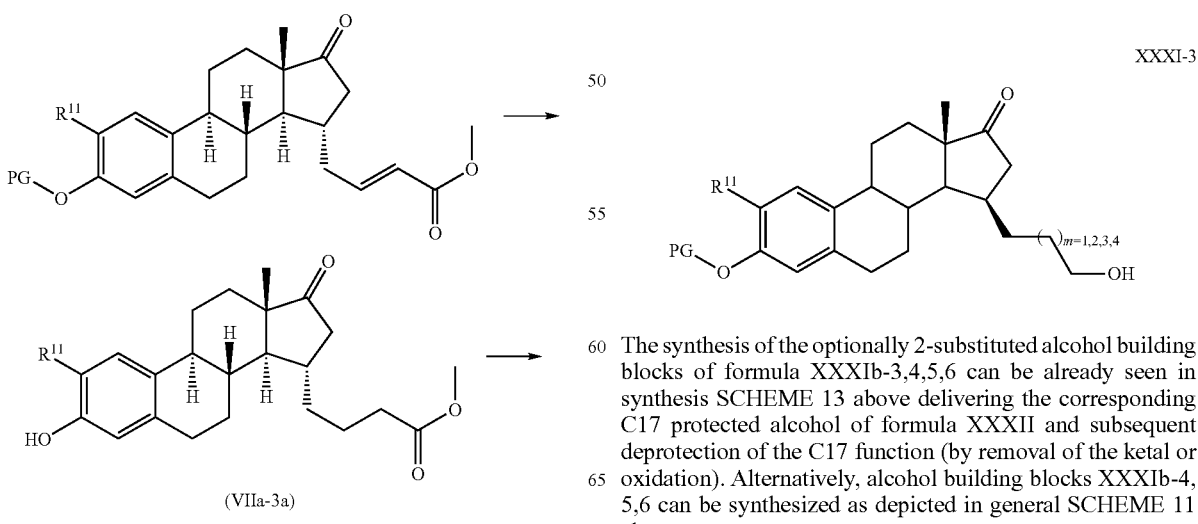

XXXI-3

The synthesis of the optionally 2-substituted alcohol building blocks of formula XXXIb-3,4,5,6 can be already seen in synthesis SCHEME 13 above delivering the corresponding C17 protected alcohol of formula XXXII and subsequent deprotection of the C17 function (by removal of the ketal or oxidation). Alternatively, alcohol building blocks XXXIb-4,5,6 can be synthesized as depicted in general SCHEME 11 above.

IIId. Optionally 2-Substituted Compounds of Formula IV with Difluorination of the C17 Keto Function The synthesis of C17 difluorinated building blocks of formula IV can be achieved according to the following protocols given for exemplary compounds IVβ-2 and IVα-3:

3-(17,17-Difluoro-3-hydroxy-estra-1,3,5(10)-trien-15β-yl)-propanoic acid (F,F-IVβ-2a)

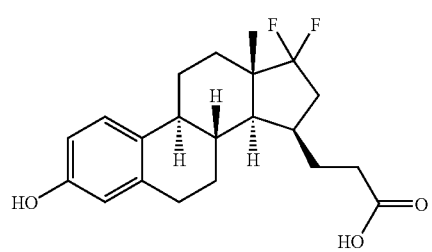

F,F-IVβ-2a

The individual steps in the synthesis of the acid building block of the formula F,F-IVβ-2a are depicted in the following SCHEME 16

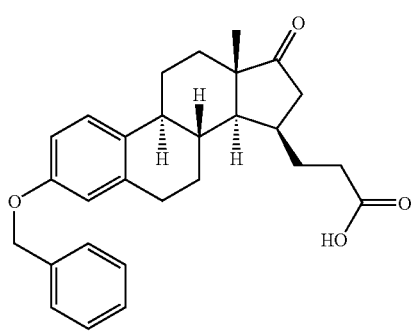

IVβ-2c

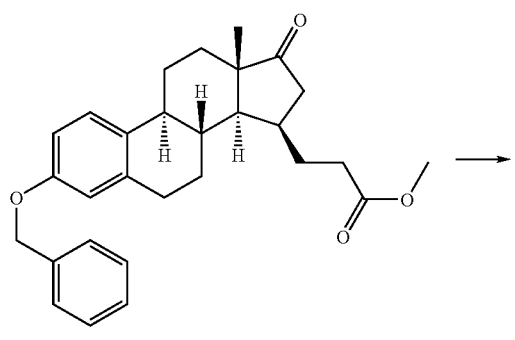

VIIβ-2c

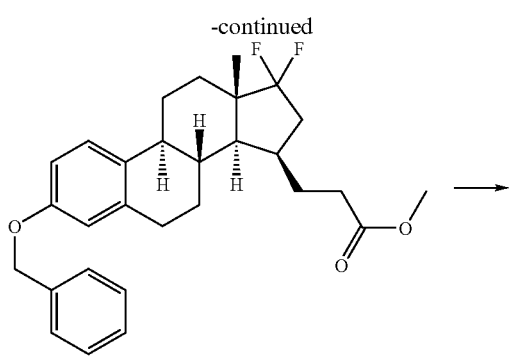

F,F-VIIβ-2c

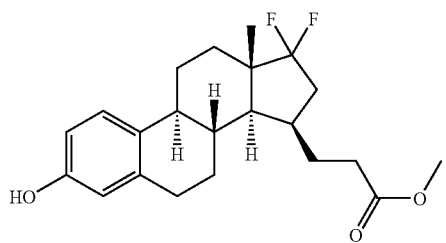

F,F-VIIβ-2a

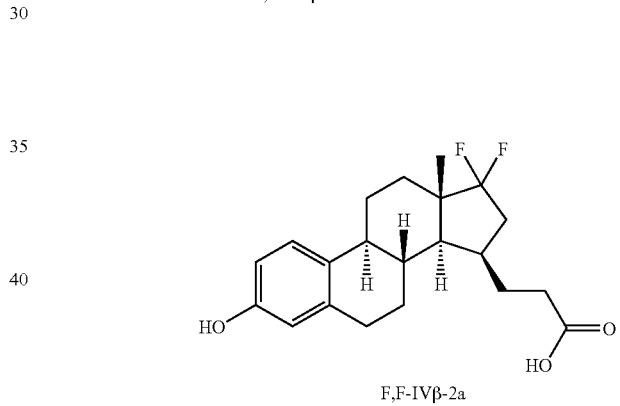

F,F-IVβ-2a 3-(3-Benzyloxy-17-oxo-estra-1,3,5(10)-trien-15β-yl)-propanoic acid of formula IVβ-2c is used as educt. Optionally, also the corresponding estradiol derivative (obtained after saponification of the corresponding protected $C_{1-7}$ alcohol) can be used as starting compound. The carboxylic acid is transformed in the corresponding methyl ester by an esterification reaction using an EDCl coupling (VIIβ-2c). If necessary, oxidation of the $C_{1-7}$ hydroxyl function has to be carried out to deliver compound VIIβ-2c. Fluorination of the obtained methyl ester with deoxofluor gave compound F,F-VIIβ-2c. Subsequent debenzylation (F,F-VIIβ-2a), followed by saponification with LiOH afforded the desired building block F,F-IVβ-2a.

$^1$H-NMR-listing: 1.027-1.34 (s, 3H), 1.408-2.421 (m, 15H), 2.837-2.960 (m, 2H), 6.573-6.651 (m, 2H), 7.121-7.257 (d, 1H).

$^{19}$F-NMR-listing: −104−−106 (d, 1F), −115−−117 (d, 1F).

4-(17,17-Difluoro-3-hydroxy-estra-1,3,5(10)-trien-15α-yl)-butanoic acid (F,F-IVα-3a)

F,F-IVα-3a

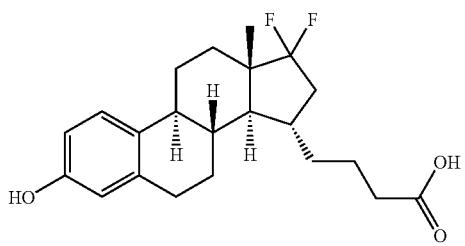

The acid building block of formula F,F-IVα-3a was synthesized starting from intermediate compound Xc and using the reaction steps as depicted in SCHEME 15: The allyl group was introduced into the 15,16-unsaturated estrone derivative of formula Xc by reaction with allylmagnesium chloride, followed by an oxy-cope rearrangement catalysed by KH and 18-Crown-6. Subsequently, the resulting compound XXX-2c was reacted with acrylic acid methyl ester using a Grubb II catalyst (olefin metathesis). Then, deviating from SCHEME 15, the 17-keto function of the resulting 4-(3-Benzyloxy-17-oxo-estra-1,3,5(10)-trien-15α-yl)but-2-enoic acid methyl ester was converted to a bisfluoro group using deoxofluor as described for F,F-VIIβ-2c. Subsequently, the well known hydrogenation step was performed to obtain the butanoic acid ester side chain, and finally the ester was hydrolysed with LiOH to give the target compound.

$^1$H-NMR-listing: 0.94 (s, 3H), 1.10-2.06 (m, 4H), 2.18-2.55 (m, 14H), 2.74-2.92 (m, 2H), 6.52 (d, 1H), 6.64 (dd, 1H), 7.15 (d, 1H)

$^{19}$F-NMR-listing: −104.5 (dd, 1F), −117.0 (d, 1F).

IIIe. Optionally 2-Substituted Boronic Acid Derivatives of Formula IVα, F,F-IVα, IVβ and F,F-IVβ

(IVb-2,3,4,5,6)-B(OH)$_2$

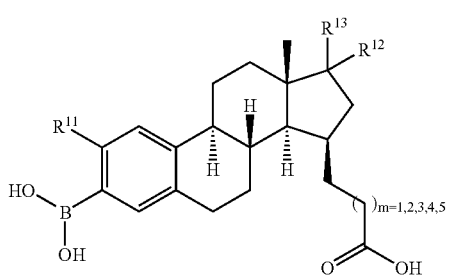

(IVα-3)-B(OH)$_2$

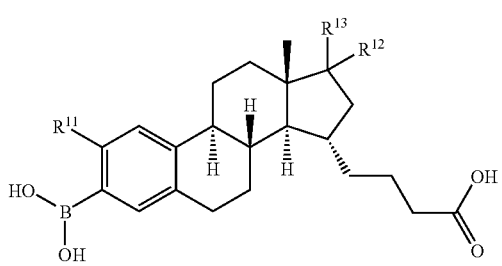

The synthesis of the boronic acid derivatives might be achieved as described in the general synthesis section for SCHEME 5.

Detailed synthesis for 4-(15α-{3-[boronic acid]}estronyl])-butanoic acid (IVα-3)-B(OH)$_2$

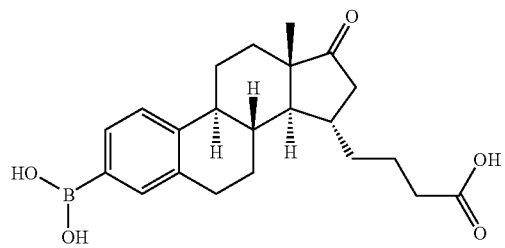

4-(15α-[3-triflate-estronyl])-butyric acid methyl ester I-13

4-(15α-[3-hydroxy-estronyl])-butyric acid methyl ester VIIα-3a (7.0 g, 18.89 mmol, see SCHEME 15) was dissolved in a mixture of DCM (50 mL) and 2,6-lutidine (11.0 mL, 10.1 g, 94.5 mmol) under N$_2$ atmosphere. At 0° C. trifluoromethane sulfonic acid anhydride (3.81 mL, 6.39 g, 22.67 mmol) in DCM (20 mL) was added dropwise. The reaction mixture was stirred at ambient temperature for 18 h and then quenched with water (150 mL). The water layer was extracted with DCM (3×150 mL) and the combined organic layers washed with 1N aq. HCl (150 mL), brine (150 mL) and dried with Na$_2$SO$_4$. The organic layer was concentrated in vacuo yielding crude compound I-13 (8.17 g, 16.26 mmol, 86%) as a slightly brown oil, which contained some unreacted VIIα-3a. Some pure 13 (2.79 g, 5.55 mmol, 29%) could be obtained by column chromatography (SiO$_2$, 0-10% EtOH in DCM). The residual crude material was again subjected to the reaction conditions using 1.5 eq. trifluoromethane sulfonic anhydride and more pure I-13 (3.95 g, 7.86 mmol, 42%) could be obtained.

4-(15α-{3-[pinacolatoboro]}estronyl])-butanoic acid methyl ester (I-14)

I-13 (7.5 g, 14.92 mmol), bis(pinacolato)diboron (4.93 g, 19.40 mmol), potassium acetate (2.93 g, 29.84 mmol) were suspended in a dried (mol. sieves 4 Å) and degassed (nitrogen) mixture of 1,4-dioxane (50 mL) and DMSO (4 mL). This mixture was again degassed by bubbling nitrogen through the solution for 30 m. Then Pd(dppf)Cl$_2$*2 DCM (2.00 g, 2.45 mmol) was added and the solution degassed for 15 m. After heating to 100° C. external temperature for 20 h the reaction mixture was diluted with ethyl acetate/water (50 mL/50 mL) and the water layer extracted with ethyl acetate (4×50 mL). The combined organic layers were washed with brine (50 mL), dried (Na$_2$SO$_4$) and evaporated in vacuo to yield I-14 (3.18 g, 6.61 mmol, 44%) after automated column chromatography (SiO$_2$, ISCO, 10-25% EA in heptane).

4-(15α-{3-[boronic acid]}estronyl])-butanoic acid ((IVα-3)-B(OH)$_2$)

I-14 (2.0 g, 4.16 mmol) and LiOH*1H$_2$O (1.05 g, 24.97 mmol) were suspended in a mixture of THF (50 mL). and water (50 mL). After stirring for 24 h at room temperature the mixture was concentrated to ca. ⅓ of its initial volume in vacuo. The watery reaction mixture was diluted with water (25 mL) and washed with DCM (1×50 mL). Then the mixture was acidified with aq. 1N HCl (50 mL), stirred for 1 h at ambient temperature, the precipitate filtered off and washed with water (50 mL) and dichloromethane (25 mL). Drying in vacuo afforded pure (IVα-3)-B(OH)$_2$ (1.21 g, 3.14 mmol, 76%).

Detailed synthesis for 4-(15α-{3-[boronic acid]}-17, 17-difluoro-estronyl])-butanoic acid (F,F-IVα-3)-B(OH)$_2$

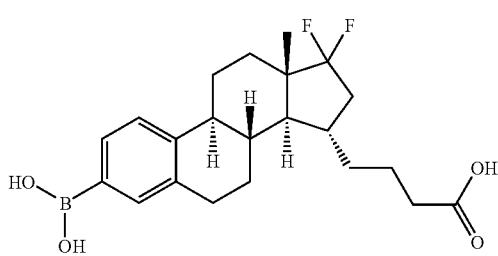

4-(15α-[3-triflate-17,17-difluoro-estronyl])-butyric acid methyl ester (I-16)

4-(17,17-Difluoro-3-hydroxy-estra-1,3,5(10)-trien-15α-yl)-butyric acid methyl ester (F,F-VIIα-3a, obtained during synthesis of F,F-IVα-3a) (2.31 g, 5.89 mmol) was dissolved in a mixture of DCM (50 mL) and 2,6-lutidine (3.52 mL, 3.15 g, 29.45 mmol) under a nitrogen atmosphere. At 0° C. trifluoromethane sulfonic acid anhydride (1.49 mL, 2.49 g, 8.83 mmol) in DCM (20 mL) was added dropwise. The reaction mixture was stirred at ambient temperature for 18 h and then quenched with water (50 mL). The water layer was extracted with DCM (3×50 mL) and the combined organic layers washed with 1 N aq. HCl (50 mL), brine (50 mL) and dried with Na$_2$SO$_4$. The organic layer was concentrated in vacuo yielding compound I-16 (3.02 g, 5.75 mmol, 97%) as a clear oil that was not purified prior to further use.

4-(15α-[3-(pinacolatoboro)-17,17-difluoro-estronyl])-butyric acid methyl ester (I-17)

I-16 (3.02 g, 5.76 mmol), bis(pinacolato)diboron (1.90 g, 7.48 mmol) and potassium acetate (1.13 g, 11.51 mmol) were suspended in a dried (mol. sieves 4A) and degassed (nitrogen) mixture of 1,4-doxane (50 mL) and DMSO (4 mL). This mixture was again degassed by bubbling nitrogen through the solution for 30 m. Then Pd(dppf)Cl$_2$*2 DCM (500 mg, 0.62 mmol) was added and the solution degassed for 15 m. After heating to 100° C. external temperature for 20 h the reaction mixture was diluted with ethyl acetate/water (50 mL/50 mL) and the water layer extracted with ethyl acetate (4×50 mL). The combined organic layers were washed with brine (50 mL), dried (Na$_2$SO$_4$) and evaporated in vacuo to yield I-17 (2.41 g, 4.79 mmol, 83%) after automated column chromatography (ISCO, 5-30% ethyl acetate in heptane, SiO$_2$).

4-(15α-[3-(pinacolatoboro)-17,17-difluoro-estronyl])-butanoic acid I-18

I-17 (3.2 g, 6.36 mmol) and LiOH*1H$_2$O (1.60 g, 38.16 mmol) were suspended in a mixture of THF (75 mL) and water (75 mL). After stirring for 18 h at room temperature the mixture was concentrated to ca. ⅓ of its initial volume in vacuo. The watery reaction mixture was diluted with water (25 mL) and washed with DCM (1×50 mL). Then the mixture was acidified with aq. 1N HCl (50 mL), stirred for 1 h at ambient temperature and extracted with DCM (3×50 mL). After drying (Na$_2$SO$_4$) and evaporation of the solvent in vacuo crude I-18 (1.91 g, 3.91 mmol, 61%) was obtained.

4-(15α-[3-(Potassium-trifluoro-boro)-17,17-difluoroestronyl])-butanoic acid I-19

I-18 (1.12 mmol) was dissolved in in methanol, and KHF2 (0.49 g, 6.27 mmol) was dissolved in water. Both solutions were mixed and stirred for 2 h at RT. After evaporation of the solvent, the residue is dissolved in hot acetone. After reduction of the organic phase, the residue I-19 can be further purified by washing with ether or was directly used in the next reaction step.

4-(15α-{3-[boronic acid]}-17,17-difluoroestronyl])-butanoic acid (F,F-IVα-3)-B(OH)$_2$ I-19 (0.58 mmol) was combined with TMSCl (0.38 g, 3.5 mmol) and water (63 mg, 3.5 mmol) in acetonitrile and stirred for 1 h at RT. After addition of saturated NaHCO$_3$ solution (1 ml), a white precipitate was filtered out. The organic phase was dried over Na$_2$SO$_4$. After evaporation of the solvent in vacuo crude (F,F-IVα-3)-B(OH)$_2$ was obtained, which can be further purified.

Detailed synthesis for 4-(15α-{3-[boronic acid]}estronyl])-propanoic acid (IVβ-2)-B(OH)$_2$

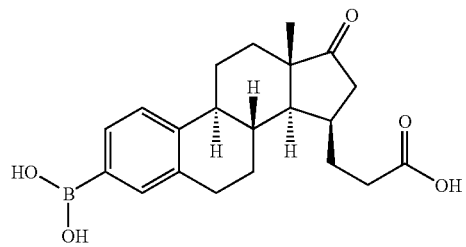

(IVb-2)-B(OH)$_2$ 3-(15β-[3-hydroxyestronyl])propanoic acid methyl ester (I-29)

A mixture of VIIβ-2b (11.26 g, 25.2 mmol, can be obtained according to SCHEME 16), Pd/C (1.6 g), methanol (300 mL) and EtOAc (120 mL) was stirred at 1 bar H$_2$ for 20 h. Pd/C (2.0 g) was added and the mixture was stirred for another 20 h at 1 bar. The reaction mixture was filtered over Celite and the filter cake was washed with MeOH (200 mL) and EtOAc (200 mL). The filtrate was concentrated in vacuo to yield I-29 (9.35 g, max. 25.2 mmol, quantitative yield) as brown foam.

3-(15β-[3-triflate-estronyl])propanoic acid methyl ester (I-30)

A solution of I-29 (7.35 g, 20.6 mmol) and 2,6-lutidine (12.0 mL, 103 mmol) in DCM (140 mL) was cooled to 0° C. A solution of trifluoromethanesulfonic anhydride (5.2 mL, 30.9 mmol) in DCM (40 mL) was added. The mixture was allowed to attain room temperature overnight. The mixture was quenched with water (110 mL). The layers were separated and the aqueous layer was extracted with DCM (2×75 mL). The combined organic layers were washed with 2N HCl (150 mL) and brine (150 mL). The organic layer was dried over $Na_2SO_4$ and concentrated in vacuo to yield 30 (11.2 g) as a red oil. This was combined with an earlier batch (2.0 g) and purified by column chromatography ($SiO_2$, 5‰ MeOH in DCM) to give I-30 (10.8, 22.1 mmol, 84%) as an orange oil.

3-(15β-[3-(Pinacolatoboro)-estronyl])propanoic acid methyl ester (31)

A mixture of I-30 (7.4 g, 15.1 mmol), DMSO (8.0 mL) and dioxane (90 mL) was degassed for 30 min. by bubbling $N_2$ through the mixture. After addition of Bis-(pinacolato)-diBor (4.99 g, 19.6 mmol) and potassium acetic acid salt (2.96 g, 30.2 mmol) degassing proceeded for another 30 min. After addition of $Pd(dppf)Cl_2.DCM$ (1.97 g, 2.4 mmol) and degassing for the third time for 30 min. the mixture was refluxed for 20 h. EtOAc (150 mL) and water (150 mL) were added and the layers were separated. The aqueous layer was extracted with EtOAc (2×100 mL). The combined organic layers were washed with brine (200 mL), dried over $Na_2SO_4$ and concentrated in vacuo to afford I-31 (11.0 g) as a black oil. This was combined with an earlier batch (3.4 g) and purified by column chromatography ($SiO_2$, hept:EtOAc, 6-1→4-1) to yield I-31 (8.4 g, 18.0 mmol, 81%) as an off-white solid.

3-(15β-[3-(boronic acid)-estronyl])propanoic acid ((IVβ-2)-B(OH)$_2$)

LiOH×$H_2O$ (4.0 g, 95.4 mol) was added to a suspension of I-31 (7.4 g, 15.9 mmol), water (185 mL) and THF (185 mL). The mixture was stirred overnight. THF was evaporated in vacuo and water (200 mL) was added. The pH was adjusted to 3 with 1N HCl and the mixture was stirred for 1 h and filtered. The filter cake was washed with water/acetonitrile (9:1, 50 mL) and DCM (50 mL). The filter cake was dried in vacuo to yield the corresponding bohr-acid of (IVβ-2)-B(OH)$_2$ (4.23 g, 11.4 mmol, 72%) as an off-white solid.

Detailed synthesis for 4-(15α-{3-[boronic acid]}-17,17-difluoroestronyl])-propanoic acid (F,F-IVβ-2)-B(OH)$_2$

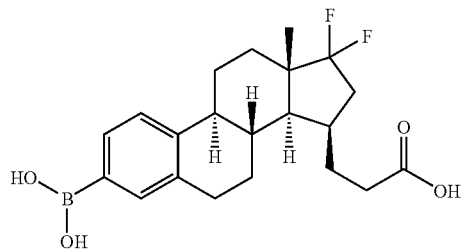

F,F-(IVb-2)-B(OH)$_2$

3-(15β-[3-triflate-17,17-difluoroestronyl])propanoic acid methyl ester (I-32)

A solution of F,F-VIIβ-2a (2.6 g, 6.9 mmol, can be obtained as depicted in SCHEME 16) and 2,6-lutidine (4.0 mL, 34 mmol) in DCM (50 mL) was cooled to 0° C. A solution of trifluoromethanesulfonic anhydride (1.7 mL, 10.4 mmol) in DCM (15 mL) was added. The mixture was allowed to attain room temperature overnight. The mixture was quenched with water (60 mL). The layers were separated and the aqueous layer was extracted with DCM (2×50 mL). The combined organic layers were washed with 2N HCl (100 mL) and brine (100 mL). The organic layer was dried over $Na_2SO_4$ and concentrated in vacuo to yield 32 (3.14 g) as a red oil. Purification by column chromatography ($SiO_2$, hept-DCM, 1-2) gives I-32 (2.49 g, 4.9 mmol, 71%) as a colorless oil.

3-(15β-[3-(pinacolatoboro)-17,17-difluoroestronyl]) propanoic acid methyl ester (I-33)

A mixture of I-32 (1.97 g, 3.8 mmol), DMSO (2.0 mL) and dioxane (25 mL) was degassed for 30 min. by bubbling $N_2$ through the mixture. After addition of bis-(pinacolato)-diBor (1.27 g, 5.0 mmol) and potassium acetic acid salt (745 mg, 7.6 mmol) degassing proceeded for another 30 min. After addition of $Pd(dppf)Cl_2.DCM$ (496 mg, 0.6 mmol) and degassing for the third time for 30 min. the mixture was refluxed for 20 h. EtOAc (100 mL) and water (100 mL) were added and the layers were separated. The aqueous layer was extracted with EtOAc (2×100 mL). The combined organic layers were washed with brine (200 mL), dried over $Na_2SO_4$ and concentrated in vacuo to afford 33 (3.3 g) as a black tar. Purification by column chromatography ($SiO_2$, hept:EtOAc, 9-1) to yield 33 (1.4 g, 2.9 mmol, 76%) as an off-white solid.

3-(15β-3-(boronic acid)-17,17-difluoroestronyl]) propanoic acid (F,F-IVβ-2)-B(OH)$_2$ LiOH×$H_2O$ (726 mg g, 17.3 mmol) was added to a suspension of 33 (1.41 g, 2.9 mmol), water (40 mL) and THF (40 mL). The mixture was stirred overnight. THF was evaporated in vacuo and water (200 mL) was added. The pH was adjusted to 3 with 1N HCl. The mixture was stirred for 1 h and extracted with DCM (2×100 mL). The combined organic layers were dried over $Na_2SO_4$ and concentrated in vacuo to afford a crude mixture (1.25 g, 2.6 mmol, 91%) of 3-(15β-[3-(pinacolatoboro)-17,17-difluoroestronyl])propanoic acid and the corresponding boronic acid (F,F-IVβ-2)-B(OH)$_2$.

IIIf. Optionally 2-Substituted Compounds of Formula XV (Protected Amine Building Block) (n=1-6)

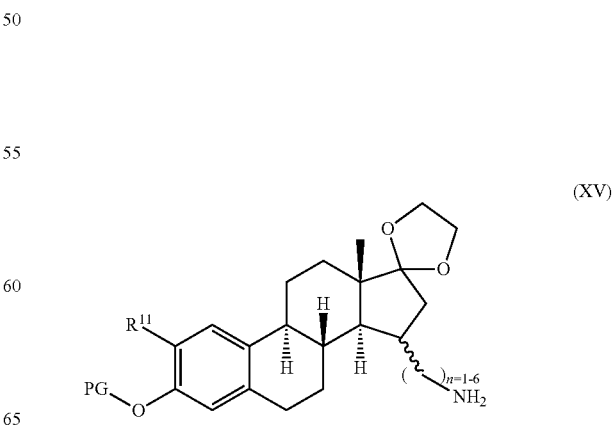

(XV)

Protected Amine Building Block XV-1 (n=1)

The individual steps in the synthesis of amine building block of the formula XV-1 are depicted in the following SCHEME 17

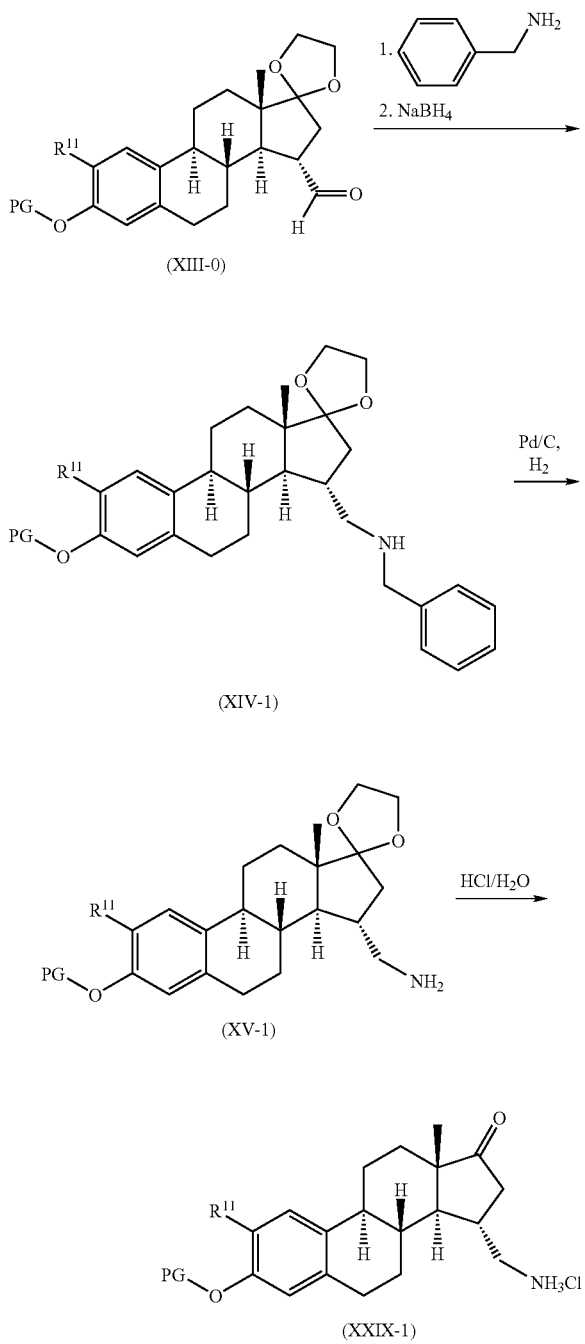

(XIII-0)

(XIV-1)

(XV-1)

(XXIX-1)

Dissolving aldehydes XIII-0b (PG=CH$_3$) or XIII-0c (PG=benzyl) in benzylamine and reduction of the residual imine in THF gave benzylamine XIV-1b (PG=CH$_3$) and XIV-1c (PG=benzyl), which were debenzylated to XV-1b (PG=CH$_3$) and XV-1a (PG=H), using Pd/C and H$_2$ at 5 bar, and dissolved in dilute HCl to give the respective ammonium chlorides XXIX-1b (PG=CH$_3$) and XXIX-1a (PG=H). Standard purification methods failed due to what seems to be instability of these ammonium salts. For these amines it was known that these should be treated as HCl salts since the free amine is not stable (ene-amines), but even the salts seem to be at least heat-sensitive. The crude reaction mixture has a purity of ~90% (HPLC-MS).

Amine Building Blocks XVα-3. XVα-4 XVα-5 and XVα-6

The individual steps in the synthesis of amine building block of the formula XVα-3 are depicted in the following SCHEME 18.

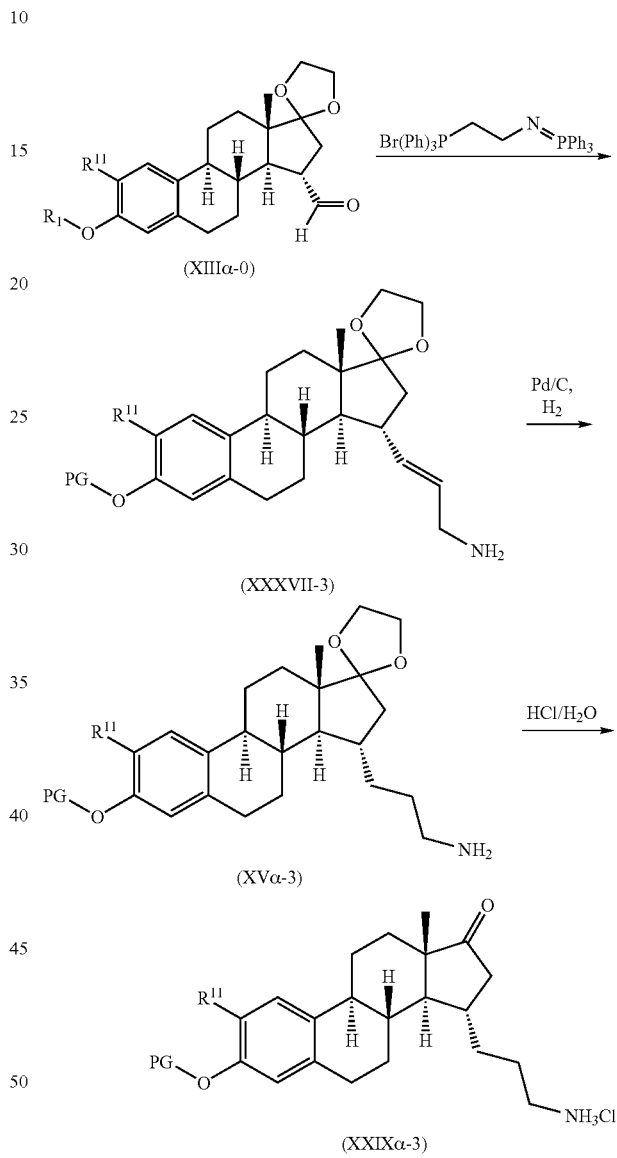

(XIIIα-0)

(XXXVII-3)

(XVα-3)

(XXIXα-3)

The protected aldehyde derivative of formula (XIIIα-0) is converted into the corresponding aminopropenyl by a Wittig reaction (see also SCHEME 9). The aminopropenyl (XXX-VII-3) is subsequently reduced to the 15-aminopropyl derivative of formula XVα-3. The protecting ketal group is converted into the 17-oxo group via acid hydrolysis. The same kind of procedure can be applied using different Wittig reagents of the general formula Hal(Ph)$_3$P—(CH$_2$)$_{n=3-5}$—R* in order to obtain amine building blocks with longer side chains (i.e. n=4, 5, or 6), wherein R* for example represents —N=P(Ph)$_3$, —N$_3$, or —NH—CO—O—CH$_3$.

Amine Building Blocks XVβ-4, XVβ-5, XVβ-6:

The individual steps in the synthesis of amine building block of the formula XVβ-4/5/6 with β configuration at the C15 atom of the steroidal core are depicted in the following SCHEME 19:

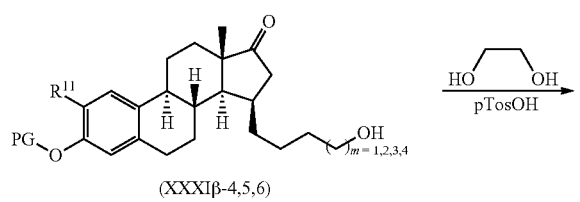

(XXXIβ-4,5,6)

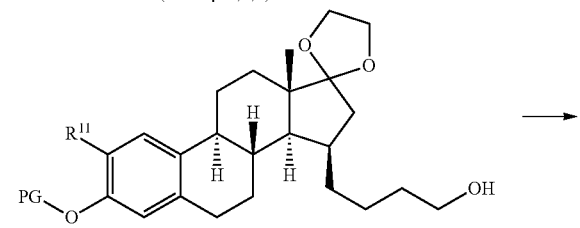

(XXXIIβ-4,5,6)

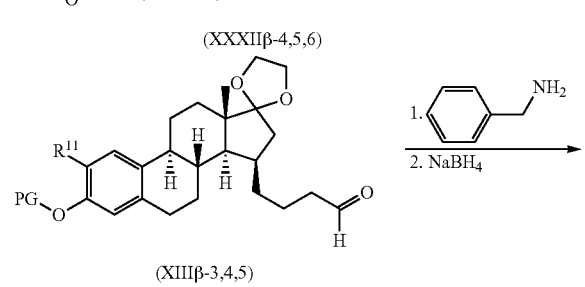

(XIIIβ-3,4,5)

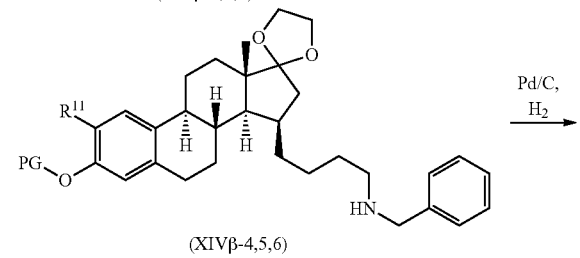

(XIVβ-4,5,6)

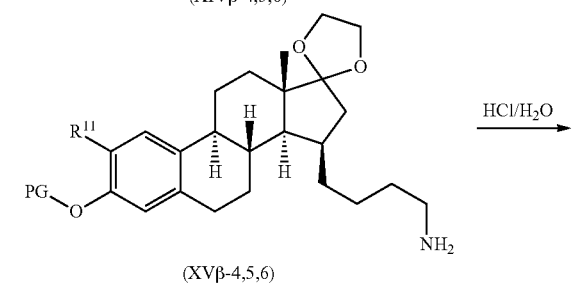

(XVβ-4,5,6)

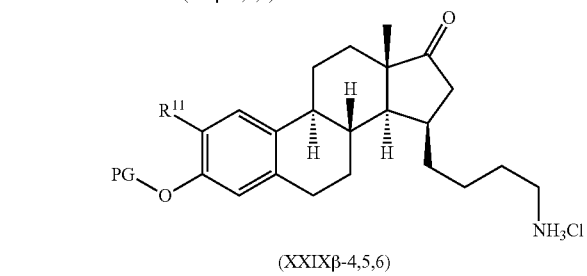

(XXIXβ-4,5,6)

In a first step, the 17 oxo function of the butanol derivative of the formula XXXIβ (for synthesis of XXXIβ) is converted into the ketal group (compound of formula XXXIIβ). Then, the alcohol function is selectively reduced to the aldehyde giving compound of the formula XIIIβ. The protected aldehyde derivative of the formula XIIIβ is converted into a secondary amine by addition of Benzylamine and subsequent reduction (reductive amination). Further reduction of the secondary amine delivers the desired, still protected amine building block of the formula XVβ. The protecting ketal group can be converted into the 17-oxo group via acid hydrolysis.

IIIg. Amine and Azide Building Block (n=1-6) of General Formula XXIX and XLIII

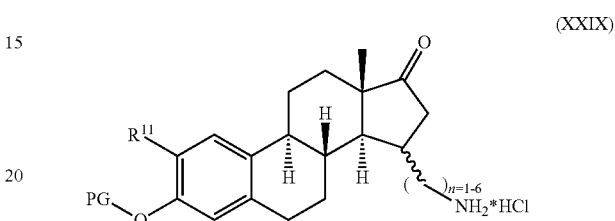

(XXIX)

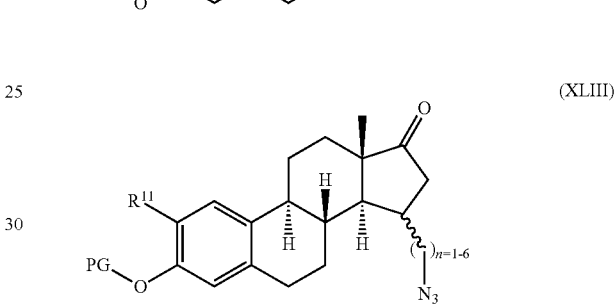

(XLIII)

Alternatively, the synthesis of the amine and azide building blocks of general formula XXIX and XLIII, respectively, can also be performed starting with an activated alcohol function and a subsequence substitution reaction, and does not need any protection of the estrone-C17 keto function according to the following general SCHEME 20

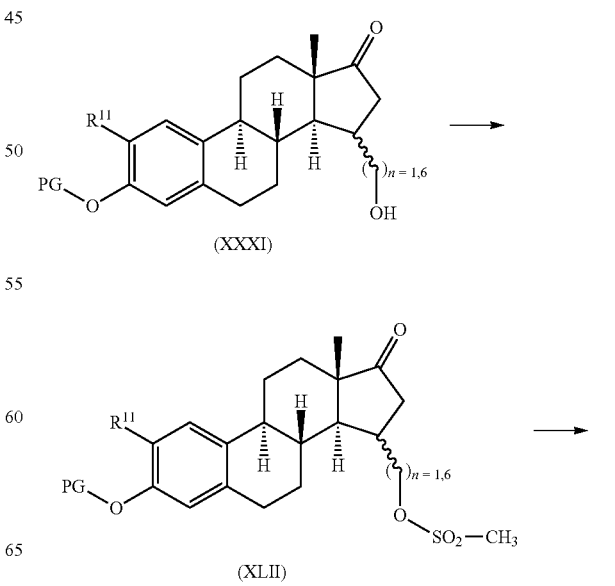

(XXXI)

(XLII)

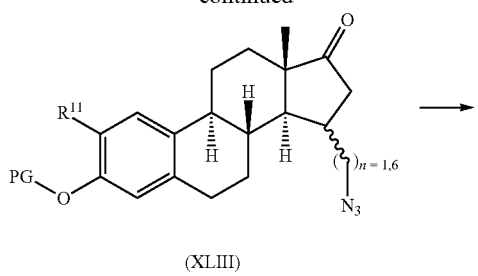

(XLIII)

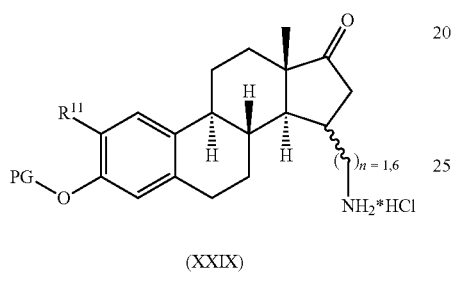

(XXIX)

After protection of the alcohol by mesylation, the azidation reaction can take place. If desired the azide is then further reduced to the corresponding amine. Alternative synthesis ways to obtain the azide building block of formula XLIII are disclosed within International patent application PCT/EP2007/059785 (unpublished).

IV. Step C(II)-Synthesis of Intermediates of general formula C-(I) with $R^{14}$=H

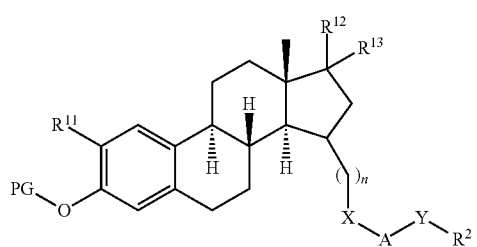

C2-(I)

The synthesis of a variety of intermediates falling under the general formula C2-(I), wherein $R^{11}$ represents H and $R^{12}$ and $R^{13}$ together represent =O, is fully disclosed in international patent application WO2005/047303 for different kinds of —X-A-Y— and $R^2$ and $R^4$ substituents. The synthesis of a variety of intermediates falling under the general formula C2-(I), wherein $R^{11}$ is different from H and/or wherein $R^{12}$ and $R^{13}$ each individually represent F, is fully disclosed in international patent application WO2006/125800 for different kinds of —X-A-Y— and $R^2$ and $R^4$ substituents. In general, this synthesis step can be performed starting from the building blocks described herein according to the reaction schemes depicted in general flow diagrams I to XVI.

V. Step E—Intermediates

IVa General Synthesis of Optionally Substituted Estron-Triflate Intermediates

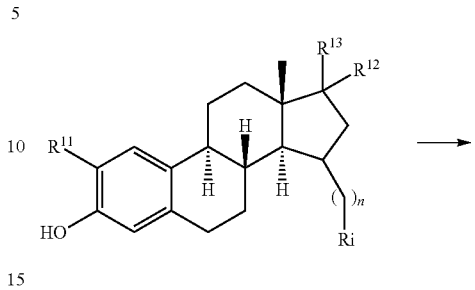

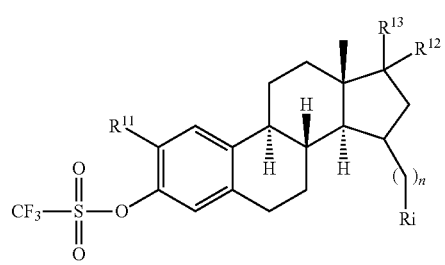

The synthesis of the corresponding optionally substituted estrone triflate from the corresponding estrone is exemplified for the synthesis of unsubstituted estrone triflate:

Estrone Triflate

A solution of triflic anhydride (169.3 mg, 0.6 mmol) in dry DCM (1 mL) was added dropwise to the stirred mixture of estrone (135.2 mg, 0.5 mmol) and 2,6-lutidine (267.9 mg, 2.5 mmol) in dry DCM (3 mL) at 0° C. The mixture was stirred for 30 min at 0° C. and overnight at RT. Then, it was quenched with water (5 mL). DCM (7 mL) was added, the organic layer was separated and washed with 2N HCl (5 mL), water (5 mL), brine (5 mL), and dried over $Na_2SO_4$. Concentration under reduced pressure and flash chromatography on silica gel (eluent hexane:ethyl acetate=4:1) afforded triflate estrone triflate as a very viscous oil which solidified during the drying in vacuum (white solid, mp 83-84° C., 177 mg, yield 88%).

$^1$H-NMR (CDCl$_3$), δ: 0.92 (s, 3H, CH$_3$), 1.43-1.68 (m, 6H), 1.91-2.19 (m, 4H), 2.23-2.32 (m, 1H), 2.37-2.43 (m, 1H), 2.48-2.56 (m, 1H), 2.94 (dd, J=8.6, 4.2 Hz, 2H, CH$_2$C=O), 6.99 (d, J=2.6 Hz, 1H$_{ar}$), 7.03 (dd, J=8.6, 2.6 Hz, 1H$_{ar}$), 7.34 (d, J=8.6 Hz, 1H$_{ar}$).

$^{13}$C-NMR (CDCl$_3$), δ: 13.93, 21.71, 25.82, 26.22, 29.52, 31.61, 35.94, 37.88, 44.23, 47.99, 50.51, 118.45, 118.88 (q, $J_{C,F}$=321.3 Hz, CF$_3$), 121.38, 127.33, 139.43, 140.41, 147.72, 220.57.

EXAMPLES

In order to more fully illustrate the nature of the invention and the manner of practicing the same, the following examples are presented, but they should not be taken as limiting.

Example 1

15α-(4-morpholin-4-yl-4-oxobutyl)-17-oxoestra-1(10),2,4-triene-3-carboxamide

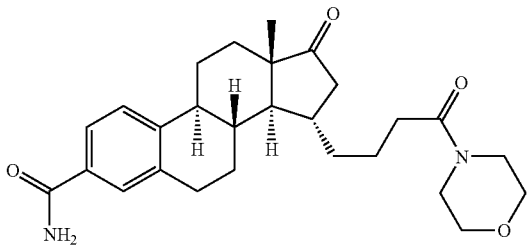

Example 1 was prepared according to the procedure displayed in SCHEME 6B and 6C(I) and starting from 3-Hydroxy-15α-(4-morpholin-4-yl-4-oxo-butyl)-estra-1,3,5(10)-trien-17-one, the detailed synthesis of which is displayed within international patent application WO2005/047303 (Example 40 therein) and can be generally achieved following reactions of SCHEME 1, SCHEME 14 or 15 and of flow diagram Ia or Ib.

15α-(4-morpholin-4-yl-4-oxo-butyl)-3-triflate-estra-1,3,5(10)-trien-17-one 5.4 g 3-Hydroxy-15α-(4-morpholin-4-yl-4-oxo-butyl)-estra-1,3,5(10)-trien-17-one is dissolved in 120 ml dry DCM. 10.72 g 2,6-lutidine is added slowly. 6.76 g trifluoromethanesulfonic acid anhydrate in 40 ml dry DCM is added slowly at 0° C. After stirring at 0° C. for 30 min, the reaction mixture remains over night at RT and is quenched with $H_2O$. 70 ml DM is added and the organic layer is extracted twice with 2N $HCl_{aq}$, twice with $H_2O$, twice with brine. After drying over $Na_2SO_4$ and reducing, the crude product is purified by flash column purification (DCM/EtOH 100:2), to give 5.5 g 15α-(4-morpholin-4-yl-4-oxo-butyl)-3-triflate-estra-1,3,5(10)-trien-17-one 15α-(4-morpholin-4-yl-4-oxobutyl)-17-oxoestra-1(10),2,4-triene-3-carboxylic acid butyl ester 2 g 15α-(4-morpholin-4-yl-4-oxo-butyl)-3-triflate-estra-1,3,5(10)-trien-17-one, 170 mg Hermann's catalyst, 880 mg DMAP, 1260 µl Huening Base and 110 mg Fu-salt in 100 ml BuOH are charged into a microwave vessel. 2.5 eq $Mo(CO)_6$ is added and the mixture is immediately heated by microwaves for 15 min at 240° C. The reaction mixture is filtered over Celite and reduced to obtain 3 g crude 15α-(4-morpholin-4-yl-4-oxobutyl)-17-oxoestra-1(10),2,4-triene-3-carboxylic acid butyl ester (a compound also falling under the scope of the present invention), which is directly used in the next reaction.

15α-(4-morpholin-4-yl-4-oxobutyl)-17-oxoestra-1(10),2,4-triene-3-carboxylic acid 3.5 g 5α-(4-morpholin-4-yl-4-oxobutyl)-17-oxoestra-1(10),2,4-triene-3-carboxylic acid butyl ester and 1.5 g LiOH are mixed with 100 ml THF, 100 ml MeOH and 100 ml $H_2O$ and stirred for 6 h at 60° C. (water bath). After reducing the solvents, $H_2O$ is added, the reaction mixture is extracted with EtOAc. The organic layer is washed with $KOH_{aq}$. The combined aquatic layers are acidified with $KHSO_{4aq}$ to pH 2-3, extracted with EtOAc. This organic layer is washed with brine, dried ($Na_2SO_4$) and the solvent removed. Purifying by column chromatography (EtOAc/IPE, 95:5 to EtOAc/IPA/AcOH 2:1:0.1) give 158 mg pure 15α-(4-morpholin-4-yl-4-oxobutyl)-17-oxoestra-1(10),2,4-triene-3-carboxylic acid (=EXAMPLE 2, NMR data see below).

15α-(4-morpholin-4-yl-4-oxobutyl)-17-oxoestra-1(10),2,4-triene-3-carboxamide 430 mg 15α-(4-morpholin-4-yl-4-oxoestra-1(10),2,4-triene-3-carboxylic acid is dissolved in DCM. 3 eq $NH_3$ solution (0.5 M in 1,4 dioxane), 3 eq 4-methyl morpholine, 1.75 eq hydroxybenztriazole and 2 eq EDCl are added slowly in an ice-bath. After stirring at RT for a couple of hours, the reaction mixture is left over night without stirring. The mixture is extracted twice with $NaHCO_3$ (5% in $H_2O$), twice with 1M $KHSO_4$ and with brine. The combined organic layers are dried ($Na_2SO_4$) and the solvent removed. Purifying by column chromatography (EtOAc/EtOH, 25:1) gives 135 mg pure 15α-(4-morpholin-4-yl-4-oxobutyl)-17-oxoestra-1(10),2,4-triene-3-carboxamide (EXAMPLE 1)

$^{13}C$ NMR (126 MHz, CHLOROFORM-d)

δ ppm 15.6 (q, 1 C) 23.7 (t, 1 C) 26.3 (t, 1 C) 27.6 (t, 1 C) 29.6 (t, 1 C) 31.6 (t, 1 C) 33.1 (t, 1 C) 36.2 (d, 1 C) 36.4 (t, 1 C) 39.2 (d, 1 C) 42.0 (t, 1 C) 43.1 (t, 1 C) 44.9 (d, 1 C) 46.0 (t, 1 C) 50.3 (s, 1 C) 54.9 (d, 1 C) 66.6 (t, 1 C) 67.0 (t, 1 C) 124.5 (d, 1 C) 126.0 (d, 1 C) 128.1 (d, 1 C) 130.7 (s, 1 C) 136.7 (s, 1 C) 144.0 (s, 1 C) 169.3 (s, 1 C) 171.2 (s, 1 C) 219.2 (s, 1 C)

$^1H$ NMR (501 MHz, CHLOROFORM-d)

δ ppm 0.98 (s, 3 H) 1.21-1.36 (m, 2 H) 1.44-1.88 (m, 6 H) 1.89-1.96 (m, 1 H) 1.96-2.06 (m, 2 H) 2.17-2.47 (m, 5 H) 2.82 (dd, J=19.2, 8.9 Hz, 1 H) 2.88-2.97 (m, 2 H) 3.43-3.52 (m, 2 H) 3.60-3.68 (m, 6 H) 5.61-6.22 (m, 2 H) 7.36 (d, J=8.2 Hz, 1 H) 7.53-7.59 (m, 2 H)

Example 2

15alpha-(4-morpholin-4-yl-4-oxobutyl)-17-oxoestra-1(10),2,4-triene-3-carboxylic acid

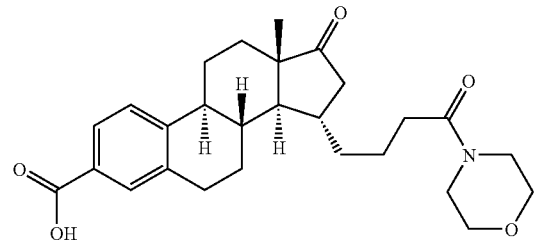

Example 2 was prepared according to the procedure displayed in SCHEME 6B and starting from 3-Hydroxy-15α-(4-morpholin-4-yl-4-oxo-butyl)-estra-1,3,5(10)-trien-17-one, the detailed synthesis of which is disclosed in published PCT application no. WO 2005/047303 (Example 40 therein) and can be generally achieved following reactions of SCHEME 1, SCHEME 14 or 15 and of flow diagram Ia or Ib. The detailed synthesis of EXAMPLE 2 is already described during the synthesis of EXAMPLE 1.

$^{13}C$ NMR (126 MHz, CHLOROFORM-d)

δ ppm 15.6 (q, 1 C) 23.7 (t, 1 C) 26.2 (t, 1 C) 27.6 (t, 1 C) 29.5 (t, 1 C) 31.6 (t, 1 C) 33.1 (t, 1 C) 36.2 (d, 1 C) 36.3 (t, 1 C) 39.2 (d, 1 C) 42.1 (t, 1 C) 43.1 (t, 1 C) 45.0 (d, 1 C) 46.1 (t, 1 C) 50.3 (s, 1 C) 54.8 (d, 1 C) 66.6 (t, 1 C) 67.0 (t, 1 C) 126.0 (d, 1 C) 127.0 (s, 1 C) 127.5 (d, 1 C) 130.6 (d, 1 C) 136.5 (s, 1 C) 145.7 (s, 1 C) 170.8 (s, 1 C) 171.6 (s, 1 C) 219.3 (s, 1 C)

$^1H$ NMR (501 MHz, CHLOROFORM-d)

δ ppm 0.97 (s, 3 H) 1.25-1.35 (m, 2 H) 1.45-1.60 (m, 3 H) 1.62-1.76 (m, 2 H) 1.79-1.87 (m, 2 H) 1.88-1.98 (m, 1 H) 1.98-2.09 (m, 1 H) 2.19-2.28 (m, 2 H) 2.30-2.51 (m, 4 H) 2.82 (dd, J=19.1, 8.7 Hz, 1 H) 2.88-2.96 (m, J=4.3 Hz, 2 H)

3.45-3.53 (m, 2 H) 3.63-3.71 (m, 6H) 7.37 (d, J=8.2 Hz, 1 H) 7.78-7.82 (m, 1 H) 7.84 (dd, J=8.5 Hz, 1 H)

Example 3

15β-{3-[(5-methyl-1,3-thiazol-2-yl)amino]-3-oxopropyl}-17-oxoestra-1(10),2,4-triene-3-carboxamide

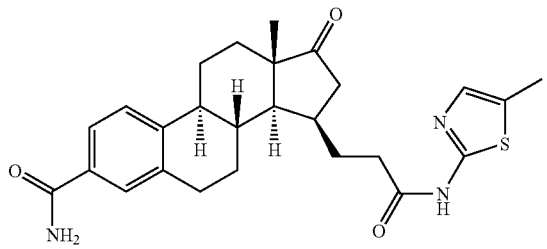

Example 3 was prepared according to the procedure displayed in SCHEME 6B and 6C(I) and as described for Example 1 herewithin starting from 3-(3-Hydroxy-17-oxo-estra-1,3,5(10)-trien-15β-yl)-N-(5-methyl-thiazol-2-yl)-propionamide, the detailed synthesis of which is disclosed in published PCT application no. WO 2005/047303 (Example 329A therein) and can be generally achieved following reactions of SCHEME 1, SCHEME 13 and of flow diagram Ia or Ib herewithin.

3-(17-oxo-3-triflate-estra-1,3,5(10)-trien-15β-yl)-N-(5-methyl-thiazol-2-yl)-propionamide This intermediate is prepared from 3-(3-Hydroxy-17-oxo-estra-1,3,5(10)-trien-15β-yl)-N-(5-methyl-thiazol-2-yl)-propionamide according to the procedure described in Example 1.

15β-{3-[(5-methyl-1,3-thiazol-2-yl)amino]-3-oxopropyl}-17-oxoestra-1(10),2,4-triene-3-carboxylic acid methyl ester 2 g 3-(17-oxo-3-triflate-estra-1,3,5(10)-trien-15β-yl)-N-(5-methyl-thiazol-2-yl)-propionamide steroid, 2.2 eq TEA, 0.03 eq Pd(II) acetate, 0.03 eq 1,3 bis (diphenylphosphino) propane (dppp) are given into a mixture of 6 ml DMSO and 4 ml MeOH and heated to 70° C. CO is passed through the reaction for 4 days. Then EtOAc is added and the organic layer is washed with $H_2O$, 1M $HCl_{aq}$ and sat. $NaHCO_{3aq}$. The combined aquatic layers are extracted with EtOAc. The combined organic layers are then dried over $Na_2SO_4$ and reduced to give 15β-{3-[(5-methyl-1,3-thiazol-2-yl)amino]-3-oxopropyl}-17-oxoestra-1(10),2,4-triene-3-carboxylic acid methyl ester (95.34%) (a compound also falling under the scope of the present invention), which is directly used in the next reaction.

15β-{3-[(5-methyl-1,3-thiazol-2-yl)amino]-3-oxopropyl}-17-oxoestra-1(10), 2,4-triene-3-carboxylic acid 350 mg 15β-{3-[(5-methyl-1,3-thiazol-2-yl)amino]-3-oxopropyl}-17-oxoestra-1(10),2,4-triene-3-carboxylic acid methyl ester and 5 eq LiOH are mixed with 30 ml MeOH and 10 ml $H_2O$ and stirred at 50° C. (water bath) for about 4 h. Then a few mg LiOH, 30 ml MeOH and 10 ml $H_2O$ were added and the reaction mixture was stirred for another 2 h at 50° C. After reducing the solvents, $H_2O$ is added, the reaction mixture is extracted with EtOAc. The combined aquatic layers are acidified with $KHSO_{4aq}$ to pH 2-3, and extracted twice with EtOAc. The latter organic layers are combined, washed with brine, dried ($Na_2SO_4$) and the solvent removed. Purifying by column chromatography ($CH_2Cl_2$: MeOH:AcOH 37:3:0.1) give 150 mg pure 15β-{3-[(5-methyl-1,3-thiazol-2-yl)amino]-3-oxopropyl}-17-oxoestra-1(10),2,4-triene-3-carboxylic acid (=EXAMPLE 4, NMR data see below).

15β-{3-[(5-methyl-1,3-thiazol-2-yl)amino]-3-oxopropyl}-17-oxoestra-1(10),2,4-triene-3-carboxamide 0.5 g 15β-{3-[(5-methyl-1,3-thiazol-2-yl)amino]-3-oxopropyl}-17-oxoestra-1(10),2,4-triene-3-carboxylic acid is dissolved in DCM. 3 eq $NH_3$ solution (0.5 M in 1,4 dioxane), 3 eq 4-methyl morpholine, 1.75 eq hydroxybenztriazole and 2 eq EDCl are added slowly in an ice-bath and the reaction is carried out as described in Example 1. Purification by column chromatography (EtOAc/EtOH, 6:1) gives pure 15β-{3-[(5-methyl-1,3-thiazol-2-yl)amino]-3-oxopropyl}-17-oxoestra-1(10),2,4-triene-3-carboxamide (EXAMPLE 3)

$^{13}C$ NMR (126 MHz, DMSO-$d_6$)

δ ppm 11.0 (q, 1 C) 17.2 (q, 1 C) 24.7 (t, 1 C) 25.8 (t, 1 C) 25.9 (t, 1 C) 28.7 (t, 1 C) 33.4 (d, 1 C) 33.6 (t, 1 C) 34.7 (t, 1 C) 35.0 (d, 1 C) 41.4 (t, 1 C) 44.5 (d, 1 C) 46.3 (s, 1 C) 51.8 (d, 1 C) 124.6 (d, 1 C) 124.7 (d, 1 C) 125.9 (s, 1 C) 127.9 (d, 1 C) 131.5 (s, 1 C) 134.6 (d, 1 C) 136.2 (s, 1 C) 143.1 (s, 1 C) 156.1 (s, 1 C) 167.8 (s, 1 C) 170.7 (s, 1 C) 219.5 (s, 1 C)

Example 4

15beta-{3-[(5-methyl-1,3-thiazol-2-yl)amino]-3-oxopropyl}-17-oxoestra-1(10),2,4-triene-3-carboxylic acid

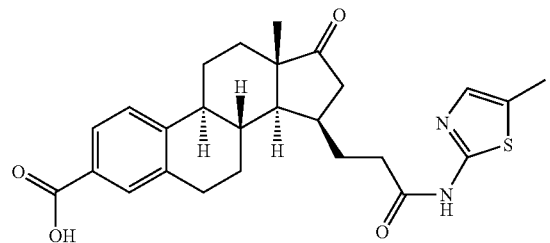

Example 4 was prepared according to the procedure displayed in SCHEME 6B and as described for Example 2 herewithin starting from 3-(3-Hydroxy-17-oxo-estra-1,3,5 (10)-trien-15β-yl)-N-(5-methyl-thiazol-2-yl)-propionamide, the detailed synthesis of which is displayed within international patent application WO2005/047303 (Example 329A therein) and can be generally achieved following reactions of SCHEME 1, SCHEME 13 and of flow diagram Ia or Ib herewithin. The detailed synthesis of EXAMPLE 4 is already described during the synthesis of EXAMPLE 3.

$^{13}C$ NMR (126 MHz, DMSO-$d_6$)

δ ppm 11.0 (q, 1 C) 17.2 (q, 1 C) 24.7 (t, 1 C) 25.7 (t, 1 C) 25.9 (t, 1 C) 28.6 (t, 1 C) 33.4 (d, 1 C) 33.6 (t, 1 C) 34.7 (t, 1 C) 34.9 (d, 1 C) 41.4 (t, 1 C) 44.6 (d, 1 C) 46.3 (s, 1 C) 51.8 (d, 1 C) 125.1 (d, 1 C) 125.9 (s, 1 C) 126.5 (d, 1 C) 128.3 (s, 1 C) 129.6 (d, 1 C) 134.6 (d, 1 C) 136.6 (s, 1 C) 144.9 (s, 1 C) 156.2 (s, 1 C) 167.4 (s, 1 C) 170.7 (s, 1 C) 219.5 (s, 1 C)

$^1H$ NMR (501 MHz, DMSO-$d_6$)

δ ppm 0.98 (s, 3 H) 1.33-1.50 (m, 3 H) 1.57-1.69 (m, 1 H) 1.70-1.78 (m, 3 H) 1.88-1.97 (m, 1 H) 2.07-2.15 (m, 1 H)

2.19-2.49 (m, 10 H) 2.89-2.98 (m, 2 H) 7.11 (d, J=1.2 Hz, 1 H) 7.38 (d, J=8.2 Hz, 1 H) 7.63-7.71 (m, 2 H) 11.66-12.05 (m, 1 H)

Example 5

N-butyl-N-methyl-15beta-{3-[(5-methyl-1,3-thiazol-2-yl)amino]-3-oxopropyl}-17-oxoestra-1(10),2,4-triene-3-carboxamide

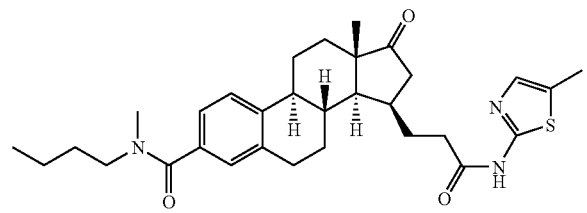

Example 5 was prepared from 15beta-{3-[(5-methyl-1,3-thiazol-2-yl)amino]-3-oxopropyl}-17-oxoestra-1(10),2,4-triene-3-carboxylic acid (Example 4) according to the procedure displayed in SCHEME 6C-I.

25 mg 15beta-{3-[(5-methyl-1,3-thiazol-2-yl)amino]-3-oxopropyl}-17-oxoestra-1(10),2,4-triene-3-carboxylic acid is dissolved in DCM. 2.5 eq N-Butylmethylamine (11.8 mg, 0.135 mmol), 3 eq 4-methyl morpholine, 1.7 eq HOBT and 2.2 eq EDCl are added slowly in an ice-bath. After stirring at RT for a couple of hours, the reaction mixture is left over night without stirring. The mixture is extracted twice with NaHCO$_3$ (5% in H$_2$O), twice with 1M KHSO$_4$ and with brine. The combined organic layers are dried (Na$_2$SO$_4$) and the solvent removed. Purifying by column chromatography (EtOAc/EtOH, 1:5) gives 21.1 mg pure N-butyl-N-methyl-15beta-{3-[(5-methyl-1,3-thiazol-2-yl)amino]-3-oxopropyl}-17-oxoestra-1(10),2,4-triene-3-carboxamide.

$^{13}$C NMR (126 MHz, CHLOROFORM-d)
δ ppm 11.60 (q, 1 C) 17.78 (q, 1 C) 22.70 (t, 1 C) 25.22 (t, 1 C) 26.21 (t, 1 C) 26.56 (t, 1 C) 29.15 (t, 1 C) 29.67 (t, 1 C) 33.91 (d, 1 C) 33.93 (t, 1 C) 35.53 (t, 1 C) 35.62 (d, 1 C) 41.98 (t, 1 C) 45.06 (d, 1 C) 47.06 (s, 1 C) 52.91 (d, 1 C) 70.62 (t, 1 C) 124.00 (d, 1 C) 124.83 (d, 1 C) 127.40 (d, 1 C) 127.69 (s, 1 C) 133.23 (d, 1 C) 134.47 (s, 1 C) 136.68 (s, 1 C) 141.15 (s, 1 C) 157.88 (s, 1 C) 170.09 (s, 1 C) 219.93 (s, 1 C)

Example 6

17,17-difluoro-15alpha-(4-morpholin-4-yl-4-oxobutyl)estra-1(10),2,4-triene-3-carboxamide

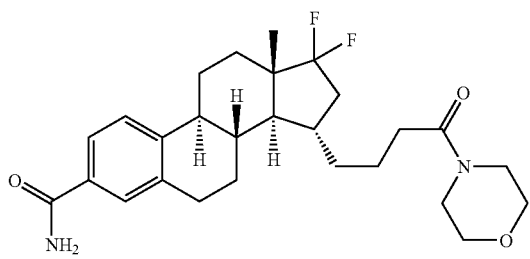

Example 6 was prepared according to the procedure displayed in SCHEME 6B and 6C(I) and starting from 4-(17,17-Difluoro-3-hydroxy-estra-1,3,5(10)-trien-15α-yl)-1-morpholin-4-yl-butan-1-one, the detailed synthesis of which is displayed within international patent application WO2006/125800 (Example 91 therein) and can be generally achieved following reactions of SCHEME 1, SCHEME 14 or 15, as described for Intermediate F,F-IVα-3a and of flow diagram Ia or Ib herewithin.

4-(17,17-Difluoro-3-triflate-estra-1,3,5(10)-trien-15α-yl)-1-morpholin-4-yl-butan-1-one
is prepared from 4-(17,17-Difluoro-3-hydroxy-estra-1,3,5(10)-trien-15α-yl)-1-morpholin-4-yl-butan-1-one according to the procedure described in Example 1, first step.

15α-(4-morpholin-4-yl-4-oxobutyl)-17,17-difluoro-estra-1(10),2,4-triene-3-carboxylic acid butyl ester 900 mg 4-(17,17-Difluoro-3-triflate-estra-1,3,5(10)-trien-15α-yl)-1-morpholin-4-yl-butan-1-one, 2.2 eq TEA, 0.03 eq Pd(II) acetate, 0.03 eq 1,3 bis(diphenylphosphino)propane (dppp) are given into a mixture of 6 ml DMSO and 4 ml MeOH and heated to 70° C. CO is passed through the reaction mixture over night. Then EtOAc is added and the organic layer is washed with H$_2$O, 1M HCl$_{aq}$ and sat. NaHCO$_{3aq}$. The combined aquatic layers are extracted with EtOAc. The combined organic layers are then dried over Na$_2$SO$_4$ and reduced to give 796 mg 15α-(4-morpholin-4-yl-4-oxobutyl)-17,17-difluoro-estra-1(10),2,4-triene-3-carboxylic acid butyl ester (also a compound falling under the scope of the present invention), which is directly used in the next reaction.

15α-(4-morpholin-4-yl-4-oxobutyl)-17,17-difluoro-estra-1(10),2,4-triene-3-carboxylic acid
796 mg 15α-(4-morpholin-4-yl-4-oxobutyl)-17,17-difluoro-estra-1(10),2,4-triene-3-carboxylic acid butyl ester and 5 eq LiOH are mixed with 30 ml MeOH and 10 ml H$_2$O and stirred at 50° C. (water bath) for about 4 h. Then a few mg LiOH, 30 ml MeOH and 10 ml H$_2$O were added and the reaction mixture was stirred for another 2 h at 50° C. After reducing the solvents, H$_2$O is added, the reaction mixture is extracted with EtOAc. The combined aquatic layers are acidified with KHSO$_{4aq}$ to pH 2-3, and extracted twice with EtOAc. The latter organic layers are combined, washed with brine, dried (Na$_2$SO$_4$) and the solvent removed. Purifying by column chromatography (CH$_2$Cl$_2$: MeOH:AcOH 37:3:0.1) give 191 mg of pure 15α-(4-morpholin-4-yl-4-oxobutyl)-17,17-difluoro-estra-1(10),2,4-triene-3-carboxylic acid (=EXAMPLE 7, for NMR see below).

15α-(4-morpholin-4-yl-4-oxobutyl)-17,17-difluoro-estra-1(10),2,4-triene-3-carboxamide 190 mg 15α-(4-morpholin-4-yl-4-oxobutyl)-17,17-difluoro-estra-1(10),2,4-triene-3-carboxylic acid is dissolved in DCM. 3 eq NH$_3$ solution (0.5 M in 1,4 dioxane), 3 eq 4-methyl morpholine, 1.75 eq hydroxybenztriazole and 2 eq EDCl are added slowly in an ice-bath. After stirring at RT for a couple of hours, the reaction mixture is left over night without stirring. The mixture is extracted twice with NaHCO$_3$ (5% in H$_2$O), twice with 1M KHSO$_4$ and with brine. The combined organic layers are dried (Na$_2$SO$_4$) and the solvent removed. Purifying by column chromatography (EtOAc/EtOH, 25:1) gives 126 mg pure EXAMPLE 6.

$^1$H NMR (501 MHz, CHLOROFORM-d)
δ ppm 0.96 (s, 3 H) 1.21-1.34 (m, 2 H) 1.37-1.88 (m, 9 H) 1.91-2.03 (m, 1 H) 2.04-2.12 (m, 1 H) 2.26-2.56 (m, 5 H) 2.84-2.97 (m, 2 H) 3.42-3.50 (m, 2 H) 3.61-3.69 (m, 6 H) 5.56-6.26 (m, 2 H) 7.36 (d, J=7.9 Hz, 1 H) 7.52-7.59 (m, 2 H)
$^{13}$C NMR (126 MHz, CHLOROFORM-d)
δ ppm 14.9 (q, J$_{C,F}$=3.9 Hz, 1 C) 23.8 (t, 1 C) 26.0 (t, 1 C) 27.5 (t, 1 C) 28.6 (t, J$_{C,F}$=4.9 Hz, 1 C) 29.6 (t, 1 C) 33.1 (t, 1 C) 36.1 (d, J$_{C,F}$=6.7 Hz, 1 C) 37.0 (t, 1 C) 39.1 (d, 1 C) 39.4-39.9 (t, J$_{C,F}$, 1 C) 42.0 (t, 1 C) 44.6 (d, 1 C) 46.0 (t, 1 C)

46.8 (s, $J_{C,F}$=20.0 Hz, 1 C) 53.4 (d, $J_{C,F}$=4.4 Hz, 1 C) 66.7 (t, 1 C) 67.0 (t, 1 C) 124.5 (d, 1 C) 126.0 (d, 1 C) 128.2 (d, 1 C) 129.0-133.1 (s, $J_{C,F}$, 1 C) 130.7 (s, 1 C) 136.7 (s, 1 C) 144.0 (s, 1 C) 169.3 (s, 1 C) 171.3 (s, 1 C)

Example 7

17,17-difluoro-15alpha-(4-morpholin-4-yl-4-oxobutyl)estra-1(10),2,4-triene-3-carboxylic acid

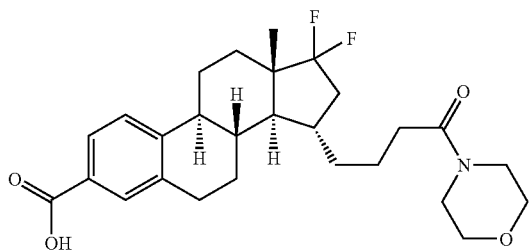

Example 7 was prepared according to the procedure displayed in SCHEME 6B and starting from 4-(17,17-Difluoro-3-hydroxy-estra-1,3,5(10)-trien-15α-yl)-1-morpholin-4-yl-butan-1-one, the detailed synthesis of which is disclosed in published PCT application no. WO 2006/125800 (Example 91 therein) and can be generally achieved following reactions of SCHEME 1, SCHEME 14 or 15, as described for Intermediate F,F-IVα-3a and of flow diagram Ia or Ib herewithin. The detailed synthesis of EXAMPLE 7 is already described during the synthesis of EXAMPLE 6.

$^{13}$C NMR (126 MHz, CHLOROFORM-d)

δ ppm 14.9 (q, $J_{C,F}$=3.6 Hz, 1 C) 23.8 (t, 1 C) 25.91 (t, 1 C) 27.5 (t, 1 C) 28.7 (d, $J_{C,F}$=4.4 Hz, 1 C) 29.6 (t, 1 C) 33.1 (t, 1 C) 36.0 (d, $J_{C,F}$=6.7 Hz, 1 C) 36.9 (t, 1 C) 39.0 (d, 1 C) 39.4-39.9 (t, $J_{C,F}$, 1 C) 42.1 (t, 1 C) 44.8 (d, 1 C) 46.1 (t, 1 C) 46.8 (s, $J_{C,F}$=20.1 Hz, 1 C) 53.3 (d, $J_{C,F}$=4.2 Hz, 1 C) 66.7 (t, 1 C) 67.0 (t, 1 C) 125.9 (d, 1 C) 127.0 (s, 1 C) 127.4 (d, 1 C) 128.9-133.1 (s, $J_{C,F}$, 1 C) 130.7 (d, 1 C) 136.5 (s, 1 C) 145.8 (s, 1 C) 171.0 (s, 1 C) 171.71 (s, 1 C)

$^{1}$H NMR (501 MHz, CHLOROFORM-d)

δ ppm 0.96 (s, 3 H) 1.22-1.33 (m, 1 H) 1.36-1.88 (m, 10 H) 1.93-2.02 (m, 1 H) 2.05-2.11 (m, 1 H) 2.31-2.56 (m, 5 H) 2.83-2.97 (m, 2 H) 3.45-3.53 (m, 2 H) 3.63-3.70 (m, 6 H) 7.37 (d, J=8.2 Hz, 1 H) 7.80 (d, J=1.5 Hz, 1 H) 7.85 (dd, J=8.2, 1.8 Hz, 1 H)

Example 8

17,17-difluoro-15beta-{3-[(5-methyl-1,3-thiazol-2-yl)amino]-3-oxopropyl}estra-1(10),2,4-triene-3-carboxamide

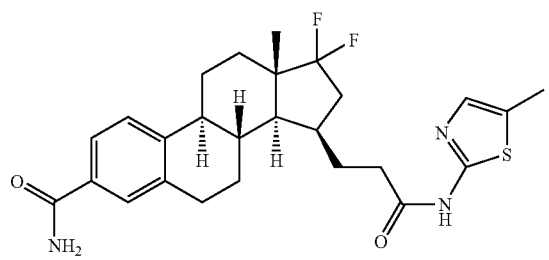

Example 8 was prepared according to the procedure displayed in SCHEME 6B and 6C(I) and starting from 3-(17,17-Difluoro-3-hydroxy-estra-1,3,5(10)-trien-15β-yl)-N-(5-methyl-thiazol-2-yl)-propionamide, the detailed synthesis of which is displayed within international patent application WO2006/125800 (Example 93 therein) and can be generally achieved following reactions of SCHEME 1, SCHEME 13, SCHEME 16 and of flow diagram Ia or Ib herewithin.

3-(17,17-Difluoro-3-triflate-estra-1,3,5(10)-trien-15β-yl)-N-(5-methyl-thiazol-2-yl)-propionamide The compound was prepared from 3-(17,17-Difluoro-3-hydroxy-estra-1,3,5(10)-trien-15β-yl)-N-(5-methyl-thiazol-2-yl)-propionamide using the procedure as described in Example 1 (step 1).

17,17-difluoro-15beta-{3-[(5-methyl-1,3-thiazol-2-yl)amino]-3-oxopropyl}estra-1(10),2,4-triene-3-carboxylic acid methyl ester The compound was prepared from 3-(17,17-Difluoro-3-triflate-estra-1,3,5(10)-trien-15β-yl)-N-(5-methyl-thiazol-2-yl)-propionamide using the procedure as described in Example 6 (step 2)

17,17-difluoro-15beta-[3-[(5-methyl-1,3-thiazol-2-yl)amino]-3-oxopropyl]estra-1(10),2,4-triene-3-carboxylic acid 0.9 g 17,17-difluoro-15beta-{3-[(5-methyl-1,3-thiazol-2-yl)amino]-3-oxopropyl}estra-1(10),2,4-triene-3-carboxylic acid methyl ester and 0.5 g LiOH are mixed with 30 ml MeOH, 50 ml THF and 30 ml H$_2$O and stirred at 80° C. (water bath) for about 30 min. H$_2$O is added, the reaction mixture is extracted with EtOAc three times. The combined aquatic layers are acidified with KHSO$_{4aq}$ to pH 2-3, and extracted the times with EtOAc. The latter organic layers are combined, washed with brine, dried (Na$_2$SO$_4$) and the solvent removed. 620 mg crude compound was obtained which was used in the following step without further purification. Purifying by column chromatography (CH$_2$Cl$_2$: MeOH:AcOH 37:3:0.1) give 77 mg of pure 17,17-difluoro-15beta-{3-[(5-methyl-1,3-thiazol-2-yl)amino]-3-oxopropyl}estra-1(10),2,4-triene-3-carboxylic acid (=EXAMPLE 9, NMR spectra see below).

17,17-difluoro-15beta-{3-[(5-methyl-1,3-thiazol-2-yl)amino]-3-oxopropyl}estra-1(10),2,4-triene-3-carboxamide 0.5 g 17,17-difluoro-15beta-{3-[(5-methyl-1,3-thiazol-2-yl)amino]-3-oxopropyl}estra-1(10),2,4-triene-3-carboxylic acid is dissolved in CH$_2$Cl$_2$. 3 eq NH$_3$ solution (0.5 M in 1,4 dioxane), 3 eq 4-methyl morpholine, 1.7 eq hydroxybenztriazole and 2 eq EDCl are added slowly in an ice-bath. After stirring at RT for a couple of hours, the reaction mixture is left over night without stirring. The mixture is extracted twice with NaHCO$_3$ (5% in H$_2$O), twice with 1M KHSO$_4$ and with brine. The combined organic layers are dried (Na$_2$SO$_4$) and the solvent removed. Purifying by column chromatography (EtOAc/EtOH, 6:1) gives 130 mg pure EXAMPLE 8.

$^{13}$C NMR (126 MHz, DMSO-d$_6$)

δ ppm 11.0 (q, 1 C) 16.6 (q, 1 C) 24.1 (t, 1 C) 26.4 (t, 1 C) 26.8 (t, 1 C) 28.6 (t, 1 C) 30.4 (t, 1 C) 33.5 (d, 1 C) 34.2 (t, 1 C) 34.9 (d, 1 C) 44.1 (d, 1 C) 49.9 (d, 1 C) 124.6 (d, 1 C) 124.7 (d, 1 C) 125.9 (s, 1 C) 127.8 (d, 1 C) 131.6 (s, 1 C) 134.6 (d, 1 C) 136.2 (s, 1 C) 143.1 (s, 1 C) 156.1 (s, 1 C) 167.8 (s, 1 C) 170.7 (s, 1 C)

Example 9

17,17-difluoro-15beta-{3-[(5-methyl-1,3-thiazol-2-yl)amino]-3-oxopropyl}estra-1(10),2,4-triene-3-carboxylic acid

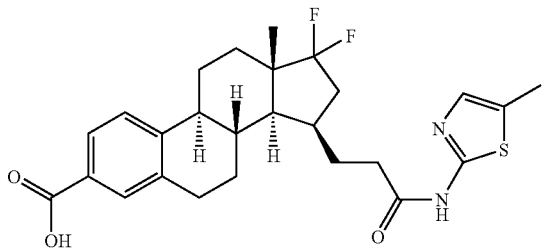

Example 9 was prepared according to the procedure displayed in SCHEME 6B and starting from 3-(17,17-Difluoro-3-hydroxy-estra-1,3,5(10)-trien-15β-yl)-N-(5-methyl-thiazol-2-yl)-propionamide, the detailed synthesis of which is displayed within international patent application WO2006/125800 (Example 93 therein) and can be generally achieved following reactions of SCHEME 1, SCHEME 13, SCHEME 16 and of flow diagram Ia or Ib herewithin. The detailed synthesis of EXAMPLE 9 is already described during the synthesis of EXAMPLE 8.

$^{13}$C NMR (126 MHz, DMSO-d$_6$)

δ ppm 11.0 (q, 1 C) 16.6 (q, 1 C) 24.1 (t, 1 C) 26.4 (t, 1 C) 26.9 (t, 1 C) 28.5 (t, 1 C) 30.4 (t, J$_{(C,F)}$=4.9 Hz, 1 C) 33.5 (d, J$_{(C,F)}$=6.5 Hz, 1 C) 34.2 (t, 1 C) 34.8 (d, 1 C) 44.2 (d, 1 C) 44.7 (s, J$_{(C,F)}$=19.9 Hz, 1 C) 49.9 (d, J$_{(C,F)}$=4.9 Hz, 1 C) 125.1 (d, 1 C) 126.0 (s, 1 C) 126.6 (d, 1 C) 128.1 (s, 1 C) 129.6 (d, 1 C) 130.5-135.0 (s, J=$_{(C,F)}$, 1 C) 134.6 (d, 1 C) 136.7 (s, 1 C) 145.1 (s, 1 C) 156.2 (s, 1 C) 167.4 (s, 1 C) 170.7 (s, 1 C)

$^1$H NMR (501 MHz, DMSO-d$_6$)

δ ppm 1.02 (s, 3 H) 1.37-1.46 (m, 2 H) 1.51-1.78 (m, 5 H) 1.87-1.97 (m, 1 H) 2.01-2.21 (m, 3 H) 2.25-2.48 (m, 8 H) 2.85-2.93 (m, 2 H) 7.10 (d, J=1.2 Hz, 1 H) 7.38 (d, J=8.2 Hz, 1 H) 7.66 (d, J=1.5 Hz, 1 H) 7.69 (dd, J=7.9, 1.8 Hz, 1 H) 11.86 (s, 1 H)

Example 10

[15α-(4-morpholin-4-yl-4-oxobutyl)-17-oxoestra-1(10),2,4-trien-3-yl]boronic acid

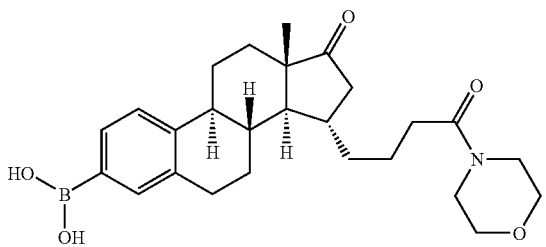

Example 10 was prepared according to the procedure displayed in SCHEME 5 and starting from 3-Hydroxy-15α-(4-morpholin-4-yl-4-oxo-butyl)-estra-1,3,5(10)-trien-17-one, the detailed synthesis of which is displayed within international patent application WO2005/047303 (Example 40 therein) and can be generally achieved following reactions of SCHEME 1, SCHEME 14 or 15 and of flow diagram Ia or Ib.

15α-(4-morpholin-4-yl-4-oxo-butyl)-3-triflate-estra-1,3,5(10)-trien-17-one 1.35 g 3-Hydroxy-15α-(4-morpholin-4-yl-4-oxo-butyl)-estra-1,3,5(10)-trien-17-one were dissolved in 30 ml dry DCM. 2.68 g 2,6-lutidine were added and the reaction mixture cooled to 0° C. At this temperature 1.69 g trifluoro methane sulfonic acid anhydride dissolved in 10 ml DCM were added drop wise. The reaction mixture was stirred for 30 min at 0° C. and left over night at ambient temperature. TLC control (cyclohexane/ethylactate/methanol 15:15:0.1) show complete conversion. The reaction mixture was quenched by adding 50 ml waster. Additional 70 ml DCM were used to enlarge the organic layer. After separation the organic layer was washed with 2N HCl-solution, water and 1 molare NaCl solution. After drying the organic layer over Na$_2$SO$_4$ the organic layer was evaporated to dryness. 1.7 g crude product were obtained, which have been purified further by flash chromatography (DCM/EtOH 100:2) yielding 0.87 g 15α-(4-morpholin-4-yl-4-oxo-butyl)-3-triflate-estra-1,3,5(10)-trien-17-one which was used in the next reaction.

15α-(4-morpholin-4-yl-4-oxo-butyl)-3-pinacolatoboro-estra-1,3,5(10)-trien-17-one 200 ml dioxane were degassed by bubbling N$_2$ through the solvent for 30 min. Than 1 g of 15α-(4-morpholin-4-yl-4-oxo-butyl)-3-triflate-estra-1,3,5(10)-trien-17-one, 670 mg bis (pinacolato)-diborane, 530 mg potassium acetate and 110 mg PdCl$_2$(dppf) were added and the reaction mixture refluxed for 10 hours under N$_2$ atmosphere. For work up most of the dioxane were evaporated before 200 ml ethyl acetate were added. The organic layer was washed with water and 1 molare NaCl solution dried over Na$_2$SO$_4$ and evaporated to dryness. 1.6 g crude product were obtained, which have been purified further by flash chromatography (dichloromethane/methanol 200:1) yielding 0.6 g 15α-(4-morpholin-4-yl-4-oxo-butyl)-3-pinacolatoboro-estra-1,3,5(10)-trien-17-one, which was used in the next reaction.

15α-(4-morpholin-4-yl-4-oxo-butyl)-(3-[potassium trifluoro-borate])-estra-1,3,5(10)-trien-17-one 600 mg 15α-(4-morpholin-4-yl-4-oxo-butyl)-3-pinacolatoboro-estra-1,3,5(10)-trien-17-one were dissolved in 10 ml methanol. 490 mg potassiumbifluoride (KHF2) and 5 ml water were added at ambient temperature. After 2 hours at ambient temperature most of the solvent was removed by evaporation. The crude material was washed 3 times with hot acetone. The acetone evaporated to dryness yielding 700 mg yellow foam. (TLC control: dichloromethane/methanol 10:1). The crude material was several times washed with EtOAc yielding 580 mg pure 15α-(4-morpholin-4-yl-4-oxo-butyl)-(3-[potassium trifluoro-borate])-estra-1,3,5(10)-trien-17-one.

15α-(3-[boronic acid])-(4-morpholin-4-yl-4-oxo-butyl)-estra-1,3,5(10)-trien-17-one 300 mg of 15α-(4-morpholin-4-yl-4-oxo-butyl)-(3-[potassium trifluoro-borate])-estra-1,3,5(10)-trien-17-one, 441 µl TMSCl, 63 µl water and 10 ml acetonitrile were stirred for 1 hour at ambient temperature. The reaction mixture was quenched with 0.3 ml conc. NaHCO$_3$. The pH of the solution was adjusted to approx. 3 with 1 M KHSO$_4$ solution very few drops. A white precipitate was removed by filtration. The filtrate washed with acetone. For further removal of the remaining water Na$_2$SO$_4$ was used. The solid material was washed several times with acetone. The acetone solutions were combined and evaporated to dryness. 240 mg foam were obtained which semi-crystallized after adding ethylacetate. After filtration and drying 170 mg solid 15α-(3-[boronic acid])-(4-morpholin-4-yl-4-oxo-butyl)-estra-1,3,5(10)-trien-17-one (EXAMPLE 10) were obtained.

$^{13}$C NMR (126 MHz, DMSO-d$_6$)

δ ppm 15.2 (q, 1 C) 23.4 (t, 1 C) 25.8 (t, 1 C) 27.4 (t, 1 C) 29.2 (t, 1 C) 31.4 (t, 1 C) 32.1 (t, 1 C) 35.3 (d, 1 C) 35.6 (t, 1 C) 38.9 (d, 1 C) 41.4 (d, 1 C) 42.5 (t, 1 C) 44.3 (d, 1 C) 45.4 (t, 1 C) 49.7 (s, 1 C) 54.1 (d, 1 C) 66.2 (t, 1 C) 66.2 (t, 1 C) 124.6 (d, 1 C) 130.9 (s, 1 C) 131.5 (d, 1 C) 134.5 (s, 1 C) 134.7 (d, 1 C) 141.3 (s, 1 C) 170.8 (s, 1 C) 218.7 (s, 1 C)

Example 11

[15β-{3-[(5-methyl-1,3-thiazol-2-yl)amino]-3-oxo-propyl}-17-oxoestra-1(10),2,4-trien-3-yl]boronic acid

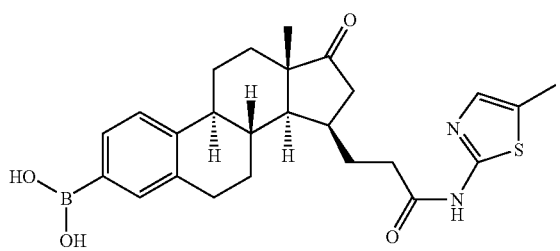

Example 11 was prepared according to the procedure displayed in SCHEME 5 and as described for Example 10 herewithin starting from 3-(3-Hydroxy-17-oxo-estra-1,3,5(10)-trien-15β-yl)-N-(5-methyl-thiazol-2-yl)-propionamide, the detailed synthesis of which is displayed within international patent application WO2005/047303 (Example 329A therein) and can be generally achieved following reactions of SCHEME 1, SCHEME 13 and of flow diagram Ia or Ib herewithin.

$^{13}$C NMR (126 MHz, DMSO-d$_6$)

δ ppm 11.0 (q, 1 C) 17.3 (q, 1 C) 24.8 (t, 1 C) 25.9 (t, 1 C) 26.0 (t, 1 C) 28.8 (t, 1 C) 33.4 (d, 1 C) 33.7 (t, 1 C) 34.7 (t, 1 C) 35.2 (d, 1 C) 41.5 (t, 1 C) 44.6 (d, 1 C) 46.3 (s, 1 C) 51.9 (d, 1 C) 123.8 (d, 1 C) 125.9 (s, 1 C) 131.4 (d, 1 C) 134.5 (d, 1 C) 134.8 (d, 1 C) 134.9 (s, 1 C) 141.7 (s, 1 C) 156.1 (s, 1 C) 170.7 (s, 1 C) 219.6 (s, 1 C)

$^1$H NMR (501 MHz, DMSO-d$_6$)

δ ppm 0.98 (s, 3 H) 1.31-1.49 (m, 3 H) 1.57-1.79 (m, 4 H) 1.88-1.98 (m, 1 H) 2.06-2.14 (m, 1 H) 2.19-2.46 (m, 9 H) 2.80-2.96 (m, 2 H) 7.11 (s, 1 H) 7.23 (d, J=7.6 Hz, 1 H) 7.50-7.57 (m, 2 H) 7.60-8.20 (s, 2 H) 11.91 (s, 1 H)

Example 47

[17,17-difluoro-15alpha-(4-morpholin-4-yl-4-oxobutyl)estra-1(10),2,4-trien-3-yl]boronic acid

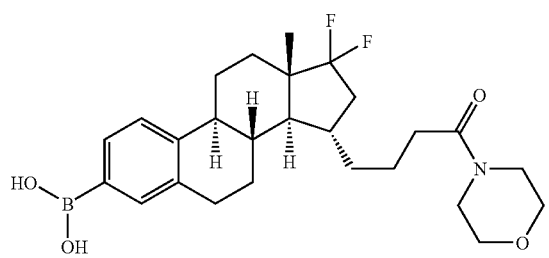

Example 47 was prepared according to the procedure displayed in SCHEME 5 and as described for Example 10 herewithin starting from 4-(17,17-Difluoro-3-hydroxy-estra-1,3,5(10)-trien-15α-yl)-1-morpholin-4-yl-butan-1-one, the detailed synthesis of which is displayed within international patent application WO2006/125800 (Example 91 therein) and can be generally achieved following reactions of SCHEME 1, SCHEME 14 or 15, as described for Intermediate F,F-IVα-3a and of flow diagram Ia or Ib herewithin $^{13}$C NMR (126 MHz, DMSO-d$_6$)

δ ppm 14.6 (q, 1 C) 23.1 (t, 1 C) 25.4 (t, 1 C) 27.1 (t, 1 C) 28.4 (t, J$_{(C,F)}$=4.4 Hz, 1 C) 29.1 (t, 1 C) 31.8 (t, 1 C) 35.1 (d, J$_{(C,F)}$=6.7 Hz, 1 C) 36.2 (t, 1 C) 38.6 (d, 1 C) 41.3 (t, 1 C) 44.0 (d, 1 C) 45.3 (t, 1 C) 46.0-46.5 (s, J$_{(CF)}$=19.7 Hz, 1 C) 52.8 (d, J$_{(CF)}$=3.9 Hz, 1 C) 66.1 (t, 2 C) 124.5 (d, 1 C) 129.1-133.8 (s, 1 C) 131.4 (d, 1 C) 134.4 (s, 1 C) 134.7 (d, 1 C) 141.1 (s, 1 C) 170.7 (s, 1 C)

$^1$H NMR (501 MHz, DMSO-d$_6$)

δ ppm 0.93 (s, 3 H) 1.10-1.81 (m, 11 H) 1.94-2.10 (m, 2 H) 2.23-2.65 (m, 5 H) 2.75-2.88 (m, 2 H) 3.40-3.46 (m, 4 H) 3.49-3.59 (m, 4 H) 7.24 (d, J=7.9 Hz, 1 H) 7.47-7.48 (m, 1 H) 7.52 (d, J=7.9 Hz, 1 H) 7.83 (s, 2 H)

Example 58

[17,17-difluoro-15β-{3-[(5-methyl-1,3-thiazol-2-yl)amino]-3-oxopropyl}estra-1(10),2,4-trien-3-yl]boronic acid

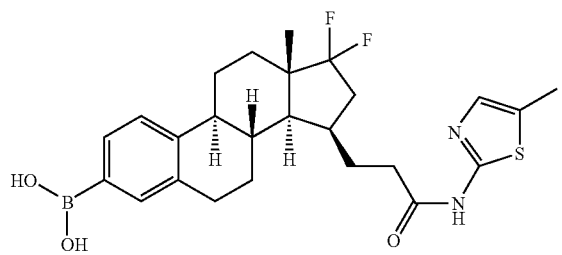

Example 58 was prepared according to the procedure displayed in SCHEME 5 and as described for Example 10 herewithin starting from 3-(17,17-Difluoro-3-hydroxy-estra-1,3,5(10)-trien-15β-yl)-N-(5-methyl-thiazol-2-yl)-propionamide, the detailed synthesis of which is displayed within international patent application WO2006/125800 (Example 93 therein) and can be generally achieved following reactions of SCHEME 1, SCHEME 13, SCHEME 16 and of flow diagram Ia or Ib herewithin.

$^{13}$C NMR (126 MHz, DMSO-d$_6$)

δ ppm 11.0 (q, 1 C) 16.6 (q, 1 C) 24.2 (t, 1 C) 26.8 (t, 1 C) 26.9 (t, 1 C) 28.7 (t, 1 C) 30.5 (t, 1 C) 34.2 (t, 1 C) 35.2 (d, 1 C) 44.3 (d, 1 C) 50.0 (d, 1 C) 123.8 (d, 1 C) 126.0 (s, 1 C) 131.5 (d, 1 C) 134.6 (d, 1 C) 134.7 (d, 1 C) 134.9 (s, 1 C) 141.7 (s, 1 C) 156.2 (s, 1 C) 170.7 (s, 1 C)

Further Boronic Acid Derivatives—Examples 12 to 28, 29 to 45, 48 to 57 and 59 to 74

A variety of compounds numbered 12 to 28, 29 to 45, 48 to 57 and 59 to 74 and falling under the scope of general formula (I), in which X-A-Y represents —CO—$NR^4$, $R^1$ represents —$B(OH)_2$, and $R^{11}$ represents —H were prepared by parallel chemistry using a reaction according to general flow diagram Ib using 4-(15α-{3-[boronic acid]}estronyl])-butanoic acid ((IVα-3)-$B(OH)_2$), 4-(15α-{3-[boronic acid]}estronyl])-propanoic acid ((IVβ-2)-$B(OH)_2$), 4-(15α-{3-[boronic acid]}-17,17-difluoro-estronyl])-butanoic acid ((F,F-IVα-3)-$B(OH)_2$), and 4-(15α-{3-[boronic acid]}-17,17-difluoroestronyl])-propanoic acid ((F,F-IVβ-2)-$B(OH)_2$), respectively, as building blocks.

Synthesis Protocol: 0.084 mmol HOBT and 155 mg PS-carbodiimid are provided in each reaction flask. A solution of 0.07 mmol of the respective steroidal building block ((IVα-3)-$B(OH)_2$), ((IVβ-2)-$B(OH)_2$), ((F,F-IVα-3)-$B(OH)_2$) or ((F,F-IVβ-2)-$B(OH)_2$) in 3 ml DCM was added per reaction flask and stirred shortly at RT. Then separate solutions of 0.07 mmol of the individual amines in 2 ml ACN were added to the respective reaction flasks. The reaction mixture was stirred for 24 h at ambient temperature. Afterwards, approx. 56 mg polymer bound trisaminoeethlyamine were added and the reaction mixture was stirred for another 24 h. After filtration and evaporating to dryness, the crude product is dissolved in 4 ml EtOAc and extracted with 4 ml $H_2O$. The organic phases were dried with $Na_2SO_4$ and evaporated in a vacuum centrifuge yielding the desired product. If still necessary, products were further purified by flash chromatography (4 g silica gel, eluent EtOAc/cyclohexane).

The following table lists the compounds prepared by this method:

| No. | m | stereo | $R^{13}$ | $R^2$ | $R^4$ | MW | HPLC Rt [min] |
|---|---|---|---|---|---|---|---|
| 12 | 2 | α | =O | 3,4-dihydroxybenzyl | H | 505.4 | 4.67 |
| 13 | 2 | α | =O | Benzo[1,3]dioxol-5-yl | H | 503.4 | 5.44 |
| 14 | 2 | α | =O | cyclopropyl | H | 423.4 | 4.78 |
| 15 | 2 | α | =O | 2-(7-methyl-1H-indol-3-yl)-ethyl | H | 540.5 | 5.51 |
| 16 | 2 | α | =O | 5-methyl-thiazol-2-yl | H | 480.4 | 5.39 |
| 17 | 2 | α | =O | cyclohexyl | H | 465.4 | 5.40 |
| 18 | 2 | α | =O | 1-methyl-1H-imidazol-4-ylmethyl | H | 477.4 | 4.30 |
| 19 | 2 | α | =O | Benzo[1,3]dioxol-5-ylmethyl | H | 517.4 | 5.26 |
| 20 | 2 | α | =O | piperidin-1-yl | | 451.4 | 5.37 |
| 21 | 2 | α | =O | pyridin-3-1-methyl | H | 474.4 | 4.62 |
| 22 | 2 | α | =O | benzyl | Methyl | 487.4 | 5.68 |
| 23 | 2 | α | =O | benzyl | H | 473.4 | 5.34 |
| 24 | 2 | α | =O | ethyl | Ethyl | 439.4 | 5.27 |
| 25 | 2 | α | =O | 2-methoxy-ethyl | H | 441.4 | 4.64 |
| 26 | 2 | α | =O | 2-(3,4-dimethoxy-phenyl)-ethyl | H | 561.5 | 5.40 |
| 27 | 2 | α | =O | 2,4-difluorobenzyl | H | 509.4 | 5.51 |
| 28 | 2 | α | =O | 4-isopropyl-piperazin-1-yl | | 494.5 | 4.32 |
| 29 | 1 | β | =O | cyclopropyl | H | 409.3 | 4.67 |
| 30 | 1 | β | =O | 2-(7-methyl-1H-indol-3-yl)-ethyl | H | 526.5 | 5.38 |
| 31 | 1 | β | =O | 5-methyl-thiazol-2-yl | H | 466.4 | 5.23 |
| 32 | 1 | β | =O | cyclohexyl | H | 451.4 | 5.38 |
| 33 | 1 | β | =O | 1-morpholin-4-yl | | 439.4 | 4.66 |
| 34 | 1 | β | =O | Benzo[1,3]dioxol-5-ylmethyl | H | 503.4 | 5.20 |
| 35 | 1 | β | =O | piperidin-1-yl | | 437.4 | 5.24 |
| 36 | 1 | β | =O | 2-pyridin-2-yl-ethyl | H | 474.4 | 4.59 |
| 37 | 1 | β | =O | benzyl | Methyl | 473.4 | 5.61 |
| 38 | 1 | β | =O | pyridin-3-yl-methyl | H | 460.4 | 4.51 |
| 39 | 1 | β | =O | ethyl | Ethyl | 425.4 | 5.19 |
| 40 | 1 | β | =O | benzyl | H | 459.4 | 5.26 |
| 41 | 1 | β | =O | 2-(3,4-dimethoxy-phenyl)-ethyl | H | 547.5 | 5.31 |
| 42 | 1 | β | =O | 2-methoxy-ethyl | H | 427.3 | 4.52 |
| 43 | 1 | β | =O | 4-isopropyl-piperazin-1-yl | | 480.5 | 4.21 |
| 44 | 1 | β | =O | 3,5-dimethoxybenzyl | H | 519.4 | 5.30 |
| 45 | 1 | β | =O | Benzo[1,3]dioxol-5-yl | H | 489.4 | 5.35 |
| 48 | 2 | α | F, F | cyclohexyl | H | 487.4 | 6.30 |
| 49 | 2 | α | F, F | Benzo[1,3]dioxol-5-ylmethyl | H | 539.4 | 6.04 |
| 50 | 2 | α | F, F | 2-pyridin-2-yl-ethyl | H | 510.4 | 5.52 |
| 51 | 2 | α | F, F | pyridin-3-yl-methyl | H | 496.4 | 5.44 |
| 52 | 2 | α | F, F | benzyl | H | 495.4 | 6.16 |
| 53 | 2 | α | F, F | 2-methoxy-ethyl | H | 463.4 | 5.52 |
| 54 | 2 | α | F, F | 2-(7-methyl-1H-indol-3-yl)-ethyl | H | 562.5 | 6.29 |
| 55 | 2 | α | F, F | piperidin-1-yl | | 473.4 | 6.33 |
| 56 | 2 | α | F, F | ethyl | Ethyl | 461.4 | 6.23 |
| 57 | 2 | α | F, F | 2-(3,4-dimethoxy-phenyl)-ethyl | Methyl | 583.5 | 6.25 |
| 59 | 1 | β | F, F | piperidin-1-yl | | 473.4 | 6.24 |
| 60 | 1 | β | F, F | Benzo[1,3]dioxol-5-ylmethyl | H | 525.4 | 5.95 |

-continued

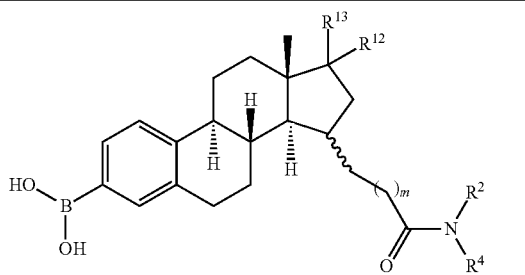

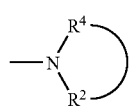

| No. | m | stereo | R¹³ | R² | R⁴ | MW | HPLC Rt [min] |
|---|---|---|---|---|---|---|---|
| 61 | 1 | β | F, F | 2-pyridin-2-yl-ethyl | H | 496.4 | 5.39 |
| 62 | 1 | β | F, F | pyridin-3-yl-methyl | H | 482.4 | 5.32 |
| 63 | 1 | β | F, F | benzyl | H | 481.4 | 6.05 |
| 64 | 1 | β | F, F | 2-methoxy-ethyl | H | 449.3 | 5.38 |
| 65 | 1 | β | F, F | 2,4-difluorobenzyl | H | 517.4 | 6.18 |
| 66 | 1 | β | F, F | 3,5-dimethoxybenzyl | H | 541.4 | 6.02 |
| 67 | 1 | β | F, F | 2-(7-methyl-1H-indol-3-yl)ethyl | H | 548.5 | 6.17 |
| 68 | 1 | β | F, F | 1-methyl-1H-imidazol-4-ylmethyl | H | 485.4 | 4.96 |
| 69 | 1 | β | F, F | piperidin-1-yl | | 459.4 | 6.21 |
| 70 | 1 | β | F, F | benzyl | Methyl | 495.4 | 6.48 |
| 71 | 1 | β | F, F | ethyl | Ethyl | 447.4 | 6.17 |
| 72 | 1 | β | F, F | 2-(3,4-dimethoxy-phenyl)-ethyl | H | 569.5 | 6.17 |
| 73 | 1 | β | F, F | 4-isopropyl-piperazin-1-yl | | 502.5 | 4.97 |
| 74 | 1 | β | F, F | Benzo[1,3]dioxol-5-yl | H | 511.4 | 6.13 |

Further Compounds—C3 Amine Derivatives—Examples 75 to 98

A variety of compounds numbered 75 to 98 and falling under the scope of general formula (I), in which X-A-Y represents —CO—NR⁴, R¹ represents —NR⁷R⁸, R¹¹ represents —H, R¹² and R¹³ together represent =O, n represents 3, and R² and R⁴ together with the nitrogen atom to which they are attached form a 1-morpholin-4-yl group were prepared by parallel chemistry using a reaction according to general SCHEME 6D using 15α-(4-morpholin-4-yl-4-oxo-butyl-3-triflate)-estra-1,3,5(10)-trien-17-one as building block, the synthesis of which is described in EXAMPLE 10 herewithin.
Detailed Synthesis:
a) Stock solution: 15α-(4-morpholin-4-yl-4-oxo-butyl-3-triflate)-estra-1,3,5(10)-trien-17-one (1204.5 mg, 2.160 mmol) were dissolved in 220 ml DMF (degassed)
b) Amines: each amine (0.043 mmol) was dissolved in 2 ml DMF (degassed)
c) Other reagents: amounts per reaction vial
  ~0.5 mg Pd(II)acetate
  ~1 mg X-Phos (2-dicyclohexylphosphino-2',4',6'-triisopropylbiphenyl)
  11.7 mg cesium carbonate
Protocol:
Pd(II)acetate, X-Phos and cesium carbonate were weighed into glass insets of the Synthos 3000 microwave. Then 2 ml of the stock solution and the corresponding amine were added into each vial. The mixtures were flushed with nitrogen and then capped. The reaction vials were conducted with the Anton Paar microwave device at 160° C. for 20 minutes (no ramp, hold time was 20 min). After cooling down, the reaction mixtures were filtrated with Celite® 503. Then most of the DMF was removed under reduced pressure at 40° C. The residues were solved in EtOAc and then extracted twice with an aqueous NaCl solution (5%). Subsequently, the aqueous layers were extracted twice with EtOAc. The organic layers were combined and filtrated over Na₂SO₄. The filtrates were dried under reduced pressure and the yields were determined. Samples for LC-MS were taken; based on the analytical results the products were purified (see section "Remarks" below).
Remarks:
Compounds No. 76, No. 82, No. 90 and No. 92 were purified with PL-NCO (Isocyanate) resin.
Compounds No. 81, No. 83, No. 89, No. 91 and No. 84 were purified by liquid chromatography.
Compounds No. 75 and No. 88 were first treated with PL-NCO (Isocyanate) resin and then purified by liquid chromatography.
The following table lists the compounds prepared by this method:

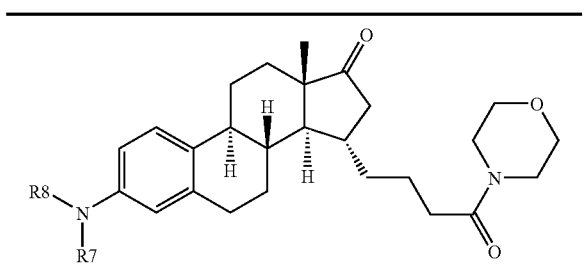

| No. | R⁷ | R⁸ | MW | HPLC Rt [min] |
|---|---|---|---|---|
| 75 | 3-methoxy-5-(trifluoromethyl)phenyl | H | 598.7 | 7.00 |
| 76 | 3-(morpholin-4-ylsulfonyl)phenyl | H | 649.8 | 6.03 |
| 77 | 4-(3-methoxyphenyl)piperazin-1-yl | | 599.8 | 6.91 |
| 78 | 3,5-bis(trifluoromethyl)phenyl | H | 636.7 | 7.52 |
| 79 | 3-(2-oxopyrrolidin-1-yl)propyl | H | 549.8 | 5.14 |
| 80 | 2-oxo-1,3-oxazolidin-3-yl | | 494.6 | 5.26 |
| 81 | 1H-indol-5-yl | H | 539.7 | 6.03 |
| 82 | pyrrolidin-1-yl | | 478.7 | 7.05 |
| 83 | Quinolin-3-yl | H | 551.7 | 6.15 |
| 84 | 4-phenylpiperazin-1-yl | | 569.8 | 7.05 |
| 85 | 3-cyano-phenyl | H | 525.7 | 6.33 |
| 86 | 4-benzylpiperazin-1-yl | | 583.8 | 5.98 |
| 87 | 3,4-difluorophenyl | H | 536.7 | 6.69 |
| 88 | 2-pyridin-2-yl-ethyl | methyl | 543.7 | 6.13 |
| 89 | 3-oxo-1,3-dihydro-2-benzofuran-5-yl | H | 556.7 | 5.83 |
| 90 | 3,4-dihydroisoquinolin-2(1H)-yl | | 540.7 | 7.19 |
| 91 | 1,1-dioxido-1-benzothien-6-yl | H | 588.8 | 5.86 |
| 92 | 4-(3-chlorophenyl)piperazin-1-yl | | 604.2 | 7.49 |
| 93 | pentyl | H | 494.7 | 7.11 |
| 94 | 2-oxopyrrolidin-1-yl | | 492.6 | 5.30 |
| 95 | phenyl | H | 500.7 | 6.57 |
| 96 | pyrrolidin-1-yl | | 478.7 | 7.04 |
| 97 | 1,3-benzodioxol-5-yl | H | 544.7 | 6.32 |
| 98 | benzyl | H | 514.7 | 6.52 |

Biological Testing Materials and Methods

Screening Strategy for 17βHSD1, 2 and/or 3 Inhibitors

The screening to assess that the compounds of the invention are inhibitors of the 17βHSD enzymes and are suited for the treatment of the aforementioned estrogen- and/or androgen dependent disorders is carried out in five major steps:
- recombinant HPLC assay for 17βHSD1 and 17βHSD2
- 17βHSD1-MCF-7, 17βHSD2-MCF-7 and/or 17βHSD3-MCF-7 cell assay
- estrogen receptor binding and functional assay
- in vivo assays, e.g. UWT assay, tumor model, and disease-oriented models, thereby first focusing on the effect on enzymatic activity of recombinant human 17βHSD1 and on selectivity towards recombinant human 17β-hydroxysteroid dehydrogenase type 2 (17βHSD2), the enzyme catalysing the reverse reaction as 17βHSD1 by conversion of E2 to E1 (method as described in WO2005/047303$^{Error!\ Bookmark\ not\ defined.}$). These protein-based tests are followed by the corresponding cell-based assays (as described in WO2005/032527). Another important factor is selectivity towards the estrogen receptor that is studied in a commercially available binding assay (PanVera LCC, Madison, Wis.) as well as in a functional ERE-LUC receptor gene assay as described by Burow et al. (2001) and explained in more detail below. After determining metabolic and physicochemical stability of a compound the first set of in vivo experiments is started. Lack of estrogenic activity in vivo is proven using the classical uterine growth test in immature rats (Lauson et al. (1939)). Efficacy of 17βHSD1-inhibition is demonstrated by reduction of 17βHSD1-dependent growth of tumor xenografts in immunodeficient mice as described by Husen et al. (2006). Finally disease-oriented models as disclosed by Grümmer et al. (2001) and Einspanier et al. (2006) determine the proof of concept of these compounds.

Some of the above-mentioned as well as alternative assays are described in more detail below:

1. Inhibition of the Recombinant Human 17β-HSD1 or 17β-HSD2 enzyme

17β-HSD1 or 17β-HSD2 purification: Recombinant 17β-HSD1 and 17β-HSD2 baculoviruses were generated by the "Bac to Bac Expression System" (Invitrogen). Recombinant 17β-HSD1 or 17β-HSD2 bacmids were transfected to Sf9 insect cells using "Cellfectin Reagent" (Invitrogen). 60 h later cells were harvested; the fractions including 17β-HSD1 or 17β-HSD2 were isolated as described by Puranen et al. (1994). Aliquots were stored frozen until determination of enzymatic activity.

Inhibition of Recombinant Human 17β-HSD1 or 17β-HSD2

Recombinant 17β-HSD1 assay: Recombinant protein homogenate (0.1 μg/ml) was incubated in 20 mM $KH_2PO_4$ pH 7.4 reaction buffer, including protease inhibitors (Complete Protease Inhibitor Cocktail tablet, Roche Diagnostics, 1697498), with 30 nM estrone (Sigma, E9750) as substrate, 800 000 cpm/ml $^3$H-estrone (PerkinElmer, NET319001MC) as a tracer substrate, and 1 mM NADPH (Sigma, N1630) as a co-factor for 30 min at RT, in the presence of potential inhibitors at concentrations of 1 μM or 0.1 μM. Inhibitor stock solutions were prepared in DMSO. The enzyme reaction was stopped by addition of trichloroacetic acid (1% final concentration). Samples were centrifuged in a microtiter plate at 4000 rpm for 10 min. Supernatants were applied to reverse phase HPLC on a Waters Symmetry C18 column, equipped with a Waters Sentry Guard column. Isocratic HPLC runs were performed at RT at a flow rate of 1 ml/min of acetonitrile:water 48:52 as running solvent. Radioactivity was monitored in the eluate by a Packard Flow Scintillation Analyzer. Total radioactivity for estrone and estradiol were determined in each sample and percent inhibition of estradiol conversion by the respective inhibitor was calculated Recombinant 17β-HSD2 assay: Recombinant 17β-HSD2 assay was performed as described for 17β-HSD1 but with following modifications: 6 μg/ml of recombinant protein homogenate, 50 nM Estradiol (Sigma, E8875) as a substrate, 800 000 cpm/ml $^3$H-estradiol (PerkinElmer, NET317) as a tracer substrate and 1 mM β-NAD (Sigma N7004) as a co-factor were used. Total radioactivity for estrone and estradiol were determined in each sample and percent inhibition of estrone conversion by the respective inhibitor was calculated.

For the calculation of % inhibition the following formula was used:

$$\% \text{ conversion} = 100 \times \frac{\{(cpm \text{ 'end product' in sample with inhibitor})/[(cpm \text{ 'substrate' in sample with inhibitor}) + (cpm \text{ 'end product' in sample with inhibitor})]\}}{\{(cpm \text{ end product in sample without inhibitor})/[(cpm\text{'substrate' in sample with inhibitor}) + (cpm \text{ 'end product' in sample with inhibitor})]\}}$$

Percent inhibition was calculated as follows: % inhibition=100−% conversion

The values "% inhibition" were determined for exemplified compounds, and the results are summarized in the following table "Inhibition of 17β-HSD enzyme type 1 and/or type 2".

TABLE

Inhibition of 17β-HSD enzyme type 1 and/or type 2

| Compound No. | Compound Name [IUPAC V 9.04] | Inhibition of rec. 17β-HSD1 100 nM | Inhibition of rec. 17β-HSD1 1 μm | Inhibition of rec. 17β-HSD2 100 nM | Inhibition of rec. 17β-HSD2 1 μm |
|---|---|---|---|---|---|
| 3 | 15beta-{3-[(5-methyl-1,3-thiazol-2-yl)amino]-3-oxopropyl}-17-oxoestra-1(10),2,4-triene-3-carboxamide | 20 | 74 | −1.8 | 8.6 |
| 11 | [15alpha-{3-[(5-methyl-1,3-thiazol-2-yl)amino]-3-oxopropyl}-17-oxoestra-1(10),2,4-trien-3-yl]boronic acid | 62 | 88 | 4.2 | 5.5 |
| 12 | [15alpha-{4-[(3,4-dihydroxybenzyl)amino]-4-oxobutyl}-17-oxoestra-1(10),2,4-trien-3-yl]boronic acid | 32 | 57 | −5.0 | 6.2 |

TABLE-continued

Inhibition of 17β-HSD enzyme type 1 and/or type 2

| Compound No. | Compound Name [IUPAC V 9.04] | Inhibition of rec. 17β-HSD1 100 nM | Inhibition of rec. 17β-HSD1 1 μm | Inhibition of rec. 17β-HSD2 100 nM | Inhibition of rec. 17β-HSD2 1 μm |
|---|---|---|---|---|---|
| 13 | [15alpha-[4-(1,3-benzodioxol-5-ylamino)-4-oxobutyl]-17-oxoestra-1(10),2,4-trien-3-yl]boronic acid | 27 | 52 | −7.6 | 2.0 |
| 16 | [15alpha-{4-[(5-methyl-1,3-thiazol-2-yl)amino]-4-oxobutyl}-17-oxoestra-1(10),2,4-trien-3-yl]boronic acid | 30 | 59 | n.d. | n.d. |
| 17 | [15alpha-[4-(cyclohexylamino)-4-oxobutyl]-17-oxoestra-1(10),2,4-trien-3-yl]boronic acid | 24 | 31 | −5.4 | 1.8 |
| 19 | [15alpha-{4-[(1,3-benzodioxol-5-ylmethyl)amino]-4-oxobutyl}-17-oxoestra-1(10),2,4-trien-3-yl]boronic acid | 19 | 43 | −2.4 | 0.1 |
| 22 | [15alpha-{4-[benzyl(methyl)amino]-4-oxobutyl}-17-oxoestra-1(10),2,4-trien-3-yl]boronic acid | 37 | 60 | n.d. | n.d. |
| 23 | [15alpha-[4-(benzylamino)-4-oxobutyl]-17-oxoestra-1(10),2,4-trien-3-yl]boronic acid | 76 | 54 | 1.8 | 0.4 |
| 26 | [15alpha-(4-{[2-(3,4-dimethoxyphenyl)ethyl](methyl)amino}-4-oxobutyl)-17-oxoestra-1(10),2,4-trien-3-yl]boronic acid | 21 | 41 | n.d. | n.d. |
| 30 | [15beta-(3-{[2-(7-methyl-1H-indol-3-yl)ethyl]amino}-3-oxopropyl)-17-oxoestra-1(10),2,4-trien-3-yl]boronic acid | 50 | 56 | 1.3 | 6.3 |
| 31 | [15beta-{3-[(5-methyl-1,3-thiazol-2-yl)amino]-3-oxopropyl}-17-oxoestra-1(10),2,4-trien-3-yl]boronic acid | 82 | 90 | 2.6 | 1.6 |
| 32 | [15beta-[3-(cyclohexylamino)-3-oxopropyl]-17-oxoestra-1(10),2,4-trien-3-yl]boronic acid | 77 | 91 | 1.1 | 3.5 |
| 33 | [15beta-(3-morpholin-4-yl-3-oxopropyl)-17-oxoestra-1(10),2,4-trien-3-yl]boronic acid | 20 | 59 | −2.3 | −1.1 |
| 34 | [15beta-{3-[(1,3-benzodioxol-5-ylmethyl)amino]-3-oxopropyl}-17-oxoestra-1(10),2,4-trien-3-yl]boronic acid | 47 | 65 | 3.2 | 0.4 |
| 35 | [17-oxo-15beta-(3-oxo-3-piperidin-1-ylpropyl)estra-1(10),2,4-trien-3-yl]boronic acid | 57 | 56 | 4.0 | 1.5 |
| 37 | [15beta-{3-[benzyl(methyl)amino]-3-oxopropyl}-17-oxoestra-1(10),2,4-trien-3-yl]boronic acid | 22 | 49 | n.d. | n.d. |
| 39 | [15beta-[3-(diethylamino)-3-oxopropyl]-17-oxoestra-1(10),2,4-trien-3-yl]boronic acid | 74 | 88 | 1.8 | −0.6 |
| 45 | [15beta-[3-(1,3-benzodioxol-5-ylamino)-3-oxopropyl]-17-oxoestra-1(10),2,4-trien-3-yl]boronic acid | 49 | 66 | −1.0 | −1.1 |
| 47 | [17,17-difluoro-15alpha-(4-morpholin-4-yl-4-oxobutyl)estra-1(10),2,4-trien-3-yl]boronic acid | 10 | 61 | 3.8 | 12.9 |
| 48 | [15alpha-[4-(cyclohexylamino)-4-oxobutyl]-17,17-difluoroestra-1(10),2,4-trien-3-yl]boronic acid | 25 | 50 | 6.4 | 12.8 |
| 49 | [15alpha-[4-(diethylamino)-4-oxobutyl]-17,17-difluoroestra-1(10),2,4-trien-3-yl]boronic acid | 29 | 50 | 7.7 | 11.6 |
| 50 | [15alpha-{4-[(1,3-benzodioxol-5-ylmethyl)amino]-4-oxobutyl}-17,17-difluoroestra-1(10),2,4-trien-3-yl]boronic acid | 40 | 57 | 8.0 | 32.8 |
| 51 | [15alpha-(4-{[2-(3,4-dimethoxyphenyl)ethyl](methyl)amino}-4-oxobutyl)-17,17-difluoroestra-1(10),2,4-trien-3-yl]boronic acid | 37 | 62 | 2.8 | 7.8 |
| 53 | [17,17-difluoro-15alpha-{4-oxo-4-[(pyridin-3-ylmethyl)amino]butyl}estra-1(10),2,4-trien-3-yl]boronic acid | 19 | 50 | 5.0 | 8.6 |
| 54 | [15alpha-[4-(benzylamino)-4-oxobutyl]-17,17-difluoroestra-1(10),2,4-trien-3-yl]boronic acid | 41 | 58 | 7.6 | 25.2 |
| 58 | [17,17-difluoro-15beta-{3-[(5-methyl-1,3-thiazol-2-yl)amino]-3-oxopropyl}estra-1(10),2,4-trien-3-yl]boronic acid | 23 | 55 | 6.8 | 11.6 |
| 59 | [15beta-[3-(cyclohexylamino)-3-oxopropyl]-17,17-difluoroestra-1(10),2,4-trien-3-yl]boronic acid | 69 | 84 | 0.6 | 15.2 |
| 60 | [15beta-{3-[(1,3-benzodioxol-5-ylmethyl)amino]-3-oxopropyl}-17,17-difluoroestra-1(10),2,4-trien-3-yl]boronic acid | 46 | 71 | 9.5 | 12.5 |
| 62 | [17,17-Difluoro-15beta-{3-oxo-3-[(pyridin-3-ylmethyl)amino]propyl}estra-1(10),2,4-trien-3-yl]boronic acid | 36 | 56 | 6.2 | 8.3 |
| 63 | [15beta-[3-(benzylamino)-3-oxopropyl]-17,17-difluoroestra-1(10),2,4-trien-3-yl]boronic acid | 51 | 66 | 12.8 | 16.9 |

TABLE-continued

Inhibition of 17β-HSD enzyme type 1 and/or type 2

| Compound | | Inhibition of rec. 17β-HSD1 | | Inhibition of rec. 17β-HSD2 | |
|---|---|---|---|---|---|
| No. | Compound Name [IUPAC V 9.04] | 100 nM | 1 μm | 100 nM | 1 μm |
| 65 | [15beta-{3-[(2,4-difluorobenzyl)amino]-3-oxopropyl}-17,17-difluoroestra-1(10),2,4-trien-3-yl]boronic acid | 32 | 63 | 5.8 | 9.8 |
| 67 | [17,17-difluoro-15beta-(3-{[2-(7-methyl-1H-indol-3-yl)ethyl]amino}-3-oxopropyl)estra-1(10),2,4-trien-3-yl]boronic acid | 47 | 66 | 10.0 | 15.8 |
| 71 | [15beta-[3-(diethylamino)-3-oxopropyl]-17,17-difluoroestra-1(10),2,4-trien-3-yl]boronic acid | 78 | 85 | 7.9 | 16.3 |
| 72 | [15beta-(3-{[2-(3,4-dimethoxyphenyl)ethyl](methyl)amino}-3-oxopropyl)-17,17-difluoroestra-1(10),2,4-trien-3-yl]boronic acid | 39 | 77 | −2.4 | 5.3 |
| 74 | [15beta-[3-(1,3-benzodioxol-5-ylamino)-3-oxopropyl]-17,17-difluoroestra-1(10),2,4-trien-3-yl]boronic acid | 55.6 | 71.4 | 4.9 | 5.5 |
| 75 | 3-{[3-methoxy-5-(trifluoromethyl)phenyl]amino}-15alpha-(4-morpholin-4-yl-4-oxobutyl)estra-1(10),2,4-trien-17-one | 36 | 50 | n.d. | n.d. |
| 76 | 15alpha-(4-morpholin-4-yl-4-oxobutyl)-3-{[3-(morpholin-4-ylsulfonyl)phenyl]amino}estra-1(10),2,4-trien-17-one | 29 | 26 | n.d. | n.d. |
| 83 | 15alpha-(4-morpholin-4-yl-4-oxobutyl)-3-(quinolin-3-ylamino)estra-1(10),2,4-trien-17-one | 19 | 50 | n.d. | n.d. |
| 91 | 3-[(1,1-dioxido-1-benzothien-6-yl)amino]-15alpha-(4-morpholin-4-yl-4-oxobutyl)estra-1(10),2,4-trien-17-one | 36 | 69 | 0.7 | 5.7 |

2. Inhibition of the 17β-HSD Type 3 Enzyme

The compounds were screened in respect of 17β-HSD3 enzyme activity in vitro on established MCF-7 cell lines, each stably expressing the 17β-HSD3 enzyme. The interconversion of substrate by 17β-HSD3 and the 17β-HSD3 inhibiting activity of chemical compounds in these cell lines were detected by HPLC system.

Varying amounts of the test compounds were incubated in the growth medium of the 17β-HSD3 expressing cells together tritium labeled androstenedione (2 nM). The medium samples were removed after exact incubation time and the reaction is stopped by trichloroacetic acid (TCA). The samples were analyzed by HPLC-coupled flow scintillation analysis.

Conversion: The 17β-HSD3 inhibiting activity of an individual test compound was calculated by comparing the conversion of a control sample without any test compound (referred to as "Negative Control") to the (reduced) conversion of the test sample containing the particular compound to be tested (referred to as "Test Sample").

$$\% \text{ inhibition} = 100 \times \frac{(\text{Conversion in Negative Control} - \text{Conversion in Test Sample})}{(\text{Conversion Negative Control})}$$

The values "% inhibition" were determined for exemplified compounds, whereby two concentrations of each compound were used. The number of the compound refers to the numbers indicated in the Experimental Section. The results are summarized in the following table "Inhibition of 17β-HSD enzyme type 3".

TABLE

Inhibition of 17β-HSD enzyme type 3

| Compound | | Inhibition of 17β-HSD3 | |
|---|---|---|---|
| No. | Compound Name [IUPAC V 9.04] | 1 μM | 10 μM |
| 8 | 17,17-difluoro-15beta-{3-[(5-methyl-1,3-thiazol-2-yl)amino]-3-oxopropyl}estra-1(10),2,4-triene-3-carboxamide | 4 | 46 |
| 13 | [15alpha-[4-(1,3-benzodioxol-5-ylamino)-4-oxobutyl]-17-oxoestra-1(10),2,4-trien-3-yl]boronic acid | 18 | 22 |
| 17 | [15alpha-[4-(cyclohexylamino)-4-oxobutyl]-17-oxoestra-1(10),2,4-trien-3-yl]boronic acid | 6 | 45 |
| 20 | [17-oxo-15alpha-(4-oxo-4-piperidin-1-ylbutyl)estra-1(10),2,4-trien-3-yl]boronic acid | 15 | 57 |

TABLE-continued

Inhibition of 17β-HSD enzyme type 3

| Compound No. | Compound Name [IUPAC V 9.04] | Inhibition of 17β-HSD3 1 μM | 10 μM |
|---|---|---|---|
| 48 | [15alpha-[4-(cyclohexylamino)-4-oxobutyl]-17,17-difluoroestra-1(10),2,4-trien-3-yl]boronic acid | 13 | 63 |
| 49 | [15alpha-[4-(diethylamino)-4-oxobutyl]-17,17-difluoroestra-1(10),2,4-trien-3-yl]boronic acid | 62 | 89 |
| 53 | [17,17-difluoro-15alpha-{4-oxo-4-[(pyridin-3-ylmethyl)amino]butyl}estra-1(10),2,4-trien-3-yl]boronic acid | 4 | 50 |
| 57 | [17,17-difluoro-15alpha-(4-oxo-4-piperidin-1-ylbutyl)estra-1(10),2,4-trien-3-yl]boronic acid | 28 | 78 |
| 60 | [15beta-{3-[(1,3-benzodioxol-5-ylmethyl)amino]-3-oxopropyl}-17,17-difluoroestra-1(10),2,4-trien-3-yl]boronic acid | 28 | 67 |
| 63 | [15beta-[3-(benzylamino)-3-oxopropyl]-17,17-difluoroestra-1(10),2,4-trien-3-yl]boronic acid | 41 | 88 |
| 67 | [17,17-difluoro-15beta-(3-{[2-(7-methyl-1H-indol-3-yl)ethyl]amino}-3-oxopropyl)estra-1(10),2,4-trien-3-yl]boronic acid | 40 | 84 |
| 71 | [15beta-[3-(diethylamino)-3-oxopropyl]-17,17-difluoroestra-1(10),2,4-trien-3-yl]boronic acid | 31 | 60 |
| 72 | [15beta-(3-{[2-(3,4-dimethoxyphenyl)ethyl](methyl)amino}-3-oxopropyl)-17,17-difluoroestra-1(10),2,4-trien-3-yl]boronic acid | 45 | 71 |
| 91 | 3-[(1,1-dioxido-1-benzothien-6-yl)amino]-15alpha-(4-morpholin-4-yl-4-oxobutyl)estra-1(10),2,4-trien-17-one | 7 | 52 |
| 98 | 3-(benzylamino)-15alpha-(4-morpholin-4-yl-4-oxobutyl)estra-1(10),2,4-trien-17-one | 15 | 48 |

3. Estrogen Receptor Binding Assay

The binding affinity of the compounds of the invention to the estrogen receptor α and to the estrogen receptor β may be determined according to the in vitro ER binding assays described by Koffman et al (1991). Alternatively, an estrogen receptor binding assay may be performed according to published PCT application no. WO 00/07996.

4. Estrogen Receptor Transactivation Assays

Compounds of the invention showing binding affinity towards the estrogen receptor may be further tested with regard to their individual estrogenic or anti-estrogenic potential (agonistic binding or antagonistic binding to the ERα or ERβ). The determination of the estrogen receptor agonist activity may be performed according to an in vitro assay system using the MMTV-ERE-LUC reporter system which is for example described within published US patent application US2003/0170292:

To assay estrogen receptor agonist activity, Hela cells are grown in 24-well microtiter plates and then transiently co-transfected with two plasmids using lipofectamine. The first plasmid comprises DNA encoding human estrogen receptor (either ER-alpha or ER-beta), and the second plasmid comprises an estrogen-driven reporter system comprising: a luciferase reporter gene (LUC) whose transcription is under the control of upstream regulatory elements comprising 4 copies of the vitellogenin estrogen response element (ERE) cloned into the mouse mammary tumor virus (MMTV) promoter (the full name for the reporter system being "MMTV-ERE-LUC"). Cells are exposed to the compounds of the invention in RPMI 1640 medium, supplemented with 10% charcoal-treated fetal calf serum, 2 mM L-glutamine, 0.1 mM non-essential amino acids and 1 mM sodium pyruvate for 42-48 h at 37° C. in a 5% carbon dioxide incubator. Concurrently, cells exposed to estradiol (1 nM) serve as positive controls. Replicate wells exposed to the solvent in which the compounds of the invention are dissolved (i.e. ethanol or methanol) are used as negative controls. After the 42-48 h incubation period, cells are rinsed with phosphate buffered saline (PBS), lysis buffer (Promega Corp) is added, and cell lysates are collected for measurement of luciferase activity with a luminometer. Estrogenic activity of the compounds of the invention is expressed as fold-increase in luciferase activity as compared to that observed in negative control cells.

Alternatively, the determination of the estrogen receptor transactivation activity (estrogenicity assay or agonist assay) and of the inhibitory potency of transactivation activity (anti-estrogenicity assay or antagonist assay) may be performed according to published PCT application no. WO 00/07996.

Conclusion

The compounds of the invention show good inhibitory potential of the 17β-HSD1, 17β-HSD2 and/or of the 17β-HSD3 enzyme. As explained in more detail above, the compounds of the invention are therefore regarded as being suited for the treatment of several estrogen and androgen dependent diseases and disorders, respectively. In particular, since several malign and benign pathologies such as e.g. breast cancer, endometriosis and uterine leiomyomas are all 17β-estradiol dependent, a reduction of the endogenous 17β-estradiol concentration in the respective tissue, e.g. by inhibition of the 17β-HSD1 enzyme, will result in an impaired or reduced proliferation of the 17β-estradiol dependent cells in said tissues as can be demonstrated by the above described in vivo assays. Therefore, the selective inhibitors of the 17β-HSD1 enzyme as described herein are well suited to impair also endogenous productions of estrogens, in particular of 17β-estradiol, in myomas, endometriotic, adenomyotic and endometrial tissue. The application of a compound acting as selective inhibitor on the 17β-HSD1 enzyme, which preferentially catalyzes the reductive reaction, will result in a lowered intracellular estradiol-concentration, since the reductive conversion of the estrone into the active estradiol is reduced or suppressed, and will therefore impair or even reduce the proliferation of the 17β-estradiol dependent cells in the malignant or benign tissue.

Illustrative Pharmaceutical Compositions

The following examples provide illustrative pharmaceutical composition formulations:

I. Hard Gelatin Capsules

Hard gelatin capsules are prepared using the following ingredients:

| Ingredient | Quantity (mg/capsule) |
|---|---|
| COMPOUND No. 1 | 0.5 |
| Starch, dried | 105.5 |
| Magnesium stearate | 14.0 |
| Total | 120.0 |

The above ingredients are mixed and filled into hard gelatin capsules in 120 mg quantities.

II. Tablets

A tablet is prepared using the ingredients below:

| Ingredient | Quantity (mg/tablet) |
|---|---|
| COMPOUND No. 10 | 0.5 |
| Cellulose, microcrystalline | 209.5 |
| Silicon dioxide, fumed | 10.0 |
| Stearic acid | 10.0 |
| Total | 230.0 |

The components are blended and compressed to form tablets each weighing 230 mg.

III. Suppositories

Suppositories, each containing 1 mg of active ingredient, may be made as follows:

| Ingredient | Quantity (mg/suppository) |
|---|---|
| COMPOUND No. 6 | 1 |
| Saturated fatty acid glycerides | 2,000 |
| Total | 2,001 |

The active ingredient is passed through a appropriately sized mesh sieve and suspended in the saturated fatty acid glycerides previously melted using the minimum heat necessary. The mixture is then poured into a suppository mold of normal 2 g capacity and allowed to cool.

IV. Intravenous Formulation

An intravenous formulation may be prepared as follows:

| Ingredient | Quantity |
|---|---|
| COMPOUND No. 8 | 5 mg |
| Isotonic saline | 1000 ml |
| Glycerol | 100 ml |

The compound is dissolved in the glycerol and then the solution is slowly diluted with isotonic saline.

GENERAL PROVISIONS

The scope of the invention is not to be limited by the description of the examples. Modifications and alterations of the present invention will be apparent to those skilled in the art without departing from the scope and spirit of the present invention. Therefore, it should be understood that the scope of this invention is defined by the appended claims, rather than by the specific examples which have been presented by way of example.

CITED LITERATURE

Ahmed V, Liu Y, Silvestro C, Taylor S D (2006) "Boronic acids as inhibitors of steroid sulfatase" Bioorg. Med. Chem. 14(24):8564-8573.

Andersen J, Bolvig S, Liang X (2005) "Efficient One-Pot Synthesis of 1-Aryl 1,2,3-Triazoles from Aryl Halides and Terminal Alkynes in the Presence of Sodium Azide" Synlett, 2005, 19:2941

Andersson S (1995) "Molecular genetics of androgenic 17β-Hydroxysteroid Dehydrogenases. J. Steroid Biochem. Molec. Biol., 55:533-534

Boivin R P, Luu-The V, Lachance R, Labrie F, Poirier D. (2000) "Structure-activity relationships of 17alpha-derivatives of estradiol as inhibitors of steroid sulfatase." J Med. Chem. 2000 Nov. 16; 43(23):4465-78.

Burow M E, Boue S M, Collins-Burow B M, Melnik L I, Duong B N, Carter-Wientjes C H, Li S, Wiese T E, Cleveland T E, McLachlan J A (2001) "Phytochemical glyceollins, isolated from soy, mediate antihormonal effects through estrogen receptor alpha and beta. J. Clin. Endocrinol. Metab. 86 (4), 1750-1758

Ciobanu L C & Poirier D (2006) "Synthesis of libraries of 16beta-aminopropyl estradiol derivatives for targeting two key steroidogenic enzymes" ChemMedChem. 1(11): 1249-59.

Cushman et al (1995) "Synthesis, antitubulin and antimitotic activity, and cytotoxicity of analogs of 2-methoxyestradiol, an endogenous mammalian metabolite of estradiol that inhibits tubulin polymerization by binding to the colchicine binding site." J Med. Chem. 38(12): 2041-9.

Cushman et al (2002) "The effect of exchanging various substituents at the 2-position of 2-methoxyestradiol on cytotoxicity in human cancer cell cultures and inhibition of tubulin polymerization." J Med. Chem. 45(21):4748-54.

Day et al (2003) "The effects of 2-substituted oestrogen sulfamates on the growth of prostate and ovarian cancer cells." J Steroid Biochem Mol. Biol. 2003 84(2-3):317-25.

Dong et al. (1998) "17β-hydroxysteroid dehydrogenases in human bone cells" J. Bone Min. Res., 13:1539-1546

Einspanier A, Lieder K, Brüns A, Husen B, Thole H, Simon C. (2006) "Induction of endometriosis in the marmoset monkey (*Callithrix jacchus*)" Mol Hum Reprod. 2006 May; 12(5):291-9. Epub 2006 Apr. 11

EP0367576

EP0977555

Ettmayer P, Amidon G L, Clement B, Testa B (2004) "Lessons learned from marketed and investigational prodrugs", J. Med. Chem. 47(10): 2393-2404.

Geissler W M et al. (1994) "Male pseudohermaphroditism caused by mutations of testicular 17beta-hydroxysteroid dehydrogenase 3." Nat. Genet., 7:34-9

Gonzalez et al (1982) "Synthesis and pharmacological evaluation of 8alpha-estradiol derivatives" Steroids 40(2): 171-188

Gruemmer R, Schwarzer F, Bainczyk K, Hess-Stumpp H, Regidor P A, Schindler A E, Winterhager E (2001) "Peritoneal endometriosis: validation of an in vivo model". Hum. Reprod. 16 (8), 1736-1743.

Husen B, Huhtinen K, Poutanen M, Kangas L, Messinger J, Thole H (2006) "Evaluation of inhibitors for 17beta-hydroxysteroid dehydrogenase type 1 in vivo in immunodeficient mice inoculated with MCF-7 cells stably expressing the recombinant human enzyme" Mol Cell Endocrinol. 2006 Mar. 27; 248(1-2):109-13. Epub 2006 Jan. 10.

Koffman et al (1991) "Evidence for involvement of tyrosine in estradiol binding by rat uterus estrogen receptor." J. Steroid. Biochem. Mol. Biol. 38(2):135

Labaree et al. (2003) "Synthesis and Evaluation of B-, C- and D-ring substituted estradiol carboxylic acid esters as locally active estrogens" J. Med. Chem. 46:1886-1904

Labrie et al (1997) "The key role of 17 beta-hydroxysteroid dehydrogenases in sex steroid biology." Steroids, 62:148-58

Labrie et al. (2000) "Role of 17 beta-hydroxysteroid dehydrogenases in sex steroid formation in peripheral intracrine tissues" Trends Endocrinol Metab., 11:421-7

Lauson H D, Heller C G, Golden J B, Severinghaus E L (1939) "The immature rat uterus in the assay of estrogenic substances, a comparison of estradiol, estrone and estriol". Endocrinoloy 24, 35-44.

Lawrence et al (2005) "Novel and potent 17beta-hydroxysteroid dehydrogenase type 1 inhibitors." J Med. Chem. 48(8):2759-62

Lesma G; Sacchetti A, Silvani A (2006) "Palladium-Catalyzed Hydroxycarbonylation of Aryl and Vinyl Triflates by in situ Generated Carbon Monoxide under Microwave Irradiation" Synthesis 4: 594-96

Ley et al (1994) "Tetrapropylammonium perruthenate, Pr4N+RuO4-, TPAP: a catalytic oxidant for organic synthesis" Synthesis. 07:639-666

Li P K, Pillai R and Dibbelt L (1995) "Estrone sulfate analogs as estrone sulfatase inhibitors" Steroids 60(3): 299-306

Liu et al (1992) "Synthesis of high affinity fluorine-substituted ligands for the androgen receptor. Potential agents for imaging prostatic cancer by positron emission tomography." J Med. Chem. 35(11):2113-29

Lunn & Farkas (1968) "The adamantyl carbonium ion as a dehydrogenating agent, its reactions with estrone" Tetrahedron 24(23):6773-6776.

Mindnich et al (2004) "The role of 17 beta-hydroxysteroid dehydrogenases" Mol Cell Endocrinol. 218(1-2):7-20. Review Mohanakrishnan & Cushman (1999) "Pd(0)-Mediated Cross Coupling of 2-Iodoestradiol with Organozinc Bromides: A General Route to the Synthesis of 2-Alkynyl, 2-Alkenyl and 2-Alkylestradiol Analogs" Synlett 1999(07): 1097-1099

Morera E & Ortar G (1998) "A palladium-catalyzed carbonylative route to primary amides" Tetrahedron Letters, 39(18): 2835-2838

Nambara et al. (1976) "Synthesis of Estetrol Monoglucuronides" Steroids 27:111-122

Oefelein M G & Cornum R (2000) "Failure to achieve castrate levels of testosterone during luteinizing hormone releasing hormone agonist therapy: the case for monitoring serum testosterone and a treatment decision algorithm." J Urol.; 164:726-9

PCT/EP2007/059785 (not yet published)

Pelletier & Poirier (1996) "Synthesis and evaluation of estradiol derivatives with 16α-(bromoalkylamide), 16α-(bromoalkyl) or 16α-(bromoalkynyl) side chain as inhibitors of 17β-hydroxysteroid dehydrogenase type 1 without estrogenic activity" Bioorg Med Chem, 4(10): 1617-1628

Poirier (2003) "Inhibitors of 17 beta-hydroxysteroid dehydrogenases" Curr Med. Chem. 10:453-77

Poirier et al (1991) "Synthesis of 17β-estradiol derivatives with N-Butyl, N-methyl alkylamide side chain at position 15." Tetrahedron, 47(37):7751-7766

Poirier et al (1996) "D-Ring alkylamine derivatives of estradiol: effect on ER-binding affinity and antiestrogenic activity" Bioorg Med Chem Lett 6(21):2537-2542

Poirier et al (1998) "A 6β-(Thiaheptanamide) Derivative of Estradiol as inhibitor of 17β-Hydroxysteroid Dehydrogenase Type 1", J. Steroid Biochem. Molec. Biol., 64:83-90

Poirier D, Ciobanu L C, Bérubé M. (2002) "A multidetachable sulfamate linker successfully used in a solid-phase strategy to generate libraries of sulfamate and phenol derivatives" Bioorg Med Chem. Lett. 2002 Oct. 21; 12(20):2833-8.

Puranen et al (1994) "Site-directed mutagenesis of the putative active site of human 17 beta-hydroxysteroid dehydrogenase type 1" Biochem. J. 304:289-93.

Rao & Cessac (2002) "A new, practical synthesis of 2-methoxyestradiols." Steroids. 67(13-14):1065-70.

Sam et al. (1998) "C16 and C17 Derivatives of Estradiol as Inhibitors of 17β-Hydroxysteroid Dehydrogenase Type 1: Chemical Synthesis and Structure-Activity Relationships", Drug Design and Discovery, 15:157-180

Schoen U, Messinger J, Buchholz M, Reinecker U, Thole H, Prabhu MKS, Konda A (2005) "An improved synthesis of 3-aminoestrone" Tetrahedron Letters 46(42): 7111-7115

Stella P (2004) "Prodrugs as therapeutics" Expert Opin. Ther. Patents, 14(3): 277-280

Tamaya et al. (1985) "Comparison of cellular levels of steroid receptors in uterine leiomyoma and myometrium." Acta Obstet Gynecol Scand., 64:307-9

Tremblay & Poirier (1998) "Overview of a Rational Approach to Design Type I 17β-Hydroxysteroid Dehydrogenase Inhibitors Without Estrogenic Activity: Chemical Synthesis and Biological Evaluation", J. Steroid Biochem. Molec. Biol., 66:179-191

US2003/0170292
U.S. Pat. No. 3,347,878
U.S. Pat. No. 3,413,321
U.S. Pat. No. 5,571,933
U.S. Pat. No. 5,677,292
U.S. Pat. No. 5,866,603
U.S. Pat. No. 6,043,236
U.S. Pat. No. 6,541,463
WO00/07996
WO01/42181
WO02/26706
WO02/32409
WO2003/017973
WO2003/022835
WO2003/033487
WO2003/101972
WO2004/046111
WO2004/060488

WO2004/080271
WO2004/085345
WO2004/085457
WO2004/085459
WO2004/110459
WO2005/032527
WO2005/047303
WO2005/084295
WO2006/003012
WO2006/003013
WO2006/027347
WO2006/063585
WO2006/125800
WO99/46279

Yoshikawa et al. (2002) "Diastereo- and Enantioselective Direct Catalytic Aldol Reaction of 2-Hydroxyacetophenones with Aldehydes Promoted by a Heteropolymetallic Complex: Catalytic Asymmetric Synthesis of anti-1, 2-Diols" J. Org. Chem. 67(8); 2556-2565.

Yuen A K L & Hutton C A (2005) "Deprotection of pinacolyl boronate esters via hydrolysis of intermediate potassium trifluoroborates" Tetrahedron letters, 46(46): 7899-7903

Zeitoun K, Takayama K, Sasano H, Suzuki T, Moghrabi N, Andersson S, Johns A, Meng L, Putman M, Carr B, Bulun S E (1998) "Deficient 17beta-hydroxysteroid dehydrogenase type 2 expression in endometriosis: failure to metabolize 17beta-estradiol." J Clin Endocrinol Metab. 1998 December; 83(12):4474-80.

What is claimed is:

1. A compound corresponding to formula (I)

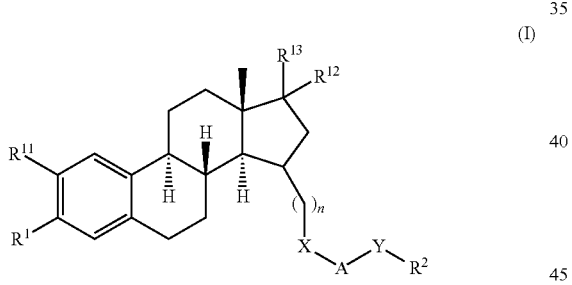

wherein

—X-A-Y— together represent a group selected from the group consisting of:
(a) —CO—NR$^4$—,
(b) —CO—O—,
(c) —CO—,
(d) —CO—NH—NR$^4$—,
(e) —NR$^3$—CO—NR$^4$—
(f) —NR$^3$—CO—O—,
(g) —NR$^3$—CO—,
(h) —NR$^3$—CO—NH—SO$_2$—,
(i) —NR$^3$—SO$_2$—NR$^4$—
(j) —NR$^3$—SO$_2$—O—,
(k) —NR$^3$—SO$_2$—
(l) —O—CO—NR$^4$—,
(m) —O—CO—,
(n) —O—CO—NH—SO$_2$—NR$^4$—,
(o) —O—, and
(p) the groups

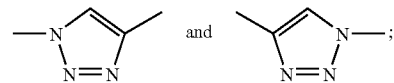

wherein R$^3$ represents —H or —(C$_1$-C$_4$)alkyl;

R$^1$ is selected from the group consisting of:
(a) —B(OR$^9$)(OR$^{10}$)
(b) —CO—OR$^6$
(c) —CO—NR$^7$R$^8$
(d) —NR$^7$R$^8$
(e) —NR$^5$—CO—R$^6$, and
(f) —NR$^5$—SO$_2$—R$^6$;

wherein

R$^5$ represents —H or —(C$_1$-C$_4$)alkyl; and

R$^6$, R$^7$, R$^8$, R$^9$ and R$^{10}$ are independently selected from the group consisting of:
(a) —H
(b) optionally substituted —(C$_1$-C$_{14}$)alkyl,
(c) optionally substituted aryl or aryl-(C$_1$-C$_{14}$)alkyl,
(d) optionally substituted heteroaryl or heteroaryl-(C$_1$-C$_{14}$)alkyl, and
(e) optionally substituted cycloheteroalkyl or cycloheteroalkyl-(C$_1$-C$_{14}$)alkyl; or R$^7$ and R$^8$ form together with the nitrogen atom, to which they are attached, a heterocyclic 4, 5, 6, 7 or 8 membered ring, which is optionally saturated, partly unsaturated or aromatic; which optionally contains 1, 2 or 3 additional heteroatoms selected from the group consisting of N, O or S, the number of additional N atoms being 0, 1, 2 or 3 and the number of O and S atoms each being 0, 1 or 2; and which ring is optionally part of a multiple condensed ring system, wherein the ring or the ring-system is optionally substituted;

and if R$^1$ is —NR$^5$—CO—R$^6$, then R$^5$ and R$^6$ together with the nitrogen atom to which R$^5$ is attached and the carbonyl group to which R$^6$ is attached may also form a 4, 5, 6, 7 or 8 membered lactam ring;

and if R$^1$ is —NR$^5$—SO$_2$—R$^6$, then R$^5$ and R$^6$ together with the nitrogen atom to which R$^5$ is attached and the sulfoxyd group to which R$^6$ is attached may also form a 4, 5, 6, 7 or 8 membered sultam ring; or R$^9$ and R$^{10}$ together with the boronic acid group to which they are attached form a 5 or 6 membered ring, which is optionally substituted with 1, 2, 3 or 4 —(C$_1$-C$_4$) alkyl groups;

n represents 1, 2, 3, 4, 5 or 6, or, if —X-A-Y— represents —CO—NR$^4$—, —CO—O—, —CO— or —CO—NH—NR$^4$—, then n may also represent 0;

R$^{11}$ represents H, —(C$_1$-C$_{14}$)alkyl, (C$_1$-C$_{14}$)alkoxy, or (C$_1$-C$_{14}$)alkoxy-(C$_1$-C$_{14}$)alkyl;

R$^{12}$ and R$^{13}$ together represent =O, or R$^{12}$ and R$^{13}$ each individually represent F;

R$^2$ and R$^4$ are independently selected from the group consisting of:
(a) —H;
(b) optionally substituted —(C$_1$-C$_{14}$)alkyl,
(c) optionally substituted acyl, with the proviso that —X-A-Y— together represent —CO—NH—NR$^4$— or a group

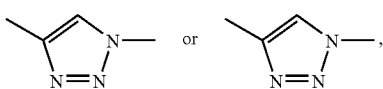 or (d) optionally substituted aryl or aryl-$(C_1-C_{14})$alkyl,
(e) optionally substituted heteroaryl or heteroaryl-$(C_1-C_{14})$alkyl, and
(f) optionally substituted cycloheteroalkyl or cycloheteroalkyl-$(C_1-C_{14})$alkyl; or $R^2$ and $R^4$ together with the nitrogen atom to which $R^2$ and $R^4$ are attached form a heterocyclic 4, 5, 6:7 or 8 memberred ring, which is optionally saturated, partly unsaturated or aromatic; which optionally contains 1, 2 or 3 additional heteroatoms selected from N, O and S, the number of additional N atoms being 0, 1, 2 or 3 and the number of O and S atoms each being 0, 1 or 2; and which ring is optionally part of a multiple condensed ring-system, wherein the ring or the ring-system is optionally substituted;
or a pharmaceutically acceptable salt thereof.

2. A compound according to claim 1, which is an optically pure enantiomer having the formula (II)

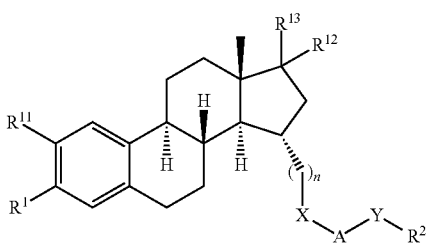

(II)

or a pharmaceutically acceptable salt thereof.

3. A compound according to claim 1, which is an optically pure enantiomer having the formula (III)

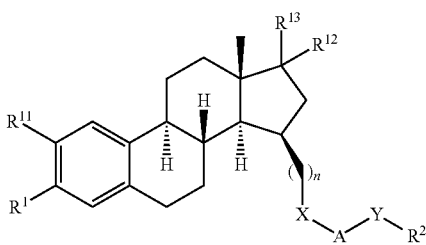

(III)

or a pharmaceutically acceptable salt thereof.

4. A compound according to claim 1, wherein —X-A-Y— together represent a group selected from the group consisting of:
(a) —CO—NR$^4$—,
(b) —CO—O—,
(c) —CO—,
(d) —CO—NH—NR$^4$—,
(e) —NH—CO—NH—,
(f) —NH—CO—O—,
(g) —NH—CO—,
(h) —NH—CO—NH—SO$_2$—,
(i) —NH—SO$_2$—NH—,
(j) —NH—SO$_2$—O—,
(k) —NH—SO$_2$
(l) —O—CO—NH—,
(m) —O—CO—,
(n) —O—CO—NH—SO$_2$—NR$^4$—,
(o) —O—, and
(p) the groups

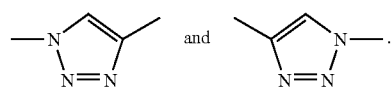

5. A compound according to claim 4, wherein —X-A-Y— together represent a group selected from the group consisting of:
(a) —CO—NR$^4$—, and
(b) the groups

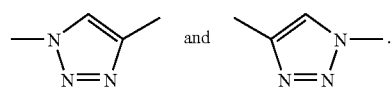

6. A compound according to claim 1, wherein $R^2$ and $R^4$ are independently selected from the group consisting of:
(a) —H, wherein, if —X-A-Y— together represents —CO—O— or —CO—, then $R^2$ is different from —H,
(b) —$(C_1-C_{12})$alkyl, which is optionally substituted with one or more substituents independently selected from the group consisting of halogen, —CN, —OR$^{14}$, —SR$^{14}$, —NR$^{15}$R$^{16}$, CONR$^{15}$R$^{16}$, —SO$_2$NR$^{15}$R$^{16}$—CO—R$^{17}$—COOR$^{14}$—NH—CO—R$^{17}$ and —O—SO$_2$—R$^{18}$; the number of said substituents being 1, 2, 3, 4 or 5 for halogen, and 1 or 2 for any combination of substituents;
(c) acyl —(C=O)—Z, wherein Z represents hydrogen, $(C_1-C_4)$alkyl, aryl, aryl—$(C_1-C_4)$alkyl or heteroaryl-$(C_1-C_4)$alkyl;
wherein each aryl or aryl-$(C_1-C_4)$alkyl is optionally substituted in the aryl moiety with 1, 2 or 3 substituents independently selected from the group consisting of hydroxyl, halogen, —O—$(C_1-C_4)$alkyl, —$(C_1-C_4)$alkyl or halogenated —$(C_1-C_4)$alkyl;
(d) aryl and aryl-$(C_1-C_{12})$alkyl, in which the aryl moiety is optionally substituted with one or more substituents independently selected from the group consisting of halogen, —OR$^{14}$, —$(C_1-C_6)$alkyl, halogenated —$(C_1-C_6)$alkyl, —COOR$^{14}$, —$(C_1-C_6)$alkyl-COOR$^{14}$, —CONR$^{15}$R$^{16}$—CN, —CO—R$^{17}$, —SR$^{14}$, —SO$_2$—R$^{18}$, —SO$_2$NR$^{15}$R$^{16}$, —NO$_2$, —NR$^{15}$R$^{16}$, —NH CO—R$^{17}$ and heteroaryl; the number of said substituents being 1, 2, 3, 4 or 5 for halogen, and 1, 2 or 3 for any combination of said substituents, and in which each heteroaryl is optionally substituted with 1 or 2 substituents independently selected from oxo, halogen, —$(C_1-C_4)$alkyl and halogenated —$(C_1-C_4)$alkyl; or
wherein the aryl moiety is optionally substituted by two groups which are attached to adjacent carbon atoms and are combined into a saturated or partly unsaturated cyclic 5, 6, 7, or 8 membered ring system, optionally containing 1, 2 or 3 heteroatoms selected from the group consisting of N, O and S, the number of N atoms being 0, 1, 2 or 3 and the number of O and S atoms each being 0, 1 or 2; and
wherein the $(C_1-C_{12})$alkyl moiety is optionally substituted by 1, 2 or 3 halogens or 1 or 2 hydroxyl groups;

(e) heteroaryl and heteroaryl-$(C_1-C_{12})$alkyl, in which the heteroaryl moiety is optionally substituted with one or more substituents independently selected from the group consisting of halogen, —$OR^{14}$, —$(C_1-C_6)$alkyl, halogenated —$(C_1-C_6)$alkyl, —$(C_1-C_6)$alkyl-$COOR^{14}$—$COR^{14}$, —$CONR^{15}R^{16}$, —CN, —CO—$R^{17}$, —$SR^{14}$, —$SO_2$—$R^{18}$, —$SO_2NR^{15}R^{16}$, —$NR^{15}R^{16}$, —NH—CO—$R^{17}$, aryl-$(C_1-C_4)$-alkyl and aryl, the number of said substituents being 1, 2, 3, 4 or 5 for halogen, and 1, 2 or 3 for any combination of said substituents,
and wherein each aryl is optionally substituted with 1, 2 or 3 substituents independently selected from the group consisting of hydroxyl, halogen, —$(C_1-C_6)$alkoxy, —$(C_1-C_6)$alkyl, halogenated —$(C_1-C_6)$alkyl and halogenated —$(C_1-C_6)$alkoxy;
and wherein the $(C_1-C_{12})$alkyl moiety is optionally substituted by 1, 2 or 3 halogens; and
(f) cycloheteroalkyl and cycloheteroalkyl-$(C_1-C_{12})$alkyl, in which the cycloheteroalkyl moiety is optionally substituted with one or more substituents independently selected from the group consisting of oxo, —$(C_1-C_6)$-alkyl, aryl, aryl-$(C_1-C_4)$-alkyl, —$OR^{14}$, —$COOR^{14}$ $(C_1-C_6)$alkyl-$COOR^{14}$—$SR^{14}$—CN, —$SO_2NR^{15}R^{16}$, —$NR^{15}R^{16}$, —$CONR^{15}R^{16}$, —CO—$R^{17}$ and —NH—CO—$R^{17}$, the number of said substituents being 1, 2, 3, 4 or 5 for halogen, and 1, 2 or 3 for any combination of said substituents, and in which each aryl group is optionally substituted with 1, 2 or 3 substituents independently selected from the group consisting of hydroxyl, halogen, $(C_1-C_6)$alkoxy, —$(C_1-C_6)$alkyl, halogenated —$(C_1-C_6)$alkyl and halogenated —$(C_1-C_6)$alkoxy;
or $R^2$ and $R^4$ together with the nitrogen atom to which $R^2$ and $R^4$ are attached form a heterocyclic 4, 5, 6, 7 or 8 membered ring, which is optionally saturated or partly unsaturated; which optionally contains 1, 2 or 3 additional heteroatoms selected from N, O and S, the number of additional N atoms being 0, 1, 2 or 3 and the number of O and S atoms each being 0, 1 or 2; and which ring is optionally part of a multiple condensed ring-system,
which ring or ring-system is optionally substituted with 1, 2 or 3 substituents independently selected from the group consisting of oxo, —$(C_1-C_6)$alkyl, halogen, —$OR^{14}$, —$COOR^{14}$, —$(C_1-C_6)$alkyl-$COOR^{14}$, —$SR^{14}$, —CN, —$NR^{15}R^{16}$—$CONR^{15}R^{16}$, —$SO_2NR^{15}R^{16}$, aryl, aryl-$(C_1-C_4)$-alkyl, heteroaryl and cycloheteroalkyl,
wherein each $(C_1-C_6)$alkyl group is optionally substituted with 1, 2 or 3 substituents independently selected among hydroxyl, halogen, —$(C_1-C_4)$alkoxy or halogenated —$(C_1-C_4)$alkoxy,
wherein each aryl or heteroaryl moiety is optionally substituted with 1, 2 or 3 substituents independently selected from the group consisting of hydroxyl, halogen, —$(C_1-C_6)$alkyl, —$(C_1-C_6)$alkoxy, halogenated —$(C_1-C_6)$alkyl, halogenated —$(C_1-C_6)$alkoxy, —$(C_1-C_6)$alkyl-$COOR^{14}$ and —$COOR^{14}$, or in which each aryl moiety optionally substituted by two groups which are attached to adjacent carbon atoms and are combined into a saturated or partly unsaturated cyclic 5, 6 or 7 membered ring system, optionally containing 1 or 2 heteroatoms selected from N, O and S, the number of N atoms being 0, 1 or 2 and the number of O and S atoms each being 0, 1 or 2; and
wherein each cycloheteroalkyl is optionally substituted with 1, 2 or 3 substituents independently selected from the group consisting of oxo, —$(C_1-C_6)$alkyl, aryl, aryl-$(C_1-C_4)$alkyl, hydroxyl, —$(C_1-C_6)$alkoxy, —$(C_1-C_6)$alkyl-$COOR^{14}$ and —$COOR^{14}$;
or which ring is optionally substituted by two groups which are attached to the same carbon atom and are combined into a saturated or partly unsaturated cyclic 4, 5, 6, 7 or 8 membered ring system, optionally containing 1, 2 or 3 heteroatoms selected from N, O and S, the number of N atoms being 0, 1, 2 or 3 and the number of O and S atoms each being 0, 1 or 2, and which cyclic ring system is optionally substituted by 1 or 2 substituents independently selected from the group consisting of oxo, $(C_1-C_6)$alkyl, aryl and aryl-$(C_1-C_4)$-alkyl;
wherein $R^{14}$, $R^{15}$, $R^{16}$, $R^{17}$ and $R^{18}$ are independently selected from the group consisting of —H, —$(C_1-C_4)$alkyl, halogenated —$(C_1-C_4)$alkyl, aryl and aryl-$(C_1-C_4)$alkyl, or wherein $R^{15}$ and $R^{16}$ form together with the nitrogen atom, to which they are attached, a heterocyclic 5, 6 or 7 membered ring, optionally containing 1 or 2 additional heteroatoms selected from N, O and S, the number of N atoms being 0, 1 or 2 and the number of O and S atoms each being 0 or 1,
and wherein n represents
(a) 1, 2, 3, 4, 5 or 6, if —X-A-Y— together represent —NH—CO—$NR^4$—, —NH—CO—O—, —NH—CO—, —NH—CO—NH—$SO_2$—, —NH—$SO_2$—$NR^4$—, —NH—$SO_2$—O—, —NH—$SO_2$—, —O—CO—$NR^4$—, —O—CO—, —O—CO—NH—$SO_2$—$NR^4$—, or —O—, or
(b) 0, 1, 2, 3, 4, or 5, if —X-A-Y— together represent —CO—$NR^4$—, —CO—O—, —CO—, or —CO—NH—$NR^4$—.

7. A compound according to claim 1, wherein $R^6$, $R^7$, $R^8$, $R^9$ and $R^{10}$ are each independently selected from the group consisting of:
(a) —H
(b) —$(C_1-C_{12})$alkyl, which is optionally substituted by halogen, —CN, —$R^{14}$, —$SR^{14}$, —$NR^{15}R^{16}$, —$CONR^{15}R^{16}$—$SO_2NR^{15}R^{16}$, —CO—$R^{17}$, —$COOR^{14}$—NH—CO—$R^{17}$, or —O—$SO_2$—$R^{18}$; the number of said substituents being up to five for halogen, and 1 or 2 for any combination of substituents;
(c) aryl and aryl-$(C_1-C_{12})$alkyl, in which the aryl moiety of the aryl or aryl-$(C_1-C_{12})$alkyl group is optionally substituted with one or more substituents independently selected from the group consisting of halogen, —$OR^{19}$, —$(C_1-C_6)$alkyl, halogenated —$(C_1-C_6)$alkyl, —$COOR^{19}$, —$(C_1-C_6)$alkyl-$COOR^{19}$, —$CONR^{20}R^{21}$, —CN, —CO—$R^{22}$, $SR^{19}$, —$SO_2$—$R^{23}$, —$SO_2NR^{20}R^{21}$, —$NO_2$, —$NR^{20}R^{21}$, —NH—CO—$R^{22}$ and heteroaryl; the number of said substituents being 1, 2, 3, 4 or 5 for halogen, and 1, 2 or 3 for any combination of said substituents, and
wherein each heteroaryl is optionally substituted with 1 or 2 substituents independently selected from oxo, halogen, —$(C_1-C_4)$alkyl and halogenated —$(C_1-C_4)$alkyl; or
wherein the aryl moiety of the aryl or aryl-$(C_1-C_{12})$alkyl group is optionally substituted by two groups which are attached to adjacent carbon atoms and are combined into a saturated or partly unsaturated cyclic 5, 6, 7, or 8 membered ring system, optionally containing 1, 2 or 3 heteroatoms selected from the group consisting of N, O and S, the number of N atoms being 0, 1, 2 or 3 and the number of O and S atoms each being 0, 1 or 2, and which ring system is optionally substituted with 1 or 2 oxo groups; and wherein the $(C_1-C_{12})$alkyl moiety is optionally substituted by 1, 2 or 3 halogens or 1 or 2 hydroxyl groups;

(d) heteroaryl and heteroaryl-$(C_1-C_{12})$alkyl, in which the heteroaryl moiety is optionally substituted with one or more substituents independently selected from the group consisting of halogen, oxo, —$OR^{19}$, —$(C_1-C_6)$alkyl, halogenated —$(C_1-C_6)$alkyl, —$COOR^{19}$, —$(C_1-C_6)$alkyl-$COOR^{19}$, —$CONR^{20}R^{21}$ —CN, —CO—$R^{22}$, —$SR^{19}$, —$SO_2$—$R^{23}$, —$SO_2NR^{20}R^{21}$, —$NR^{20}R^{21}$, —NH—CO—$R^{22}$, aryl-$(C_1-C_4)$-alkyl and aryl, the number of said substituents being 1, 2, 3, 4 or 5 for halogen, and 1, 2 or 3 for any combination of said substituents, and wherein each aryl is optionally substituted with 1, 2 or 3 substituents independently selected from the group consisting of hydroxyl, halogen, —$(C_1-C_6)$alkoxy, —$(C_1-C_6)$alkyl, halogenated —$(C_1-C_6)$alkyl and halogenated —$(C_1-C_6)$alkoxy; and wherein the $(C_1-C_{12})$alkyl moiety is optionally substituted by 1, 2 or 3 halogens; and (e) cycloheteroalkyl and cycloheteroalkyl-$(C_1-C_{12})$alkyl, in which the cycloheteroalkyl moiety is optionally substituted with one or more substituents independently selected from the group consisting of oxo, —$(C_1-C_6)$-alkyl, aryl, aryl-$(C_1-C_4)$-alkyl, —$OR^{19}$, —$COOR^{19}$, —$(C_1-C_6)$alkyl-$COOR^{19}$, —$SR^{19}$, —CN, —$SO_2NR^{20}R^{21}$, —$NR^{20}R^{21}$, —$CONR^{20}R^{21}$, —CO—$R^{22}$ and —NH—CO—$R^{22}$, the number of said substituents being 1, 2, 3, 4 or 5 for halogen, and 1, 2 or 3 for any combination of said substituents, and in which each aryl group is optionally substituted with 1, 2 or 3 substituents independently selected from the group consisting of hydroxyl, halogen, $(C_1-C_6)$alkoxy, —$(C_1-C_6)$alkyl, halogenated —$(C_1-C_6)$alkyl and halogenated —$(C_1-C_6)$alkoxy;

or $R^7$ and $R^8$ together with the nitrogen atom to which they are attached form a heterocyclic 4, 5, 6, 7 or 8 membered ring, which is optionally saturated, partly unsaturated or aromatic; which optionally contains 1, 2 or 3 additional heteroatoms selected from the group consisting of N, O or S, the number of additional N atoms being 0, 1, 2 or 3 and the number of O and S atoms each being 0, 1 or 2; and which ring is optionally part of a multiple condensed ring system, and which ring or ring-system is optionally substituted by 1, 2 or 3 substituents independently selected from the group consisting of oxo, —$(C_1-C_6)$alkyl, halogen, —$OR^{19}$, —$COOR^{19}$, —$(C_1-C_6)$alkyl-$COOR^{19}$, —$SR^{19}$, —CN, —$NR^{20}R^{21}$, —$CONR^{20}R^{21}$, —$SO_2NR^{20}R^{21}$, aryl and aryl-$(C_1-C_4)$-alkyl, wherein each $(C_1-C_6)$alkyl group is optionally substituted with 1, 2 or 3 substituents independently selected among hydroxyl, halogen, —$(C_1-C_4)$alkoxy or halogenated —$(C_1-C_4)$alkoxy, wherein each aryl moiety is optionally substituted with 1, 2 or 3 substituents independently selected from the group consisting of hydroxyl, halogen, —$(C_1-C_6)$alkyl, —$(C_1-C_6)$alkoxy, halogenated —$(C_1-C_6)$alkyl, halogenated —$(C_1-C_6)$alkoxy, —$(C_1-C_6)$alkyl-$COOR^{19}$ and —$COOR^{19}$; or wherein $R^{19}$, $R^{20}$, $R^{21}$, $R^{22}$ and $R^{23}$ are independently selected from the group consisting of —H, —$(C_1-C_4)$alkyl, halogenated —$(C_1-C_4)$alkyl, aryl and aryl-$(C_1-C_4)$alkyl, or wherein $R^{20}$ and $R^{21}$ form together with the nitrogen atom, to which they are attached, a heterocyclic 5, 6 or 7 membered ring, optionally containing 1 or 2 additional heteroatoms selected from N, O and S, the number of N atoms being 0, 1 or 2 and the number of O and S atoms each being 0 or 1, and if $R^1$ is —$NR^5$—CO—$R^6$, then $R^5$ and $R^6$ together with the nitrogen atom to which $R^5$ is attached and the carbonyl group to which $R^6$ is attached may also form a heterocyclic 4, 5, 6, 7 or 8 membered lactam ring, and if $R^1$ is —$NR^5$—$SO_2$—$R^6$, then $R^5$ and $R^6$ together with the nitrogen atom to which $R^5$ is attached and the sulfoxyd group to which $R^6$ is attached may also form a heterocyclic 4, 5, 6, 7 or 8 membered sultam ring, or $R^9$ and $R^{10}$ form together with the boron atom, to which they are attached, a heterocyclic 5 or 6 membered ring, which is optionally substituted with 1, 2, 3 or 4-$(C_1-C_4)$ alkyl groups.

8. A compound according to claim 1, wherein $R^1$ is selected from the group consisting of:
(a) —$B(OH)_2$.
(b) —CO—OH
(c) —CO—$NR^7R^8$,
(d) —$NR^7R^8$, and
(e) —$NR^5$—CO—$R^6$.

9. A compound according to claim 8, wherein
$R^1$ is —CO—$NR^7R^8$, and
$R^7$ and $R^8$ are independently selected from the group consisting of —H and —$(C_1-C_6)$alkyl.

10. A compound according to claim 8, wherein
$R^1$ is —$NR^5$—CO—$R^6$, and
$R^5$ and $R^6$ together with the nitrogen atom to which $R^5$ is attached and the carbonyl group to which $R^6$ is attached form a heterocyclic 5 or 6-membered lactam ring.

11. A compound according to claim 8, wherein
$R^1$ is —$NR^7R^8$, and
$R^7$ and $R^8$ are independently selected from the group consisting of:
(a) —H
(b) —$(C_1-C_6)$alkyl;
(c) phenyl and phenyl-$(C_1-C_4)$alkyl,
wherein the phenyl moiety is optionally substituted with 1 or 2 substituents independently selected from the group consisting of halogen, —$OR^{19}$, —$(C_1-C_4)$alkyl, halogenated —$(C_1-C_4)$alkyl, —CN and —$SO_2NR^{20}R^{21}$; or
wherein the phenyl moiety is optionally substituted by two groups which are attached to adjacent carbon atoms and are combined into a saturated or partly unsaturated cyclic 5 or 6 membered ring system, optionally containing 1 or 2 heteroatoms selected from the group consisting of O and S, the number of O and S atoms each being 0, 1 or 2, and which ring system is optionally substituted with 1 or 2 oxo groups;

(d) heteroaryl and heteroaryl-$(C_1-C_4)$alkyl, which heteroaryl moiety is optionally substituted with 1 or 2 oxo groups;

(e) cycloheteroalkyl and cycloheteroalkyl-$(C_1-C_4)$alkyl, in which the cycloheteroalkyl moiety is optionally substituted with an oxo group;

or $R^7$ and $R^8$ together with the nitrogen atom to which they are attached form a heterocyclic 5, 6 or 7 membered ring, which is optionally saturated, partly unsaturated or aromatic;

which optionally contains 1 or 2 additional heteroatoms selected from the group consisting of N, O or S, the number of additional N atoms being 0, 1 or 2 and the number of O and S atoms each being 0 or 1; and which ring is optionally part of a multiple condensed ring system, and which ring or ring-system is optionally substituted by 1 or 2 substituents independently selected from the group consisting of oxo, —($C_1$-$C_4$)alkyl, —$OR^{19}$, aryl and aryl-($C_1$-$C_2$)-alkyl,
in which each aryl moiety is optionally substituted with 1, 2 or 3 substituents independently selected from the group consisting of hydroxyl, halogen, —($C_1$-$C_4$)alkyl, —($C_1$-$C_4$)alkoxy, halogenated —($C_1$-$C_4$)alkyl and halogenated —($C_1$-$C_4$)alkoxy;
wherein $R^{19}$, $R^{20}$ and $R^{21}$ are independently selected from the group consisting of —H, —($C_1$-$C_4$)alkyl and halogenated —($C_1$-$C_4$)alkyl, or
wherein $R^{20}$ and $R^{21}$ together with the nitrogen atom to which they are attached form a heterocyclic 5 or 6 membered ring, optionally containing 1 additional heteroatom selected from the group consisting of N, O and S.

12. A compound according to claim 6, wherein $R^2$ and $R^4$ are each independently selected from the group consisting of:
(a) —H, provided that —X-A-Y— is not —CO—O— or —CO—,
(b) —($C_1$-$C_6$)alkyl and —($C_1$-$C_6$)cycloalkyl, which are optionally substituted with 1 or 2 substituents independently selected from the group consisting of halogen and —$OR^{14}$;
(c) phenyl and phenyl-($C_1$-$C_4$)alkyl,
wherein the phenyl moiety is optionally substituted with 1 or 2 substituents independently selected from the group consisting of halogen, —$OR^{14}$, —($C_1$-$C_6$)alkyl and halogenated —($C_1$-$C_6$)alkyl, or
wherein the phenyl moiety is optionally substituted by two groups which are attached to adjacent carbon atoms and are combined into a saturated or partly unsaturated cyclic 5 or 6 membered ring system, optionally containing 1 or 2 heteroatoms independently selected from the group consisting of N, O and S, the number of N, O and S atoms each being 0, 1 or 2;
(d) heteroaryl and heteroaryl-($C_1$-$C_4$)alkyl, in which the heteroaryl moiety is optionally substituted with 1 or 2 substituents independently selected from the group consisting of halogen, —$OR^{14}$, —($C_1$-$C_6$)alkyl and halogenated —($C_1$-$C_6$)alkyl;
or $R^2$ and $R^4$ together with the nitrogen atom to which $R^2$ and $R^4$ are attached form a heterocyclic 5, 6 or 7 membered ring, which is optionally saturated or partly unsaturated; which optionally contains 1 or 2 additional heteroatoms selected from the group consisting of N, O and S, the number of additional N atoms being 0, 1 or 2 and the number of O and S atoms each being 0 or 1; and which ring is optionally part of a multiple condensed ring-system,
wherein said heterocyclic ring or ring-system is optionally substituted with 1 or 2 substituents independently selected from the group consisting of oxo, —($C_1$-$C_6$)alkyl, halogen and —$OR^{14}$, wherein $R^{14}$ is selected from the group consisting of —H, —($C_1$-$C_4$)alkyl and halogenated —($C_1$-$C_4$)alkyl.

13. A compound according to claim 1, wherein $R^{11}$ represents H, —($C_1$-$C_4$)alkyl, ($C_1$-$C_4$)alkoxy, or ($C_1$-$C_4$)alkoxy-($C_1$-$C_4$)alkyl.

14. A compound according to claim 13, wherein $R^{11}$ represents H, ethyl, propyl, methoxyethyl, methoxy, ethoxy or methoxyethoxy.

15. A compound according to claim 14, wherein $R^{11}$ represents H.

16. A compound according claim 1, wherein n represents 2, 3 or 4.

17. A compound according to claim 16, wherein
n represents 2, and
the compound is an optically pure enantiomer corresponding to formula (III-b)

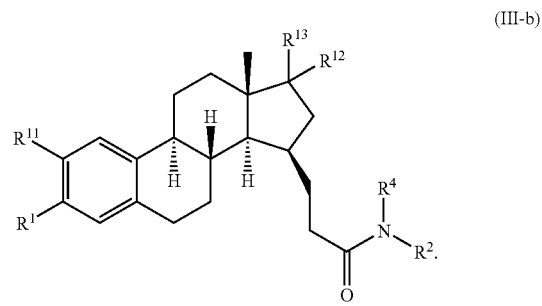

(III-b)

18. A compound according to 16, wherein
n represents 3, and
the compound is an optically pure enantiomer corresponding to formula (II)

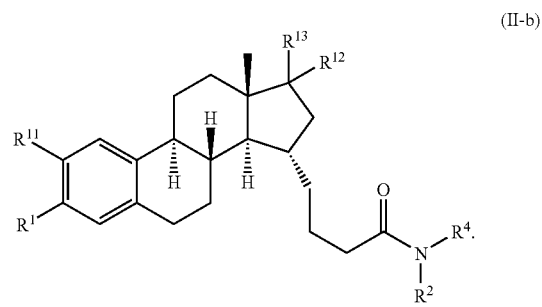

(II-b)

19. A compound according to claim 1, wherein $R^{12}$ and $R^{13}$ together represent =O.

20. A compound according to claim 1, wherein $R^{12}$ and $R^{13}$ each individually represent F.

21. A compound according to claim 1, wherein
—X-A-Y— together represent —CO—$NR^4$—;
$R^1$ is selected from the group consisting of
(a) —$B(OH)_2$.
(b) —CO—OH
(c) —CO—$NR^7R^8$, wherein $R^7$ and $R^8$ are independently selected from —H and —($C_1$-$C_4$)alkyl
(d) —$NR^5$—CO—$R^6$, wherein $R^5$ and $R^6$ together with the nitrogen atom to which $R^5$ is attached and the carbonyl group to which $R^6$ is attached form a heterocyclic 5 membered lactam ring, and
(e) —$NR^7R^8$;
$R^{11}$ represents —H;
$R^{12}$ and $R^{13}$ together represent =O, or $R^{12}$ and $R^{13}$ each individually represent F; and
n represents 2 or 3.

22. A compound according to claim 21, wherein
$R^1$ represents —CO—OH or —CO—$NR^7R^8$, wherein $R^7$ and $R^8$ are each independently selected from —H and —($C_1$-$C_4$)alkyl;
—X-A-Y— together represent —CO—$NR^4$—;
$R^{11}$ represents —H;
$R^{12}$ and $R^{13}$ together represent =O, or $R^{12}$ and $R^{13}$ each individually represent F; and
n represents 2 or 3.

23. A compound according to claim 21, wherein
$R^1$ represents —B(OH)$_2$,
—X-A-Y— together represent —CO—NR$^4$—;
$R^{11}$ represents —H;
$R^{12}$ and $R^{13}$ together represent =O, or $R^{12}$ and $R^{13}$ each individually represent F; and
n represents 2 or 3.

24. A compound according to claim 21, wherein
$R^1$ represents —NR$^5$—CO—R$^6$, wherein $R^5$ and $R^6$ together with the nitrogen atom to which $R^5$ is attached and the carbonyl group to which $R^6$ is attached form a heterocyclic 5 membered lactam ring;
—X-A-Y— together represent —CO—NR$^4$—;
$R^{11}$ represents —H;
$R^{12}$ and $R^{13}$ together represent =O, or $R^{12}$ and $R^{13}$ each individually represent F; and
n represents 2 or 3.

25. A compound according to claim 21, wherein
$R^1$ represents —NR$^7$R$^8$,
—X-A-Y— together represent —CO—NR$^4$—;
$R^{11}$ represents —H;
$R^{12}$ and $R^{13}$ together represent =O, or $R^{12}$ and $R^{13}$ each individually represent F; and
n represents 2 or 3.

26. A compound according to claim 25, wherein $R^7$ and $R^8$ are each independently selected from the group consisting of:
(a) —H
(b) —(C$_1$-C$_6$)alkyl;
(c) phenyl and phenyl-(C$_1$-C$_2$)alkyl,
 wherein the phenyl moiety is optionally substituted with 1 or 2 substituents independently selected from the group consisting of halogen, —OR$^{19}$, —(C$_1$-C$_4$)alkyl, halogenated —(C$_1$-C$_4$)alkyl, —CN and —SO$_2$NR$^{20}$R$^{21}$; or
 wherein the phenyl moiety is optionally substituted by two groups which are attached to adjacent carbon atoms and are combined into a saturated or partly unsaturated cyclic 5 or 6 membered ring system, optionally containing 1 or 2 heteroatoms selected from the group consisting of O and S, the number of O and S atoms each being 0, 1 or 2, and which ring system is optionally substituted with 1 or 2 oxo groups;
(d) heteroaryl and heteroaryl-(C$_1$-C$_2$)alkyl, in which the heteroaryl moiety is selected from the group consisting of indolyl, quinolinyl, benzothienyl and pyridinyl, which heteroaryl moiety is optionally substituted with 1 or 2 oxo groups;
(e) cycloheteroalkyl and cycloheteroalkyl-(C$_1$-C$_4$)alkyl, in which the cycloheteroalkyl moiety is selected from the group consisting of pyrrolidinyl and oxazolidinyl, and in which the cycloheteroalkyl moiety is optionally substituted with an oxo group;
or $R^7$ and $R^8$ together with the nitrogen atom to which they are attached form a heterocyclic 5 or 6 membered saturated ring, which is saturated or partly unsaturated, which optionally contains 1 additional heteroatom selected from the group consisting of N and O; and
which ring is optionally part of a multiple condensed ring system, and which ring or ring-system is optionally substituted by a substituent selected from the group consisting of oxo, phenyl and phenyl-(C$_1$-C$_2$)-alkyl, wherein each phenyl moiety is optionally substituted with a substituent selected from the group consisting of halogen and —(C$_1$-C$_4$)alkoxy;
wherein $R^{19}$, $R^{20}$ and $R^{21}$ are independently selected from the group consisting of —H, —(C$_1$-C$_4$)alkyl and halogenated —(C$_1$-C$_4$)alkyl, or
wherein $R^{20}$ and $R^{21}$ together with the nitrogen atom to which they are attached form a heterocyclic 6 membered ring, optionally containing 1 additional heteroatom selected from N and O.

27. A compound according to claim 21, wherein $R^2$ and $R^4$ are independently selected from:
(a) —H,
(b) —(C$_1$-C$_4$)alkyl, which is optionally substituted with —OR$^{14}$, wherein $R^{14}$ is selected from the group consisting of —H, —(C$_1$-C$_4$)alkyl and halogenated —(C$_1$-C$_4$)alkyl;
(c) —(C$_1$-C$_6$)cycloalkyl;
(d) phenyl and phenyl-(C$_1$-C$_2$)alkyl,
 wherein the phenyl moiety is optionally substituted with 1 or 2 substituents independently selected from the group consisting of halogen and —OR$^{14}$, or
 wherein the phenyl moiety is optionally substituted by two groups which are attached to adjacent carbon atoms and are combined into a saturated cyclic 5 or 6 membered ring system, optionally containing 1 or 2 heteroatoms independently selected from the group consisting of N, O and S, the number of N, O and S atoms each being 0, 1 or 2;
(e) heteroaryl and heteroaryl-(C$_1$-C$_2$)alkyl, in which the heteroaryl moiety is selected from the group consisting of imidazolyl, pyridinyl, indolyl and thiazolyl, and in which the heteroaryl moiety is optionally substituted with —(C$_1$-C$_4$)alkyl;
or $R^2$ and $R^4$ together with the nitrogen atom to which $R^2$ and $R^4$ are attached form a heterocyclic 5, 6 or 7 membered saturated ring, which optionally contains 1 additional heteroatom selected from N and O; which ring is optionally substituted with —(C$_1$-C$_4$)alkyl.

28. A compound according to claim 1, wherein
$R^1$ represents —B(OH)$_2$,
—X-A-Y— together represent a group

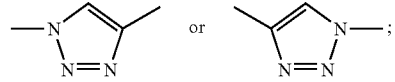

$R^{11}$ represents H, ethyl, propyl, methoxyethyl, methoxy, ethoxy or methoxyethoxy;
$R^{12}$ and $R^{13}$ together represent =O, or $R^{12}$ and $R^{13}$ each individually represent F; and
n represents 2 or 3.

29. A compound according to claim 28, wherein $R^2$ is selected from the group consisting of
(a) —(C$_1$-C$_6$)alkyl,
(b) (C$_1$-C$_6$)cycloalkyl-(C$_1$-C$_4$)alkyl, and
(c) phenyl and phenyl-(C$_1$-C$_2$)alkyl, in which the phenyl moiety is optionally substituted with 1 or 2 substituents independently selected from the group consisting of halogen, —(C$_1$-C$_4$)alkyl, halogenated —(C$_1$-C$_4$)alkyl, —OR$^{14}$, and —COOR$^{14}$, wherein $R^{14}$ is selected from the group consisting of —H, —(C$_1$-C$_4$)alkyl and halogenated —(C$_1$-C$_4$)alkyl.

30. A compound according to claim 1, selected from the group consisting of compounds:
No. 3  15beta-{3-[(5-methyl-1,3-thiazol-2-yl)amino]-3-oxopropyl}-17-oxoestra-1(10),2,4-triene-3-carboxamide, No. 8 17,17-difluoro-15beta-{3-[(5-methyl-1,3-thiazol-2-yl)amino]-3-oxopropyl}estra-1(10),2,4-triene-3-carboxamide,
No. 11 [15alpha-{3-[(5-methyl-1,3-thiazol-2-yl)amino]-3-oxopropyl}-17-oxoestra-1(10),2,4-trien-3-yl]boronic acid,
No. 12 [15alpha-{4-[(3,4-dihydroxybenzyl)amino]-4-oxobutyl}-17-oxoestra-1(10),2,4-trien-3-yl]boronic acid,
No. 13 [15alpha-[4-(1,3-benzodioxol-5-ylamino)-4-oxobutyl]-17-oxoestra-1(10),2,4-trien-3-yl]boronic acid,
No. 16 [15alpha-{4-[(5-methyl-1,3-thiazol-2-yl)amino]-4-oxobutyl}-17-oxoestra-1(10),2,4-trien-3-yl]boronic acid,
No. 17 [15alpha-[4-(cyclohexylamino)-4-oxobutyl]-17-oxoestra-1(10),2,4-trien-3-yl]boronic acid,
No. 19 [15alpha-{4-[(1,3-benzodioxol-5-ylmethyl)amino]-4-oxobutyl}-17-oxoestra-1(10),2,4-trien-3-yl]boronic acid,
No. 20 [17-oxo-15alpha-(4-oxo-4-piperidin-1-ylbutyl)estra-1(10),2,4-trien-3-yl]boronic acid,
No. 22 [15alpha-{4-[benzyl(methyl)amino]-4-oxobutyl}-17-oxoestra-1(10),2,4-trien-3-yl]boronic acid,
No. 23 [15alpha-[4-(benzylamino)-4-oxobutyl]-17-oxoestra-1(10),2,4-trien-3-yl]boronic acid,
No. 26 [15alpha-(4-{[2-(3,4-dimethoxyphenyl)ethyl](methyl)amino}-4-oxobutyl)-17-oxoestra-1(10),2,4-trien-3-yl]boronic acid,
No. 30 [15beta-(3-{[2-(7-methyl-1H-indol-3-yl)ethyl]amino}-3-oxopropyl)-17-oxoestra-1(10),2,4-trien-3-yl]boronic acid,
No. 31 [15beta-{3-[(5-methyl-1,3-thiazol-2-yl)amino]-3-oxopropyl}-17-oxoestra-1(10),2,4-trien-3-yl]boronic acid,
No. 32 [15beta-[3-(cyclohexylamino)-3-oxopropyl]-17-oxoestra-1(10),2,4-trien-3-yl]boronic acid,
No. 33 [15beta-(3-morpholin-4-yl-3-oxopropyl)-17-oxoestra-1(10),2,4-trien-3-yl]boronic acid,
No. 34 [15beta-{3-[(1,3-benzodioxol-5-ylmethyl)amino]-3-oxopropyl}-17-oxoestra-1(10),2,4-trien-3-yl]boronic acid,
No. 35 [17-oxo-15beta-(3-oxo-3-piperidin-1-ylpropyl)estra-1(10),2,4-trien-3-yl]boronic acid,
No. 37 [15beta-{3-[benzyl(methyl)amino]-3-oxopropyl}-17-oxoestra-1(10),2,4-trien-3-yl]boronic acid,
No. 39 [15beta-[3-(diethylamino)-3-oxopropyl]-17-oxoestra-1(10),2,4-trien-3-yl]boronic acid,
No. 45 [15beta-[3-(1,3-benzodioxol-5-ylamino)-3-oxopropyl]-17-oxoestra-1(10),2,4-trien-3-yl]boronic acid,
No. 48 [15alpha-[4-(cyclohexylamino)-4-oxobutyl]-17,17-difluoroestra-1(10),2,4-trien-3-yl]boronic acid,
No. 49 [15alpha-[4-(diethylamino)-4-oxobutyl]-17,17-difluoroestra-1(10),2,4-trien-3-yl]boronic acid,
No. 50 [15alpha-{4-[(1,3-benzodioxol-5-ylmethyl)amino]-4-oxobutyl}-17,17-difluoroestra-1(10),2,4-trien-3-yl]boronic acid,
No. 51 [15alpha-(4-{[2-(3,4-dimethoxyphenyl)ethyl](methyl)amino}-4-oxobutyl)-17,17-difluoroestra-1(10),2,4-trien-3-yl]boronic acid,
No. 53 [17,17-difluoro-15alpha-{4-oxo-4-[(pyridin-3-ylmethyl)amino]butyl}estra-1(10),2,4-trien-3-yl]boronic acid,
No. 54 [15alpha-[4-(benzylamino)-4-oxobutyl]-17,17-difluoroestra-1(10),2,4-trien-3-yl]boronic acid,
No. 57 [17,17-difluoro-15alpha-(4-oxo-4-piperidin-1-ylbutyl)estra-1(10),2,4-trien-3-yl]boronic acid,
No. 58 [17,17-difluoro-15beta-{3-[(5-methyl-1,3-thiazol-2-yl)amino]-3-oxopropyl}estra-1(10),2,4-trien-3-yl]boronic acid,
No. 75 3-{[3-methoxy-5-(trifluoromethyl)phenyl]amino}-15alpha-(4-morpholin-4-yl-4-oxobutyl)estra-1(10),2,4-trien-17-one,
No. 76 15alpha-(4-morpholin-4-yl-4-oxobutyl)-3-{[3-(morpholin-4-ylsulfonyl)phenyl]amino}estra-1(10),2,4-trien-17-one,
No. 83 15alpha-(4-morpholin-4-yl-4-oxobutyl)-3-(quinolin-3-ylamino)estra-1(10),2,4-trien-17-one,
No. 91 3-[(1,1-dioxido-1-benzothien-6-yl)amino]-15alpha-(4-morpholin-4-yl-4-oxobutyl)estra-1(10),2,4-trien-17-one,
No. 98 3-(benzylamino)-15alpha-(4-morpholin-4-yl-4-oxobutyl)estra-1(10),2,4-trien-17-one,
and pharmaceutically acceptable salts thereof.

31. A pharmaceutical composition comprising a compound according to claim 1 and at least one pharmaceutically acceptable carrier or excipient.

32. A method of treating breast cancer in a mammal, said method comprising administering to said mammal a pharmacologically effective amount of a compound according to claim 1.

33. A method according to claim 32, wherein the breast cancer is characterized by a detectable level of 17β-HSD1 within a cancer tissue sample.

34. A method according to claim 32, wherein the mammal is a human post-menopausal female.

\* \* \* \* \*

UNITED STATES PATENT AND TRADEMARK OFFICE
CERTIFICATE OF CORRECTION

PATENT NO. : 8,288,367 B2
APPLICATION NO. : 11/947025
DATED : October 16, 2012
INVENTOR(S) : Messinger et al.

It is certified that error appears in the above-identified patent and that said Letters Patent is hereby corrected as shown below:

In the Claims,

Column 137, line 61, claim 1: "-$NR^3$-$SO_2$" to read as -- -$NR^3$-$SO_2$-, --

Column 139, line 11, claim 1: "6:7" to read as -- 6, 7 --

Column 140, line 01, claim 4: "-NH-$SO_2$" to read as -- -$NHSO_2$-, --

Column 140, line 32, claim 6: "-$SO_2NR^{15}R^{16}$-CO-$R^{17}$-$COOR^{14}$-NH-CO-$R^{17}$" to read as -- -$SO_2NR^{15}R^{16}$, -CO-$R^{17}$, -$COOR^{14}$, -NH-CO-$R^{17}$ --

Column 140, line 50, claim 6: "-$CONR^{15}R^{16}$-CN," to read as -- -$CONR^{15}R^{16}$, -CN, --

Column 141, line 05, claim 6: "-($C_1$-$C_6$)alkyl-$COOR^{14}$-$COR^{14}$," to read as -- -($C_1$-$C_6$)alkyl-$COOR^{14}$, -$COOR^{14}$, --

Column 141, line 31, claim 6: "($C_1$-$C_6$)alkoxy," to read as -- -($C_1$-$C_6$)alkoxy, --

Column 141, line 45, claim 6: "-$NR^{15}R^{16}$-$CONR^{15}R^{16}$," to read as -- -$NR^{15}R^{16}$, $CONR^{15}R^{16}$, --

Column 141, line 58, claim 6: "each aryl moiety optionally substituted" to read as -- each aryl moiety is optionally substituted --

Column 142, line 39, claim 7: "-$CONR^{15}R^{16}$-$SO_2$-$NR^{15}R^{16}$," to read as -- -$CONR^{15}R^{16}$, -$SO_2$-$NR^{15}R^{16}$, --

Column 142, line 49, claim 7: "-CO-$R^{22}$,$SR^{19}$," to read as -- -CO-$R^{22}$, -$SR^{19}$, --

Column 142, line 65, claim 7: "Satoms" to read as -- 5 atoms --

Column 144, line 13, claim 7: "4-($C_1$-$C_4$)alkyl" to read as -- 4 -($C_1$-$C_4$)alkyl --

Signed and Sealed this
Seventeenth Day of March, 2015

Michelle K. Lee
*Director of the United States Patent and Trademark Office*